(12) United States Patent
Tung et al.

(10) Patent No.: US 7,432,379 B2
(45) Date of Patent: Oct. 7, 2008

(54) SUBSTITUTED PYRAZOLE DERIVATIVES AND RELATED COMPOUNDS AS BRADYKININ B₁ RECEPTOR ANTAGONISTS

(75) Inventors: Jay S. Tung, Belmont, CA (US); Albert W. Garofalo, South San Francisco, CA (US); Michael A. Pleiss, Sunnyvale, CA (US); Jing Wu, Redwood City, CA (US); David W. G. Wone, Newark, CA (US); Ashley C. Guinn, Pacifica, CA (US); Darren B. Dressen, San Mateo, CA (US); R. Jeffrey Neitz, San Francisco, CA (US); Jennifer Marugg, San Jose, CA (US); Martin Neitzel, Pacifica, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 560 days.

(21) Appl. No.: 10/837,231

(22) Filed: Apr. 30, 2004

(65) Prior Publication Data

US 2005/0020659 A1 Jan. 27, 2005

Related U.S. Application Data

(60) Provisional application No. 60/467,695, filed on May 2, 2003, provisional application No. 60/539,546, filed on Jan. 27, 2004.

(51) Int. Cl.
*C07D 401/12* (2006.01)
(52) U.S. Cl. ..................................................... 546/211
(58) Field of Classification Search .................. 546/211
See application file for complete search history.

(56) References Cited

U.S. PATENT DOCUMENTS

| | | | |
|---|---|---|---|
| 3,654,275 A | 4/1972 | McManus | |
| 5,753,629 A * | 5/1998 | Beria et al. ................... | 514/18 |
| 5,916,908 A | 6/1999 | Giese et al. | |
| 6,433,185 B1 | 8/2002 | Ferrari et al. | |
| 2002/0037856 A1 | 3/2002 | Zhang et al. | |
| 2003/0119749 A1 | 6/2003 | Zhang et al. | |
| 2003/0212113 A1 | 11/2003 | Dyatkina et al. | |
| 2004/0063658 A1 | 4/2004 | Roberts et al. | |
| 2004/0116353 A1 | 6/2004 | Ferrari et al. | |
| 2004/0142997 A1 | 7/2004 | Chen et al. | |
| 2005/0032868 A1 | 2/2005 | Tung et al. | |
| 2005/0038099 A1 | 2/2005 | Tung et al. | |
| 2006/0281733 A1 | 12/2006 | Tung et al. | |
| 2007/0123531 A1 | 5/2007 | Garofalo et al. | |

FOREIGN PATENT DOCUMENTS

| | | |
|---|---|---|
| DE | 3421386 | 12/1985 |
| DE | 19854081 | 5/2000 |
| EP | 1304325 | 4/2003 |
| GB | 2310207 | 8/1997 |
| JP | 49100080 | 9/1974 |
| JP | 3-168743 | 7/1991 |
| WO | WO/96/05196 | 2/1996 |
| WO | WO98/11101 | 3/1998 |
| WO | WO/98/11101 | 3/1998 |
| WO | WO98/28268 | 7/1998 |
| WO | WO/99/27939 | 6/1999 |
| WO | WO00/31066 | 6/2000 |
| WO | WO/00/50418 | 8/2000 |
| WO | WO00/50418 | 8/2000 |
| WO | WO01/05783 A1 | 1/2001 |
| WO | WO01/57034 | 8/2001 |
| WO | WO/01/87888 | 11/2001 |
| WO | WO01/87888 | 11/2001 |
| WO | WO/02/02523 | 1/2002 |
| WO | WO02/02523 | 1/2002 |
| WO | WO02/04424 | 1/2002 |
| WO | WO/02/08196 | 1/2002 |
| WO | WO/02/22655 | 3/2002 |
| WO | WO02/099388 | 12/2002 |
| WO | WO03/007945 | 1/2003 |
| WO | WO03/007958 | 1/2003 |
| WO | WO/03/015774 | 2/2003 |
| WO | WO03/015774 | 2/2003 |
| WO | WO/03/095429 | 11/2003 |
| WO | WO03/095429 | 11/2003 |
| WO | WO2004/033434 | 4/2004 |

OTHER PUBLICATIONS

Baraldi et al. "Benzoyl Nitrogen Mustard Derivatives of Benzoheterocyclic Analogues of Netropsin: Synthesis and Biological Activity" *Bioorganic & Medicinal Chemistry* 11:2381-2388 (2003).

(Continued)

*Primary Examiner*—Rebecca L Anderson
*Assistant Examiner*—Robert Havlin
(74) *Attorney, Agent, or Firm*—Foley & Lardner LLP

(57) ABSTRACT

Disclosed are compounds that are bradykinin B₁ receptor antagonists and are useful for treating diseases, or relieving adverse symptoms associated with disease conditions, in mammals mediated by bradykinin B₁ receptor. Certain of the compounds exhibit increased potency and are also expected to exhibit increased duration of action.

12 Claims, No Drawings

OTHER PUBLICATIONS

Baraldi et al. "Synthesis and Antitumor Activity of New Benzoheterocyclic Derivatives of Distamycin A" *J. Med. Chem.* 42:2675-2684 (2000).

Baraldi et al. "Novel Benzoyl Nitrogen Mustard Derivatives of Pyrazole Analogues of Distamycin A: Synthesis and Antileukemic Activity" *Bioorganic & Medicinal Chemistry* 7:251-262 (1999).

Baraldi et al. "Structure-Activity Relationship of novel Tallimustine Derivatives: Synthesis and Antitumor Activity" *Bioorganic & Medicinal Chemistry* 6(11):1247-1252.

Baraldi et al. "Synthesis and Antitumor Activity of Novel Distamycin Derivatives" *Bioorganic & Medicinal Chemistry* 6(11):1241-1246 (1996).

Atwell et al. 5-Amino-1-(chloromethyl)-1,2-dihydro-3*H*-benz[*e*]indoles: Relationships between Structure and Cytotoxicity for Analogues Bearing Different DNA Minor Groove Binding Subunits *J. Med. Chem.* 42:3400-3411 (1999).

Database CA Online XP002301180 Database Accession No. 1998:302076 Marchini et al. "Sequence-specific DNA alkylation of novel tallimustine derivatives" *Anti-Cancer Drug Design* 13(3):193-205 (1998).

Database CA Online XP-002301181 Database Accession No. 1992:173857 Lee et al. "Pyrazole analogs of the dispyrrolecarboxamide anti-tumor antibiotics: Synthesis, DNA binding and anti-tumor properties" *Anti-Cancer Drug Design* 6(5):501-517.

Database CA Online XP-002301226 Database Accession No. 1998:233560 Abdallah et al. "A convenient synthesis of 5-amino-4-(2-benzothiazolyl)pyrazoles" *Indian Journal of Chemistry, Section B: Organic Chemistry Including Medicinal Chemistry* 36(12):1175-1177 (1997).

Abdallah, et al. "A convenient synthesis of 5-amino-4-(2-benzothiazolyl) pyrazoles" *Indian J. of Chem.* 36B:1175-1177 (1997).

Eighandour, Ahmed "Hydrazonoyl Halides in Heterocyclic Chemistry: Synthesis of New Polyfunctionally Substituted Pyrazoles, Pyridazines and Pyrazolo [3,4-*d*]pyridazines" *J. Chem.. Research(s)* 358-359 (1993).

Ibrahim, et al. "Utility of Hydrazidoyl Chlorides: Synthesis of New Pyrazoles, Pyrazolo [3,4-*d*]pyridazines, Pyrazolo [4,5-*b*]pyridines and Pyrazolo [4,5-*d*]pyrimidine Derivatives" *J. Indian Chem. Soc.* 69:378-380 (1992).

Lee, et al. "Pyrazole analogues of the bispyrrolecarboxamide anti-tumour antibiotics: synthesis, DNA binding and anti-tumour properties" *Anti-Cancer Drug Design* 6:501-517 (1991).

J.G. Menke, et al., "Expression Cloning of a Human $B_1$ Bradykinin Receptor," *J. Biol. Chem.*, 269(34);21583-21586 (1994).

J. F. Hess, "Cloning and Pharmacological Characterization of a Human Bradykinin (BK-2) Receptor" *Biochem.and, Biophys. Res. Commun.*, 184:260-268 (1992).

Burch et al., "Bradykinin Receptor Antagonists", *Med. Res. Reviews*, 10(2):237-269 (1990).

Clark, W.G. "Kinins and the Peripheral Central Nervous Systems", Handbook of Experimental Pharmacology, vol. XXV: Bradykinin, Kallidin, and Kallikrein. Erdo, E.G. (Ed.), 311-322 (1979).

Ammons, W.S., et al., "Effects of Intracardiac Bradykinin on $T_2$-$T_5$ Medial Spinothalamic Cells", *American Journal of Physiology*, 249, R145-152 (1985).

Costello, A.H. et al., "Suppression of Carageenan-Induced Hyperalgesia, Hyperthermia and Edema by a Bradykinin Antagonist", *European Journal of Pharmacology*, 171:259-263 (1989).

Laneuville, et al., "Bradykinin Analogue Blocks Bradykinin-induced Inhibition of a Spinal Nociceptive Reflex in the Rat", *European Journal of Pharmacology*, 137:281-285 (1987).

Steranka, et al., "Antinociceptive Effects of Bradykinin Antagonists", *European Journal of Pharmacology*, 136:261-262 (1987).

Steranka, et al., "Bradykinin as a Pain Mediator: Receptors are Localized to Sensory Neurons, and Antagonists have Analgesic Actions", *Neurobiology*, 85:3245-3249 (1987).

Whalley, et al., in *Naunyn Schmiederberg's Arch. Pharmacol.*, 336:652-655 (1987).

Back, et al., "Determination of Components of the Kallikrein-Kinin System in the Cerebrospinal Fluid of Patients with Various Diseases", *Res. Clin.Stud. Headaches*, 3:219-226 (1972).

Ness, et al., "Visceral pain: a Review of Experimental Studies", *Pain*, 41:167-234 (1990).

Aasen, et al., "Plasma Kallikrein Activity and Prekallikrein Levels during Endotoxin Shock in Dogs", *Eur. Surg.*, 10:50-62(1977).

Aasen, et al., "Plasma Kallikrein-Kinin System in Septicemia", *Arch. Surg.*, 118:343-346 (1983).

Katori, et al., "Evidence for the Involvement of a Plasma Kallikrein/Kinin System in the Immediate Hypotension Produced by Endotoxin in Anaesthetized Rats", *Br. J. Pharmacol.*, 98:1383-1391 (1989).

Marceau, et al., "Pharmacology of Kinins: Their Relevance to Tissue Injury and Inflammation", *Gen. Pharmacol.*, 14:209-229 (1982).

Weipert, et al., "Attenuation of arterial blood pressure fall in endotoxin shock in the rat using the competitive bradykinin antagonist I vs-I vs-[Hyp$^{2,}$ Thi$^{5,8}$ DPhe$^7$]-Bk (B4148)" *Brit J Pharm* 94:282-284 (1988).

Haberland, "The Role of Kininogenases, Kinin Formation and Kininogenase Inhibitor in Post Traumatic Shock and Related Conditions", *Klinische Woochen-Schrift*, 56:325-331 (1978).

Ellis, et al., "Inhibition of Bradykinin-and Kallikrein-Induced Cerebral Arteriolar Dilation by Specific Bradykinin Antagonist", *Stroke*, 18:792-795 (1987).

Kamitani, et al., "Evidence for a Possible Role of the Brain Kallikrein-Kinin System in the Modulation of the Cerebral Circulation", *Circ. Res.*, 57:545-552 (1985).

Barnes, "Inflammatory Mediator Receptors and Asthma", *Am. Rev. Respir. Dis.*, 135:S26-S31 (1987).

Fuller, et al., "Bradykinin-induced Bronchoconstriction in Humans", *Am. Rev. Respir. Dis.*, 135:176-180 (1987).

Jin, et al., "Inhibition of Bradykinin-Induced Bronchoconstriction in the Guinea-Pig by a Synthetic $B_2$ Receptor Antagonist", *Br. J. Pharmacol.*, 97:598-602 (1989).

Polosa, et al., "Contribution of Histamine and Prostanoids to Bronchoconstriction Provoked by Inhaled Bradykinin in Atopic Asthma", *Allergy*, 45:174-182 (1990).

Baumgarten, et al., "Concentrations of Glandular Kallikrein in Human Nasal Secretions Increase During Experimentally Induced Allergic Rhinitis", *J. Immunology*, 137:1323-1328 (1986).

Proud, et al., "Nasal Provocation with Bradykinin Induces Symptoms of Rhinitis and a Sore Throat", *Am. Rev. Respir Dis.*, 137:613-616 (1988).

Stewart and Vavrek in "Chemistry of Peptide Bradykinin Antagonists" *Basic and Chemical Research*, R. M. Burch (Ed.), pp. 51-96 (1991).

Seabrook, et al., Expression of B1 and B2 Bradykinin Receptor mRNA and Their Functional Roles in Sympathetic Ganglia and Sensory Dorsal Root Ganglia Neurons from Wild-type and B2 Receptor Knockout Mice, *Neuropharmacology*, 36(7):1009-17 (1997).

Elguero, et al., Nonconventional Analgesics: Bradykinin Antagonists, *An. R. Acad. Farm.*, 63(1):173-90 (Spa) (1997).

Marceau, "Kinin $B_1$ Receptors: A Review," *Immunopharmacology*, 30:1-26 (1995).

Gavrilenko, et al. "Synthesis and properties of 3-amino-3-pyrazolin-5-ones" *Journal of Organic Chemistry* 40(19) 2720-2724 (1975).

Atwell, et al. "5-Amino-1-(chloromethyl)-1,2-dihydro-3H-benz'eindoles..." *Journal of Medicinal Chemistry* 42(17) 3400-3411 (1999).

Rzepecki, et al. "Aminopyrazole oligomers for .beta.-sheet stabilization of peptides" Database accession No. 2003:732768 *Database Chemabs Online*; & Synthesis 12:1815-1826 (2003).

Rzepecki et al., "New Heterocyclic beta-Sheet Ligands with Peptidic Recognition Elements" *Journal of Organic chemistry* 69(16) 5168-5171 (2004).

U.S. Appl. No. 10/555,515, filed Aug. 25, 2006, Tung et al.

* cited by examiner

SEQUENCE LISTING

```
<160> NUMBER OF SEQ ID NOS: 6

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: may be des-Arg

<400> SEQUENCE: 1

Arg Pro Pro Gly Phe Ser Pro Phe Arg
 1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Arg Pro Pro Gly Phe Ser Pro Phe Arg
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Met Lys Arg Pro Pro Gly Phe Ser Pro Phe Arg
  1               5                  10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Ser Arg Pro Pro Gly Phe Ser Pro Phe Arg
  1               5                  10

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hyp

<400> SEQUENCE: 5

Arg Pro Xaa Gly Phe Ser Pro Phe Arg
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Hyp

<400> SEQUENCE: 6

Arg Pro Pro Xaa Phe Ser Pro Phe Arg
  1               5
```

SUBSTITUTED PYRAZOLE DERIVATIVES AND RELATED COMPOUNDS AS BRADYKININ B₁ RECEPTOR ANTAGONISTS

CROSS-REFERENCE TO RELATED APPLICATIONS

This application claims the benefit of U.S. Provisional Application Ser. No. 60/467,695, filed on May 2, 2003 and U.S. Provisional Application Ser. No. 60/539,546, filed on Jan. 27, 2004, which are each incorporated herein in their entirety.

BACKGROUND OF THE INVENTION

Field of the Invention

This invention is directed to certain 3-amido-5-substituted pyrazole derivatives and related compounds. These compounds are useful as bradykinin $B_1$ receptor antagonists to relieve adverse symptoms in mammals mediated, at least in part, by bradykinin $B_1$ receptor including pain, inflammation, septic shock, the scarring process, and the like. This invention is also directed to pharmaceutical compositions comprising such compounds as well as to methods for mediating adverse symptoms in a mammal mediated, at least in part, by the bradykin $B_1$ receptor.

REFERENCES

The following publications are cited in this application as superscript numbers.

[1] J. G. Menke, et al., *J. Biol. Chem.*, 269(34):21583-21586 (1994)

[2] J. F. Hess, Biochem. Human $B_2$ Receptor, *Biophys. Res. Commun.*, 184:260-268 (1992)

[3] R. M. Burch, et al., "Bradykinin Receptor Antagonists", *Med. Res. Rev.*, 10(2):237-269 (1990).

[4] Clark, W. G. "Kinins and the Peripheral Central Nervous Systems", Handbook of Experimental Pharmacology, Vol. XXV: Bradykinin, Kallidin, and Kallikrein. Erdo, E. G. (Ed.), 311-322 (1979).

[5] Ammons, W. S., et al., "Effects of Intracardiac Bradykinin on $T_2$-$T_5$ Medial Spinothalamic Cells", *American Journal of Physiology*, 249, R145-152 (1985).

[6] Costello, A. H. et al., "Suppression of Carageenan-Induced Hyperalgesia, Hyperthermia and Edema by a Bradykinin Antagonist", *European Journal of Pharmacology*, 171:259-263 (1989).

[7] Laneuville, et al., "Bradykinin Analogue Blocks Bradykinin-induced Inhibition of a Spinal Nociceptive Reflex in the Rat", *European Journal of Pharmacology*, 137: 281-285 (1987).

[8] Steranka, et al., "Antinociceptive Effects of Bradykinin Antagonists", *European Journal of Pharmacology*, 136: 261-262 (1987).

[9] Steranka, et al., "Bradykinin as a Pain Mediator: Receptors are Localized to Sensory Neurons, and Antagonists have Analgesic Actions", *Neurobiology*, 85:3245-3249 (1987).

[10] Whalley, et al., in *Naunyn Schmiederberg's Arch. Pharmacol.*, 336:652-655 (1987).

[11] Back, et al., "Determination of Components of the Kallikrein-Kinin System in the Cerebrospinal Fluid of Patients with Various Diseases", *Res. Clin. Stud. Headaches*, 3:219-226 (1972).

[12] Ness, et al., "Visceral pain: a Review of Experimental Studies", *Pain*, 41:167-234 (1990).

[13] Aasen, et al., "Plasma kallikrein Activity and Prekallikrein Levels during Endotoxin Shock in Dogs", *Eur. Surg.*, 10:5062(1977).

[14] Aasen, et al., "Plasma Kallikrein-Kinin System in Septicemia", *Arch. Surg.*, 118:343-346 (1983).

[15] Katori, et al., "Evidence for the Involvement of a Plasma Kallikrein/Kinin System in the Immediate Hypotension Produced by Endotoxin in Anaesthetized Rats", *Br. J. Pharmacol.*, 98:1383-1391 (1989).

[16] Marceau, et al., "Pharmacology of Kinins: Their Relevance to Tissue Injury and Inflammation", *Gen. Pharmacol.*, 14:209-229 (1982).

[17] Weipert, et al., *Brit J. Pharm.*, 94:282-284 (1988).

[18] Haberland, "The Role of Kininogenases, Kinin Formation and Kininogenase Inhibitor in Post Traumatic Shock and Related Conditions", *Klinische Woochenschrift*, 56:325-331 (1978).

[19] Ellis, et al., "Inhibition of Bradykinin-and Kallikrein-Induced Cerebral Arteriolar Dilation by Specific Bradykinin Antagonist", *Stroke*, 18:792-795 (1987).

[20] Kamitani, et al., "Evidence for a Possible Role of the Brain Kallikrein-Kinin System in the Modulation of the Cerebral Circulation", *Circ. Res.*, 57:545-552 (1985).

[21] Barnes, "Inflammatory Mediator Receptors and Asthma", *Am. Rev. Respir. Dis.*, 135:S26-S31 (1987).

[22] R. M. Burch, et al., "Bradykinin Receptor Antagonists", *Med. Res. Rev.*, 10(2):237-269 (1990).

[23] Fuller, et al., "Bradykinin-induced Bronchoconstriction in Humans", *Am. Rev. Respir. Dis.*, 135:176-180 (1987).

[24] Jin, et al., "Inhibition of Bradykinin-Induced Bronchoconstriction in the Guinea-Pig by a Synthetic $B_2$ Receptor Antagonist", *Br. J. Pharmacol*, 97:598-602 (1989).

[25] Polosa, et al., "Contribution of Histamine and Prostanoids to Bronchoconstriction Provoked by Inhaled Bradykinin in Atopic Asthma", *Allergy*, 45:174-182 (1990).

[26] Baumgarten, et al., "Concentrations of Glandular Kallikrein in Human Nasal Secretions Increase During Experimentally Induced Allergic Rhinitis", *J. Immunology*, 137:1323-1328 (1986).

[27] Proud, et al., "Nasal Provocation with Bradykinin Induces Symptoms of Rhinitis and a Sore Throat", *Am. Rev. Respir Dis.*, 137:613-616 (1988).

[28] Steward and Vavrek in "Chemistry of Peptide Bradykinin Antagonists" *Basic and Chemical Research*, R. M. Burch (Ed.), pages 51-96 (1991).

[29] Seabrook, et al., Expression of B1 and B2 Bradykinin Receptor mRNA and Their Functional Roles in Sympathetic Ganglia and Sensory Dorsal Root Ganglia Neurons from Wild-type and B2 Receptor Knockout Mice, *Neuropharmacology*, 36(7):1009-17 (1997)

[30] Elguero, et al., Nonconventional Analgesics: Bradykinin Antagonists, *An. R. Acad. Farm.*, 63(1):173-90 (Spa) (1997)

[31] McManus, U.S. Pat. No. 3,654,275, Quinoxalinecarboxamide Antiinflammatory Agents, issued Apr. 4, 1972

[32] Beyreuther, B.; et al., International Patent application publication number WO 03/007958 A1 published on Jan. 30, 2003.

[33] Marceau, "Kinin $B_1$ Receptors: A Review," *Immunopharmacology*, 30:1-26 (1995).

[34] Giese, et al., U.S. Pat. No. 5,916,908, issued Jun. 29, 1999

[35] Yoshida, et al., Japanese Patent Application Serial No. 49100080

[36] Oxford Dictionary of Biochemistry and Molecular Biology. Oxford University Press, 2001.

All of the above-identified publications are herein incorporated by reference in their entirety to the same extent as if each individual publication was specifically and individually incorporated by reference in its entirety.

Notwithstanding the above, it is understood that superscript numbers after a three letter amino acid residue abbreviation refers to its location in the peptide sequence using conventional numbering where the amino terminus is referred to as "1" and the counting increases seriatum until the last amino acid residue is reached which is the carboxyl terminus of the peptide chain.

STATE OF THE ART

Bradykinin or kinin-9 (BK) is a vasoactive nonapeptide, H-Arg$^1$-Pro$^2$-Pro$^3$-Gly$^4$-Phe$^5$-Ser$^6$-Pro$^7$-Phe$^8$-Arg$^9$-OH (SEQ. ID. NO. 1), formed by the action of plasma kallikrein, which hydrolyzes the sequence out of the plasma globulin kininogen. Plasma kallikrein circulates as an inactive zymogen, from which active kallikrein is released by Hageman factor. Tissue kallikrein appears to be located predominantly on the outer surface of epithelial cell membranes at sites thought to be involved in transcellular electrolyte transport.

Glandular kallikrein cleaves kininogen one residue earlier to give the decapeptide Lys-bradykinin (kallidin, Lys-BK) (SEQ. ID. NO. 2). Met-Lys-bradykinin (SEQ. ID. NO. 3) is also formed, perhaps by the action of leukocyte kallikrein. Pharmacologically important analogues include des-Arg$^9$ (amino acid 1-8 of SEQ. ID. NO. 1) or BK$_{1-8}$ and Ile-Ser-bradykinin (or T-kinin) (SEQ. ID. NO. 4), [Hyp$^3$]bradykinin (SEQ. ID. NO. 5), and [Hyp$^4$]bradykinin (SEQ. ID. NO. 6).[36]

Bradykinin (BK) is known to be one of the most potent naturally occurring stimulators of C-fiber afferents mediating pain. It also is a powerful blood-vessel dilator, increasing vascular permeability and causing a fall in blood pressure, edema-producing agent, and stimulator of various vascular and non-vascular smooth muscles in tissues such as uterus, gut and bronchiole. Bradykinin is formed in a variety of inflammatory conditions and in experimental anaphylactic shock. The kinin/kininogen activation pathway has also been described as playing a pivotal role in a variety of physiologic and pathophysiologic processes, being one of the first systems to be activated in the inflammatory response and one of the most potent simulators of: (i) phospholipase A$_2$ and, hence, the generation of prostaglandins and leukotrienes; and (ii) phospholipase C and thus, the release of inositol phosphates and diacylgylcerol. These effects are mediated predominantly via activation of BK receptors of the B$_2$ type.

Bradykinin receptor is any membrane protein that binds bradykinin (BK) and mediates its intracellular effects. Two types of receptors are recognized: B$_1$, on which order of potency is des-Arg$^9$-bradykinin (BK$_{1-8}$ or amino acid 1-8 of SEQ. ID. NO. 1)=kallidin (SEQ. ID. NO. 2)>BK(SEQ. ID. NO. 1); and B$_2$, with order of potency kallidin (SEQ. ID. NO. 2)>BK (SEQ. ID. NO. 1)>>BK$_{1-8}$. Hence, BK$_{1-8}$ is a powerful discriminator.[36] B$_1$ receptors are considerably less common than B$_2$ receptors, which are present in most tissues. The rat B$_2$ receptor is a seven-transmembrane-domain protein which has been shown on activation to stimulate phosphoinositide turnover. The B$_1$ subtype is induced by inflammatory processes.[33] The distribution of receptor B$_1$ is very limited since this receptor is only expressed during states of inflammation. Bradykinin receptors have been cloned for different species, notably the human B1 receptor (see J. G. Menke et al.[1], and human B2 receptor J. F. Hess[2]). Examples: B$_1$, database code BRB1_HUMAN, 353 amino acids (40.00 kDa); B$_2$, database code BRB2_HUMAN, 364 amino acids (41.44 kDa).[36]

Two major kinin precursor proteins, high molecular weight and low molecular weight kininogen are synthesized in the liver, circulate in plasma, and are found in secretions such as urine and nasal fluid. High molecular weight kininogen is cleaved by plasma kallikrein, yielding BK, or by tissue kallikrein, yielding kallidin. Low molecular weight kininogen, however, is a substrate only for tissue kallikrein. In addition, some conversion of kallidin to BK may occur inasmuch as the amino terminal lysine residue of kallidin is removed by plasma aminopeptidases. Plasma half-lives for kinins are approximately 15 seconds, with a single passage through the pulmonary vascular bed resulting in 80-90% destruction. The principle catabolic enzyme in vascular beds is the dipeptidyl carboxypeptidase kininase II or angiotensin-converting enzyme (ACE). A slower acting enzyme, kininase I, or carboxypeptidase N, which removes the carboxyl terminal Arg, circulates in plasma in great abundance. This suggests that it may be the more important catabolic enzyme physiologically. Des-Arg$^9$-bradykinin (amino acid 1-8 of SEQ. ID. NO. 1) as well as des-Arg$^{10}$-kallidin (amino acid 1-9 of SEQ. ID. NO. 2) formed by kininase I acting on BK or kallidin, respectively, are acting BK$_1$ receptor agonists, but are relatively inactive at the more abundant BK$_2$ receptor at which both BK and kallidin are potent agonists.

Direct application of bradykinin to denuded skin or intra-arterial or visceral injection results in the sensation of pain in mammals including humans. Kinin-like materials have been isolated from inflammatory sites produced by a variety of stimuli. In addition, bradykinin receptors have been localized to nociceptive peripheral nerve pathways and BK has been demonstrated to stimulate central fibers mediating pain sensation. Bradykinin has also been shown to be capable of causing hyperalgesia in animal models of pain. See, Burch, et al.[3] and Clark, W. G.[4]

These observations have led to considerable attention being focused on the use of BK antagonists as analgesics. A number of studies have demonstrated that bradykinin antagonists are capable of blocking or ameliorating both pain as well as hyperalgesia in mammals including humans. See, Ammons, W. S., et al.[5], Clark, W. G.[4], Costello, A. H., et al.[6], Laneuville, et al.[7], Steranka, et al.[8] and Steranka, et al.[9]

Currently accepted therapeutic approaches to analgesia have significant limitations. While mild to moderate pain can be alleviated with the use of non-steroidal anti-inflammatory drugs and other mild analgesics, severe pain such as that accompanying surgical procedures, burns and severe trauma requires the use of narcotic analgesics. These drugs carry the limitations of abuse potential, physical and psychological dependence, altered mental status and respiratory depression which significantly limit their usefulness.

Prior efforts in the field of BK antagonists indicate that such antagonists can be useful in a variety of roles. These include use in the treatment of burns, perioperative pain, migraine and other forms of pain, shock, central nervous system injury, asthma, rhinitis, premature labor, inflammatory arthritis, inflammatory bowel disease, neuropathic pain, etc. For example, Whalley, et al.[10] has demonstrated that BK antagonists are capable of blocking BK-induced pain in a human blister base model. This suggests that topical application of such antagonists would be capable of inhibiting pain in burned skin, e.g., in severely burned patients that require large doses of narcotics over long periods of time and for the local treatment of relatively minor burns or other forms of local skin injury.

The management of perioperative pain requires the use of adequate doses of narcotic analgesics to alleviate pain while not inducing excessive respiratory depression. Post-operative narcotic-induced hypoventilation predisposes patients to collapse of segments of the lungs, a common cause of post-operative fever, and frequently delays discontinuation of mechanical ventilation. The availability of a potent non-narcotic parenteral analgesic could be a significant addition to the treatment of perioperative pain. While no currently available BK antagonist has the appropriate pharmacodynamic profile to be used for the management of chronic pain, frequent dosing and continuous infusions are already commonly used by anesthesiologists and surgeons in the management of perioperative pain.

Several lines of evidence suggest that the kallikrein/kinin pathway may be involved in the initiation or amplification of vascular reactivity and sterile inflammation in migraine. (See, Back, et al.[11]). Because of the limited success of both prophylactic and non-narcotic therapeutic regimens for migraine as well as the potential for narcotic dependence in these patients, the use of BK antagonists offers a highly desirable alternative approach to the therapy of migraine.

Bradykinin is produced during tissue injury and can be found in coronary sinus blood after experimental occlusion of the coronary arteries. In addition, when directly injected into the peritoneal cavity, BK produces a visceral type of pain. (See, Ness, et al.[12]). While multiple other mediators are also clearly involved in the production of pain and hyperalgesia in settings other than those described above, it is also believed that antagonists of BK have a place in the alleviation of such forms of pain as well.

Shock related to bacterial infections is a major health problem. It is estimated that 400,000 cases of bacterial sepsis occur in the United States yearly; of those, 200,000 progress to shock, and 50% of these patients die. Current therapy is supportive, with some suggestion in recent studies that monoclonal antibodies to Gram-negative endotoxin may have a positive effect on disease outcome. Mortality is still high, even in the face of this specific therapy, and a significant percentage of patients with sepsis are infected with Gram-positive organisms that would not be amenable to anti-endotoxin therapy.

Multiple studies have suggested a role for the kallikrein/kinin system in the production of shock associated with endotoxin. See, Aasen, et al.[13], Aasen, et al.[14], Katori, et al.[15] and Marceau, et al.[16] Recent studies using newly available BK antagonists have demonstrated in animal models that these compounds can profoundly affect the progress of endotoxic shock. (See, Weipert, et al.[17]). Less data is available regarding the role of BK and other mediators in the production of septic shock due to Gram-positive organisms. However, it appears likely that similar mechanisms are involved. Shock secondary to trauma, while frequently due to blood loss, is also accompanied by activation of the kallikrein/kinin system. (See, Haberland.[18])

Numerous studies have also demonstrated significant levels of activity of the kallikrein/kinin system in the brain. Both kallikrein and BK dilate cerebral vessels in animal models of CNS injury. (See Ellis, et al.[19] and Kamitani, et al.[20]). Bradykinin antagonists have also been shown to reduce cerebral edema in animals after brain trauma. Based on the above, it is believed that BK antagonists should be useful in the management of stroke and head trauma.

Other studies have demonstrated that BK receptors are present in the lung, that BK can cause bronchoconstriction in both animals and man and that a heightened sensitivity to the bronchoconstrictive effect of BK is present in asthmatics. Some studies have been able to demonstrate inhibition of both BK and allergen-induced bronchoconstriction in animal models using BK antagonists. These studies indicate a potential role for the use of BK antagonists as clinical agents in the treatment of asthma. (See Barnes[21], Burch, et al.[22], Fuller, et al.[23], Jin, et al.[24] and Polosa, et al.[25].)

Bradykinin has also been implicated in the production of histamine and prostanoids to bronchoconstriction provoked by inhaled bradykinin in atopic asthma.[25] Bradykinin has also been implicated in the production of symptoms in both allergic and viral rhinitis. These studies include the demonstration of both kallikrein and BK in nasal lavage fluids and that levels of these substances correlate well with symptoms of rhinitis. (See, Baumgarten, et al.[26], Jin, et al.[24], and Proud, et al.[27])

In addition, studies have demonstrated that BK itself can cause symptoms of rhinitis. Stewart and Vavrek[28] discuss peptidic BK antagonists and their possible use against effects of BK.

A great deal of research effort has been expended towards developing such antagonists with improved properties. However, notwithstanding extensive efforts to find such improved BK antagonists, there remains a need for additional and more effective BK antagonists. Two of the major problems with presently available BK antagonists are their low levels of potency and their extremely short durations of activity. Thus there is a special need for BK antagonists having increased potency and for duration of action.

Two generations of peptidic antagonists of the B2 receptor have been developed. The second generation has compounds two orders of magnitude more potent as analgesics than first generation compounds and the most important derivative was icatibant. The first non-peptidic antagonist of the B2 receptor, described in 1993, has two phosphonium cations separated by a modified amino acid. Many derivatives of this di-cationic compound have been prepared. Another non-peptidic compound antagonist of B2 is the natural product Martinelline. See Elguero.[30] See also Seabrook.[29]

U.S. Pat. No. 3,654,275[31] teaches that certain 1,2,3,4-tetrahydro-1-acyl-3-oxo-2-quinoxalinecarboxamides have anti-inflammatory activity.

International Patent Application WO 03/007958 filed on Jul. 2, 2002 and published on Jan. 30, 2003 discloses tetrahydroquinoxalines acting as Bradykinin antagonists.[32]

U.S. Pat. No. 5,916,908[34] teaches the use of 3,5-disubstituted pyrazoles or 3,4,5-trisubstituted pyrazoles as kinase inhibitors.

Japanese Patent Application Serial No. 49100080[35] teaches 2-aminopyrazoles as anti-inflammatory agents.

Currently there is no marketed therapeutic agent for the inhibition of bradykinin $B_1$ receptor. In view of the above, compounds which are bradykinin $B_1$ receptor antagonists would be particularly advantageous in treating those diseases mediated by bradykinin $B_1$ receptor.

SUMMARY OF THE INVENTION

This invention is directed, in part, to compounds that are bradykinin $B_1$ receptor antagonist. It is also directed to compounds that are useful for treating diseases or relieving adverse symptoms associated with disease conditions in mammals, where the disease is mediated at least in part by bradykinin $B_1$ receptor. For example, inhibition of the bradykinin $B_1$ receptor is useful for the moderation of pain, inflammation, septic shock, the scarring process, etc. These compounds are preferably selective for antagonism of the $B_1$ receptor over the $B_2$ receptor. This selectivity may be therapeutically beneficial due to the up-regulation of the $B_1$ receptor following tissue damage or inflammation. Certain of the compounds exhibit increased potency and are contemplated to also exhibit an increased duration of action.

In one embodiment, this invention provides compounds of Formula (I) and/or Formula (II):

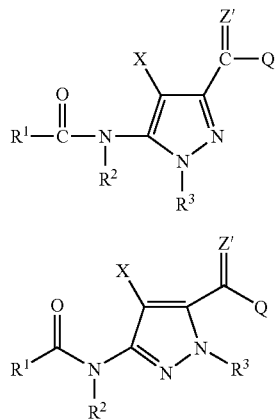

wherein

Z' is selected from O, S and NH;

Q is selected from the group consisting of —$NR^4R^5$, —OH, alkyl, substituted alkyl, alkenyl, substituted alkenyl, alkynyl, substituted alkynyl, cycloalkyl, substituted cycloalkyl, heterocyclic, substituted heterocyclic, alkoxy, substituted alkoxy, aryl, substituted aryl, heteroaryl and substituted heteroaryl;

$R^1$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic and substituted heterocyclic;

$R^2$ and $R^3$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic and substituted heterocyclic;

$R^4$ and $R^5$ are independently selected from the group consisting of hydrogen, alkyl, substituted alkyl, alkoxy, substituted alkoxy, cycloalkyl, substituted cycloalkyl, heterocyclic, substituted heterocyclic and where $R^4$ and $R^5$, together with the nitrogen atom pendent thereto are joined to form a heterocyclic, a substituted heterocyclic, a heteroaryl or a substituted heteroaryl group, provide that when $R^4$ or $R^5$ is a substituted alkyl group this group is not —$CHR^a$—C(O)—$NR^bR^c$ or —$CHR^a$—C(O)—$OR^b$, wherein $R^a$ is the side chain of a natural or unnatural amino acid, and $R^b$ and $R^c$ are independently selected from the group consisting of hydrogen, alkyl, substituted alkyl, aryl, substituted aryl, heteroaryl, or substituted heteroaryl, alkenyl, substituted alkenyl, alkynyl, substituted alkynyl, cycloalkyl, substituted cycloalkyl, heterocyclic, and substituted heterocyclic;

X is selected from the group consisting of hydrogen, halogen, alkyl, substituted alkyl, nitro, cyano, hydroxyl, alkoxy, substituted alkoxy, carboxy, carboxyl esters, aryl, substituted aryl, heteroaryl, substituted heteroaryl, amino, substituted amino, acylamino, aminoacyl, and —C(O)$NR^7R^8$ wherein $R^7$ and $R^8$ are independently selected from the group consisting of hydrogen, alkyl, substituted alkyl, cycloalkyl, substituted cycloalkyl, heterocyclic and substituted heterocyclic, or $R^7$ and $R^8$ together with the nitrogen atom to which they are joined form a heteroaryl, substituted heteroaryl, heterocyclic, and substituted heterocyclic;

or pharmaceutically acceptable salts, prodrugs or isomers thereof;

with the following provisos:

A) when Z' is O; $R^2$ is H; $R^3$ is 5-(2, 4-dichlorophenyl)-imidazol-4-ylidene-[2-methyl-4-(N-(1-methylsufonyleth-2-yl)-N-ethylamino)phenyl]-amine; X is H; and $R^1$ is 1-(3-t-butyl-4-hydroxyphenyloxy)tridec-1-yl; then Q is not ethoxy;

B) when Z' is O; $R^2$ is H; $R^3$ is 4-chlorophenyl; X is aminoacyl; and $R^1$ is methyl or phenyl; then Q is not methyl;

C) when Z' is O; $R^2$ is H; $R^3$ is 4-chlorophenyl or 4-methylphenyl; X is cyano; and $R^1$ is methyl; then Q is not methyl;

D) when Z' is O; $R^2$ is H; $R^3$ is H; X is H; and $R^1$ is 1-[(1-cyclohexyl-2-(furan-3-yl)-1H-benzoimidazol-5-yl)acylamino]cyclopent-1-yl; then Q is not hydroxy;

E) when Z' is O; $R^2$ is H; $R^3$ is H; X is H; and $R^1$ is 3-isobutoxy-5-isopropylphenyl or isopropyl; then Q is not methoxy;

F) when Z' is O; $R^2$ is H; $R^3$ is methyl; X is H; and $R^1$ is 2-methyl-3-acetamidopyrazol-5-yl; then Q is not hydroxy or methoxy;

G) when Z' is O; $R^2$ is H; $R^3$ is H; X is isobutoxycarbonyl or n-propoxycarbonyl; and $R^1$ is methyl; then Q is not methoxy;

H) when Z' is O; $R^2$ is H; $R^3$ is methyl; X is H; and $R^1$ is 2-(3-trifluoromethyl-phenoxy)pyridine-3-yl; then Q is not ethoxy;

I) when Z' is O; $R^2$ is 3-cyanobenzyl; $R^3$ is methyl; X is H; and $R^1$ is methyl; then Q is not isopropyl;

J) when Z' is O; $R^2$ is H; $R^3$ is methyl; X is H; and $R^1$ is 1-methyl-3-(benzyloxycarbonylamino)pyrazol-5-yl; then Q is not N,N-dimethylamino-ethylamino, methoxy or hydroxy;

K) when Z' is O; $R^2$ is H; $R^3$ is methyl; X is H; and $R^1$ is 1-methyl-3-(N,N-dimethylaminoethylcarbonylamino)pyrazol-5-yl; then Q is not N,N-dimethylamino-ethylamino;

L) when Z' is O; $R^2$ is H; $R^3$ is methyl; X is H; and $R^1$ is 1-methyl-5-aminopyrazol-3-yl; then Q is not N,N-dimethylaminoethylamino or methoxy;

M) when Z' is O; $R^2$ is H; $R^3$ is methyl; X is H; and $R^1$ is 1-methyl-5-acetamidopyrazol-3-yl-; then Q is not hydroxy or methoxy;

N) when Z' is O; $R^2$ is H; $R^3$ is methyl; X is H; and $R^1$ is 1-methyl-5-(benzyloxycarbonylamino)pyrazol-3-yl; then Q is not N,N-dimethylaminoethylamino, methoxy or hydroxy;

O) when Z' is O; $R^2$ is H; $R^3$ is methyl; X is H; and $R^1$ is 1-methyl-5-(N,N-dimethylaminoethylcarbonylamino)pyrazol-3-yl; then Q is not N,N-dimethylamino-ethylamino;

P) when Z' is O; $R^2$ is H; $R^3$ is methyl; X is H; and $R^1$ is 1-methyl-5-methylcarbonylaminopyrazol-3-yl; then Q is not 1-chloromethyl-5-nitro-2,3-dihydro-1(H)-benzo[e]indol-3-yl or 1-chloromethyl-5-amino-2,3-dihydro-1(H)-benzo[e]indol-3-yl;

Q) when Z' is O; $R^2$ is H; $R^3$ is phenyl; X is benzothiazol-2-yl; and $R^1$ is methyl; then Q is not ethoxy; or R) when Q is —$NR^4R^5$, —OH, alkoxy or substituted alkoxy; $R^1$ is substituted aryl or substituted heteroaryl, the aryl or heteroaryl group is not substituted with —C(O)NH—W'—C(O)$OR^b$ or —C(O)NH—W'—C(O)$NR^bR^c$, where W is aryl, substituted aryl, heteroaryl or substituted heteroaryl;

and further with the proviso that the compound in Formula (I) is not

A') 4-bromo-5-(2-chloro-benzoylamino)-1H-pyrazole-3-carboxylic acid; or

B') 5-(2-chloro-benzoylamino)-1H-pyrazole-3-carboxylic acid (2-dimethylamino-1-methyl-ethyl)-amide.

In Formula (I) or Formula (II) preferred Q groups are —NR$^4$R$^5$, —OH, alkyl, and aryl. For example, preferred alkyl groups are methyl, ethyl and propyl. The preferred aryl group is phenyl. Preferred R$^4$ and R$^5$ groups are detailed below.

Z' is preferably O.

In Formula (I) or Formula (II) preferred R$^1$ groups include aryl and substituted aryl groups. Some examples of aryl groups include phenyl, naphth-2-yl, naphth-1-yl; and the like. Some preferred substituted aryl groups include monosubstituted phenyls, disubstituted phenyls and trisubstituted phenyls such as 5-dimethylaminonaphth-1-yl, 2-chlorophenyl, 2-fluorophenyl, 2-bromophenyl, 2-hydroxyphenyl, 2-nitrophenyl, 2-methylphenyl, 2-methoxyphenyl, 2-phenoxyphenyl, 2-trifluoromethylphenyl, 4-fluorophenyl, 4-chlorophenyl, 4-bromophenyl, 4-nitrophenyl, 4-methylphenyl, 4-hydroxyphenyl, 4-methoxyphenyl, 4-ethoxyphenyl, 4-butoxyphenyl, 4-isopropylphenyl, 4-phenoxyphenyl, 4-trifluoromethylphenyl, 4-hydroxymethylphenyl, 3-methoxyphenyl, 3-hydroxyphenyl, 3-nitrophenyl, 3-fluorophenyl, 3-chlorophenyl, 3-bromophenyl, 3-phenoxyphenyl, 3-thiomethoxyphenyl, 3-methylphenyl, 3-trifluoromethylphenyl, 2,3-dichlorophenyl, 2,3-difluorophenyl, 2,4-dichlorophenyl, 2,5-dimethoxyphenyl, 3,4-dichlorophenyl, 3,4-difluorophenyl, 3,4-methylenedioxyphenyl, 3,4-dimethoxyphenyl, 3,5-difluorophenyl, 3,5-dichlorophenyl, 3,5-di-(trifluoromethyl)phenyl, 3,5-dimethoxyphenyl, 2,4-dichlorophenyl, 2,4-difluorophenyl, 2,6-difluorophenyl, 3,4,5-trifluorophenyl, 3,4,5-trimethoxyphenyl, 3,4,5-tri-(trifluoromethyl)phenyl, 2,4,6-trifluorophenyl, 2,4,6-trimethylphenyl, 2,4,6-tri-(trifluoromethyl)phenyl, 2,3,5-trifluorophenyl, 2,4,5-trifluorophenyl, 2,5-difluorophenyl, 2-fluoro-3-trifluoromethylphenyl, 4-fluoro-2-trifluoromethylphenyl, 2-fluoro-4-trifluoromethylphenyl, 4-benzyloxyphenyl, 2-chloro-6-fluorophenyl, 2,3,4,5,6-pentafluorophenyl, 2,5-dimethylphenyl, 4-phenylphenyl and 2-fluoro-3-trifluoromethylphenyl, 2-(quinolin-8-yl) sulfanylmethyl)phenyl, 2-((3-methylphen-1-ylsufanyl)methyl)phenyl, and the like.

Preferred R$^1$ substituted alkyl groups include alkaryl groups which include, by way of example, benzyl, 2-phenyleth-1-yl, 3-phenyl-n-prop-1-yl, and the like.

Preferred R$^1$ alkyl, alkenyl, cycloalkyl and cycloalkenyl groups in Formula (I) or Formula (II) include, by way of example, isopropyl, n-propyl, n-butyl, isobutyl, sec-butyl, t-butyl, —CH$_2$CH=CH$_2$, —CH$_2$CH=CH(CH$_2$)$_4$CH$_3$, cyclopropyl, cyclobutyl, cyclohexyl, cyclopentyl, cyclohex-1-enyl, —CH$_2$-cyclopropyl, —CH$_2$-cyclobutyl, —CH$_2$-cyclohexyl, —CH$_2$-cyclopentyl, —CH$_2$CH$_2$-cyclopropyl, —CH$_2$CH$_2$-cyclobutyl, —CH$_2$CH$_2$-cyclohexyl, —CH$_2$CH$_2$-cyclopentyl, and the like.

Preferred R$^1$ heteroaryls and substituted heteroaryls in Formula (I) or Formula (II) include, by way of example, pyrid-2-yl, pyrid-3-yl, pyrid-4-yl, fluoropyridyls (including 5-fluoropyrid-3-yl), chloropyridyls (including 5-chloropyrid-3-yl), thiophen-2-yl, thiophen-3-yl, benzothiazol-4-yl, 2-phenylbenzoxazol-5-yl, furan-2-yl, benzofuran-2-yl, thionaphthen-2-yl, 2-chlorothiophen-5-yl, 3-methylisoxazol-5-yl, 2-(thiophenyl)thiophen-5-yl, 6-methoxythionaphthen-2-yl, 3-phenyl-1,2,4-thiooxadiazol-5-yl, 2-phenyloxazol-4-yl, 5-chloro-1,3-dimethylpyrazol-4-yl; 2-methoxycarbonyl-thiophen-3-yl; 2,3-dimethylimidazol-5-yl; 2-methylcarbonylamino-4-methyl-thiazol-5-yl; quinolin-8-yl; thiophen-2-yl; 1-methylimidiazol-4-yl; 3,5-dimethylisoxazol-4-yl; and the like.

Particularly preferred R$^1$ groups are 2-chlorophenyl, 2-fluorophenyl, 2-(quinolin-8-yl) sulfanylmethyl)phen-1-yl, 2-((3-methylphen-1-ylsufanyl)methyl)phen-1-yl, and methyl.

R$^1$ may be also be a sulfonated aminoalkyl such as Formula (V) below, wherein R$^{21}$ is hydrogen or alkyl, and R$^{20}$ is an amino acid side chain or where R$^{20}$ and R$^{21}$ and the atoms to which they are attached form a heterocyclic or heteroaryl group of from 4 to 12 ring atoms, and R$^{22}$ is alkyl, substituted alkyl, aryl or substituted aryl.

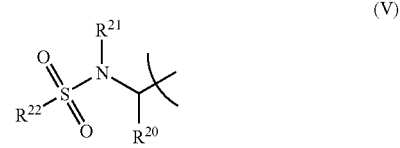

(V)

In one embodiment, R$^1$ is N-(4-methylbenzenesulfonyl)pyrrol-2-yl, N-(4-chloro-2,5-dimethylbenzenesulfonyl)pyrrol-2-yl, N-(napthylsulfonyl)pyrrol-2-yl, N-(benzylsulfonyl)pyrrol-2-yl; N-(4-chloro-2,5-dimethylbenzenesulfonyl)azetidin-2-yl, N-(4-chloro-2,5-dimethylbenzenesulfonyl)piperidin-2-yl, 1-(4-chloro-2,5-dimethylbenzenesulfonyl)-1,2,3,4-tetrahydroisoquinolin-2-yl, N-(4-chloro-2,5-dimethylbenzenesulfonyl)-N-methyl-aminomethyl; and 1-[N-(4-chloro-2,5-dimethylbenzenesulfonyl)amino]eth-1-yl; and the like.

R$^{22}$ is preferably selected from the group consisting of phenyl, 4-methylphenyl, 2,5-dimethylphenyl, 4-chlorophenyl, 2,5-dimethyl-4-chlorophenyl, benzyl, naphthyl, 1,2,3,4-tetrahydroisoquinoline, and the like.

R$^{20}$ is preferably hydrogen.

R$^{21}$ is preferably hydrogen, methyl, or ethyl.

Preferably R$^{20}$ and R$^{21}$ are joined to form a heterocyclic group, such as azetidinyl, pyrrolyl, piperidinyl, 1,2,3,4-tetrahydroisoquinolinyl, and the like.

Preferred R$^2$ groups include hydrogen, methyl, ethyl, isopropyl, 2-methoxyeth-1-yl, pyrid-3-ylmethyl, benzyl, t-butoxycarbonyl-methyl and the like. The particularly preferred R$^2$ is hydrogen.

Preferred R$^3$ groups include hydrogen, methyl, ethyl, isopropyl, 2-methoxyeth-1-yl, pyrid-3-ylmethyl, benzyl, t-butoxycarbonyl-methyl and the like. Additional Preferred R$^3$ groups are also listed in Table II below. Particularly preferred R$^3$ groups include hydrogen, C$_{1-4}$alkyl, optionally substituted monocyclic aryl, and optionally substituted monocyclic heteroaryl. More preferred R$^3$ groups are hydrogen, methyl and phenyl.

In one preferred embodiment, R$^4$ is a group selected from 2-[N-(α-aminoacetyl)piperid-4-yl]eth-1-yl; 4-aminobenzyl; 2-[4-(aminoethylene-amidino)phenyl]eth-1-yl; 2-[N-(1-amino-1-methylethylcarbonyl)piperid-4-yl]eth-1-yl; 2-(4-aminophenyl)eth-1-yl; 2-aminothiazol-5-ylmethyl; (2-aminopyrid-4-yl)methyl; 2-bromoeth-1-yl; 1-(S)-carbamyol-2-(phenyl)eth-1-yl; 4-carboxybenzyl; 2-chloroeth-1-yl; cyanomethyl; 2-(4-cyanophenyl)eth-1-yl; cyclohexylmethyl; 2-(N-cyclopropylpiperidin-4-yl)eth-1-yl; 2-[4-(N,N-dimethylamino]phenethyl; ethyl; 4-fluorophenethyl; hydrogen; 2-(N-hydroxypyrid-4-yl)eth-1-yl; 2-[4-(imidazolin-2-yl)phenyl]eth-1-yl; methoxy; 4-(methoxycarbonyl)benzyl; 2-methoxyeth-1-yl; 2-[4-(methylcarbonylamino]phenethyl;

2-(4-methylpiperazin-1-yl)eth-1-yl; (N-methylpiperidin-2-yl)methyl; 2-(N-methylpiperidin-2-yl)eth-1-yl; 2-(N-methylpiperidin-3-yl)eth-1-yl; 2-(N-methyl-1,2,5,6-tetrahydropyrid-4-yl)eth-1-yl; n-hexyl; 4-nitrobenzyl; 4-phenylbut-1-yl; 2-(piperidin-2-yl)eth-1-yl; 2-(piperidin-3-yl)eth-1-yl; 2-(piperidin-4-yl)eth-1-yl; (piperid-1-yl)carbonylmethyl; 2-(pyrid-2-yl)eth-1-yl; 2-(pyrid-3-yl)eth-1-yl; and 2-[N-(t-butoxycarbonylmethyl)piperid-4-yl]eth-1-yl.

In one embodiment, Q is selected from (1-(benzyloxyacetyl)-azepan-3-yl)amino; (1,5-dimethyl-2,3,4,5-tetrahydro-1H-benzo[b][1,4]diazepin-3-yl)amino; (1,5-dimethyl-2-oxo-2,3,4,5-tetrahydro-1H-benzo[b][1,4]diazepin-3-yl) amino; (1-cyclopropylmethyl-2-oxo-azepan-3-yl)amino; (1-cyclopropylmethyl-5-methyl-2-oxo-2,3,4,5-tetrahydro-1H-benzo[b][1,4]diazepin-3-yl)amino; (1-cyclopropylmethyl-azepan-3-yl)amino; (1-ethyl-2-oxo-5-phenyl-2,3-dihydro-1H-benzo[e][1,4]diazepin-3-yl)amino; (1'-methyl-[1,4']bipiperidin-4-yl)methylamino; (1-methyl-piperidin-4-ylmethyl)amino; (1-pyridin-4-ylmethyl-piperidin-4-yl)amino; (1-pyridin-4-ylmethyl-piperidin-4-ylmethyl)amino; (2-oxo-1-propyl-azepan-3-yl)amino; (2-oxo-5-phenethyl-1-propyl-2,3-dihydro-1H-benzo[e][1,4]diazepin-3-yl)amino; (3,4,5,6-tetrahydro-2H-[1,4']bipyridin-4-yl)methylamino; (5-methyl-2-oxo-2,3,4,5-tetrahydro-1H-benzo[b][1,4]diazepin-3-yl)amino; (5-methyl-6-oxo-6,7,8,9-tetrahydro-5H-pyrido[3,2-b]azepin-7-yl)amino; (indan-2-yl)amino; (N-(benzyloxyacetyl)piperidin-4-yl)amino; (N-(pyridin-4-ylcarbonyl)piperidin-4-yl)methylamino; [1-(2-dimethylamino-ethyl)-2-oxo-azepan-3-yl]amino; [1-(2-pyridin-4-yl-ethyl)-piperidin-4-yl]amino; [1-(2-pyridin-4-yl-ethyl)-piperidin-4-ylmethyl]amino; [1-(pyridin-4-ylcarbonyl)-piperidin-4-yl]amino; [2-(1'-methyl-[1,4']bipiperidin-4-yl)-ethyl]amino; [2-(1-pyridin-4-ylmethyl-piperidin-4-yl)-ethyl]amino; [2-(4-pyridin-4-yl-piperazin-1-yl)ethyl]amino; [2-(pyridine-4-yl)ethyl]amino; [5-(3-azabicyclo[3.2.2]non-3-yl)-1-methyl-2-oxo-2,3-dihydro-1H-benzo[e][1,4]diazepin-3-yl]amino; [5-(benzyloxycarbonyl)-2-oxo-2,3,4,5-tetrahydro-1H-benzo[b][1,4]diazepin-3-yl]amino; {2-[1-(2-pyridin-4-yl-ethyl)-piperidin-4-yl]-ethyl}amino; {2-[1-(N,N-dimethylaminocarbonyl)-piperidin-4-yl]ethyl}amino; {2-[1-(pyridin-4-ylcarbonyl)-piperidin-4-yl]ethyl}amino; 2-(3-methoxy-4-hydroxyphenyl)ethylamino; 2-(N-(4-1H-benzimidazol-2-yl)piperin-4-yl)ethylamino; 2-(N-(4-benzimidazol-2-yl)piperin-4-yl) ethylamino; 2-(N-methyl-N-pyridin-4-yl)ethylamino; 2-[1,4']bipiperidinyl-2-cyano-ethylamino; 2-[1,4']bipiperidinylethylamino; 2-[2-phenyl-1H-benzo[d]imidazole]ethylamino; 2-[4-(pyridin-4-yl)piperidin-1-yl]ethylamino; 2-[N-((pyridin-4-yl)acetyl)piperidin-4-yl]ethylamino; 2-[N-(2,2,2-trichloroethoxyacetyl) piperidin-4-yl]ethylamino; 5-(t-butoxycarbonyl)aminopentylamino; 5-aminopentylamino; N-((pyridin-4-yl)acetyl)piperidin-4-ylamino; and piperidin-4-ylamino.

In another preferred embodiment, Q is —NR$^4$R$^5$ which, in turn, is derived from one of the following amines:
 1-(2-aminoethyl)piperidine;
 1-(2-pyridinyl)-4-piperidinamine;
 1-(2-pyridinyl)-4-piperidinethanamine;
 1-(4-chlorophenyl)ethylamine;
 1-(4-fluorophenyl)ethylamine;
 1-(4-methoxyphenyl)ethylamine;
 1-(4-methyl)-4-piperidinepropan-2-amine;
 1-(4-pyridinyl)-4-piperidinamine;
 1-(4-pyridyl)-4-piperidineethanamine;
 1,5-dimethyl-1H-pyrazole-3-methanamine;
 1-amino-2-indanol;
 1-aminopiperidine;
 1-benzyl-3-aminopyrrolidine;
 1-dimethylamino-2-propylamine;
 1-methyl-1H-pyrrole-2-methanamine;
 1-methyl-3-piperidinamine;
 1-methyl-4-piperidineethanamine;
 1-methylpiperazine;
 1-phenyl-4-(2-aminoethyl)piperidine;
 1-phenylpiperazine;
 alpha-methyl-1-piperidineethanamine;
 2-(2-aminoethyl)-1-methylpyrrolidine;
 2-(4-benzylpiperazin-1-yl)ethylamine;
 2-(4-methylpiperazin-1-yl)ethylamine;
 2-(aminomethyl)-1-ethylpyrrolidine;
 2-(aminomethyl)-5-methylpyrazine;
 2-amino-4-phenyl-1-piperidin-1-ylbutane;
 2-benzyloxycyclopentylamine;
 2-methylcyclohexylamine;
 2-phenylglycinol;
 2-picolylamine;
 3-(1H-pyrrol-1-yl)-benzenemethanamine;
 3-amino-1,3,4,5-tetrahydro-2H-1-benzazepin-2-one;
 3-amino-1,3-dihydro-1-methyl-5-phenyl-2H-1,4-benzodiazepin-2-one;
 3-amino-1,3-dihydro-5-phenyl-2H-1,4-benzodiazepin-2-one;
 3-amino-1,3-dihydro-5-cyclohexyl-2H-1,4-benzodiazepin-2-one;
 3-amino-1-ethylhexahydro-2H-azepin-2-one;
 3-amino-1-methyl-2-piperidinone;
 3-amino-2-oxo-1,2,3,4-tetrahydroquinoline;
 3-amino-3-methyl-2-piperidone;
 3-amino-7-chloro-1,3-dihydro-5-phenyl-2H-1,4-benzodiazepin-2-one;
 3-amino-7-chloro-5-(2-chlorophenyl)-1,3-dihydro-2H-1,4-benzodiazepin-2-one;
 3-aminohexahydro-1-(phenylmethyl)-2H-azepin-2-one;
 3-aminomethylbenzothiophene;
 3-aminoquinuclidine;
 3-dimethylamino-1-propylamine;
 3-morpholinopropylamine;
 3-picolylamine;
 4-(1-aminoethyl)phenol;
 4-(2-aminoethyl)morpholine;
 4-(2-aminoethyl)pyridine;
 4-amino-1-benzylpiperidine;
 4-amino-2-butanol;
 4-picolylamine;
 1-methyl-4-piperidinamine;
 5-methyl-3-Isoxazolemethanamine;
 alaninol;
 alpha-N,N-dimethylbenzylamine;
 alpha-amine-epsilon-N-methyl-caprolactam;
 alpha-aminodiphenylmethane;
 alpha-amino-epsilon-caprolactam;
 alpha-methyl-4-morpholineethanamine;
 alpha-methylbenzylamine;
 azepan-3-ylamine;
 benzylamine;
 beta-methyl-1-pyrrolidineethanamine;
 cumylamine;
 cyclohexylamine;

endo-8-methyl-8-azabicyclo[3.2.1]octan-3-amine;
ethanolamine;
hexahydro-1-methyl-1H-azepin-3-amine;
histamine;
isopropylamine;
methylamine;
morpholine;
N-(2-aminoethyl)-2-benzyl-N-methylaniline;
N-(2-aminoethyl)acetamide;
N-(2-aminoethyl)pyrrolidine;
N,N,N'-trimethylethylenediamine;
N,N-dimethylethylenediamine;
N,O-dimethylhydroxylamine;
N-alpha-dimethylbenzylamine;
phenethylamine;
trans-2-aminocyclohexanol;
trans-4-aminocyclohexanol;
tryptamine;
tyramine;
valinol;
N,N-diethyl-1,2-propanediamine;
N-ethyl-N-methyl-1,2-propanediamine;
1-phenylsulfonyl-4-piperidineamine;
alpha-phenyl-1-piperidineethanamine;
N,N-dimethyl-1,2-butanediamine;
3,4-dihydro-1-(2H)-quinolineethanamine;
1-amino-2-propanol;
beta-alaninamide;
beta-alanine t-butyl ester;
alpha-methyl-4-(methylsulfonyl)-benzenemethanamine;
1-[2-pyrrolidinylmethyl]-pyrrolidine;
alpha-methylbenzylamine;
alpha methyl-1-pyrrolidineethanamine;
N,N-dimethyl-4-phenyl-1,2-butanediamine;
N-acetyl-N-methyl-1,2-propanediamine;
N-methyl-N-phenyl-1,2-ethanediamine;
N-cyclopropyl-N-methyl-1,2-propanediamine;
(4-phenyl-morpholin-2-yl)-methyl amine;
1-(1-naphthyl)ethylamine;
1,2,3,4-tetrahydro-1-naphthylamine;
1-aminoethylphosphonic acid;
1-cyclohexylethylamine;
1-ethynylcyclohexylamine;
1-methoxy-3-phenyl-2-propylamine;
2-(aminomethyl)benzimidazole;
2-(diisobutylamino)ethylamine;
2-(diisopropylamino)ethylamine;
2,2,2-trifluoroethylamine;
2,2-diphenylethylamine;
2,6-bis(dimethylamino)benzylamine;
2-[2-(aminomethyl)phenylthio]benzyl alcohol;
2-amino-1,2-diphenylethanol;
2-amino-4'-bromoacetophenone;
2-aminoacetophenone;
2-(aminoethyl)-2-thiopseudourea;
2-aziridinoethylamine;
2-methoxyisopropylamine;
2-methylallylamine;
3,3-diphenylpropylamine;
3,4-methylenedioxyamphetamine;
3-aminocyclohexanecarboxylic acid;
3-aminopyrrolidine;
3-nitrophenacylamine;
4-(2-aminoethyl)-1-methylpiperidine;
4-(2-aminoethyl)benzenesulfonamide;
4-amino-1-diethylaminopentane;
7-amino-5-methyl-5H,7H-dibenzo[b,d]azepin-6-one;
agmatine;
alpha-1-amino-2-propanol;
alpha-ethylbenzylamine;
aminoacetamidine;
aminoacetonitrile;
beta-methylphenethylamine;
cathinone;
cyclobutylamine;
cyclohexanemethylamine;
cyclopropylamine;
cycloserine;
homocysteine thiolactone;
menthylamine;
methioninol;
muscimol;
N-(3'-aminopropyl)-2-pyrrolidinone;
N-(3-aminopropyl)diethanolamine;
N,N-dimethyl-1,4-diaminobutane;
N-benzylethylenediamine;
N-ethyl-N-butylethylenediamine;
norephedrine;
O-benzylhydroxylamine;
phenylisopropylamine;
p-methoxyamphetamine; and
tetrahydrofurfarylamine.

Preferred $R^5$ groups include hydrogen, methyl, ethyl, isopropyl, 2-methoxyethyl, and pyrid-3-yl-methyl.

Other preferred Q groups also include hydroxy, alkyl, substituted alkyl, cycloalkyl, substituted cycloalkyl, alkoxy, substituted alkoxy, aryl, and substituted aryl. For example, Q may be —OH, methyl, ethyl, methoxy, ethoxy, phenyl, benzyl, and the like.

Preferred cyclic groups defined by Q include cycloalkyl, lactone, lactam, benzazepinone, dibenzazepinone and benzodiazepine groups, such as, (2-oxo-1,3,4,5-tetrahydro-2H-1-benzazepin-3-yl)amino; (2-oxo-7-chloro-1,3-dihydro-5-phenyl-2H-1,4-benzodiazepin-3-yl)amino; 2-oxo-7-chloro-5-(2-chlorophenyl)-1,3-dihydro-2H-[1,4-e]benzodiazepin-3-yl)amino; (6-oxo-5-methyl-5H,7H-dibenzo[b,d]azepin-7-yl)amino; (2-oxo 3-amino-1,3,4,5-tetrahydro-2H-1-benzazepin-3-yl)amino; (2-Oxo-5-phenyl-2,3-dihydro-1H-benzo[e][1,4]diazepin-3-yl)amino; (1-Methyl-2-oxo-5-phenyl-2,3-dihydro-1H-benzo[e][1,4]diazepin-3-yl)amino; (1-Methyl-azepan-3-yl)amino; (2-Oxo-5-phenyl-2,3-dihydro-1H-benzo[e][1,4]diazepin-3-yl)amino; and the like and derivatives and analogues thereof.

Preferred X groups include hydrogen, bromine, chlorine, fluorine and methyl.

When $R^3$ in Formula (I) or Formula (II) is other than hydrogen, two geometric isomers may exist. When $R^3$ is hydrogen Formula (I) or Formula (II) are tautomers. In those cases where the compounds of Formula (I) or Formula (II) exist as tautomers, optical isomers or geometric isomers, the above formulas are intended to represent isomer mixtures as well as the individual isomeric bradykinin B, receptor antagonist or intermediate isomers, all of which are encompassed within the scope of this invention.

Further, references to the compounds of Formula (I) or Formula (II) with respect to pharmaceutical applications thereof are also intended to include pharmaceutically acceptable salts of the compounds of Formula (I) or Formula (II).

Compounds within the scope of this invention include those set forth in Table I as follows:

TABLE I (IIIa) and (IIIb)

| Cpd # | R¹ | R² | R³ | X | Q |
|---|---|---|---|---|---|
| 201 | 2-chlorophenyl | H | H | Br | (2-(N-methylpiperidin-4-yl)eth-1-yl)amino |
| 202 | 2-chlorophenyl | H | H | Br | (2-(R or S)-2-methyl-2-(pyrrolidin-1-yl)eth-1-yl)amino |
| 203 | 2-chlorophenyl | $CH_3$ | H | Br | Methoxy |
| 204 | 2-chlorophenyl | H | H | Br | (R)-(+)-quinuclidin-3-ylamino |
| 205 | 2-chlorophenyl | H | H | Br | (S)-(−)-quinuclidin-3-ylamino |
| 206 | 2-chlorophenyl | H | H | Br | (diphenylmethyl)amino |
| 207 | 2-chlorophenyl | H | H | Br | (2-(1-phenylpiperidin-4-yl)eth-1-yl)amino |
| 208 | 2-(quinolin-8-yl)sulfanylmethyl)phenyl | H | H | Br | (2-(N-morpholino)eth-1-yl)amino |
| 209 | 2-chlorophenyl | H | H | $CH_3$ | (2-(piperidin-1-yl)eth-1-yl)amino |
| 210 | 2-chlorophenyl | H | H | $CH_3$ | Isopropylamino |
| 211 | 2-chlorophenyl | H | H | $CH_3$ | Cyclohexylamino |
| 212 | 2-chlorophenyl | H | H | $CH_3$ | N,O-Dimethylhydroxylamino |
| 213 | 2-chlorophenyl | H | H | $CH_3$ | Phenyl |
| 214 | 2-chlorophenyl | H | H | $CH_3$ | Methyl |
| 215 | 2-chlorophenyl | H | H | $CH_3$ | (1-benzylpiperidin-4-yl)amino |
| 216 | 2-chlorophenyl | H | H | $CH_3$ | (S)-(−)-α-methylbenzylamino |
| 217 | 2-chlorophenyl | H | H | Benzyl | (2-(piperidin-1-yl)eth-1-yl)amino |
| 218 | 2-((3-methylphenyl-sulfanyl)methyl)phenyl | H | H | Br | Methoxy |
| 219 | 2-chlorophenyl | H | H | Br | Methoxy |
| 220 | 2-chlorophenyl | H | H | Br | Benzylamino |
| 221 | 2-chlorophenyl | H | H | Br | Hydroxyl |
| 222 | 2-chlorophenyl | H | H | Br | Methylamino |
| 223 | 2-chlorophenyl | H | H | Br | (R)-(+)-α-methylbenzylamino |
| 224 | 2-chlorophenyl | H | H | Br | (2-(pyridin-4-yl)eth-1-yl)amino |
| 225 | 2-chlorophenyl | H | H | Br | (dimethylbenzyl)amino |
| 226 | 2-chlorophenyl | H | H | Br | (S)-(−)-α-(hydroxymethylbenzyl)amino |
| 227 | 2-chlorophenyl | H | H | Br | N-((R)-(+)-α-methylbenzyl)-N-(methyl)amino |
| 228 | 2-chlorophenyl | H | H | Br | (2-(pyrrolidin-1-yl)eth-1-yl)amino |
| 229 | 2-chlorophenyl | H | H | Br | (S)-(−)-α-methylbenzylamino |
| 230 | 2-chlorophenyl | H | H | Br | (2-(N-morpholino)eth-1-yl)amino |
| 231 | 2-chlorophenyl | H | H | Br | (3-(N-morpholino)prop-1-yl)amino |
| 232 | 2-chlorophenyl | H | H | Br | (2-(N,N-dimethylamino)eth-1-yl)amino |
| 233 | 2-chlorophenyl | H | H | Br | (3-(N,N-dimethylamino)prop-1-yl)amino |
| 234 | 2-chlorophenyl | H | H | Br | 1-methylpiperazin-4-yl |
| 235 | 2-chlorophenyl | H | H | Br | N-Morpholino |
| 236 | 2-chlorophenyl | H | H | Br | Cyclohexylamino |
| 237 | 2-chlorophenyl | H | H | Br | (2-phenyleth-1-yl)amino |
| 238 | 2-chlorophenyl | H | H | Br | (2-(S)-1-hydroxy-3-methylbut-2-yl)amino |
| 239 | 2-chlorophenyl | H | H | Br | (1-benzylpiperidin-4-yl)amino |
| 240 | 2-chlorophenyl | H | H | Br | (2-hydroxyeth-1-yl)amino |
| 241 | 2-chlorophenyl | H | H | Br | (trans-1-hydroxycyclohex-4-yl)amino |
| 242 | 2-chlorophenyl | H | H | Br | (2--methylcyclohex-1-yl)amino |
| 243 | 2-chlorophenyl | H | H | Br | (2-(1-hydroxyphen-4-yl)eth-1-yl)amino |
| 244 | 2-chlorophenyl | H | H | Br | ((1S,2S)-2-benzyl oxycyclopent-2-yl)amino |
| 245 | 2-chlorophenyl | H | H | Br | (2-(1H-indol-3-yl)eth-1-yl)amino |
| 246 | 2-chlorophenyl | H | H | Br | (2-(2H-imidazol-4-yl)eth-1-yl)amino |
| 247 | 2-chlorophenyl | H | H | Br | ((1S,2R)-(−)-cis-2-hydroxyindan-2-yl)amino |

TABLE I-continued (IIIa) and (IIIb)

| Cpd # | R¹ | R² | R³ | X | Q |
|---|---|---|---|---|---|
| 248 | 2-chlorophenyl | H | H | Br | (3-hydroxy-but-1-yl)amino |
| 249 | 2-chlorophenyl | H | H | Br | (2-(R or S)-1-(N,N-dimethylamino)prop-2-yl)amino |
| 250 | 2-chlorophenyl | H | H | Br | (trans-1-hydroxycyclohex-2-yl)amino |
| 251 | 2-chlorophenyl | H | H | Cl | (R)-(+)-α-methylbenzylamino |
| 252 | 2-chlorophenyl | H | H | Br | (2-(S)-3-(piperidin-1-yl)prop-2-yl)amino |
| 253 | 2-chlorophenyl | H | H | Br | (2-(R or S)-3-(pyrrolidin-1-yl)prop-2-yl)amino |
| 254 | 2-chlorophenyl | H | H | Br | (2-(R or S)-3-(morpholino)prop-2-yl)amino |
| 255 | 2-chlorophenyl | H | H | Br | (2-(S)-3-(hydroxy)prop-2-yl)amino |
| 256 | 2-chlorophenyl | H | H | Br | 2-(1-methylpiperidin-4-yl)eth-1-ylamino |
| 257 | 2-chlorophenyl | H | H | Br | (1-(phenylsulfonyl)piperidin-4-yl)amino |
| 258 | 2-chlorophenyl | H | H | Br | (1-methylpiperidin-4-yl)amino |
| 259 | 2-chlorophenyl | H | H | Br | (2-(R)-3-(piperidin-1-yl)prop-2-yl)amino |
| 260 | 2-chlorophenyl | H | H | Br | (2-(R)-3-(morpholino)prop-2-yl)amino |
| 261 | 2-chlorophenyl | H | H | Br | (2-(R)-1-(piperidin-1-yl)-2-(phenyl)eth-2-yl)amino |
| 262 | 2-chlorophenyl | H | H | Br | (2-(S)-1-(piperidin-1-yl)-2-(phenyl)eth-2-yl)amino |
| 263 | 2-chlorophenyl | H | H | Br | (2-(R)-3-(hydroxy)prop-2-yl)amino |
| 264 | 2-chlorophenyl | H | H | Br | (2-(R)-3-(N,N-dimethylamino)prop-2-yl)amino |
| 265 | 2-chlorophenyl | H | H | H | (R)-(+)-α-methylbenzylamino |
| 266 | 2-chlorophenyl | H | H | Br | (2-(S)-3-(N,N-dimethylamino)prop-2-yl)amino |
| 267 | 2-chlorophenyl | H | H | H | (2-(R or S)-3-(N,N-dimethylamino)prop-2-yl)amino |
| 268 | 2-chlorophenyl | H | H | Br | (2-(R)-1-(N,N-dimethylamino)but-2-yl)amino |
| 269 | 2-chlorophenyl | H | H | Br | (2-(R)-1-(N,N-diethylamino)prop-2-yl)amino |
| 270 | 2-chlorophenyl | H | H | Br | (2-(R)-3-(N-ethyl-N-methylamino)prop-2-yl)amino |
| 271 | 2-chlorophenyl | H | H | Br | (2-(acetamido)eth-1-yl)amino |
| 272 | 2-chlorophenyl | H | H | Br | (2-(R)-1-(N,N-dimethylamino)-4-(phenyl)but-2-yl)amino |
| 273 | 2-chlorophenyl | H | H | Br | (2-(R)-1-(N-methyl-acetamido)prop-2-yl)amino |
| 274 | 2-chlorophenyl | H | H | Br | (2-(N-phenyl-N-methylamino)eth-1-yl)amino |
| 275 | 2-chlorophenyl | H | H | Br | ((3S)-(+)-1-Benzylpyrrolidin-3-yl)amino |
| 276 | 2-chlorophenyl | H | H | Br | ((3R)-(−)-1-Benzylpyrrolidin-3-yl)amino |
| 277 | 2-chlorophenyl | H | H | Br | (2-(R)-3-(N-cyclopropyl-N-methylamino)prop-2-yl)amino |
| 278 | 2-chlorophenyl | H | H | Br | (N-phenylmorpholin-2-ylmethyl)amino |
| 279 | 2-chlorophenyl | H | H | Br | (2-(1,2,3,4-tetrahydroquinolin-1-yl)eth-1-yl)amino |
| 280 | 2-chlorophenyl | H | H | Br | (2-(1-methylpyrrolidin-2-yl)eth-1-yl)amino |
| 281 | 2-chlorophenyl | H | H | Br | (pyridin-2-ylmethyl)amino |
| 282 | 2-chlorophenyl | H | H | Br | (pyridin-3-ylmethyl)amino |
| 283 | 2-chlorophenyl | H | H | Br | (pyridin-4-ylmethyl)amino |
| 284 | 2-chlorophenyl | H | H | Br | (2-(piperidin-1-yl)eth-1-yl)amino |
| 285 | 2-chlorophenyl | H | H | Br | (2-(R or S)-2-(4-hydroxy-phen-1-yl)eth-2-yl)amino |

TABLE I-continued (IIIa) / (IIIb)

| Cpd # | R¹ | R² | R³ | X | Q |
|---|---|---|---|---|---|
| 286 | 2-chlorophenyl | H | H | Br | (2-(pyrrolidin-1-yl)eth-1-yl)amino |
| 287 | 2-chlorophenyl | H | H | Br | (5-methylpyrazin-2-ylmethyl)amino |
| 288 | 2-chlorophenyl | H | H | Br | (2-(R or S)-2-hydroxyprop-1-yl)amino |
| 289 | 2-chlorophenyl | H | H | Br | (piperidin-1-yl)amino |
| 290 | 2-chlorophenyl | H | H | Br | (2-(R)-2-(4-methylphen-1-yl)eth-2-yl)amino |
| 291 | 2-chlorophenyl | H | H | Br | (2-(aminocarbonyl)eth-1-yl)amino |
| 292 | | | | | |
| 293 | 2-chlorophenyl | H | H | Br | (1-(R)-1-(4-chlorophen-1-yl)eth-1-yl)amino |
| 294 | 2-chlorophenyl | H | H | Br | (2-(R)-2-(4-methoxyphen-1-yl)eth-2-yl)amino |
| 295 | 2-chlorophenyl | H | H | Br | (1-(R or S)-1-(4-methyl-sulfonylphen-1-yl)eth-1-yl)amino |
| 296 | 2-chlorophenyl | H | H | Br | N-methyl-N-(2-(dimethyl-amino)eth-1-yl)amino |
| 297 | 2-chlorophenyl | H | H | Br | 2-(R)-2-(pyrrolidin-1-ylmethyl)-pyrrolidin-1-yl |
| 298 | 2-chlorophenyl | H | H | Br | (3-(R or S)-2-oxo-azepan-3-yl)amino |
| 299 | 2-chlorophenyl | H | H | Br | 1-methylpiperazin-4-yl |
| 300 | 2-chlorophenyl | H | H | Br | 1-(phenyl)piperazin-4-yl |
| 301 | 2-chlorophenyl | H | H | Br | (2-(R or S)-1-(ethyl)pyrrolidin-2-ylmethyl)amino |
| 302 | 2-chlorophenyl | H | H | Br | (1-(R)-(4-fluorophen-1-yl)eth-1-yl)amino |
| 303 | 2-chlorophenyl | H | H | Br | (3-(S)-2-Oxo-azepan-3-yl)amino |
| 304 | 2-chlorophenyl | H | H | Br | (3-(R)-2-Oxo-azepan-3-yl)amino |
| 305 | 2-chlorophenyl | H | H | Br | (3-(S)-1-methyl-2-oxo-azepan-3-yl)amino |
| 306 | 2-chlorophenyl | H | H | Br | (3-(R)-1-Methyl-2-oxo-azepan-3-yl)amino |
| 307 | 2-chlorophenyl | H | H | Br | (3-(R or S)-2-Oxo-5-phenyl-2,3-dihydro-1H-benzo[e][1,4]diazepin-3-yl)amino |
| 308 | 2-chlorophenyl | H | H | Br | (3-(R)-1-Methyl-azepan-3-yl)amino |
| 309 | 2-chlorophenyl | H | H | Br | (3-(R or S)-1-Methyl-2-oxo-5-phenyl-2,3-dihydro-1H-benzo[e][1,4]diazepin-3-yl)amino |
| 310 | 2-chlorophenyl | H | H | H | (3-(R or S)-2-Oxo-5-phenyl-2,3-dihydro-1H-benzo[e][1,4]diazepin-3-yl)amino |
| 311 | 2-chlorophenyl | H | H | Br | (3-(R or S)-2-oxo 3-amino-1,3,4,5-tetrahydro-2H-1-benz-azepin-3-yl)amino |
| 312 | 2-chlorophenyl | H | H | Cl | (3-(R or S)-2-Oxo-5-phenyl-2,3-dihydro-1H-benzo[e][1,4]diazepin-3-yl)amino |
| 313 | 2-chlorophenyl | H | H | Br | (7-(R or S)-6-oxo-5-methyl-5H,7H-dibenzo[b,d]azepin-7-yl)amino |
| 314 | 2-chlorophenyl | H | H | Br | (3-(R or S)-2-Oxo-5-cyclo-hexyl-2,3-dihydro-1H-benzo[e][1,4]diazepin-3-yl)amino |
| 315 | 2-chlorophenyl | H | H | Br | (3-(R or S)-1-Methyl-2-oxo-5-phenyl-2,3-dihydro-1H-benzo[e][1,4]diazepin-3-yl)amino |
| 316 | 2-chlorophenyl | H | H | Br | (3-(R or S)-1-Methyl-2-oxo-5-phenyl-2,3-dihydro-1H-benzo[e][1,4]diazepin-3-yl)amino |
| 317 | 2-chlorophenyl | H | H | Br | (2-(N-methyl-N-(2-benzylphen-1-yl)amino)eth-1yl)amino |
| 318 | 2-chlorophenyl | H | H | Cl | (3-(R or S)-2-oxo-7-chloro-5-(2-chlorophenyl)-1,3-dihydro-2H-[1,4-e]benzodiazepin-3-yl)amino |

TABLE I-continued (IIIa) and (IIIb) structures shown.

| Cpd # | R¹ | R² | R³ | X | Q |
|---|---|---|---|---|---|
| 319 | 2-chlorophenyl | H | H | Cl | (3-(R or S)-2-oxo-7-chloro-1,3-dihydro-5-phenyl-2H-1,4-benzodiazepin-3-yl)amino |
| 320 | 2-chlorophenyl | H | H | Br | (2-(R)-1-(piperidin-1-yl)-4-(phenyl)but-2-yl)amino |
| 321 | 2-chlorophenyl | H | H | Br | (1,5-dimethyl-1H-pyrazol-3-ylmethyl)amino |
| 322 | 2-chlorophenyl | H | H | Br | (1-methyl-1H-pyrrol-2-ylmethyl)amino |
| 323 | 2-chlorophenyl | H | H | Br | (benzothiophen-3-ylmethyl)amino |
| 324 | 2-chlorophenyl | H | H | Br | (5-methyl-isoxazol-3-ylmethyl)amino |
| 325 | 2-chlorophenyl | H | H | Br | (3-(R or S)-3-methyl-2-oxo-piperidin-3-yl)amino |
| 326 | 2-chlorophenyl | H | H | Br | (3-(R or S)-1-methyl-2-oxo-piperidin-3-yl)amino |
| 327 | 2-chlorophenyl | H | H | Br | (3-(R or S)-1-methylpiperidin-3-yl)amino |
| 328 | 2-chlorophenyl | H | H | Br | (3-(R or S)-2-oxo-1,2,3,4-tetra-hydroquinolin-3-yl)amino |
| 329 | 2-chlorophenyl | H | H | Cl | (3-(R)-1-methyl-azepan-3-yl)amino |
| 330 | 2-chlorophenyl | H | H | Br | (3-(R)-1-(benzyl)-2-oxo-azepan-3-yl)amino |
| 331 | 2-chlorophenyl | H | H | Br | (3-(R)-1-(ethyl)-2-oxo-azepan-3-yl)amino |
| 332 | 2-chlorophenyl | CH₃ | H | Br | (2-(1-methylpiperidin-4-yl)eth-1-yl)amino |
| 333 | 2-chlorophenyl | H | H | Br | (2-(1-(pyridin-4-yl)piperidin-4-yl)eth-1-yl)amino |
| 334 | 2-chlorophenyl | H | H | Br | (2-(1-benzylpiperazin-4-yl)eth-1-yl)amino |
| 335 | 2-chlorophenyl | H | H | Br | (2-(1-methylpiperazin-4-yl)eth-1-yl)amino |
| 336 | 2-chlorophenyl | H | H | Br | (3-(1H-pyrrol-1-yl)phenylmethyl)amino |
| 337 | 2-chlorophenyl | H | H | Cl | (2-(1-(pyridin-4-yl)piperidin-4-yl)eth-1-yl)amino |
| 338 | 2-chlorophenyl | H | H | Br | endo-8-methyl-8-azabicyclo[3.2.1]octan-3-amino |
| 339 | 2-chlorophenyl | H | H | Br | (2-(R or S)-1-(1-methyl-piperidin-4-yl)prop-2-yl)amino |
| 340 | 2-chlorophenyl | H | H | Br | (1-(pyridin-4-yl)piperidin-4-yl)amino |
| 341 | 2-chlorophenyl | H | H | Br | (1-(pyridin-2-yl)piperidin-4-yleth-1-yl)amino |
| 342 | 2-chlorophenyl | H | H | H | (3-(R or S)-2-oxo-1,3,4,5-tetrahydro-2H-1-benzazepin-3-yl)amino |
| 343 | 2-chlorophenyl | H | H | Cl | (3-(R or S)-2-oxo-1,3,4,5-tetrahydro-2H-1-benzazepin-3-yl)amino |
| 344 | 2-chlorophenyl | H | H | Br | (3-(R)-1-Methyl-2-oxo-5-phenyl-2,3-dihydro-1H-benzo[e][1,4]diazepin-3-yl)amino |
| 345 | 2-chlorophenyl | H | H | Cl | (3-(S)-2-Oxo-5-phenyl-2,3-dihydro-1H-benzo[e][1,4]diazepin-3-yl)amino |
| 346 | 2-chlorophenyl | H | H | Cl | (3-(R)-2-Oxo-5-phenyl-2,3-dihydro-1H-benzo[e][1,4]diazepin-3-yl)amino |
| 347 | 2-chlorophenyl | H | H | Cl | (3-(R or S)-1-Methyl-2-oxo-5-phenyl-2,3-dihydro-1H-benzo[e][1,4]diazepin-3-yl)amino |
| 348 | 2-chlorophenyl | H | H | Br | 2-(4-cyanophenyl)ethylamino |
| 349 | 2-chlorophenyl | H | H | Br | 2-[1-(4-imidazol-2-yl)phenyl]ethylamino |
| 350 | 2-chlorophenyl | H | H | Br | N-((pyridin-4-yl)acetyl)piperidin-4-ylamino |
| 351 | 2-chlorophenyl | H | H | Br | (N-(pyridin-4-ylcarbonyl)piperidin-4-yl)methylamino |

TABLE I-continued (IIIa) (IIIb)

| Cpd # | R¹ | R² | R³ | X | Q |
|---|---|---|---|---|---|
| 352 | 2-chlorophenyl | H | H | Br | 2-[1,4']bipiperidinylethylamino |
| 353 | 2-chlorophenyl | H | H | Br | 2-[1,4']bipiperidinyl-2-cyano-ethylamino |
| 354 | 2-chlorophenyl | H | H | Br | 2-[N-((pyridin-4-yl)acetyl)piperidin-4-yl]ethylamino |
| 355 | 2-chlorophenyl | H | H | Br | (1,5-dimethyl-2,3,4,5-tetrahydro-1H-benzo[b][1,4]diazepin-3-yl)amino |
| 356 | 2-chlorophenyl | H | H | Br | 2-[4-(pyridin-4-yl)piperidin-1-yl]ethylamino |
| 357 | 2-chlorophenyl | H | H | Br | (N-(benzyloxyacetyl)piperidin-4-yl)amino |
| 358 | 2-chlorophenyl | H | H | Br | piperidin-4-ylamino |
| 360 | 2-chlorophenyl | H | H | Br | (1-(benzyloxyacetyl)-azepan-3-yl)amino |
| 361 | 2-chlorophenyl | H | H | Br | (azepan-3-yl)amino |
| 362 | 2-methylphenyl | H | H | Cl | (1-ethyl-2-oxo-5-phenyl-2,3-dihydro-1H-benzo[e][1,4]diazepin-3-yl)amino |
| 363 | 2-chlorophenyl | H | H | Br | (indan-2-yl)amino |
| 364 | 2-chlorophenyl | H | Me | Br | 2-[N-(pyridin-4-yl)piperidin-4-yl]ethylamino |
| 365 | 2-chlorophenyl | H | Me | H | (2-oxo-5-phenyl-2,3-dihydro-1H-benzo[e][1,4]diazepin-3-yl)amino |
| 366 | 2-chlorophenyl | H | Me | H | (2-oxo-5-phenyl-2,3-dihydro-1H-benzo[e][1,4]diazepin-3-yl)amino |
| 367 | 2-chlorophenyl | H | Me | H | 2-[N-(pyridin-4-yl)piperidin-4-yl]eth-1-ylamino |
| 368 | 2-chlorophenyl | H | H | Br | 2-[N-(2,2,2-trichloroethoxyacetyl)piperidin-4-yl]eth-1-ylamino |
| 369 | 2-chlorophenyl | H | Me | H | 2-[N-(pyridin-4-yl)piperidin-4-yl]eth-1-ylamino |
| 370 | 2-chlorophenyl | H | H | Br | 2-(N-(4-benzimidazol-2-yl)piperin-4-yl)eth-1-ylamino |
| 371 | 2-chlorophenyl | H | H | Br | 2-(N-(4-1H-benzimidazol-2-yl)piperin-4-yl)eth-1-ylamino |
| 372 | 2-chlorophenyl | H | H | Me | (2-oxo-5-phenyl-2,3-dihydro-1H-benzo[e][1,4]diazepin-3-yl)amino |
| 373 | 2-chlorophenyl | H | H | Br | (2-oxo-1-propyl-azepan-3-yl)amino |
| 374 | Phenyl | H | H | Cl | (2-oxo-5-phenyl-2,3-dihydro-1H-benzo[e][1,4]diazepin-3-yl)amino |
| 375 | 2-methylphenyl | H | H | Cl | (2-oxo-5-phenyl-2,3-dihydro-1H-benzo[e][1,4]diazepin-3-yl)amino |
| 376 | 3,5-dichlorophenyl | H | H | Br | (2-oxo-5-phenyl-2,3-dihydro-1H-benzo[e][1,4]diazepin-3-yl)amino |
| 377 | 4-chlorophenyl | H | H | Br | (2-oxo-5-phenyl-2,3-dihydro-1H-benzo[e][1,4]diazepin-3-yl)amino |
| 378 | 2-chlorophenyl | H | H | Br | (1-ethyl-2-oxo-5-phenyl-2,3-dihydro-1H-benzo[e][1,4]diazepin-3-yl)amino |
| 379 | 3-chlorophenyl | H | H | Br | (2-oxo-5-phenyl-2,3-dihydro-1H-benzo[e][1,4]diazepin-3-yl)amino |
| 380 | 2-chlorophenyl | H | H | Br | (1,5-dimethyl-2-oxo-2,3,4,5-tetrahydro-1H-benzo[b][1,4]diazepin-3-yl)amino |
| 381 | 3-chlorophenyl | H | H | Cl | (2-oxo-5-phenyl-2,3-dihydro-1H-benzo[e][1,4]diazepin-3-yl)amino |
| 382 | 2-chlorophenyl | H | H | Br | (1-cyclopropylmethyl-2-oxo-azepan-3-yl)amino |
| 383 | 2-chlorophenyl | H | H | F | (2-oxo-5-phenyl-2,3-dihydro-1H-benzo[e][1,4]diazepin-3-yl)amino |
| 384 | 2-fluorophenyl | H | H | Cl | (2-oxo-5-phenyl-2,3-dihydro-1H-benzo[e][1,4]diazepin-3-yl)amino |
| 385 | 2-chlorophenyl | H | H | Cl | (1-methyl-2-oxo-5-phenyl-2,3-dihydro-1H-benzo[e][1,4]diazepin-3-yl)amino |

TABLE I-continued

Structures (IIIa) and (IIIb)

| Cpd # | R¹ | R² | R³ | X | Q |
|---|---|---|---|---|---|
| 386 | 2-chlorophenyl | H | H | Br | (1-cyclopropylmethyl-azepan-3-yl)amino |
| 387 | 2-chlorophenyl | H | H | Br | 2-(N-methyl-N-pyridin-4-yl)eth-1-ylamino |
| 388 | 2-chlorophenyl | H | H | Br | (1-methyl-piperidin-4-ylmethyl)amino |
| 389 | 2-chlorophenyl | H | H | Br | [1-(2-dimethylamino-ethyl)-2-oxo-azepan-3-yl]amino |
| 390 | 2-chlorophenyl | H | H | Br | (5-methyl-6-oxo-6,7,8,9-tetrahydro-5H-pyrido[3,2-b]azepin-7-yl)amino |
| 391 | 3-chlorophenyl | H | H | H | [2-(3,4,5,6-tetrahydro-2H-[1,4']bipyridin-4-yl)-eth-1-yl]amino |
| 392 | 2-methylphenyl | H | H | Br | [2-(3,4,5,6-tetrahydro-2H-[1,4']bipyridin-4-yl)-eth-1-yl]amino |
| 393 | 2-fluorophenyl | H | H | Br | [2-(3,4,5,6-tetrahydro-2H-[1,4']bipyridin-4-yl)-eth-1-yl]amino |
| 394 | 2-chlorophenyl | H | H | Br | {2-[1-(N,N-dimethylaminocarbonyl)-piperidin-4-yl]eth-1-yl}amino |
| 395 | 2-chlorophenyl | H | H | Br | {2-[1-(pyridin-4-ylcarbonyl)-piperidin-4-yl]eth-1-yl}amino |
| 396 | 2-chlorophenyl | H | H | Br | [2-(4-pyridin-4-yl-piperazin-1-yl)eth-1-yl]amino |
| 397 | 2-chlorophenyl | H | H | Br | (1-pyridin-4-ylmethyl-piperidin-4-yl)amino |
| 398 | 2-chlorophenyl | H | H | Br | {1-[4-bromo-5-(2-chloro-benzoylamino)-1H-pyrazole-3-carbonyl]-piperidin-4-yl}amino |
| 399 | 2-chlorophenyl | H | H | Br | [2-(1-pyridin-4-ylmethyl-piperidin-4-yl)-eth-1-yl]amino |
| 400 | 2-chlorophenyl | H | H | Br | {2-[1-(2-pyridin-4-yl-ethyl)-piperidin-4-yl]-eth-1-yl}amino |
| 401 | 2-chlorophenyl | H | H | Br | (1-pyridin-4-ylmethyl-piperidin-4-ylmethyl)amino |
| 402 | 2-chlorophenyl | H | H | Br | [1-(2-pyridin-4-yl-ethyl)-piperidin-4-yl]amino |
| 403 | 2-chlorophenyl | H | H | Br | [1-(2-pyridin-4-yl-ethyl)-piperidin-4-ylmethyl]amino |
| 404 | 2-chlorophenyl | H | H | Br | [2-(1'-methyl-[1,4']bipiperidin-4-yl)-eth-1-yl]amino |
| 405 | 2-chlorophenyl | H | H | Cl | [5-(3-aza-bicyclo[3.2.2]non-3-yl)-1-methyl-2-oxo-2,3-dihydro-1H-benzo[e][1,4]diazepin-3-yl]amino |
| 406 | 2-chlorophenyl | H | H | Br | [5-(3-aza-bicyclo[3.2.2]non-3-yl)-1-methyl-2-oxo-2,3-dihydro-1H-benzo[e][1,4]diazepin-3-yl]amino |
| 407 | 2-chlorophenyl | H | H | Cl | (2-oxo-5-phenethyl-1-propyl-2,3-dihydro-1H-benzo[e][1,4]diazepin-3-yl)amino |
| 408 | 2-chlorophenyl | H | H | Cl | [5-(3-aza-bicyclo[3.2.2]non-3-yl)-1-methyl-2-oxo-2,3-dihydro-1H-benzo[e][1,4]diazepin-3-yl]amino |
| 409 | 2-chlorophenyl | H | H | Cl | [5-(3-aza-bicyclo[3.2.2]non-3-yl)-1-methyl-2-oxo-2,3-dihydro-1H-benzo[e][1,4]diazepin-3-yl]amino |
| 410 | 2-chlorophenyl | H | H | Br | (1-ethyl-2-oxo-5-phenyl-2,3-dihydro-1H-benzo[e][1,4]diazepin-3-yl)amino |
| 411 | 2-chlorophenyl | H | H | Br | (1-ethyl-2-oxo-5-phenyl-2,3-dihydro-1H-benzo[e][1,4]diazepin-3-yl)amino |
| 412 | 2-chlorophenyl | H | Me | Br | [2-(3,4,5,6-tetrahydro-2H-[1,4']bipyridin-4-yl)-eth-1-yl]amino |
| 413 | 2-chlorophenyl | H | H | Br | [1-(pyridin-4-ylcarbonyl)-piperidin-4-yl]amino |
| 414 | 2-chlorophenyl | H | H | Br | (3,4,5,6-tetrahydro-2H-[1,4']bipyridin-4-yl)methylamino |

TABLE I-continued (IIIa) (IIIb)

| Cpd # | R¹ | R² | R³ | X | Q |
|---|---|---|---|---|---|
| 415 | 2-chlorophenyl | H | Me | Br | 2-oxo-5-phenyl-2,3-dihydro-1H-benzo[e][1,4]diazepin-3-yl)amino |
| 416 | 2-chlorophenyl | H | H | Br | (5-methyl-2-oxo-2,3,4,5-tetrahydro-1H-benzo[b][1,4]diazepin-3-yl)amino |
| 417 | 2-chlorophenyl | H | H | Br | (1-cyclopropylmethyl-5-methyl-2-oxo-2,3,4,5-tetrahydro-1H-benzo[b][1,4]diazepin-3-yl)amino |
| 418 | 2-chlorophenyl | H | H | H | 2-[1-(4-imidazol-2-yl)phenyl]eth-1-ylamino |
| 419 | 2-chlorophenyl | H | H | Br | 2-(3-methoxy-4-hydroxy-phenyl)eth-1-ylamino |
| 420 | 2-fluorophenyl | H | H | Br | (1,5-dimethyl-2-oxo-2,3,4,5-tetrahydro-1H-benzo[b][1,4]diazepin-3-yl)amino |
| 421 | 2-chlorophenyl | H | H | H | (3,4,5,6-tetrahydro-2H-[1,4']bipyridin-4-yl)methylamino |
| 422 | 2-chlorophenyl | H | H | Br | [5-(benzyloxycarbonyl)-2-oxo-2,3,4,5-tetrahydro-1H-benzo[b][1,4]diazepin-3-yl]amino |
| 423 | 2-chlorophenyl | H | H | Br | (1'-methyl-[1,4']bipiperidin-4-yl)methylamino |
| 424 | 2-fluorophenyl | H | H | Br | (3,4,5,6-tetrahydro-2H-[1,4']bipyridin-4-yl)methylamino |
| 425 | 2-chlorophenyl | H | H | Br | [2-(4-methylpiperidinyl)eth-1-yl]amino |
| 426 | 2-chlorophenyl | H | Me | Br | (3,4,5,6-tetrahydro-2H-[1,4']bipyridin-4-yl)methylamino |
| 427 | 2-fluorophenyl | H | Me | Br | [2-(3,4,5,6-tetrahydro-2H-[1,4']bipyridin-4-yl)-eth-1-yl]amino |
| 428 | 2-chlorophenyl | H | H | H | [2-(pyridine-4-yl)eth-1-yl]amino |
| 429 | 2-chlorophenyl | H | H | Br | 2-[2-phenyl-1H-benzo[d]imidazole]eth-1-ylamino |
| 430 | 2-chlorophenyl | H | H | Br | 5-aminopentylamino |
| 431 | 2-chlorophenyl | H | H | Br | 5-(t-butoxycarbonyl)-aminopentylamino |
| 432 | 2-chlorophenyl | H | H | Me | {2-[1-(4-imidazol-2-yl)phenyl]eth-1-yl}amino |
| 433 | 2-chlorophenyl | H | H | Me | [2-(3,4,5,6-tetrahydro-2H-[1,4']bipyridin-4-yl)-eth-1-yl]amino |
| 434 | 2-chlorophenyl | H | t-butyl | Me | [2-(3,4,5,6-tetrahydro-2H-[1,4']bipyridin-4-yl)-eth-1-yl]amino |
| 435 | 2-chlorophenyl | H | H | Br | (1-(benzylcarbonyl)azepan-3-yl)-amino |
| 436 | 2-chlorophenyl | H | Phenyl | H | [2-(3,4,5,6-tetrahydro-2H-[1,4']bipyridin-4-yl)-ethyl]amino |
| 437 | 2-chlorophenyl | H | Phenyl | Br | [2-(3,4,5,6-tetrahydro-2H-[1,4']bipyridin-4-yl)-ethyl]amino |
| 438 | 2-chlorophenyl | H | 3,4-dichloro-phenyl | H | [2-(3,4,5,6-tetrahydro-2H-[1,4']bipyridin-4-yl)-ethyl]amino |
| 439 | 2-chlorophenyl | H | 3-trifluoro-methylphenyl | H | [2-(3,4,5,6-tetrahydro-2H-[1,4']bipyridin-4-yl)-ethyl]amino |
| 440 | 2-chlorophenyl | H | 3-trifluoro-methylphenyl | Br | [2-(3,4,5,6-tetrahydro-2H-[1,4']bipyridin-4-yl)-ethyl]amino |
| 441 | 2-chlorophenyl | H | H | Br | [2-(piperidin-4-yl)-ethyl]amino |
| 442 | 2-fluorophenyl | H | H | Br | [N-(benzothiazol-2-yl)piperidin-4-ylmethyl]amino |
| 443 | 2-chlorophenyl | H | H | Br | (azepan-3-ylmethyl)-amino |
| 444 | 2-chlorophenyl | H | H | Br | [5-(4,5-dihydro-1H-imidazol-2-yl)-pent-1-yl]amino |
| 445 | 2-chlorophenyl | H | Me | Br | [2-(4-(pyridin-4-yl)-piperazin-1-yl)ethyl]amino |
| 446 | 2-chlorophenyl | H | Me | Br | (azepan-3-yl)-amino |
| 447 | 2-chlorophenyl | H | H | Br | [4-(pyridin-4-yl)-[1,4]diazepin-6-yl]amino |

TABLE I-continued (IIIa) and (IIIb) structures shown with R¹-C(=O)-N(R²)- attached to pyrazole bearing X, C(=O)-Q, and R³ on ring nitrogen.

| Cpd # | R¹ | R² | R³ | X | Q |
|---|---|---|---|---|---|
| 448 | 2-chlorophenyl | H | Me | Br | [2-(N-methyl-piperidin-4-yl)-ethyl]amino |
| 449 | 2-chlorophenyl | H | Me | Br | {2-[4-(4,5-dihydro-1H-imidazol-2-yl)-phenyl]ethyl}amino |
| 450 | 2-chlorophenyl | H | Me | Me | [2-(3,4,5,6-tetrahydro-2H-[1,4']bipyridin-4-yl)-ethyl]amino |
| 451 | 2-chlorophenyl | H | 2-methyl-phenyl | Me | [2-(3,4,5,6-tetrahydro-2H-[1,4']bipyridin-4-yl)-ethyl]amino |
| 452 | 2-chlorophenyl | H | 3-methoxy-phenyl | Me | [2-(3,4,5,6-tetrahydro-2H-[1,4']bipyridin-4-yl)-ethyl]amino |
| 453 | 2-chlorophenyl | H | 4-fluorophenyl | Me | [2-(3,4,5,6-tetrahydro-2H-[1,4']bipyridin-4-yl)-ethyl]amino |
| 454 | 2-chlorophenyl | H | Phenyl | Me | [2-(3,4,5,6-tetrahydro-2H-[1,4']bipyridin-4-yl)-ethyl]amino |
| 455 | 2-chlorophenyl | H | Pyridin-2-yl | H | [2-(3,4,5,6-tetrahydro-2H-[1,4']bipyridin-4-yl)-ethyl]amino |
| 456 | 2-chlorophenyl | H | 4-fluorophenyl | Br | [2-(3,4,5,6-tetrahydro-2H-[1,4']bipyridin-4-yl)-ethyl]amino |
| 457 | 2-chlorophenyl | H | Pyridin-2-yl | Br | [2-(3,4,5,6-tetrahydro-2H-[1,4']bipyridin-4-yl)-ethyl]amino |
| 458 | 2-chlorophenyl | H | 4-fluorophenyl | H | [2-(3,4,5,6-tetrahydro-2H-[1,4']bipyridin-4-yl)-ethyl]amino |
| 459 | 2-chlorophenyl | H | H | H | [4-methyl-5-oxo-[1,4]diazepin-6-yl]amino |
| 460 | 2-chlorophenyl | H | Phenyl | Br | (2-oxo-azepan-3-yl)-amino |
| 461 | 2-chlorophenyl | H | Phenyl | H | (2-oxo-azepan-3-yl)-amino |
| 462 | 2-chlorophenyl | H | Pyridin-2-yl | Me | [2-(3,4,5,6-tetrahydro-2H-[1,4']bipyridin-4-yl)-ethyl]amino |
| 463 | 2-chlorophenyl | H | Pyridin-4-yl | Me | [2-(3,4,5,6-tetrahydro-2H-[1,4']bipyridin-4-yl)-ethyl]amino |
| 464 | 2-chlorophenyl | H | Pyrimidin-2-yl | Me | [2-(3,4,5,6-tetrahydro-2H-[1,4']bipyridin-4-yl)-ethyl]amino |
| 465 | 2-chlorophenyl | H | 2,6-dimethyl-pyrimidin-4-yl | Me | [2-(3,4,5,6-tetrahydro-2H-[1,4']bipyridin-4-yl)-ethyl]amino |
| 466 | 2-chlorophenyl | H | Pyridin-2-yl | Me | (2-oxo-5-phenyl-2,3-dihydro-1H-benzo[e][1,4]diazepin-3-yl)amino |
| 467 | 2-chlorophenyl | H | Phenyl | H | 2-oxo-5-phenyl-2,3-dihydro-1H-benzo[e][1,4]diazepin-3-yl)amino |
| 468 | 2-chlorophenyl | H | Phenyl | Br | (2-oxo-5-phenyl-2,3-dihydro-1H-benzo[e][1,4]diazepin-3-yl)amino |
| 469 | acetyl | H | Phenyl | H | [2-(3,4,5,6-tetrahydro-2H-[1,4']bipyridin-4-yl)-ethyl]amino |
| 470 | 2-chlorophenyl | H | 4-isopropyl-phenyl | Br | [2-(3,4,5,6-tetrahydro-2H-[1,4']bipyridin-4-yl)-ethyl]amino |
| 471 | 2-chlorophenyl | H | 4-isopropyl-phenyl | H | [2-(3,4,5,6-tetrahydro-2H-[1,4']bipyridin-4-yl)-ethyl]amino |
| 472 | 2-fluorophenyl | H | Phenyl | Br | [2-(3,4,5,6-tetrahydro-2H-[1,4']bipyridin-4-yl)-ethyl]amino |
| 473 | 2-fluorophenyl | H | Phenyl | H | [2-(3,4,5,6-tetrahydro-2H-[1,4']bipyridin-4-yl)-ethyl]amino |
| 474 | 2-chlorophenyl | H | 4-methoxy-phenyl | Br | [2-(3,4,5,6-tetrahydro-2H-[1,4']bipyridin-4-yl)-ethyl]amino |
| 475 | 2-chlorophenyl | H | 2-(N,N-dimethylamino)-eth-1-yl | Br | [2-(3,4,5,6-tetrahydro-2H-[1,4']bipyridin-4-yl)-ethyl]amino |

Particularly preferred compounds include the following compounds:

4-Bromo-5-(2-chloro-benzoylamino)-1H-pyrazole-3-carboxylic acid [2-(1-methyl-piperidin-4-yl)-ethyl]-amide;

4-Bromo-5-(2-chloro-benzoylamino)-1H-pyrazole-3-carboxylic acid (2-pyrrolidin-1-yl-prop-1-yl)-amide;

(R)-4-Bromo-5-(2-chloro-benzoylamino)-1-phenyl-pyrazole-3-carboxylic acid (2-oxo-azepan-3-yl)-amide;

(R)-4-Bromo-5-(2-chloro-benzoylamino)-1H-pyrazole-3-carboxylic acid (1-aza-bicyclo[2.2.2]oct-3-yl)-amide;

(S)-4-Bromo-5-(2-chloro-benzoylamino)-1H-pyrazole-3-carboxylic acid (1-aza-bicyclo[2.2.2]oct-3-yl)-amide;

4-Bromo-5-(2-chloro-benzoylamino)-1H-pyrazole-3-carboxylic acid benzhydryl-amide;
4-Bromo-5-(2-chloro-benzoylamino-1H-pyrazole-3-carboxylic acid [2-(1-phenyl-piperidin-4-yl)-ethyl]-amide;
4-Bromo-5-[2-(quinolin-8-ylthiomethyl)-benzoylamino]-1H-pyrazole-3-carboxylic acid (2-morpholin-4-yl-ethyl)-amide;
5-(2-Chloro-benzoylamino)-4-methyl-2H-pyrazole-3-carboxylic acid (2-piperidin-1-yl-ethyl)-amide;
5-(2-Chloro-benzoylamino)-4-methyl-1H-pyrazole-3-carboxylic acid isopropylamide;
5-(2-Chloro-benzoylamino)-4-methyl-1H-pyrazole-3-carboxylic acid cyclohexylamide;
5-(2-Chloro-benzoylamino)-4-methyl-1H-pyrazole-3-carboxylic acid methoxy-methyl-amide;
3-benzoyl-5-(2-chloro-benzoylamino) 4-methyl-1H-pyrazole;
4-methyl-5-(2-chloro-benzoylamino)-1-(pyridine-2-yl)-pyrazole-3-carboxylic acid (2-oxo-5-phenyl-2,3-dihydro-1H-benzo[e][1,4]diazepin-3-yl)amide;
5-(2-Chloro-benzoylamino)-4-methyl-1H-pyrazole-3-carboxylic acid (1-benzyl-piperidin-4-yl)-amide;
(S)-5-(2-Chloro-benzoylamino)-4-methyl-1H-pyrazole-3-carboxylic acid (1-phenyl-ethyl)-amide;
4-Benzyl-5-(2-chloro-benzoylamino)-1H-pyrazole-3-carboxylic acid (2-piperidin-1-yl-ethyl)-amide;
4-Bromo-5-(2-m-tolylthiomethyl-benzoylamino)-1H-pyrazole-3-carboxylic acid methyl ester;
4-Bromo-5-(2-chloro-benzoylamino)-1H-pyrazole-3-carboxylic acid methyl ester;
4-Bromo-5-(2-chloro-benzoylamino)-1H-pyrazole-3-carboxylic acid benzylamide;
4-Bromo-5-(2-chloro-benzoylamino)-1H-pyrazole-3-carboxylic acid methylamide;
(R)-4-Bromo-5-(2-chloro-benzoylamino)-1H-pyrazole-3-carboxylic acid (1-phenyl-ethyl)-amide;
4-Bromo-5-(2-chloro-benzoylamino)-1H-pyrazole-3-carboxylic acid (2-pyridin-4-yl-ethyl)-amide;
4-Bromo-5-(2-chloro-benzoylamino)-1H-pyrazole-3-carboxylic acid (1-methyl-1-phenyl-ethyl)-amide;
(S)-4-Bromo-5-(2-chloro-benzoylamino)-1H-pyrazole-3-carboxylic acid (2-hydroxy-1-phenyl-ethyl)-amide;
(R)-4-Bromo-5-(2-chloro-benzoylamino)-1H-pyrazole-3-carboxylic acid methyl-(1-phenyl-ethyl)-amide;
4-Bromo-5-(2-chloro-benzoylamino)-1H-pyrazole-3-carboxylic acid (2-pyrrolidin-1-yl-ethyl)-amide;
(S)-4-Bromo-5-(2-chloro-benzoylamino)-1H-pyrazole-3-carboxylic acid (1-phenyl-ethyl)-amide;
4-Bromo-5-(2-chloro-benzoylamino)-1H-pyrazole-3-carboxylic acid (2-morpholin-4-yl-ethyl)-amide;
4-Bromo-5-(2-chloro-benzoylamino)-1H-pyrazole-3-carboxylic acid (3-morpholin-4-yl-propyl)-amide;
4-Bromo-5-(2-chloro-benzoylamino)-1H-pyrazole-3-carboxylic acid (2-dimethylamino-ethyl)-amide;
4-Bromo-5-(2-chloro-benzoylamino)-1H-pyrazole-3-carboxylic acid (3-dimethylamino-propyl)-amide;
4-bromo-5-(2-chloro-benzoylamino) 1H-pyrazole-3-carboxylic acid 4-methyl-piperazin-1-yl amide;
4-bromo-5-(2-chloro-benzoylamino) 1H-pyrazole-3-carboxylic acid morpholino-4-yl amide;
4-Bromo-5-(2-chloro-benzoylamino)-1H-pyrazole-3-carboxylic acid cyclohexylamide;
4-Bromo-5-(2-chloro-benzoylamino)-1H-pyrazole-3-carboxylic acid phenethyl-amide;
(S)-4-Bromo-5-(2-chloro-benzoylamino)-1H-pyrazole-3-carboxylic acid (1-hydroxymethyl-2-methyl-propyl)-amide;
4-Bromo-5-(2-chloro-benzoylamino)-1H-pyrazole-3-carboxylic acid (1-benzyl-piperidin-4-yl)-amide;
4-Bromo-5-(2-chloro-benzoylamino)-1H-pyrazole-3-carboxylic acid (2-hydroxy-ethyl)-amide;
4-Bromo-5-(2-chloro-benzoylamino)-1H-pyrazole-3-carboxylic acid (trans-4-hydroxy-cyclohexyl)-amide;
4-Bromo-5-(2-chloro-benzoylamino)-1H-pyrazole-3-carboxylic acid (2-methyl-cyclohexyl)-amide;
4-Bromo-5-(2-chloro-benzoylamino)-1H-pyrazole-3-carboxylic acid [2-(4-hydroxy-phenyl)-ethyl]-amide;
4-Bromo-5-(2-chloro-benzoylamino)-1H-pyrazole-3-carboxylic acid (1S,2 S)-(2-benzyloxy-cyclopentyl)-amide;
4-Bromo-5-(2-chloro-benzoylamino)-1H-pyrazole-3-carboxylic acid [2-(1H-indol-3-yl)-ethyl]-amide;
4-Bromo-5-(2-chloro-benzoylamino)-1H-pyrazole-3-carboxylic acid [2-(1H-imidazol-4-yl)-ethyl]-amide;
4-Bromo-5-(2-chloro-benzoylamino)-1H-pyrazole-3-carboxylic acid (1S,2R)-(2-hydroxy-indan-1-yl)-amide;
4-Bromo-5-(2-chloro-benzoylamino)-1H-pyrazole-3-carboxylic acid (3-hydroxy-butyl)-amide;
4-Bromo-5-(2-chloro-benzoylamino)-1H-pyrazole-3-carboxylic acid (2-dimethylamino-1-methyl-ethyl)-amide;
4-Bromo-5-(2-chloro-benzoylamino)-1H-pyrazole-3-carboxylic acid (trans-2-hydroxy-cyclohexyl)-amide;
(R)-4-Chloro-5-(2-chloro-benzoylamino)-1H-pyrazole-3-carboxylic acid (1-phenyl-ethyl)-amide;
(S)-4-Bromo-5-(2-chloro-benzoylamino)-1H-pyrazole-3-carboxylic acid (1-methyl-2-piperidin-1-yl-ethyl)-amide;
4-Bromo-5-(2-chloro-benzoylamino)-1H-pyrazole-3-carboxylic acid (1-methyl-2-pyrrolidin-1-yl-ethyl)-amide;
4-Bromo-5-(2-chloro-benzoylamino)-1H-pyrazole-3-carboxylic acid (1-methyl-2-morpholin-4-yl-ethyl)-amide;
(S)-4-Bromo-5-(2-chloro-benzoylamino)-1H-pyrazole-3-carboxylic acid (2-hydroxy-1-methyl-ethyl)-amide;
4-Bromo-5-(2-chloro-benzoylamino)-1H-pyrazole-3-carboxylic acid [2-(1-methyl-piperidin-4-yl)-ethyl]-amide;
4-Bromo-5-(2-chloro-benzoylamino)-1H-pyrazole-3-carboxylic acid (1-benzenesulfonyl-piperidin-4-yl)-amide;
4-Bromo-5-(2-chloro-benzoylamino)-1H-pyrazole-3-carboxylic acid (1-methyl-piperidin-4-yl)-amide;
(R)-4-Bromo-5-(2-chloro-benzoylamino)-1H-pyrazole-3-carboxylic acid (1-methyl-2-piperidin-1-yl-ethyl)-amide;
(R)-4-Bromo-5-(2-chloro-benzoylamino)-1H-pyrazole-3-carboxylic acid (1-methyl-2-morpholin-4-yl-ethyl)-amide;
(R)-4-Bromo-5-(2-chloro-benzoylamino)-1H-pyrazole-3-carboxylic acid (1-phenyl-2-piperidin-1-yl-ethyl)-amide;
(S)-4-Bromo-5-(2-chloro-benzoylamino)-1H-pyrazole-3-carboxylic acid (1-phenyl-2-piperidin-1-yl-ethyl)-amide;
(R)-4-Bromo-5-(2-chloro-benzoylamino)-1H-pyrazole-3-carboxylic acid (2-hydroxy-1-methyl-ethyl)-amide;
(R)-4-Bromo-5-(2-chloro-benzoylamino)-1H-pyrazole-3-carboxylic acid (2-dimethylamino-1-methyl-ethyl)-amide;
(R)-5-(2-Chloro-benzoylamino)-1H-pyrazole-3-carboxylic acid (1-phenyl-ethyl)-amide;
(S)-4-Bromo-5-(2-chloro-benzoylamino)-1H-pyrazole-3-carboxylic acid (2-dimethylamino-1-methyl-ethyl)-amide;
(R)-4-Bromo-5-(2-chloro-benzoylamino)-1H-pyrazole-3-carboxylic acid (1-dimethylaminomethyl-propyl)-amide;

(R)-4-Bromo-5-(2-chloro-benzoylamino)-1H-pyrazole-3-carboxylic acid (2-diethylamino-1-methyl-ethyl)-amide;
(R)-4-Bromo-5-(2-chloro-benzoylamino)-1H-pyrazole-3-carboxylic acid [2-(ethyl-methyl-amino)-1-methyl-ethyl]-amide;
4-Bromo-5-(2-chloro-benzoylamino)-1H-pyrazole-3-carboxylic acid (2-acetylamino-ethyl)-amide;
(R)-4-Bromo-5-(2-chloro-benzoylamino)-1H-pyrazole-3-carboxylic acid (1-dimethylaminomethyl-3-phenyl-propyl)-amide;
(R)-4-Bromo-5-(2-chloro-benzoylamino)-1H-pyrazole-3-carboxylic acid [2-(acetyl-methyl-amino)-1-methyl-ethyl]-amide;
4-Bromo-5-(2-chloro-benzoylamino)-1H-pyrazole-3-carboxylic acid [2-(methyl-phenyl-amino)-ethyl]-amide;
4-Bromo-5-(2-chloro-benzoylamino)-1H-pyrazole-3-carboxylic acid ((3 S)-1-benzyl-pyrrolidin-3-yl)-amide;
4-Bromo-5-(2-chloro-benzoylamino)-1H-pyrazole-3-carboxylic acid ((3 R)-1-benzyl-pyrrolidin-3-yl)-amide;
(R)-4-Bromo-5-(2-chloro-benzoylamino)-1H-pyrazole-3-carboxylic acid [2-(cyclopropyl-methyl-amino)-1-methyl-ethyl]-amide;
4-Bromo-5-(2-chloro-benzoylamino)-1H-pyrazole-3-carboxylic acid (4-phenyl-morpholin-2-ylmethyl)-amide;
4-Bromo-5-(2-chloro-benzoylamino)-1H-pyrazole-3-carboxylic acid [2-(3,4-dihydro-2H-quinolin-1-yl)-ethyl]-amide;
4-Bromo-5-(2-chloro-benzoylamino)-1H-pyrazole-3-carboxylic acid [2-(1-methyl-pyrrolidin-2-yl)-ethyl]-amide;
4-Bromo-5-(2-chloro-benzoylamino)-1H-pyrazole-3-carboxylic acid (pyridin-2-ylmethyl)-amide;
4-Bromo-5-(2-chloro-benzoylamino)-1H-pyrazole-3-carboxylic acid (pyridin-3-ylmethyl)-amide;
4-Bromo-5-(2-chloro-benzoylamino)-1H-pyrazole-3-carboxylic acid (pyridin-4-ylmethyl)-amide;
4-Bromo-5-(2-chloro-benzoylamino)-1H-pyrazole-3-carboxylic acid (2-piperidin-1-yl-ethyl)-amide;
4-Bromo-5-(2-chloro-benzoylamino)-1H-pyrazole-3-carboxylic acid [1-(4-hydroxy-phenyl)-ethyl]-amide;
4-Bromo-5-(2-chloro-benzoylamino)-1H-pyrazole-3-carboxylic acid (2-pyrrolidin-1-yl-ethyl)-amide;
4-Bromo-5-(2-chloro-benzoylamino)-1H-pyrazole-3-carboxylic acid (5-methyl-pyrazin-2-ylmethyl)-amide;
4-Bromo-5-(2-chloro-benzoylamino)-1H-pyrazole-3-carboxylic acid (2-hydroxy-propyl)-amide;
4-Bromo-5-(2-chloro-benzoylamino)-1H-pyrazole-3-carboxylic acid piperidin-1-ylamide;
(R)-4-Bromo-5-(2-chloro-benzoylamino)-1H-pyrazole-3-carboxylic acid (1-p-tolyl-ethyl)-amide;
4-Bromo-5-(2-chloro-benzoylamino)-1H-pyrazole-3-carboxylic acid (2-aminocarbonyl-ethyl)-amide;
4-Bromo-5-(2-chloro-benzoylamino)-1H-pyrazole-3-carboxylic acid (2-(tert-butoxycarbonyl)eth-1-yl)-amide;
(R)-4-Bromo-5-(2-chloro-benzoylamino)-1H-pyrazole-3-carboxylic acid [1-(4-chloro-phenyl)-ethyl]-amide;
(R)-4-Bromo-5-(2-chloro-benzoylamino)-1H-pyrazole-3-carboxylic acid [1-(4-methoxy-phenyl)-ethyl]-amide;
4-Bromo-5-(2-chloro-benzoylamino)-1H-pyrazole-3-carboxylic acid [1-(4-methanesulfonyl-phenyl)-ethyl]-amide;
4-Bromo-5-(2-chloro-benzoylamino)-1H-pyrazole-3-carboxylic acid (2-dimethylamino-ethyl);
4-bromo-5-(2-chlorobenzoylamino)-1H-pyrazole-3-carboxylic acid [2-(pyrrolidin-1-ylmethyl)-pyrrolidin-1-yl]amide;
4-Bromo-5-(2-chloro-benzoylamino)-2H-pyrazole-3-carboxylic acid (2-oxo-azepan-3-yl)-amide;
4-bromo-5-(2-chloro-benzoylamino) 1H-pyrazole-3-carboxylic acid (4-phenylpiperzin-1-yl)amide;
4-Bromo-5-(2-chloro-benzoylamino)-1H-pyrazole-4-carboxylic acid (1-ethyl-pyrrolidin-2-ylmethyl)-amide;
(R)-4-Bromo-5-(2-chloro-benzoylamino)-1H-pyrazole-3-carboxylic acid [1-(4-fluoro-phenyl)-ethyl]-amide;
(S)-4-Bromo-5-(2-chloro-benzoylamino)-1H-pyrazole-3-carboxylic acid (2-oxo-azepan-3-yl)-amide;
(R)-4-Bromo-5-(2-chloro-benzoylamino)-1H-pyrazole-3-carboxylic acid (2-oxo-azepan-3-yl)-amide;
(S)-4-Bromo-5-(2-chloro-benzoylamino)-1H-pyrazole-3-carboxylic acid (1-methyl-2-oxo-azepan-3-yl)-amide;
(R)-4-Bromo-5-(2-chloro-benzoylamino)-1H-pyrazole-3-carboxylic acid (1-methyl-2-oxo-azepan-3-yl)-amide;
4-Bromo-5-(2-chloro-benzoylamino)-1H-pyrazole-3-carboxylic acid (2-oxo-5-phenyl-2,3-dihydro-1H-benzo[e][1,4]diazepin-3-yl)-amide;
(R)-4-Bromo-5-(2-chloro-benzoylamino)-1H-pyrazole-3-carboxylic acid (1-methyl-azepan-3-yl)-amide;
4-Bromo-5-(2-chloro-benzoylamino)-1H-pyrazole-3-carboxylic acid (1-methyl-2-oxo-5-phenyl-2,3-dihydro-1H-benzo[e][1,4]diazepin-3-yl)-amide;
5-(2-Chloro-benzoylamino)-1H-pyrazole-3-carboxylic acid (2-oxo-5-phenyl-2,3-dihydro-1H-benzo[e][1,4]diazepin-3-yl)-amide;
4-Bromo-5-(2-chloro-benzoylamino)-1H-pyrazole-3-carboxylic acid (2-oxo-2,3,4,5-tetrahydro-1H-benzo[b]azepin-3-yl)-amide;
4-Chloro-5-(2-chloro-benzoylamino)-1H-pyrazole-3-carboxylic acid (2-oxo-5-phenyl-2,3-dihydro-1H-benzo[e][1,4]diazepin-3-yl)-amide;
4-Bromo-5-(2-chloro-benzoylamino)-1H-pyrazole-3-carboxylic acid (5-methyl-6-oxo-6,7-dihydro-5H-dibenzo[b,d]azepin-7-yl)-amide;
4-Bromo-5-(2-chloro-benzoylamino)-1H-pyrazole-3-carboxylic acid (5-cyclohexyl-2-oxo-2,3-dihydro-1-H-benzo[e][1,4]diazepin-3-yl)-amide;
4-Bromo-5-(2-chloro-benzoylamino)-1H-pyrazole-3-carboxylic acid (1-methyl-2-oxo-5-phenyl-2,3-dihydro-1H-benzo[e][1,4]diazepin-3-yl)-amide;
4-methyl-5-(2-chlorobenzoylamino)-1-(3,4-dimethylpyrimidin-6-yl)-pyrazole-3-carboxylic acid [2-(3,4,5,6-tetrahydro-2H-[1,4']bipyridin-4-yl)ethyl]amide;
4-Bromo-5-(2-chloro-benzoylamino)-1H-pyrazole-3-carboxylic acid {2-[(2-benzyl-phenyl)-methyl-amino]-ethyl}-amide;
4-Chloro-5-(2-chloro-benzoylamino)-1H-pyrazole-3-carboxylic acid [7-chloro-5-(2-chloro-phenyl)-2-oxo-2,3-dihydro-1H-benzo[e][1,4]diazepin-3-yl]-amide;
4-Chloro-5-(2-chloro-benzoylamino)-1H-pyrazole-3-carboxylic acid (7-chloro-2-oxo-5-phenyl-2,3-dihydro-1H-benzo[e][1,4]diazepin-3-yl)amide;
(R)-4-Bromo-5-(2-chloro-benzoylamino)-1H-pyrazole-3-carboxylic acid (3-phenyl-1-piperidin-1-ylmethyl-propyl)amide;
4-Bromo-5-(2-chloro-benzoylamino)-1H-pyrazole-3-carboxylic acid (1,5-dimethyl-1H-pyrazol-3-ylmethyl)amide;
4-Bromo-5-(2-chloro-benzoylamino)-1H-pyrazole-3-carboxylic acid (1-methyl-1H-pyrrol-2-ylmethyl)amide;
4-Bromo-5-(2-chloro-benzoylamino)-1H-pyrazole-3-carboxylic acid (benzo[b]thiophen-3-ylmethyl)amide;
4-Bromo-5-(2-chloro-benzoylamino)-1H-pyrazole-3-carboxylic acid (5-methyl-isoxazol-3-ylmethyl)amide;

4-Bromo-5-(2-chloro-benzoylamino)-1H-pyrazole-3-carboxylic acid (3-methyl-2-oxo-piperidin-3-yl)amide;
4-Bromo-5-(2-chloro-benzoylamino)-1H-pyrazole-3-carboxylic acid (1-methyl-2-oxo-piperidin-3-yl)amide;
4-Bromo-5-(2-chloro-benzoylamino)-1H-pyrazole-3-carboxylic acid (1-methyl-piperidin-3-yl)-amide;
4-Bromo-5-(2-chloro-benzoylamino)-1H-pyrazole-3-carboxylic acid (2-oxo-1,2,3,4-tetrahydro-quinolin-3-yl)amide;
(R)-4-Chloro-5-(2-chlorobenzoylamino)-1H-pyrazole-3-carboxylic acid (1-methylazepin-3-yl)amide;
(R)-4-Bromo-5-(2-chlorobenzoylamino)-1H-pyrazole-3-carboxylic acid (1-benzyl-2-oxo-azepin-3-yl)amide;
(R)-4-Bromo-5-(2-chlorobenzoylamino)-1H-pyrazole-3-carboxylic acid (1-ethyl-2-oxo-azepin-3-yl)amide;
4-Bromo-5-[(2-chloro-benzoyl)-methyl-amino]-1H-pyrazole-3-carboxylic acid [2-(1-methyl-piperidin-4-yl)-ethyl]amide;
4-Bromo-5-(2-chlorobenzoylamino)-1H-pyrazole-3-carboxylic acid [2-(3,4,5,6-tetrahydro-2H-[1,4']bipyridin-4-yl)ethyl]amide;
4-Bromo-5-(2-chloro-benzoylamino)-1H-pyrazole-3-carboxylic acid [2-(4-benzyl-piperazin-1-yl)ethyl]amide;
4-Bromo-5-(2-chloro-benzoylamino)-1H-pyrazole-3-carboxylic acid [2-(4-methyl-piperazin-1-yl)ethyl]amide;
4-Bromo-5-(2-chloro-benzoylamino)-1H-pyrazole-3-carboxylic acid 3-pyrrol-1-yl-benzylamide;
4-Chloro-5-(2-chloro-benzoylamino)-1H-pyrazole-3-carboxylic acid [2-(3,4,5,6-tetrahydro-2H-[1,4']bipyridin-4-yl)-ethyl]amide;
endo-4-Bromo-5-(2-chloro-benzoylamino)-1H-pyrazole-3-carboxylic acid (8-methyl-8-aza-bicyclo[3.2.1]oct-3-yl)amide;
4-Bromo-5-(2-chloro-benzoylamino)-1H-pyrazole-3-carboxylic acid [1-methyl-2-(1-methyl-piperidin-4-yl)ethyl]amide;
4-Bromo-5-(2-chlorobenzoylamino)-1H-pyrazole-3-carboxylic acid (3,4,5,6-tetrahydro-2H-[1,4']bipyridin-4-yl)amide;
4-Bromo-5-(2-chlorobenzoylamino)-1H-pyrazole-3-carboxylic acid [2-(3,4,5,6-tetrahydro-2H-[1,2']bipyridin-4-yl)-ethyl]amide;
5-(2-Chloro-benzoylamino)-1H-pyrazole-3-carboxylic acid (2-oxo-2,3,4,5-tetrahydro-1H-benzo[b]azepin-3-yl)amide;
4-Chloro-5-(2-chloro-benzoylamino)-1H-pyrazole-3-carboxylic acid (2-oxo-2,3,4,5-tetrahydro-1H-benzo[b]azepin-3-yl)amide;
(R)-4-Bromo-5-(2-chloro-benzoylamino)-1H-pyrazole-3-carboxylic acid (1-methyl-2-oxo-5-phenyl-2,3-dihydro-1H-benzo[e][1,4]diazepin-3-yl)amide;
(S)-4-Chloro-5-(2-chloro-benzoylamino)-1H-pyrazole-3-carboxylic acid (2-oxo-5-phenyl-2,3-dihydro-1H-benzo[e][1,4]diazepin-3-yl)amide;
(R)-4-Chloro-5-(2-chloro-benzoylamino)-1H-pyrazole-3-carboxylic acid (2-oxo-5-phenyl-2,3-dihydro-1H-benzo[e][1,4]diazepin-3-yl)amide;
4-Chloro-5-(2-chloro-benzoylamino)-1H-pyrazole-3-carboxylic acid (1-methyl-2-oxo-5-phenyl-2,3-dihydro-1H-benzo[e][1,4]diazepin-3-yl)amide;
(R)-4-Bromo-5-(2-chlorobenzoylamino)-1H-pyrazole-3-carboxylic acid (9-methyl-8-oxo-6,7,8,9-tetrahydro-5-oxa-9-aza-benzocyclohepten-7-yl)amide;
(R)-4-Bromo-5-(2-chlorobenzoylamino)-1H-pyrazole-3-carboxylic acid (2-oxo-1-phenethyl-azepan-3-yl)amide;
4-Bromo-5-(2-chlorobenzoylamino)-1H-pyrazole-3-carboxylic acid (1,5-dimethyl-2-oxo-2,3,4,5-tetrahydro-1H-benzo[b]azepin-3-yl)amide;
(R)-4-Bromo-5-(2-chlorobenzoylamino)-1H-pyrazole-3-carboxylic acid (1-ethyl-azepan-3-yl)amide;
(R)-4-Bromo-5-(2-chlorobenzoylamino)-1H-pyrazole-3-carboxylic acid (9-ethyl-8-oxo-6,7,8,9-tetrahydro-5-oxa-9-aza-benzocyclohepten-7-yl)amide;
4-Bromo-5-(2-chlorobenzoylamino)-1H-pyrazole-3-carboxylic acid (3-methyl-2-oxo-2,3,4,5-tetrahydro-1H-benzo[d]azepin-1-yl)amide;
(R)-5-(2-Chlorobenzoylamino)-1H-pyrazole-3-carboxylic acid (9-ethyl-8-oxo-6,7,8,9-tetrahydro-5-oxa-9-aza-benzocyclohepten-7-yl)amide;
(R)-4-Bromo-5-(2-chlorobenzoylamino)-1H-pyrazole-3-carboxylic acid (1-benzoyl-azepan-3-yl)amide;
(R)-4-Bromo-5-(2-chlorobenzoylamino)-1H-pyrazole-3-carboxylic acid (1-acetyl-azepan-3-yl)amide;
4-Bromo-5-(2-chlorobenzoylamino)-1H-pyrazole-3-carboxylic acid (1,5,5-trimethyl-2-oxo-2,3,4,5-tetrahydro-1H-benzo[b]azepin-3-yl)amide;
4-Bromo-5-(2-chlorobenzoylamino)-1H-pyrazole-3-carboxylic acid [2-(1-pyrimidin-2-yl-piperidin-4-yl)-ethyl]amide;
5-(2-Chlorobenzoylamino)-1H-pyrazole-3-carboxylic acid [2-(1-methyl-piperidin-4-yl)-ethyl]amide;
4-Bromo-5-isobutyrylamino-1H-pyrazole-3-carboxylic acid (2-oxo-5-phenyl-2,3-dihydro-1H-benzo[e][1,4]diazepin-3-yl)amide;
4-Bromo-5-(2-fluorobenzoylamino)-1H-pyrazole-3-carboxylic acid (2-oxo-5-phenyl-2,3-dihydro-1H-benzo[e][1,4]diazepin-3-yl)amide;
5-Acetylamino-4-bromo-1H-pyrazole-3-carboxylic acid (2-oxo-5-phenyl-2,3-dihydro-1H-benzo[e][1,4]diazepin-3-yl)amide;
5-Benzoylamino-4-bromo-1H-pyrazole-3-carboxylic acid (2-oxo-5-phenyl-2,3-dihydro-1H-benzo[e][1,4]diazepin-3-yl)amide;
4-Bromo-5-(2-chloro-benzoylamino)-1H-pyrazole-3-carboxylic acid (2-oxo-1-propyl-azepan-3-yl)amide;
5-Benzoylamino-4-chloro-1H-pyrazole-3-carboxylic acid (2-oxo-5-phenyl-2,3-dihydro-1H-benzo[e][1,4]diazepin-3-yl)amide;
4-Chloro-5-(2-methyl-benzoylamino)-1H-pyrazole-3-carboxylic acid (2-oxo-5-phenyl-2,3-dihydro-1H-benzo[e][1,4]diazepin-3-yl)amide;
4-Bromo-5-(3,5-dichloro-benzoylamino)-1H-pyrazole-3-carboxylic acid (2-oxo-5-phenyl-2,3-dihydro-1H-benzo[e][1,4]diazepin-3-yl)amide;
4-Bromo-5-(4-chloro-benzoylamino)-1H-pyrazole-3-carboxylic acid (2-oxo-5-phenyl-2,3-dihydro-1H-benzo[e][1,4]diazepin-3-yl)amide;
4-Bromo-5-(2-chloro-benzoylamino)-1H-pyrazole-3-carboxylic acid (1-ethyl-2-oxo-5-phenyl-2,3-dihydro-1H-benzo[e][1,4]diazepin-3-yl)amide;
4-Bromo-5-(3-chloro-benzoylamino)-1H-pyrazole-3-carboxylic acid (2-oxo-5-phenyl-2,3-dihydro-1H-benzo[e][1,4]diazepin-3-yl)amide;
4-Bromo-5-(2-chloro-benzoylamino)-1H-pyrazole-3-carboxylic acid (1,5-dimethyl-2-oxo-2,3,4,5-tetrahydro-1H-benzo[b][1,4]diazepin-3-yl)amide;
4-Chloro-5-(3-chloro-benzoylamino)-1H-pyrazole-3-carboxylic acid (2-oxo-5-phenyl-2,3-dihydro-1H-benzo[e][1,4]diazepin-3-yl)amide;
4-Bromo-5-(2-chloro-benzoylamino)-1H-pyrazole-3-carboxylic acid (1-cyclopropylmethyl-2-oxo-azepan-3-yl)amide;

5-(2-Chloro-benzoylamino)-4-fluoro-1H-pyrazole-3-carboxylic acid (2-oxo-5-phenyl-2,3-dihydro-1H-benzo[e][1,4]diazepin-3-yl)amide;

Chloro-5-(2-fluoro-benzoylamino)-1H-pyrazole-3-carboxylic acid (2-oxo-5-phenyl-2,3-dihydro-1H-benzo[e][1,4]diazepin-3-yl)amide;

4-Chloro-5-(2-chloro-benzoylamino)-1H-pyrazole-3-carboxylic acid methyl-(1-methyl-2-oxo-5-phenyl-2,3-dihydro-1H-benzo[e][1,4]diazepin-3-yl)amide;

4-Bromo-5-(2-chloro-benzoylamino)-1H-pyrazole-3-carboxylic acid (1-cyclopropylmethyl-azepan-3-yl)amide;

4-Bromo-5-(2-chloro-benzoylamino)-1H-pyrazole-3-carboxylic acid [2-(N-methyl-N-pyridin-4-yl)eth-1-yl]amide;

4-Bromo-5-(2-chloro-benzoylamino)-1H-pyrazole-3-carboxylic acid (1-methyl-piperidin-4-ylmethyl)amide;

4-Bromo-5-(2-chloro-benzoylamino)-1H-pyrazole-3-carboxylic acid [1-(2-dimethylamino-ethyl)-2-oxo-azepan-3-yl]amide;

4-Bromo-5-(2-chloro-benzoylamino)-1H-pyrazole-3-carboxylic acid (5-methyl-6-oxo-6,7,8,9-tetrahydro-5H-pyrido[3,2-b]azepin-7-yl)amide;

5-(3-Chloro-benzoylamino)-1H-pyrazole-3-carboxylic acid [2-(3,4,5,6-tetrahydro-2H-[1,4']bipyridin-4-yl)-ethyl]amide;

4-Bromo-5-(2-methyl-benzoylamino)-1H-pyrazole-3-carboxylic acid [2-(3,4,5,6-tetrahydro-2H-[1,4']bipyridin-4-yl)-ethyl]amide;

4-Bromo-5-(2-fluoro-benzoylamino)-1H-pyrazole-3-carboxylic acid [2-(3,4,5,6-tetrahydro-2H-[1,4']bipyridin-4-yl)-ethyl]amide;

4-Bromo-5-(2-chloro-benzoylamino)-1H-pyrazole-3-carboxylic acid (2-(N-(N,N-dimethylaminocarbonyl)piperidin-4-yl)eth-1-yl)amide;

4-Bromo-5-(2-chloro-benzoylamino)-1H-pyrazole-3-carboxylic acid {2-[1-(pyridine-4-carbonyl)-piperidin-4-yl]-ethyl}amide;

4-Bromo-5-(2-chloro-benzoylamino)-1H-pyrazole-3-carboxylic acid [2-(4-pyridin-4-yl-piperazin-1-yl)-ethyl]amide;

4-Bromo-5-(2-chloro-benzoylamino)-1H-pyrazole-3-carboxylic acid (1-pyridin-4-ylmethyl-piperidin-4-yl)amide;

4-methyl-S -(2-chlorobenzoylamino)-1-(pyrimidin-2-yl)-pyrazole-3-carboxylic acid [2-(3,4,5,6-tetrahydro-2H-[1,4']bipyridin-4-yl)ethyl]amide;

4-Bromo-5-(2-chloro-benzoylamino)-1H-pyrazole-3-carboxylic acid [2-(1-pyridin-4-ylmethyl-piperidin-4-yl)-ethyl]amide;

4-Bromo-5-(2-chloro-benzoylamino)-1H-pyrazole-3-carboxylic acid {2-[1-(2-pyridin-4-yl-ethyl)-piperidin-4-yl]-ethyl}amide;

4-Bromo-5-(2-chloro-benzoylamino)-1H-pyrazole-3-carboxylic acid (1-pyridin-4-ylmethyl-piperidin-4-ylmethyl)amide;

4-Bromo-5-(2-chloro-benzoylamino)-1H-pyrazole-3-carboxylic acid [1-(2-pyridin-4-yl-ethyl)-piperidin-4-yl]amide;

4-Bromo-5-(2-chloro-benzoylamino)-1H-pyrazole-3-carboxylic acid [1-(2-pyridin-4-yl-ethyl)-piperidin-4-ylmethyl]amide;

4-Bromo-5-(2-chloro-benzoylamino)-1H-pyrazole-3-carboxylic acid [2-(1'-methyl-[1,4']bipiperidin-4-yl)-ethyl]amide;

4-Chloro-5-(2-chloro-benzoylamino)-1H-pyrazole-3-carboxylic acid [5-(3-aza-bicyclo[3.2.2]non-3-yl)-1-methyl-2-oxo-2,3-dihydro-1H-benzo[e][1,4]diazepin-3-yl]amide;

4-Bromo-5-(2-chloro-benzoylamino)-1H-pyrazole-3-carboxylic acid [5-(3-aza-bicyclo[3.2.2]non-3-yl)-1-methyl-2-oxo-2,3-dihydro-1H-benzo[e][1,4]diazepin-3-yl]amide;

4-Chloro-5-(2-chloro-benzoylamino)-1H-pyrazole-3-carboxylic acid (2-oxo-5-phenethyl-1-propyl-2,3-dihydro-1H-benzo[e][1,4]diazepin-3-yl)amide;

4-Chloro-5-(2-chloro-benzoylamino)-1H-pyrazole-3-carboxylic acid [5-(3-aza-bicyclo[3.2.2]non-3-yl)-1-methyl-2-oxo-2,3-dihydro-1H-benzo[e][1,4]diazepin-3-yl]amide;

4-Chloro-5-(2-chloro-benzoylamino)-1H-pyrazole-3-carboxylic acid [5-(3-aza-bicyclo[3.2.2]non-3-yl)-1-methyl-2-oxo-2,3-dihydro-1H-benzo[e][1,4]diazepin-3-yl]amide;

4-Bromo-5-(2-chloro-benzoylamino)-1H-pyrazole-3-carboxylic acid (1-ethyl-2-oxo-5-phenyl-2,3-dihydro-1H-benzo[e][1,4]diazepin-3-yl)amide;

4-Bromo-5-(2-chloro-benzoylamino)-1H-pyrazole-3-carboxylic acid (1-ethyl-2-oxo-5-phenyl-2,3-dihydro-1H-benzo[e][1,4]diazepin-3-yl)amide;

4-Bromo-3-(2-chloro-benzoylamino)-1-methyl-pyrazole-5-carboxylic acid [2-(3,4,5,6-tetrahydro-2H-[1,4']bipyridin-4-yl)-ethyl]amide;

4-Bromo-5-(2-chlorobenzoylamino)-1H-pyrazole-3-carboxylic acid [2-(4-cyano-phenyl)ethyl]amide;

4-Bromo-5-(2-chlorobenzoylamino)-1H-pyrazole-3-carboxylic acid {2-[4-(4,5-dihydro-1H-imidazol-2-yl)-phenyl]ethyl}amide;

4-Bromo-5-(2-chlorobenzoylamino)-1H-pyrazole-3-carboxylic acid [1-(2-pyridin-4-yl-acetyl)-piperidin-4-yl]amide;

4-Bromo-5-(2-chlorobenzoylamino)-1H-pyrazole-3-carboxylic acid [1-(pyridine-4-carbonyl)-piperidin-4-ylmethyl]amide;

4-Bromo-5-(2-chlorobenzoylamino)-1H-pyrazole-3-carboxylic acid (2-[1,4']bipiperidin-1'-yl-ethyl)amide;

4-Bromo-5-(2-chlorobenzoylamino)-1H-pyrazole-3-carboxylic acid (2-[1,4']bipiperidin-1'-yl-2-cyanoethyl)amide;

4-Bromo-5-(2-chlorobenzoylamino)-1H-pyrazole-3-carboxylic acid {2-[1-(2-pyridin-4-yl-acetyl)-piperidin-4-yl]ethyl}amide;

4-Bromo-5-(2-chlorobenzoylamino)-1H-pyrazole-3-carboxylic acid (1,5-dimethyl-2,3,4,5-tetrahydro-1H-benzo[b][1,4]diazepin-3-yl)amide;

4-Bromo-5-(2-chlorobenzoylamino)-1H-pyrazole-3-carboxylic acid [2-(3,4,5,6-tetrahydro-2H-[4,4']bipyridin-1-yl)ethyl]amide;

4-Bromo-5-(2-chlorobenzoylamino)-1H-pyrazole-3-carboxylic acid [N-(benzyloxycarbonyl)piperidin-4-yl]amide;

4-Bromo-5-(2-chlorobenzoylamino)-1H-pyrazole-3-carboxylic acid piperidin-4-ylamide;

1-(pyridin-4-yl)-4-methyl-5-(2-chloro-benzoylamino)-1H-pyrazole-3-carboxylic acid [2-(3,4,5,6-tetrahydro-2H-[1,4']bipyridin-4-yl)-ethyl]amide;

4-Bromo-5-(2-chlorobenzoylamino)-1H-pyrazole-3-carboxylic acid [N-(benzyloxycarbonyl)azapin-3-yl]amide;

4-Bromo-5-(2-chlorobenzoylamino)-1H-pyrazole-3-carboxylic acid azepan-3-ylamide;

4-Chloro-5-(2-methylbenzoylamino)-1H-pyrazole-3-carboxylic acid (1-ethyl-2-oxo-5-phenyl-2,3-dihydro-1H-benzo[e][1,4]diazepin-3-yl)amide;
4-Bromo-5-(2-chlorobenzoylamino)-1H-pyrazole-3-carboxylic acid indan-2-ylamide;
4-Bromo-5-(2-chlorobenzoylamino)-1-methyl-1H-pyrazole-3-carboxylic acid [2-(3,4,5,6-tetrahydro-2H-[1,4']bipyridin-4-yl)ethyl]amide;
5-(2-Chlorobenzoylamino)-1-methyl-1H-pyrazole-3-carboxylic acid (2-oxo-5-phenyl-2,3-dihydro-1H-benzo[e][1,4]diazepin-3-yl)amide;
3-(2-Chlorobenzoylamino)-1-methyl-1H-pyrazole-5-carboxylic acid (2-oxo-5-phenyl-2,3-dihydro-1H-benzo[e][1,4]diazepin-3-yl)amide;
5-(2-Chlorobenzoylamino)-1-methyl-1H-pyrazole-3-carboxylic acid [2-(3,4,5,6-tetrahydro-2H-[1,4']bipyridin-4-yl)ethyl]amide;
4-bromo-5-(2-chlorobenzoylamino)-1H-pyrazole-3-carboxylic acid [2-(N-(2,2,2-trichloroethoxycarbonyl)piperidine-4-yl)eth-1-yl]amide;
3-(2-Chlorobenzoylamino)-1-methyl-1H-pyrazole-5-carboxylic acid [2-(3,4,5,6-tetrahydro-2H-[1,4']bipyridin-4-yl)ethyl]amide;
4-Bromo-5-(2-chlorobenzoylamino)-1H-pyrazole-3-carboxylic acid {2-[1-(1H-benzoimidazol-2-yl)-piperidin-4-yl]ethyl}amide;
4-Bromo-5-(2-chlorobenzoylamino)-2H-pyrazole-3-carboxylic acid {2-[4-(1H-benzoimidazol-2-yl)-phenyl]ethyl}amide;
5-(2-Chlorobenzoylamino)-4-methyl-1H-pyrazole-3-carboxylic acid (2-oxo-5-phenyl-2,3-dihydro-1H-benzo[e][1,4]diazepin-3-yl)amide;
4-Bromo-5-(2-chlorobenzoylamino)-1H-pyrazole-3-carboxylic acid [1-(pyridine-4-carbonyl)-piperidin-4-yl]amide;
4-Bromo-5-(2-chlorobenzoylamino)-1H-pyrazole-3-carboxylic acid (3,4,5,6-tetrahydro-2H-[1,4']bipyridin-4-ylmethyl)amide;
4-Bromo-5-(2-chlorobenzoylamino)-1-methyl-1H-pyrazole-3-carboxylic acid (2-oxo-5-phenyl-2,3-dihydro-1H-benzo[e][1,4]diazepin-3-yl)amide;
(R)-4-Bromo-5-(2-chloro-benzoylamino)-1H-pyrazole-3-carboxylic acid (5-methyl-2-oxo-2,3,4,5-tetrahydro-1H-benzo[b][1,4]diazepin-3-yl)amide;
(R)-4-Bromo-5-(2-chloro-benzoylamino)-1H-pyrazole-3-carboxylic acid (1-cyclopropylmethyl-5-methyl-2-oxo-2,3,4,5-tetrahydro-1H-benzo [b][1,4]diazepin-3-yl)amide;
5-(2-chlorobenzoylamino)-1H-pyrazole-3-carboxylic acid {2-[4-(4,5-dihydro-1H-imidazol-2-yl)-phenyl]ethyl}amide;
4-Bromo-5-(2-chlorobenzoylamino)-1H-pyrazole-3-carboxylic acid {2-[3-methoxy-4-hydroxyphenyl]ethyl}amide;
(R)-4-Bromo-5-(2-fluoro-benzoylamino)-1H-pyrazole-3-carboxylic acid (1,5-dimethyl-2-oxo-2,3,4,5-tetrahydro-1H-benzo[b][1,4]diazepin-3-yl)amide;
5-(2-chloro-benzoylamino)-1H-pyrazole-3-carboxylic acid [2-(3,4,5,6-tetrahydro-2H-[1,4']bipyridin-4-yl)methyl]amide;
4-Bromo-5-(2-chloro-benzoylamino)-1H-pyrazole-3-carboxylic acid [1-benzyloxycarbonyl-5-oxo-[1,4]diazepin-6-yl;
4-Bromo-5-(2-chloro-benzoylamino)-1H-pyrazole-3-carboxylic acid [2-(1'-methyl-[1,4']bipiperidin-4-yl)-methyl]amide;
4-Bromo-5-(2-fluoro-benzoylamino)-1H-pyrazole-3-carboxylic acid [2-(3,4,5,6-tetrahydro-2H-[1,4']bipyridin-4-yl)methyl]amide;
4-Bromo-5-(2-chlorobenzoylamino)-1H-pyrazole-3-carboxylic acid (2-(4-methylpiperidinyl)ethyl)amide;
1-methyl-4-bromo-5-(2-chloro-benzoylamino)-1H-pyrazole-3-carboxylic acid [2-(3,4,5,6-tetrahydro-2H-[1,4']bipyridin-4-yl)methyl]amide;
1-methyl-4-bromo-5-(2-fluoro-benzoylamino)-1H-pyrazole-3-carboxylic acid [2-(3,4,5,6-tetrahydro-2H-[1,4']bipyridin-4-yl)-ethyl]amide;
5-(2-chlorobenzoylamino)-1H-pyrazole-3-carboxylic acid [2-(pyridin-4-yl)ethyl]amide;
4-Bromo-5-(2-chlorobenzoylamino)-1H-pyrazole-3-carboxylic acid (2-[2-phenyl-1H-benzo[d]imidazol-5-yl]ethyl)amide;
4-Bromo-5-(2-chlorobenzoylamino)-1H-pyrazole-3-carboxylic acid (5-(t-butoxycarbamoyl)aminopent-1-yl)amide;
4-Bromo-5-(2-chlorobenzoylamino)-1H-pyrazole-3-carboxylic acid (5-aminopentyl)amide;
4-methyl-5-(2-chlorobenzoylamino)-1H-pyrazole-3-carboxylic acid {2-[4-(4,5-dihydro-1H-imidazol-2-yl)-phenyl]ethyl}amide;
4-methyl-5-(2-chloro-benzoylamino)-1H-pyrazole-3-carboxylic acid [2-(3,4,5,6-tetrahydro-2H-[1,4']bipyridin-4-yl)-ethyl]amide;
1-t-butyl-4-methyl-5-(2-chloro-benzoylamino)-1H-pyrazole-3-carboxylic acid [2-(3,4,5,6-tetrahydro-2H-[1,4']bipyridin-4-yl)-ethyl]amide;
4-bromo-5-(2-chloro-benzoylamino)-1H-pyrazole-3-carboxylic acid [2-(4-(1,4,5,6-tetrahydropyrimidin-2-yl)phenyl)ethyl]amide;
4-fluoro-5-(2-chloro-benzoylamino)-1H-pyrazole-3-carboxylic acid [2-(3,4,5,6-tetrahydro-2H-[1,4']bipyridin-4-yl)-ethyl]amide;
1-(pyridin-2-yl)-4-methyl-5-(2-chloro-benzoylamino)-1H-pyrazole-3-carboxylic acid [2-(3,4,5,6-tetrahydro-2H-[1,4']bipyridin-4-yl)-ethyl]amide;
4-bromo-5-(2-chloro-benzoylamino)-1H-pyrazole-3-carboxylic acid [4-oxo-[1,4]diazepin-5-yl]amide;
4-bromo-5-(2-chlorobenzoylamino)-1H-pyrazole-3-carboxylic acid (1-methyl-5-oxo-4-(2-(N,N-dimethylamino)ethyl)-2,3,4,5-tetrahydro-1H-benzo[b][1,4]diazepin-6-yl)amide;
4-bromo-5-(2-chloro-benzoylamino)-1H-pyrazole-3-carboxylic acid [4-methyl-5-oxo-1-(benzyloxycarbonyl)-[1,4]diazepin-6-yl]amide;
4-bromo-5-(3-chloro-pyridin-4-ylcarbonyl)amino)-1H-pyrazole-3-carboxylic acid [2-(3,4,5,6-tetrahydro-2H-[1,4']bipyridin-4-yl)-ethyl]amide;
4-bromo-5-(2-chloro-benzoylamino)-1H-pyrazole-3-carboxylic acid [4-methyl-5-oxo-[1,4]diazepin-6-yl]amide;
(R)-4-Bromo-5-(2-chloro-benzoylamino)-1H-pyrazole-3-carboxylic acid (1-pyridin-4-yl)azepan-3-yl)-amide;
4-bromo-5-(2-chlorobenzoylamino)-1H-pyrazole-3-carboxylic acid (2,3,4,5-tetrahydro-1H-benzo[b]azepin-3-yl)amide;
4-Bromo-5-(2-chloro-benzoylamino)-1H-pyrazole-3-carboxylic acid [6-(benzothiazol-2-yl)hex-1-yl]amide;
(R)-5-(2-chloro-benzoylamino)-1-(phenyl)-pyrazole-3-carboxylic acid (2-oxo-azepan-3-yl)-amide;
4-bromo-5-(2-chloro-benzoylamino)-1H-pyrazole-3-carboxylic acid [1,4-dimethyl-5-oxo-[1,4]diazepan-6-yl]amide;

4-bromo-5-(2-chloro-benzoylamino)-1H-pyrazole-3-carboxylic acid [4-(4,5-dihydro-1H-imidazol-2-yl)benzyl]amide;
4-Bromo-5-(2-chloro-benzoylamino)-1H-pyrazole-3-carboxylic acid [5-(benzothiazol-2-yl)pent-1-yl]amide;
4-Bromo-5-(2-chloro-benzoylamino)-1H-pyrazole-3-carboxylic acid [N-(benzothiazol-2-yl)piperidin-4-ylmethyl]amide;
4-bromo-5-(2-fluoro-benzoylamino)-1H-pyrazole-3-carboxylic acid [N-(pyridin-4-yl)piperidin-4-ylmethyl]amide;
4-bromo-5-(2-chloro-benzoylamino)-1H-pyrazole-3-carboxylic acid [2-(4-methyl-piperidin-1-yl)ethyl]amide;
4-bromo-5-(2-fluoro-benzoylamino)-1H-pyrazole-3-carboxylic acid [2-(4-(pyridin-4-yl)-piperazin-1-yl)ethyl]amide;
4-Bromo-5-(2-bromo-benzoylamino)-1H-pyrazole-3-carboxylic acid [N-(2-aminopyridin-6-yl)piperidin-4-ylmethyl]amide;
5-(2-chloro-benzoylamino)-1H-pyrazole-3-carboxylic acid [2-(pyridine-4-yl)ethyl]amide;
4-bromo-5-(2-chloro-benzoylamino)-1H-pyrazole-3-carboxylic acid [2-(1-(4,5-dihydro-1H-imidazol-2-yl)piperidin-4-yl)ethyl]amide;
4-Bromo-5-(2-chloro-benzoylamino)-1-methyl-pyrazole-3-carboxylic acid [2-(N-(benzothiazol-2-yl)piperidin-4-yl)ethyl]amide;
4-bromo-5-(2-chloro-benzoylamino)-1H-pyrazole-3-carboxylic acid [4-(N-pyridin-4-yl)amino)butyl]amide;
4-Bromo-5-(2-chloro-benzoylamino)-1-methyl-pyrazole-3-carboxylic acid [2-N,N-dimethylamino)ethyl]amide;
(R)-4-bromo-5-(2-chlorobenzoylamino)-1-methyl-pyrazole-3-carboxylic acid (1,5-dimethyl-2-oxo-2,3,4,5-tetrahydro-1H-benzo [b][1,4]diazepin-3-yl)amide;
(R)-4-bromo-5-(2-chloro-benzoylamino)-1-methyl-pyrazole-3-carboxylic acid (2-oxo-azepan-3-yl)-amide;
4-methyl-5-(2-fluoro-benzoylamino)-1-phenyl-pyrazole-3-carboxylic acid [2-(3,4,5,6-tetrahydro-2H-[1,4']bipyridin-4-yl)-ethyl]amide;
(R)-4-Bromo-5-(2-chloro-benzoylamino)-1H-pyrazole-3-carboxylic acid (1-(benzylcarbonyl)azepan-3-yl)-amide;
4-methyl-5-(2-fluoro-benzoylamino)-1-t-butyl-pyrazole-3-carboxylic acid [2-(3,4,5,6-tetrahydro-2H-[1,4']bipyridin-4-yl)-ethyl]amide;
5-(2-chloro-benzoylamino)-1-(phenyl)-pyrazole-3-carboxylic acid [2-(3,4,5,6-tetrahydro-2H-[1,4']bipyridin-4-yl)-ethyl]amide;
4-bromo-5-(2-chloro-benzoylamino)-1-(phenyl)-pyrazole-3-carboxylic acid [2-(3,4,5,6-tetrahydro-2H-[1,4'] bipyridin-4-yl)-ethyl]amide;
5-(2-chloro-benzoylamino)-1-(3,4-dichlorophenyl)-pyrazole-3-carboxylic acid [2-(3,4,5,6-tetrahydro-2H-[1,4'] bipyridin-4-yl)-ethyl]amide;
5-(2-chloro-benzoylamino)-1-(m-trifluoromethyl-phenyl)-pyrazole-3-carboxylic acid [2-(3,4,5,6-tetrahydro-2H-[1,4']bipyridin-4-yl)-ethyl]amide;
4-bromo-5-(2-chloro-benzoylamino)-1-(m-trifluoromethyl-phenyl)-pyrazole-3-carboxylic acid [2-(3,4,5,6-tetrahydro-2H-[1,4']bipyridin-4-yl)-ethyl]amide;
4-bromo-5-(2-chloro-benzoylamino)-1H-pyrazole-3-carboxylic acid [2-(piperidin-4-yl)-ethyl]amide;
4-Bromo-5-(2-fluoro-benzoylamino)-1H-pyrazole-3-carboxylic acid [N-(benzothiazol-2-yl)piperidin-4-ylmethyl]amide;
4-Bromo-5-(2-chloro-benzoylamino)-1H-pyrazole-3-carboxylic acid (azepan-3-ylmethyl)-amide;
4-bromo-5-(2-chloro-benzoylamino)-1H-pyrazole-3-carboxylic acid [5-(4,5-dihydro-1H-imidazol-2-yl)-pent-1-yl]amide;
4-bromo-5-(2-chloro-benzoylamino)-1-methyl-pyrazole-3-carboxylic acid [2-(4-(pyridin-4-yl)-piperazin-1-yl)ethyl]amide;
(R)-4-Bromo-5-(2-chloro-benzoylamino)-1-methyl-pyrazole-3-carboxylic acid (azepan-3-yl)-amide;
4-bromo-5-(2-chloro-benzoylamino)-1H-pyrazole-3-carboxylic acid [3-(pyridin-4-yl)-[1,4]diazepin-5-yl]amide;
4-bromo-5-(2-chloro-benzoylamino)-1-methyl-pyrazole-3-carboxylic acid {2-[4-(4,5-dihydro-1H-imidazol-2-yl)-phenyl]ethyl}amide;
4-bromo-5-(2-chloro-benzoylamino)-1-methyl-pyrazole-3-carboxylic acid [2-(3,4,5,6-tetrahydro-2H-[1,4']bipyridin-4-yl)-ethyl]amide;
4-methyl-5-(2-chloro-benzoylamino)-1-methyl-pyrazole-3-carboxylic acid [2-(3,4,5,6-tetrahydro-2H-[1,4']bipyridin-4-yl)-ethyl]amide;
4-methyl-5-(2-chloro-benzoylamino)-1-(2-methyl-phenyl)-pyrazole-3-carboxylic acid [2-(3,4,5,6-tetrahydro-2H-[1,4']bipyridin-4-yl)-ethyl]amide;
4-methyl-5-(2-chloro-benzoylamino)-1-(3-methoxyphenyl)-pyrazole-3-carboxylic acid [2-(3,4,5,6-tetrahydro-2H-[1,4']bipyridin-4-yl)-ethyl]amide;
4-methyl-5-(2-chloro-benzoylamino)-1-p-fluorophenyl)-pyrazole-3-carboxylic acid [2-(3,4,5,6-tetrahydro-2H-[1,4']bipyridin-4-yl)-ethyl]amide;
4-methyl-5-(2-chloro-benzoylamino)-1-phenyl-pyrazole-3-carboxylic acid [2-(3,4,5,6-tetrahydro-2H-[1,4']bipyridin-4-yl)-ethyl]amide;
5-(2-chloro-benzoylamino)-1-(pyridine-2-yl)-pyrazole-3-carboxylic acid [2-(3,4,5,6-tetrahydro-2H-[1,4']bipyridin-4-yl)-ethyl]amide;
4-bromo-5-(2-chloro-benzoylamino)-1-(p-fluorophenyl)-pyrazole-3-carboxylic acid [2-(3,4,5,6-tetrahydro-2H-[1,4']bipyridin-4-yl)-ethyl]amide;
4-bromo-5-(2-chloro-benzoylamino)-1-(pyridin-2-yl)-pyrazole-3-carboxylic acid [2-(3,4,5,6-tetrahydro-2H-[1,4']bipyridin-4-yl)-ethyl]amide;
5-(2-chloro-benzoylamino)-1-p-fluorophenyl-pyrazole-3-carboxylic acid [2-(3,4,5,6-tetrahydro-2H-[1,4']bipyridin-4-yl)-ethyl]amide; and
5-(2-chloro-benzoylamino)-1H-pyrazole-3-carboxylic acid [4-methyl-5-oxo-[1,4]diazepin-6-yl]amide;
5-(2-chlorobenzoylamino)-1-phenyl-1H-pyrazole-3-carboxylic acid (2-oxo-5-phenyl-2,3-dihydro-1H-benzo[e][1,4]diazepin-3-yl)amide;
4-Bromo-5-(2-chlorobenzoylamino)-1-phenyl-1H-pyrazole-3-carboxylic acid (2-oxo-5-phenyl-2,3-dihydro-1H-benzo[e][1,4]diazepin-3-yl)amide;
5-acetylamino-1-phenyl-1H-pyrazole-3-carboxylic acid [2-(3,4,5,6-tetrahydro-2H-[1,4']bipyridin-4-yl)-ethyl]amide;
4-bromo-5-(2-chlorobenzoylamino)-1-(4-isopropylphenyl)-1H-pyrazole-3-carboxylic acid [2-(3,4,5,6-tetrahydro-2H-[1,4']bipyridin-4-yl)ethyl]amide;
5-(2-chlorobenzoylamino)-1-(4-isopropylphenyl)-1H-pyrazole-3-carboxylic acid [2-(3,4,5,6-tetrahydro-2H-[1,4']bipyridin-4-yl)ethyl]amide;

4-Bromo-5-(2-fluorobenzoylamino)-1-phenyl-1H-pyrazole-3-carboxylic acid [2-(3,4,5,6-tetrahydro-2H-[1,4']bipyridin-4-yl)ethyl]amide;

5-(2-Fluorobenzoylamino)-1-phenyl-1H-pyrazole-3-carboxylic acid [2-(3,4,5,6-tetrahydro-2H-[1,4']bipyridin-4-yl)ethyl]amide;

4-Bromo-5-(2-chlorobenzoylamino)-1-(4-methoxyphenyl)-1H-pyrazole-3-carboxylic acid [2-(3,4,5,6-tetrahydro-2H-[1,4']bipyridin-4-yl)ethyl]amide;

4-Bromo-5-(2-chlorobenzoylamino)-1-(2-N,N-diemthylamino)eth-1-yl)-pyrazole-3-carboxylic acid [2-(3,4,5,6-tetrahydro-2H-[1,4']bipyridin-4-yl)ethyl]amide; and pharmaceutically acceptable salts thereof.

The following compounds are also contemplated by the present invention and may be prepared using methods described herein and/or methods described in U.S. Pat. No. 4,873,334 and/or methods well known in the art.

TABLE II

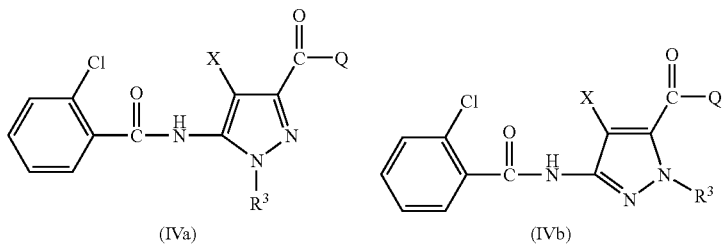

| Cpd # | X | *R³ | **Q |
|---|---|---|---|
| 1001 | Br | 5-methylpyridin-2-yl | 2-(4-(pyridin-4-yl)piperidin-1-yl)ethylamino |
| 1002 | Br | 2,6-dimethylpyrimidin-4-yl | 2-(4-(pyridin-4-yl)piperidin-1-yl)ethylamino |
| 1003 | Br | 4-trifluoromethyl-6-methylpyridin-2-yl | 2-(4-(pyridin-4-yl)piperidin-1-yl)ethylamino |
| 1004 | Br | 2,6-dichloropyridin-4-yl | 2-(4-(pyridin-4-yl)piperidin-1-yl)ethylamino |
| 1005 | Br | 2,3,5,6-tetrafluoropyridin-4-yl | 2-(4-(pyridin-4-yl)piperidin-1-yl)ethylamino |

TABLE II-continued

| Cpd # | X | *R³ | **Q |
|---|---|---|---|
| 1006 | Br | 5-methylthieno[2,3-d]pyrimidin-4-yl | 2-(1-(pyridin-4-yl)piperidin-4-yl)ethylamino |
| 1007 | Br | 7-chloroquinolin-4-yl | 2-(1-(pyridin-4-yl)piperidin-4-yl)ethylamino |
| 1008 | Br | 1,3-dimethyl-4-nitro-1H-pyrazol-5-yl | 2-(1-(pyridin-4-yl)piperidin-4-yl)ethylamino |
| 1009 | Br | 2-(methoxycarbonyl)thiophen-3-yl | 2-(1-(pyridin-4-yl)piperidin-4-yl)ethylamino |
| 1010 | Br | quinoxalin-2-yl | 2-(1-(pyridin-4-yl)piperidin-4-yl)ethylamino |
| 1011 | Br | 5-chloro-3-(trifluoromethyl)pyridin-2-yl | 2-(1-(pyridin-4-yl)piperidin-4-yl)ethylamino |

TABLE II-continued

| Cpd # | X | *R³ | **Q |
|---|---|---|---|
| 1012 | Br | 4,5-dihydro-1H-imidazol-2-yl | HN-CH₂CH₂-(4-(pyridin-4-yl)piperidin-1-yl) |
| 1013 | Br | 3-(aminosulfonyl)pyridin-4-yl | HN-CH₂CH₂-(4-(pyridin-4-yl)piperidin-1-yl) |
| 1014 | Br | 4-methylphenyl | HN-CH₂CH₂-(4-(pyridin-4-yl)piperidin-1-yl) |
| 1015 | Br | 4-chlorophenyl | HN-CH₂CH₂-(4-(pyridin-4-yl)piperidin-1-yl) |
| 1016 | Br | 4-bromophenyl | HN-CH₂CH₂-(4-(pyridin-4-yl)piperidin-1-yl) |
| 1017 | Br | 4-methoxyphenyl | HN-CH₂CH₂-(4-(pyridin-4-yl)piperidin-1-yl) |

TABLE II-continued
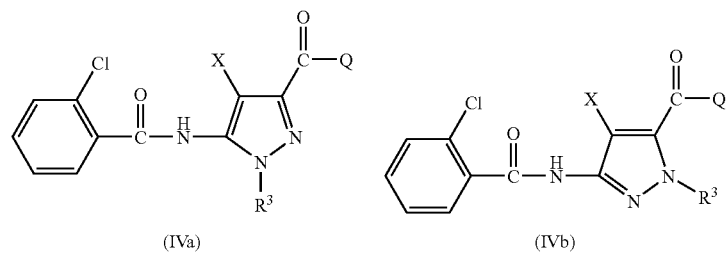
| Cpd # | X | *R³ | **Q |
|---|---|---|---|
| 1018 | Br | 4-I-phenyl | HN-CH₂CH₂-(4-(pyridin-4-yl)piperidin-1-yl) |
| 1019 | Br | 4-CF₃-phenyl | HN-CH₂CH₂-(4-(pyridin-4-yl)piperidin-1-yl) |
| 1020 | Br | 4-NO₂-phenyl | HN-CH₂CH₂-(4-(pyridin-4-yl)piperidin-1-yl) |
| 1021 | Br | 4-SO₂NH₂-phenyl | HN-CH₂CH₂-(4-(pyridin-4-yl)piperidin-1-yl) |
| 1022 | Br | 3-methyl-phenyl | HN-CH₂CH₂-(4-(pyridin-4-yl)piperidin-1-yl) |

TABLE II-continued
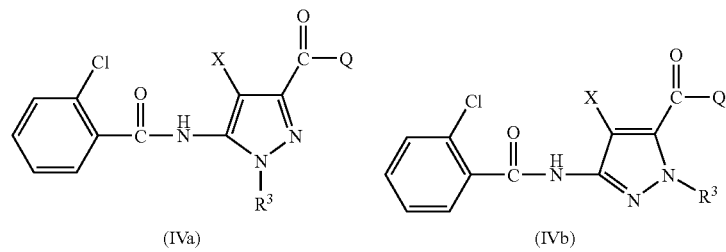
| Cpd # | X | *R³ | **Q |
|---|---|---|---|
| 1023 | Br | 3-chlorophenyl | HN-CH₂CH₂-(4-(pyridin-4-yl)piperidin-1-yl) |
| 1024 | Br | 3-bromophenyl | HN-CH₂CH₂-(4-(pyridin-4-yl)piperidin-1-yl) |
| 1025 | Br | 3-fluorophenyl | HN-CH₂CH₂-(4-(pyridin-4-yl)piperidin-1-yl) |
| 1026 | Br | 3-methoxyphenyl | HN-CH₂CH₂-(4-(pyridin-4-yl)piperidin-1-yl) |
| 1027 | Br | 3-propylphenyl | HN-CH₂CH₂-(4-(pyridin-4-yl)piperidin-1-yl) |
| 1028 | Br | 3-(trifluoromethyl)phenyl | HN-CH₂CH₂-(4-(pyridin-4-yl)piperidin-1-yl) |

TABLE II-continued

| Cpd # | X | *R³ | **Q |
|---|---|---|---|
| 1029 | Br | 3-nitrophenyl | 2-(1-(pyridin-4-yl)piperidin-4-yl)ethylamino |
| 1030 | Br | 2-methylphenyl | 2-(1-(pyridin-4-yl)piperidin-4-yl)ethylamino |
| 1031 | Br | 2-chlorophenyl | 2-(1-(pyridin-4-yl)piperidin-4-yl)ethylamino |
| 1032 | Br | 2-fluorophenyl | 2-(1-(pyridin-4-yl)piperidin-4-yl)ethylamino |
| 1033 | Br | 2-nitrophenyl | 2-(1-(pyridin-4-yl)piperidin-4-yl)ethylamino |
| 1034 | Me | pyridin-4-yl | 2-(1-(pyridin-4-yl)piperidin-4-yl)ethylamino |

TABLE II-continued
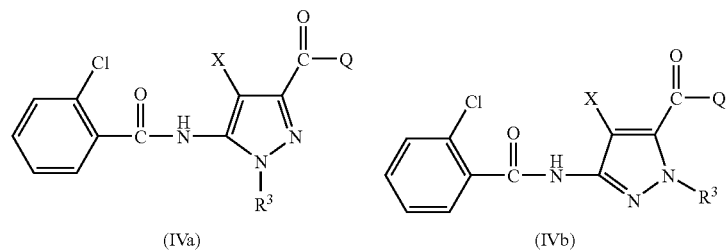
(IVa)      (IVb)
| Cpd # | X | *R³ | **Q |
|---|---|---|---|
| 1035 | Br | 4-pyridyl | HN-CH₂CH₂-(4-piperidyl)-N-(4-pyridyl) |
| 1036 | Me | 3-pyridyl | HN-CH₂CH₂-(4-piperidyl)-N-(4-pyridyl) |
| 1037 | Br | 3-pyridyl | HN-CH₂CH₂-(4-piperidyl)-N-(4-pyridyl) |
| 1038 | Me | 2-pyridyl | HN-CH₂CH₂-(4-piperidyl)-N-(4-pyridyl) |
| 1039 | Br | 2-pyridyl | HN-CH₂CH₂-(4-piperidyl)-N-(4-pyridyl) |
| 1040 | Me | 4-pyrimidinyl | HN-CH₂CH₂-(4-piperidyl)-N-(4-pyridyl) |

TABLE II-continued
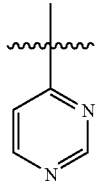
| Cpd # | X | *R³ | **Q |
|---|---|---|---|
| 1041 | Br | 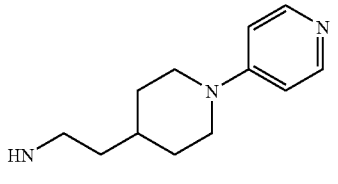 | 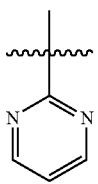 |
| 1042 | Me | 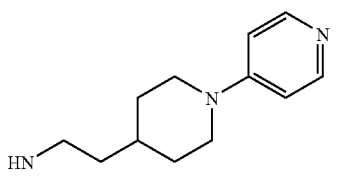 | 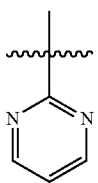 |
| 1043 | Br | 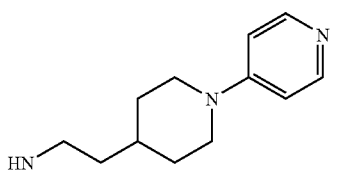 | 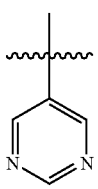 |
| 1044 | Me | 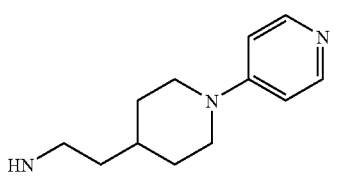 | 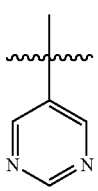 |
| 1045 | Br | 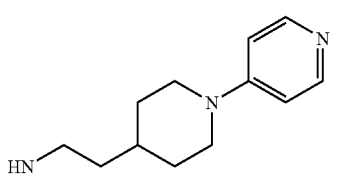 | 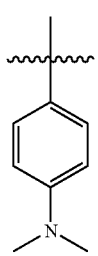 |
| 1046 | Br | 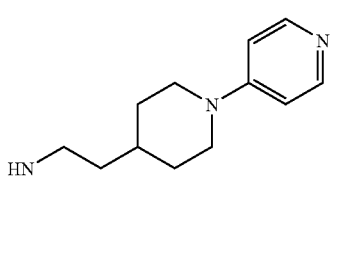 | |

TABLE II-continued
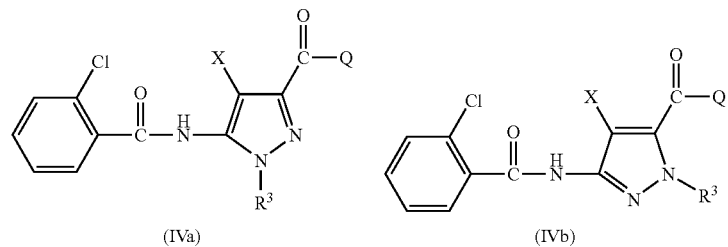
| Cpd # | X | *R³ | **Q |
|---|---|---|---|
| 1047 | Br | 3,4-dichlorophenyl (CH with wavy bond) | HN-CH2CH2-(4-(pyridin-4-yl)piperidin-1-yl) |
| 1048 | Ph | Me | HN-CH2CH2-(4-(pyridin-4-yl)piperidin-1-yl) |
| 1049 | Me | Me | HN-CH2CH2-(4-(pyridin-4-yl)piperidin-1-yl) |
| 1050 | Br | Me | HN-CH2CH2-(1-methylpiperidin-4-yl) |
| 1051 | Br | Me | HN-(azepan-3-yl) |
| 1052 | Br | Ph | HN-CH2CH2-(4-(pyridin-4-yl)piperidin-1-yl) |
| 1053 | Me | Ph | HN-CH2CH2-(4-(pyridin-4-yl)piperidin-1-yl) |

TABLE II-continued

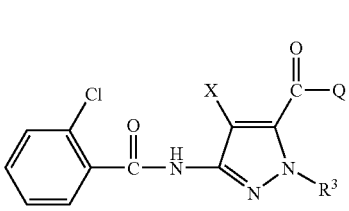

| Cpd # | X | *R³ | **Q |
|---|---|---|---|
| 1054 | H | Ph | 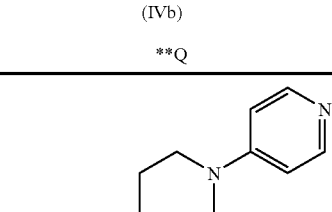 |
| 1055 | Cl | Me | 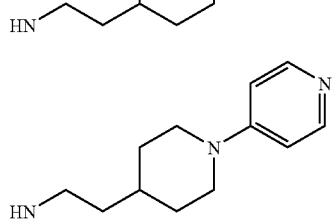 |

*the R³ groups are attached to the core structure by the bond marked with 
**The Q groups is attached to the core structure through the —NH group with unfilled valency Also contemplated are compounds for Formula I or Formula II above wherein R³ is selected from the R³ moieties listed in Table II above.

The following compounds are specifically intended not to be covered in the present application:

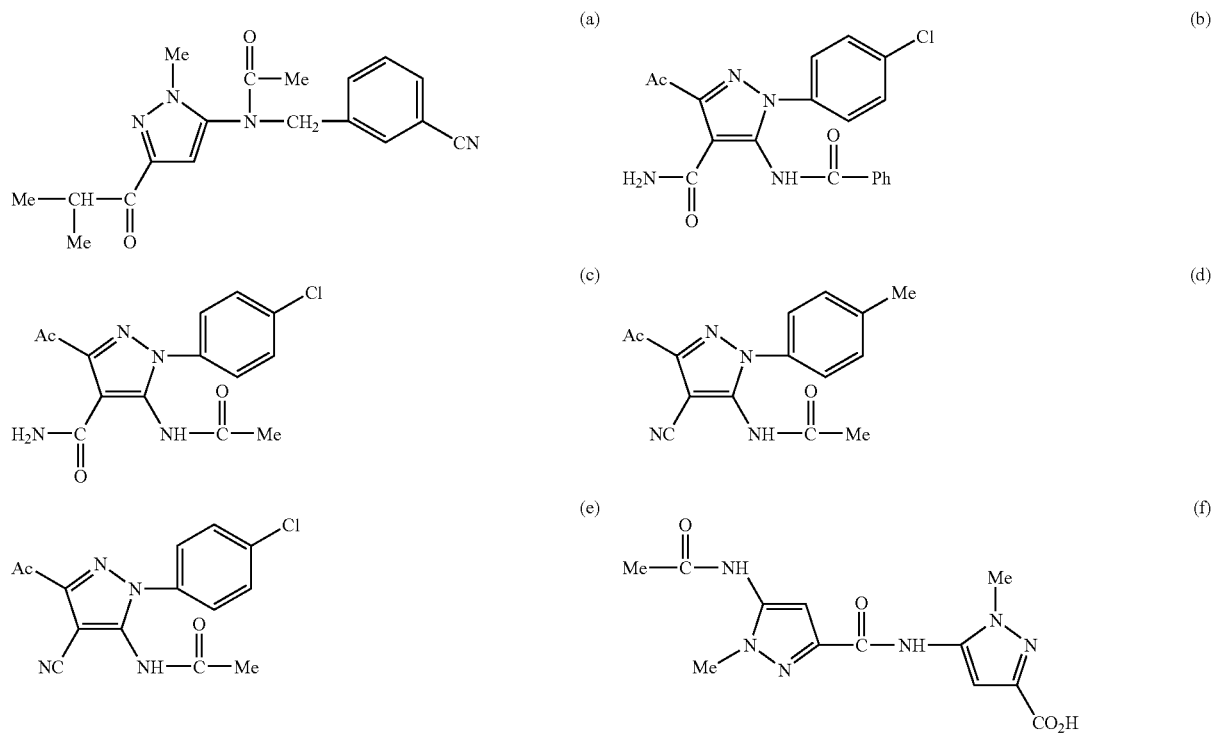

-continued
(g)
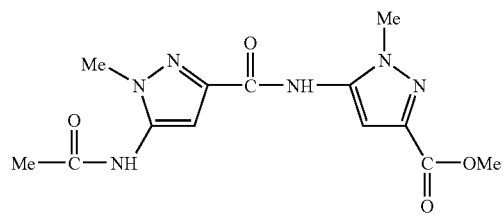
(h)
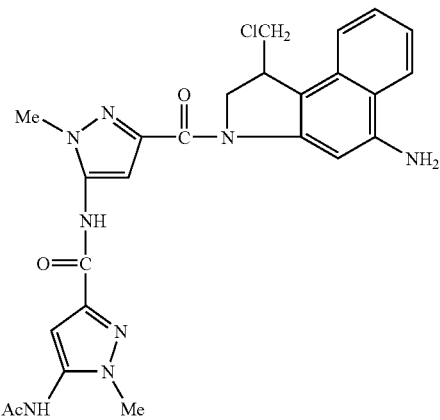
(i)
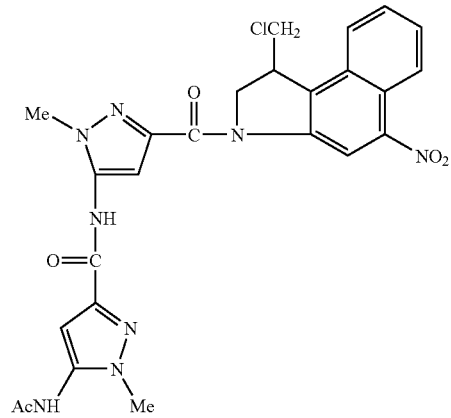
(j)
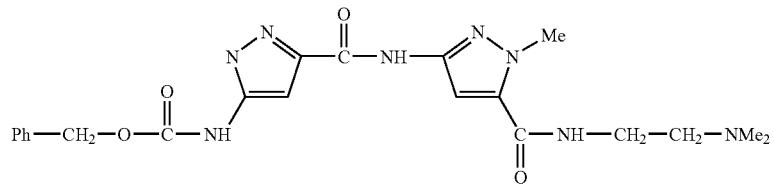
(k)
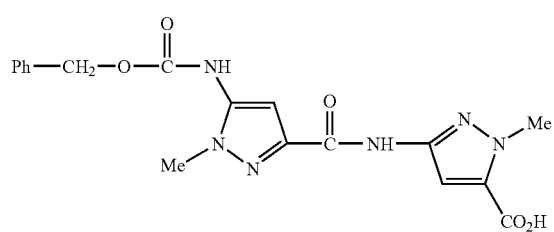
(l)
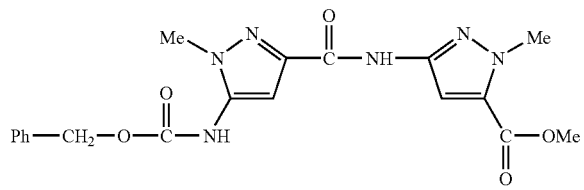
(m)
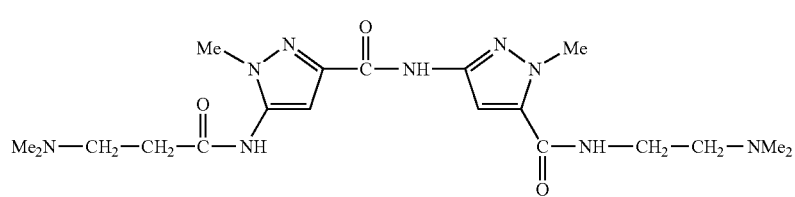

-continued
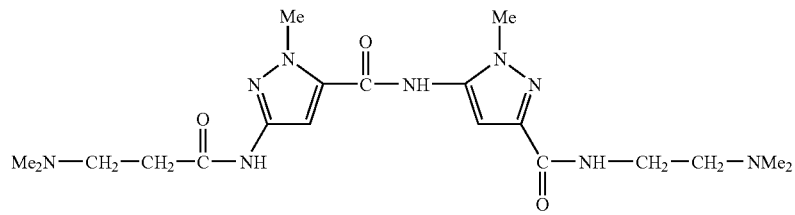
(n)
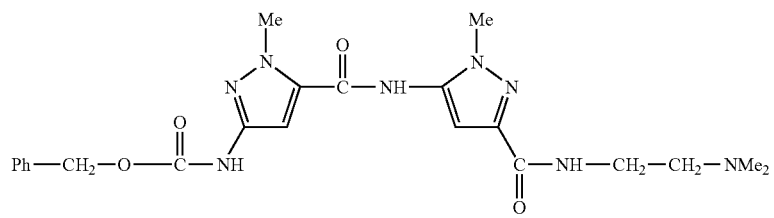
(o)
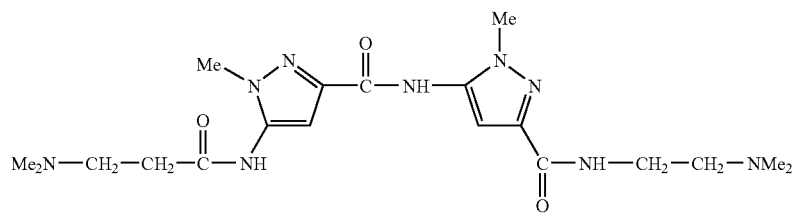
(p)
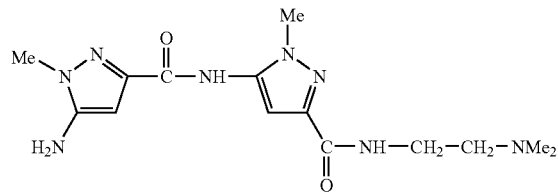
(q)
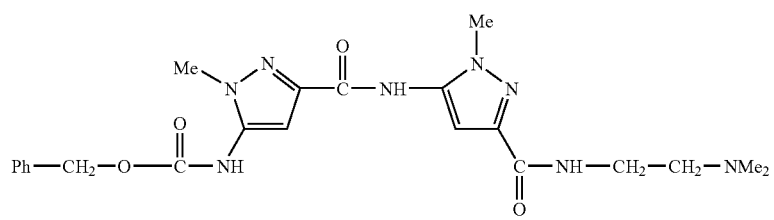
(r)
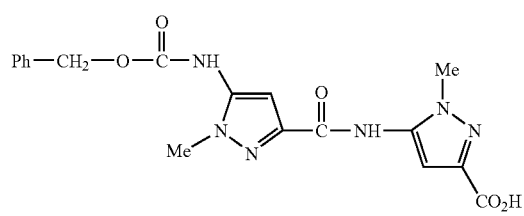
(s)
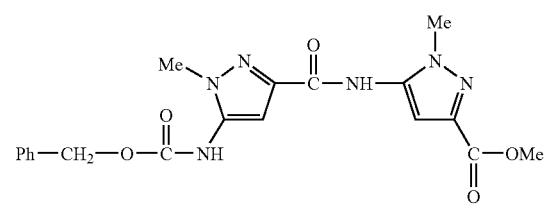
(t)
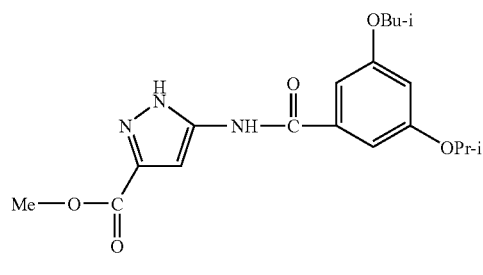
(u)
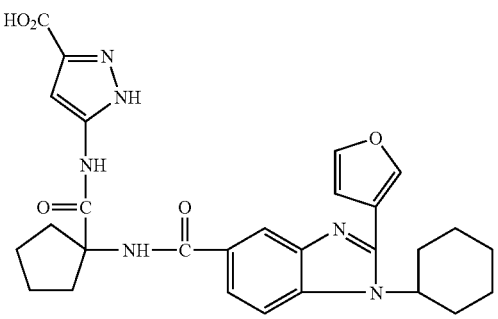
(v)

-continued
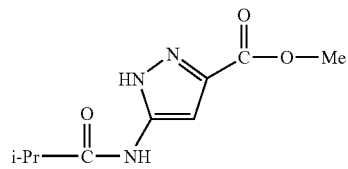
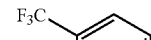
(x)
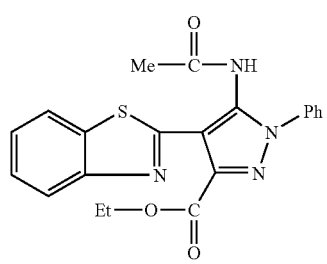
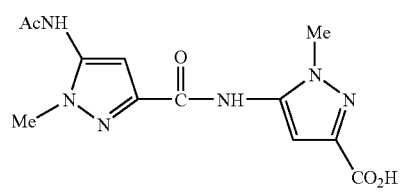
(y)
(z)
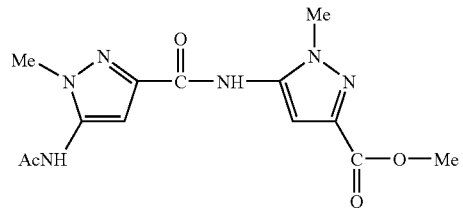
(aa)
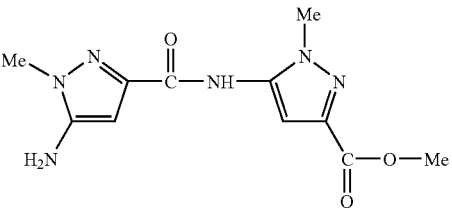
(bb)
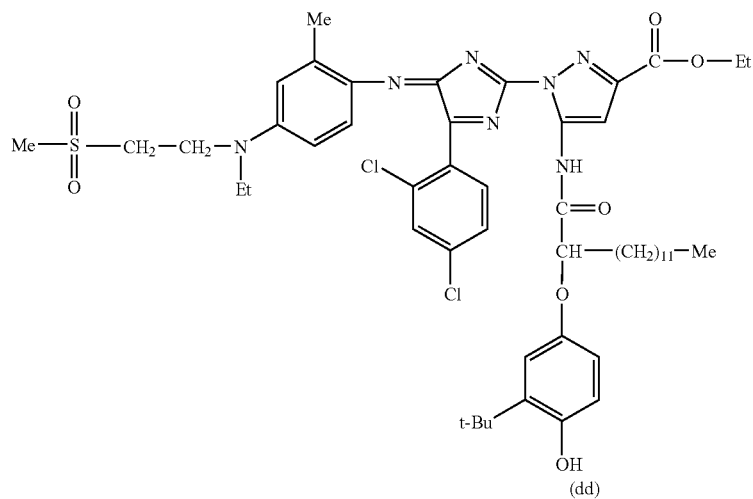
(cc)
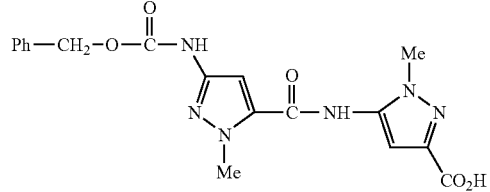
(dd)
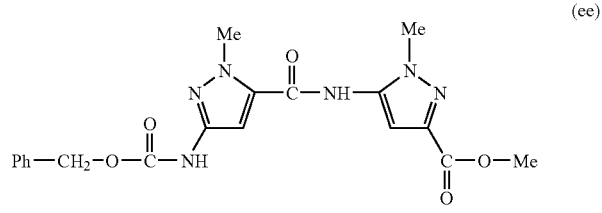
(ee)

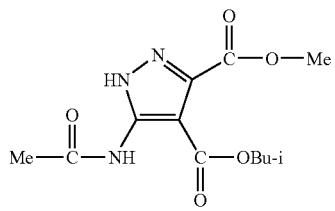
(ff)

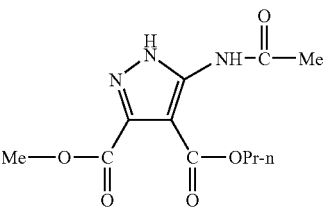
(gg)

In one preferred embodiment, in the compounds of Formula (I) and Formula (II), especially, but not necessarily, when X is hydrogen, $R^3$ is optionally not substituted aryl, or alkyl and/or $R^1$ is optionally not substituted heteroaryl.

In the selective antagonist and methods aspects of this invention compounds of Formula (I) and/or Formula (II) below maybe employed

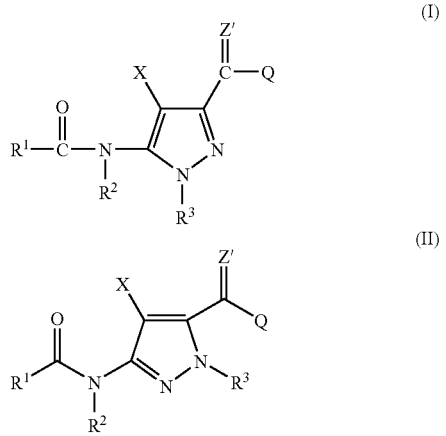

wherein

Z' is selected from O, S and NH;

Q is selected from the group consisting of —$NR^4R^5$, —OH, alkyl, substituted alkyl, alkenyl, substituted alkenyl, alkynyl, substituted alkynyl, cycloalkyl, substituted cycloalkyl, heterocyclic, substituted heterocyclic, alkoxy, substituted alkoxy, aryl, substituted aryl, heteroaryl and substituted heteroaryl;

$R^1$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic and substituted heterocyclic;

$R^2$ and $R^3$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic and substituted heterocyclic;

$R^4$ and $R^5$ are independently selected from the group consisting of hydrogen, alkyl, substituted alkyl, alkoxy, substituted alkoxy, cycloalkyl, substituted cycloalkyl, heterocyclic, substituted heterocyclic and where $R^4$ and $R^5$, together with the nitrogen atom pendent thereto, are joined to form a heterocyclic, a substituted heterocyclic, a heteroaryl or a substituted heteroaryl group, provided that when $R^4$ or $R^5$ is a substituted alkyl group this group is not —$CHR^a$—C(O)—$NR^bR^c$ or —$CHR^a$—C(O)—$OR^b$, wherein $R^a$ is the side chain of a natural or unnatural amino acid, and $R^b$ and $R^c$ are independently selected from the group consisting of hydrogen, alkyl, substituted alkyl, aryl, substituted aryl, heteroaryl, or substituted heteroaryl, alkenyl, substituted alkenyl, alkynyl, substituted alkynyl, cycloalkyl, substituted cycloalkyl, heterocyclic, and substituted heterocyclic;

X is selected from the group consisting of hydrogen, halogen, alkyl, substituted alkyl, nitro, cyano, hydroxy, alkoxy, substituted alkoxy, carboxy, carboxyl esters, aryl, substituted aryl, heteroaryl, substituted heteroaryl, amino, substituted amino, acylamino, aminoacyl, and —$C(O)NR^7R^8$ wherein $R^7$ and $R^8$ are independently selected from the group consisting of hydrogen, alkyl, substituted alkyl, cycloalkyl, substituted cycloalkyl, heterocyclic and substituted heterocyclic, or $R^7$ and $R^8$ together with the nitrogen atom to which they are joined form a heteroaryl, substituted heteroaryl, heterocyclic, and substituted heterocyclic;

or pharmaceutically acceptable salts, prodrugs or isomers thereof;

with the proviso that the compound is Formula (I) is not
- A') 4-bromo-5-(2-chloro-benzoylamino)-1H-pyrazole-3-carboxylic acid; or
- B') 5-(2-chloro-benzoylamino)-1H-pyrazole-3-carboxylic acid (2-dimethylamino-1-methyl-ethyl)-amide.

The present invention also provides a selective antagonist of bradykinin $B_1$ receptor over bradykinin $B_2$ receptor that is a compound of Formula (I) and/or Formula (II).

The present invention further provides a method for selective inhibiting bradykinin $B_1$ receptor over bradykinin $B_2$ receptor which method comprises using a compound of Formula (I) and/or Formula (II).

The present invention further provides a pharmaceutical composition comprising a pharmaceutically acceptable carrier and a therapeutically amount of a compound of Formula (I) or Formula (II) or mixtures thereof effective to treat or palliate adverse symptoms in mammals mediated by bradykinin $B_1$ receptor.

The present invention further provides a method for treating or palliating adverse symptoms in mammals mediated at least in part by bradykinin $B_1$ receptor which method comprises administering a therapeutically effective amount of a compound of Formula (I) or Formula (II) or mixtures thereof or as is more generally the case the pharmaceutical composition.

The present invention further provides a pharmaceutical composition comprising a pharmaceutically acceptable carrier and a therapeutically effective amount of a compound of Formula (I) or Formula (II) or mixtures thereof to treat or palliate adverse symptoms in mammals associated with up-regulating bradykinin $B_1$ receptor following tissue damage or inflammation.

The present invention further provides a method for treating or palliating adverse symptoms in mammals associated with up-regulating bradykinin $B_1$ receptor following tissue damage or inflammation which method comprises administering a therapeutically effective amount of a compound of Formula (I) or Formula (II) or mixtures thereof or as is more generally the case the pharmaceutical composition.

The present invention further provides a method for treating or palliating adverse symptoms associated with the presence or secretion of bradykinin $B_1$ receptor agonists in mammals which method comprises administering a therapeutically effective amount of a compound of Formula (I) or Formula (II) or mixtures thereof or as is more generally the case the pharmaceutical composition.

The present invention provides a method for treating or ameliorating pain, inflammation, septic shock or the scarring process in mammals mediated at least in part by bradykinin $B_1$ receptor in such mammals which method comprises administering a therapeutically effective amount of a compound of Formula (I) or Formula (II) or mixtures thereof or as is more generally the case the pharmaceutical composition.

The present invention provides a method for treating or ameliorating adverse symptoms associated with up-regulating bradykinin $B_1$ receptor relative to burns, perioperative pain, migraine, shock, central nervous system injury, asthma, rhinitis, premature labor, inflammatory arthritis, inflammatory bowel disease or neuropathic pain which method comprises administering a therapeutically effective amount of a compound of Formula (I) or Formula (II) or mixtures thereof or as is more generally the case the pharmaceutical composition.

The present invention further provides a method for treating or palliating adverse symptoms associated with the presence or secretion of bradykinin $B_1$ receptor agonists in mammals which method comprises administering a therapeutically effective amount of a compound of Formula (I) or Formula (II) or mixtures thereof or as is more generally the case the pharmaceutical composition.

The invention also provides a method for determining bradykinin $B_1$ receptor agonist levels in a biological sample which method comprises contacting said biological sample with a compound of Formula (I) or Formula (II), at a predetermined concentration.

DETAILED DESCRIPTION OF THE PREFERRED EMBODIMENTS

As noted above, this invention is directed to certain 3-amido-5-substituted pyrazole derivatives and related compounds which are useful as bradykinin $B_1$ receptor antagonists to relieve adverse symptoms in mammals mediated, at least in part, by bradykinin $B_1$ receptor including pain, inflammation, septic shock, the scarring process, etc. However, prior to describing this invention in further detail, the following terms will first be defined.

DEFINITIONS

Unless otherwise expressly defined with respect to a specific occurrence of the term, the following terms as used herein shall have the following meanings regardless of whether capitalized or not:

The term "alkyl" or "alk" refers to monovalent alkyl groups having from 1 to 15 carbon atoms and more preferably 1 to 6 carbon atoms and includes both straight chain and branched chain alkyl groups. This term is exemplified by groups such as methyl, t-butyl, n-heptyl, octyl and the like. The term $C_{1-4}$alkyl refers to alkyl groups with from 1 to 4 carbon atoms.

The term "substituted alkyl" refers to an alkyl group, of from 1 to 15 carbon atoms, preferably, 1 to 6 carbon atoms, having from 1 to 5 substituents, preferably 1 to 3 substituents, independently selected from the group consisting of alkoxy, substituted alkoxy, acyl, acylamino, thiocarbonylamino, acyloxy, amino, substituted amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, oxo, thioxo, carboxyl, carboxyl esters, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, OS(O)2-heteroaryl, —OS(O)$_2$-substituted heteroaryl, —OS(O)$_2$-heterocyclic, —OS(O)$_2$-substituted heterocyclic, —OSO$^2$—NR$^{40}$R$^{40}$ where each R$^{40}$ is hydrogen or alkyl, —NR$^{40}$S(O)$_2$-alkyl, —NR$^{40}$S(O)$_2$-substituted alkyl, —NR$^{40}$S(O)$_2$-aryl, —NR$^{40}$S(O)$_2$-substituted aryl, —NR$^{40}$S(O)$_2$-heteroaryl, —NR$^{40}$S(O)$_2$-substituted heteroaryl, —NR$^{40}$S(O)$_2$-heterocyclic, —NR$^{40}$S(O)$_2$-substituted heterocyclic, —NR$^{40}$S(O)$_2$—NR$^{40}$-alkyl, —NR$^{40}$S(O)$_2$—NR$^{40}$-substituted alkyl, —NR$^{40}$S(O)$_2$—NR$^{40}$-aryl, —NR$^{40}$S(O)$_2$—NR$^{40}$-substituted aryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heterocyclic, and —NR$^{40}$S(O)$_2$—NR$^{40}$-substituted heterocyclic where each R$^{40}$ is hydrogen or alkyl.

"Alkylene" refers to divalent alkylene groups having from 1 to 15 carbon atoms and more preferably 1 to 6 carbon atoms and includes both straight chain and branched chain alkylene groups. This term is exemplified by groups such as methylene, t-butylene, n-heptylene, octylene and the like.

"Substituted alkylene" refers to alkylene groups having from 1 to 5 substituents, preferably 1 to 3 substituents, independently selected from the group defined for substituted alkyl above.

"Alkoxy" refers to the group "alkyl-O—" which includes, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— provided that a nitrogen atom of the heterocyclic or substituted heterocyclic is not bound to the —C(O)— group wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amino" refers to the group —NH$_2$.

"Substituted amino" refers to the group —NR$^{41}$R$^{41}$, where each R$^{41}$ group is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, provided that both R$^{41}$ groups are not hydrogen; or the R$^{41}$ groups can be joined together with the nitrogen atom to form a heterocyclic or substituted heterocyclic ring.

The "acylamino" or as a prefix "carbamoyl" or "carboxamide" or "substituted carbamoyl" or "substituted carboxamide" refers to the group —C(O)NR$^{42}$R$^{42}$ where each R$^{42}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$^{42}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" or as a prefix "thiocarbamoyl", "thiocarboxamide" or "substituted thiocarbamoyl" or "substituted thiocarboxamide" refers to the group —C(S)NR$^{43}$R$^{43}$ where each R$^{43}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$^{43}$ is joined to form, together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups acyl-O— where acyl is as defined herein.

"Alkenyl" refers to alkenyl group having from 2 to 10 carbon atoms and preferably 2 to 6 carbon atoms and having at least 1 and preferably from 1-2 sites of alkenyl unsaturation.

"Substituted alkenyl" refers to alkenyl groups as defined herein, having from 1 to 5 substituents, preferably 1 to 3 substituents, independently selected from the group of substituents defined for substituted alkyl provided that any hydroxyl or thiol substitution is not attached to a vinyl carbon atom.

"Alkenylene" refers to divalent alkenylene groups having from 2 to 15 carbon atoms and preferably 2 to 6 carbon atoms having at least 1 and preferably 1-2 sites of alkenylene unsaturation and includes both straight chain and branched chain alkenylene groups. This term is exemplified by groups such as 1,2-ethenylene, 1,4-n-but-2-enylene, 1,7-n-hept-3-enylene, and the like.

"Substituted alkenylene" refers to alkenylene groups having from 1 to 5 substituents, preferably 1 to 3 substituents, independently selected from the group defined for substituted alkenyl above.

"Alkynyl" refers to alkynyl group having from 2 to 10 carbon atoms and preferably 3 to 6 carbon atoms and having at least 1 and preferably from 1-2 sites of alkynyl unsaturation.

"Substituted alkynyl" refers to alkynyl groups, as defined herein, having from 1 to 5, preferably 1 to 3 substituents, selected from the same group of substitutents as defined for substituted alkyl provided that any hydroxyl or thiol substitution is not attached to an acetylenic carbon atom.

"Amidino" refers to the group H$_2$NC(=NH)— and the term "alkylamidino" refers to compounds having 1 to 3 alkyl groups (e.g., alkylHNC(=NH)—) where alkyl is as defined herein.

"Thioamidino" refers to the group R$^{44}$SC(=NH)— where R$^{44}$ is hydrogen or alkyl where alkyl is as defined herein.

"Aminoacyl" refers to the groups —NR$^{45}$C(O)alkyl, —NR$^{45}$C(O)substituted alkyl, —NR$^{45}$C(O)cycloalkyl, —NR$^{45}$C(O)substituted cycloalkyl, —NR$^{45}$C(O)alkenyl, —NR$^{45}$C(O)substituted alkenyl, —NR$^{45}$C(O)alkynyl, —NR$^{45}$C(O)substituted alkynyl, —NR$^{45}$C(O)aryl, —NR$^{45}$C(O)substituted aryl, —NR$^{45}$C(O)heteroaryl, —NR$^{45}$C(O)substituted heteroaryl, —NR$^{45}$C(O)heterocyclic, and —NR$^{45}$C(O)substituted heterocyclic where R$^{45}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are defined herein.

"Aminocarbonyloxy" refers to the groups —NR$^{46}$C(O)O-alkyl, —NR$^{46}$C(O)O-substituted alkyl, —NR$^{46}$C(O)O-alkenyl, —NR$^{46}$C(O)O-substituted alkenyl, —NR$^{46}$C(O)O-alkynyl, —NR$^{46}$C(O)O-substituted alkynyl, —NR$^{46}$C(O)O-cycloalkyl, —NR$^{46}$C(O)O-substituted cycloalkyl, —NR$^{46}$C(O)O-aryl, —NR$^{46}$C(O)O-substituted aryl, —NR$^{46}$C(O)O-heteroaryl, —NR$^{46}$C(O)O-substituted heteroaryl, —NR$^{46}$C(O)O-heterocyclic, and —NR$^{46}$C(O)O-substituted heterocyclic where R$^{46}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" or as a prefix "carbamoyloxy" or "substituted carbamoyloxy" refers to the groups —OC(O)NR$^{47}$R$^{47}$ where each R$^{47}$ is independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic or where each R$^{47}$ is joined to form, together with the nitrogen atom a heterocyclic or substituted heterocyclic and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NR$^{48}$R$^{48}$ where each R$^{48}$ is independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic or where each R$^{48}$ is joined to form, together with the nitrogen atom a heterocyclic or substituted heterocyclic and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR$^{49}$C(O)NR49— where R$^{49}$ is selected from the group consisting of hydrogen and alkyl.

"Aminothiocarbonylamino" refers to the group —NR$^{50}$C(S)NR$^{50}$—where R$^{50}$ is selected from the group consisting of hydrogen and alkyl.

"Aryl" or "Ar" refers to an aromatic carbocyclic group of from 6 to 14 carbon atoms having a single ring (i.e., monocyclic) (e.g., phenyl) or multiple condensed rings (e.g., naphthyl or anthryl) which condensed rings may or may not be aromatic (e.g., 2-benzoxazolinone,2H-1,4-benzoxazin-3 (4H)-one, and the like). When at least one of the rings in the fused multicyclic ring system is non-aromatic, the point of attachment of the aryl group to the core structure is on one of the aromatic ring atoms. Preferred aryls include phenyl and naphthyl.

"Substituted aryl" refers to aryl groups, as defined herein, which are substituted with from 1 to 4, preferably 1-3, substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$- alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NR$^{51}$R$^{51}$ where each R$^{51}$ is hydrogen or alkyl, —NR$^{51}$S(O)$_2$-alkyl, —NR$^{51}$S(O)$_2$-substituted alkyl, —NR$^{51}$S(O)$_2$-aryl, —NR$^{51}$S(O)$_2$-substituted aryl, —NR$^{51}$S(O)$_2$-heteroaryl, —NR$^{51}$S(O)$_2$-substituted heteroaryl, —NR$^{51}$S(O)$_2$-heterocyclic, —NR$^{51}$S(O)$_2$-substituted heterocyclic, —NR$^{51}$S(O)$_2$—NR$^{51}$-alkyl, —NR$^{51}$S(O)$_2$—NR$^{51}$-substituted alkyl, —NR$^{51}$S(O)$_2$—NR$^{51}$-aryl, —NR$^{51}$S(O)$_2$—NR$^{51}$-substituted aryl, —NR$^{51}$S(O)$_2$—NR$^{51}$-heteroaryl, —NR$^{51}$S(O)$_2$—NR$^{51}$-substituted heteroaryl, —NR$^{51}$S(O)$_2$—NR$^{51}$-heterocyclic, —NR$^{51}$S(O)$_2$—NR$^{51}$-substituted heterocyclic where each R$^{51}$ is hydrogen or alkyl, wherein each of the terms is as defined herein.

"Aryloxy" refers to the group aryl-O— which includes, by way of example, phenoxy, naphthoxy, and the like wherein aryl is as defined herein.

"Substituted aryloxy" refers to substituted aryl-O— groups where substituted aryl is as defined herein.

"Aryloxyaryl" refers to the group -aryl-O-aryl where aryl is as defined herein.

"Substituted aryloxyaryl" refers to aryloxyaryl groups substituted with from 1 to 4, preferably 1-3 substituents on either or both aryl rings independently selected from the same group consisting of substituents as defined for substituted aryl.

"Carboxyl" refers to the group —COOH and pharmaceutically acceptable salts thereof.

"Carboxyl esters" refer to any one of the following esters: —COO-alkyl, —COO-substituted alkyl, —COO-cycloalkyl, —COO-substituted cycloalkyl, —COO-aryl, —COO-substituted aryl, —COO-hetereoaryl, —COO-substituted heteroaryl, —COO-hetereocyclic, and —COO-substituted heterocyclic.

"Cycloalkyl" refers to cyclic alkyl groups of from 3 to 20 carbon atoms having a single or multiple cyclic rings including, by way of example, cyclopropyl, cyclobutyl, cyclopentyl, cyclooctyl, adamantanyl, and the like. Cycloalkyl groups of the present invention also include fused multicyclic rings wherein one or more of the rings within the multicyclic ring system are aromatic, as long as the point of attachment to the core or backbone of the structure is on a non-aromatic ring atom.

"Substituted cycloalkyl" refers to a cycloalkyl group, as defined herein, having from 1 to 5, preferably 1-3 substituents independently selected from the same group of substituents as defined for substituted alkyl.

"Cycloalkoxy" refers to —O-cycloalkyl groups where cycloalkyl is as defined herein.

"Substituted cycloalkoxy" refers to —O-substituted cycloalkyl groups where substituted cycloalkyl is as defined herein.

"Guanidino" or "substituted guanidino" refers to the groups —NR$^{52}$C(=NR$^{52}$)NR$^{52}$R$^{52}$ where each R$^{52}$ is independently hydrogen or alkyl.

"Guanidinosulfone" refers to the groups —NR$^{53}$C(=NR$^{53}$)NRSO$_2$-alkyl, —NR$^{53}$C(=NR$^{53}$)NR$^{53}$SO$_2$-substituted alkyl, —NR$^{53}$C(=NR$^{53}$)NR$^{53}$SO$_2$-alkenyl, —NR$^{53}$C(=NR$^{53}$)NR$^{53}$SO$_2$-substituted alkenyl, —NR$^{53}$C(=NR$^{53}$)NR$^{53}$SO$_2$-alkynyl, —NR$^{53}$C(=NR$^{53}$)NR$^{53}$SO$_2$-substituted alkynyl, —NR$^{53}$C(=NR$^{53}$)NR$^{53}$SO$_2$-aryl, —NR$^{53}$C(=NR$^{53}$)NR$^{53}$SO$_2$-substituted aryl, —NR$^{53}$C(=NR$^{53}$)NR$^{53}$SO$_2$-cycloalkyl, —NR$^{53}$C(=NR$^{53}$)NR$^{53}$SO$_2$-substituted cycloalkyl, —NR$^{53}$C(=NR$^{53}$)NR$^{53}$SO$_2$-heteroaryl, —NR$^{53}$C(=NR$^{53}$)NR$^{53}$SO$_2$-substituted heteroaryl, —NR$^{53}$C(=NR$^{53}$)NR$^{53}$SO$_2$-heterocyclic, and —NR$^{53}$C(=NR$^{53}$)NR$^{53}$SO$_2$-substituted heterocyclic where each R$^{53}$ is independently hydrogen and alkyl.

"Halo" or "halogen" refers to fluoro, chloro, bromo and iodo.

"Heteroaryl" refers to an aromatic group of from 2 to 10 ring carbon atoms and 1 to 4 ring heteroatoms selected from oxygen, nitrogen and sulfur within the ring. Such heteroaryl groups can have a single ring (i.e., monocyclic) (e.g., pyridyl or furyl) or multiple condensed rings (e.g., indolizinyl or benzothienyl) which may be non-heteroaryl. When at least one of the rings in the fused multicyclic ring system is non-heteroaryl such as aryl, cycloalkyl, cycloalkenyl or heterocyclic, the point of attachment of the heteroaryl group to the core structure is on one of the heteroaryl atoms. Preferred heteroaryls include pyridyl, pyrrolyl, indolyl and furyl.

"Substituted heteroaryl" refers to heteroaryl groups, as defined above, which are substituted with from 1 to 3 substituents independently selected from the same group of substituents as defined for "substituted aryl".

"Heteroaryloxy" refers to the group —O-heteroaryl and "substituted heteroaryloxy" refers to the group —O-substituted heteroaryl where heteroaryl and substituted heteroaryl are as defined above.

"Heterocycle" or "heterocyclic" refers to a saturated or unsaturated group having a single ring or multiple condensed rings, from 2 to 20 ring carbon atoms and from 1 to 4 ring hetero atoms selected from nitrogen, sulfur or oxygen within the ring. "Heterocycle" or "heterocyclic" groups of the present invention also include fused multicyclic rings wherein one or more of the rings within the multicyclic ring system are aromatic, as long as the point of attachment to the core or backbone of the structure is on a non-aromatic ring atom.

"Saturated heterocyclic" refers to heterocycles of single or multiple condensed rings lacking unsaturation in any ring (e.g., carbon to carbon unsaturation, carbon to nitrogen unsaturation, nitrogen to nitrogen unsaturation, and the like).

"Unsaturated heterocyclic" refers to non-aromatic heterocycles of single or multiple condensed rings having unsaturation in any ring (e.g., carbon to carbon unsaturation, carbon to nitrogen unsaturation, nitrogen to nitrogen unsaturation, and the like).

"Substituted heterocyclic" refers to heterocycle groups, as defined above, which are substituted with from 1 to 3 substituents independently selected from the group consisting of oxo (=O), thioxo (=S), plus the same group of substituents as defined for substituted aryl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Substituted saturated heterocyclic" refers to substituted heterocycles, as defined above, of single or multiple condensed rings lacking unsaturation in any ring (e.g., carbon to carbon unsaturation, carbon to nitrogen unsaturation, nitrogen to nitrogen unsaturation, and the like).

"Substituted unsaturated heterocyclic" refers to non-aromatic substituted heterocycles of single or multiple condensed rings having unsaturation in any ring (e.g., carbon to carbon unsaturation, carbon to nitrogen unsaturation, nitrogen to nitrogen unsaturation, and the like).

"Heterocyclyloxy" refers to the group —O-heterocyclic and "substituted heterocyclyloxy" refers to the group —O-substituted heterocyclic where heterocyclic and substituted heterocyclyoxy are as defined above.

"Thiol" refers to the group —SH.

"Thioalkyl" and "thioalkoxy" refer to the groups —S-alkyl where alkyl is as defined above.

"Substituted thioalkyl" and "substituted thioalkoxy" refer to the group —S-substituted alkyl where substituted alkyl is as defined above.

"Thiocycloalkyl" refers to the groups —S-cycloalkyl where cycloalkyl is as defined above.

"Substituted thiocycloalkyl" refers to the group —S-substituted cycloalkyl where substituted cycloalkyl is as defined above.

"Thioaryl" refers to the group —S-aryl and "substituted thioaryl" refers to the group —S-substituted aryl where aryl and substituted aryl are as defined above.

"Thioheteroaryl" refers to the group —S-heteroaryl and "substituted thioheteroaryl" refers to the group —S-substituted heteroaryl where heteroaryl and substituted heteroaryl are as defined above.

"Thioheterocyclic" refers to the group —S-heterocyclic and "substituted thioheterocyclic" refers to the group —S-substituted heterocyclic where heterocyclic and substituted heterocyclic are as defined above.

Amino acid refers to any of the naturally occurring amino acids, as well as synthetic analogs (e.g., D-stereoisomers of the naturally occurring amino acids, such as D-threonine) and derivatives thereof. α-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). The term "naturally occurring amino acids" refers to these amino acids.

Unnatural amino acids are also known in the art, as set forth in, for example, Williams (ed.), Synthesis of Optically Active alpha.-Amino Acids, Pergamon Press (1989); Evans et al., J. Amer. Chem. Soc., 112:4011-4030 (1990); Pu et al., J. Org Chem., 56:1280-1283 (1991); Williams et al., J. Amer. Chem. Soc., 113:9276-9286 (1991); and all references cited therein.

"Pharmaceutically acceptable salt" refers to pharmaceutically acceptable salts of a compound of Formula (I) or Formula (II) which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

It is understood that the substitution patterns defined herein do not include any chemically impossible substitution patterns. Moreover, when a group is defined by the term "substituted" such as substituted aryl and a possible substituent is the substituted group itself, e.g., substituted aryl substituted with substituted aryl, it is not intended that such substitution patterns be repeated indefinitely such as to produce a polymer,e.g., (substituted aryl)$_n$. Accordingly, in all cases, the maximum number of repetitions is 4. That is too say that n is an integer from 1 to 4.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis,* Third Edition, Wiley, New York, 1999, and references cited therein.

The compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4$^{th}$ Edition), and Larock's Comprehensive Organic Transformations (VCH Publishers Inc., 1989).

Specifically, the substituted pyrazoles and various intermediates useful in the preparation of substituted pyrazoles are preferably prepared as shown in the following Schemes.

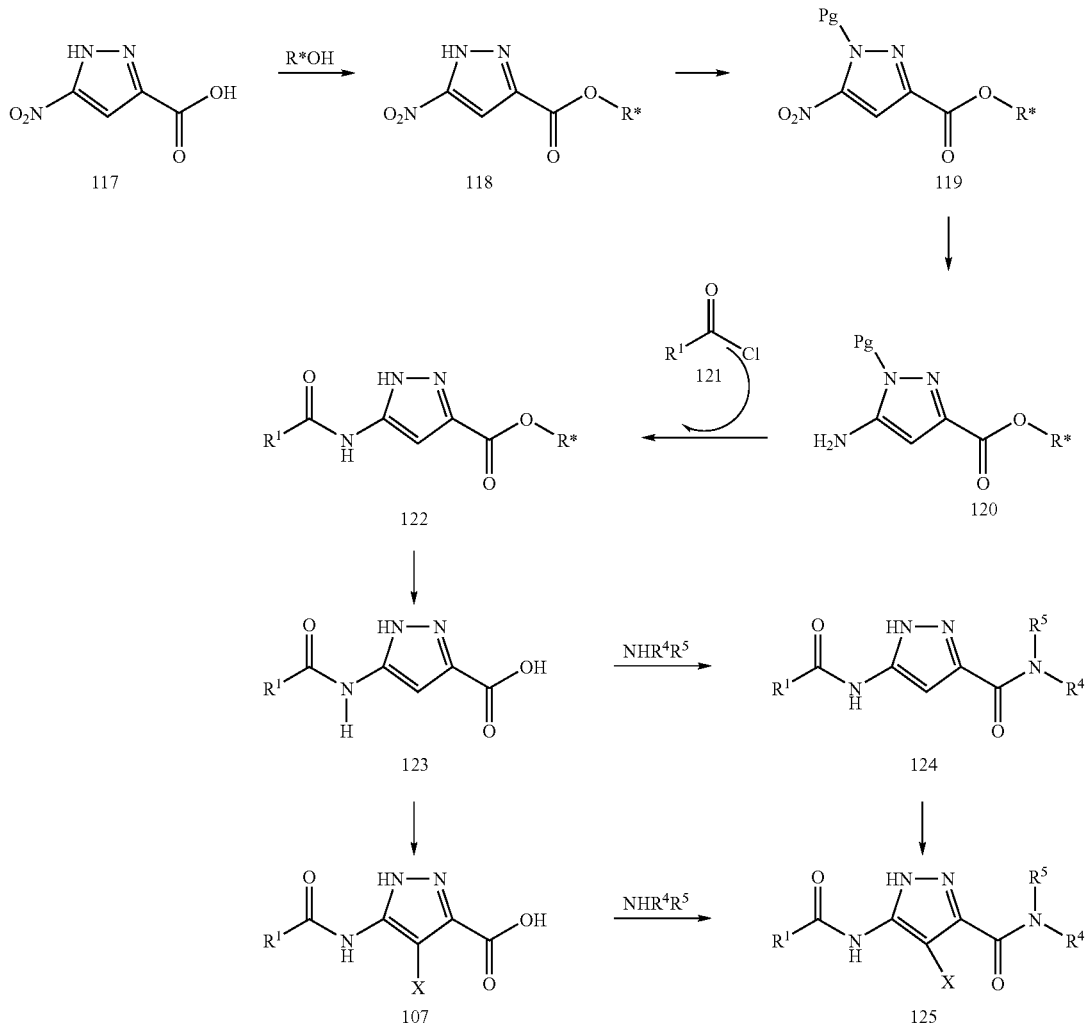

Specifically, in Scheme 1 (where $R^1$, $R^3$, $R^4$, $R^5$, X, are as defined above and R* is alkyl), commercially available 3-nitro-5-carboxyl pyrazole, compound 117, is esterified under conventional conditions using a suitable alcohol, such as methanol, in acidic medium to provide for the corresponding ester, 118. The particular alcohol employed is not critical and is typically selected based on ease of synthesis and costs. The reaction is preferably conducted at an elevated temperature of from about 25 to about 100° C. until the reaction is substantially complete, which is typically 2 to 12 hours. The resulting product, compound 118, can be recovered by conventional methods, such as chromatography, filtration, evaporation, crystallization, and the like or, alternatively, used in the next step without purification and/or isolation.

The 3-nitro-5-carboxyl ester pyrazole, compound 118, is protected with a conventional protecting group, Pg, under conventional conditions. The selected protecting group is one that is removed under conditions other than hydrogenation. A preferred protecting group is the Boc group.

The nitro group of the protected 3-nitro-5-carboxyl ester pyrazole, compound 119, is reduced to an amine using standard reduction reactions. For example, compound 119 is reacted with hydrogen gas at about 10 to 60 psi, in the presence of a suitable catalyst such as palladium on carbon to afford the corresponding amine, compound 120. The reaction is preferably conducted at a temperature of from about 20 to about 80° C. until the reaction is substantially complete, which is typically 1 to 5 hours. The resulting amine, compound 120, can be recovered by conventional methods, such as chromatography, filtration, crystallization, and the like or, alternatively, used in the next step without purification and/or isolation.

The 3-amino-5-carboxyl ester pyrazole, compound 120, is acylated under conventional conditions by reaction with at least a stoichiometric amount and preferably an excess of a desired acyl chloride, compound 121. The reaction is preferably conducted in the presence of a conventional activating agent such as DMAP in the presence of a base such as pyridine that scavenges the acid generated. The reaction is preferably conducted in an inert solvent such as dichloromethane, chloroform and the like although a liquid base such as pyridine can be employed as the solvent and to scavenge the acid generated. The reaction is preferably conducted at a temperature of from about −5 to about 35° C. until the reaction is substantially complete, which is typically 2 to 12 hours. The resulting product, compound 122, is obtained after a standard deprotection reaction, and can be recovered by conventional methods, such as chromatography, filtration, evaporation crystallization, and the like or, alternatively, used in the next step without purification and/or isolation.

Hydrolysis of compound 122, using conventional conditions such as lithium hydroxide and water in methanol and/or THF, affords the 3-($R^1$CONH—)-5-carboxylic acid pyrazole, compound 123.

Compound 123 is functionalized at the 4-position of the pyrazole ring by conventional methods to provide for compound 107. For example, when X is halo, compound 123 is contacted with at least a stoichiometric amount of a suitable halogenation agent such as N-halo succinimide, bromine, and the like. The reaction is conducted in an inert diluent such as dimethylformamide, dichloromethane, and the like at a temperature sufficient to effect halogenation. Typically, the reaction is conducted at from about 0° to about 40° C. until the reaction is substantially complete which typically occurs in about 0.1 to 10 hours. The resulting product, compound 107, can be recovered by conventional methods, such as chromatography, filtration, evaporation, crystallization, and the like or, alternatively, used in the next step without purification and/or isolation.

Subsequently, the carboxylic acid group of compound 107 is amidated using at least a stoichiometric amount and preferably an excess of a suitable amine, $HNR^4R^5$, under conventional conditions well known in the art preferably using an activating agent to effect coupling such as HOBT, EDC.HCl, NMM and the like. The resulting compound 125 can be recovered by conventional methods, such as chromatography, filtration, evaporation, crystallization, and the like.

Alternatively, compound 123 may be amidated as described above to form compound 124, which can be recovered by conventional methods, such as chromatography, filtration, evaporation, crystallization, and the like. Compound 124 can be functionalized at the 4-position of the pyrazole ring by conventional methods to provide for compound 125 using the same methods described for the conversion of compound 123 to compound 107.

In an alternative synthetic embodiment, compounds of Formula (I) or Formula (II) where X is alkyl can be prepared as shown in Scheme 2 below:

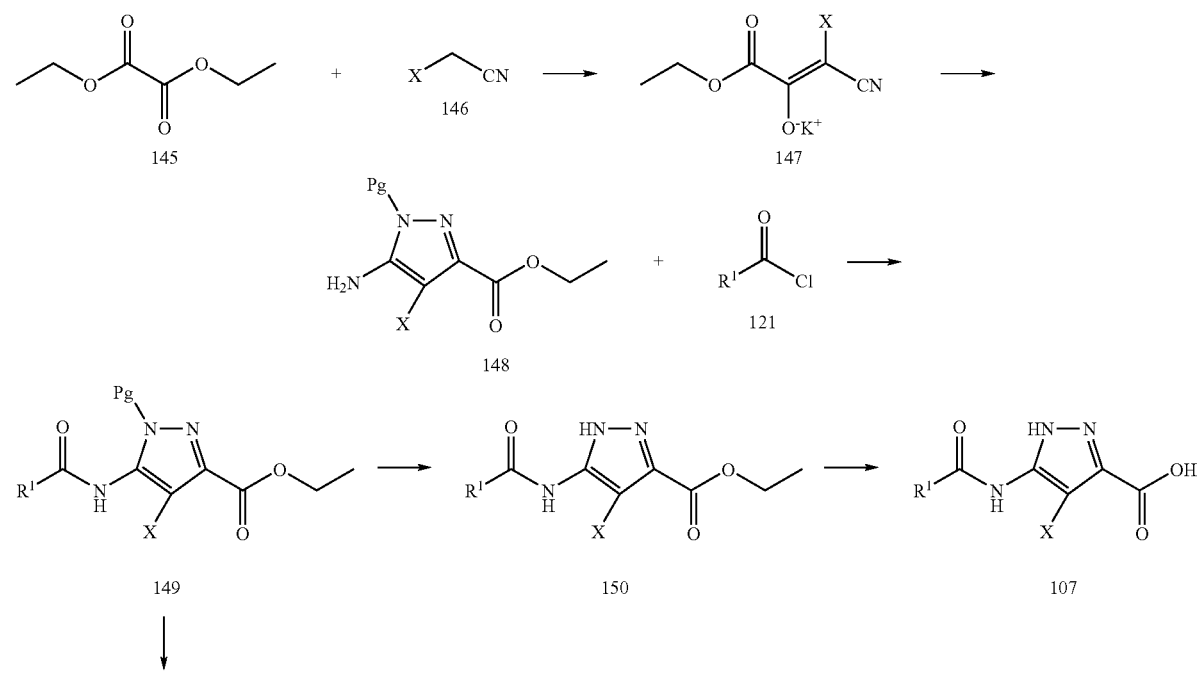

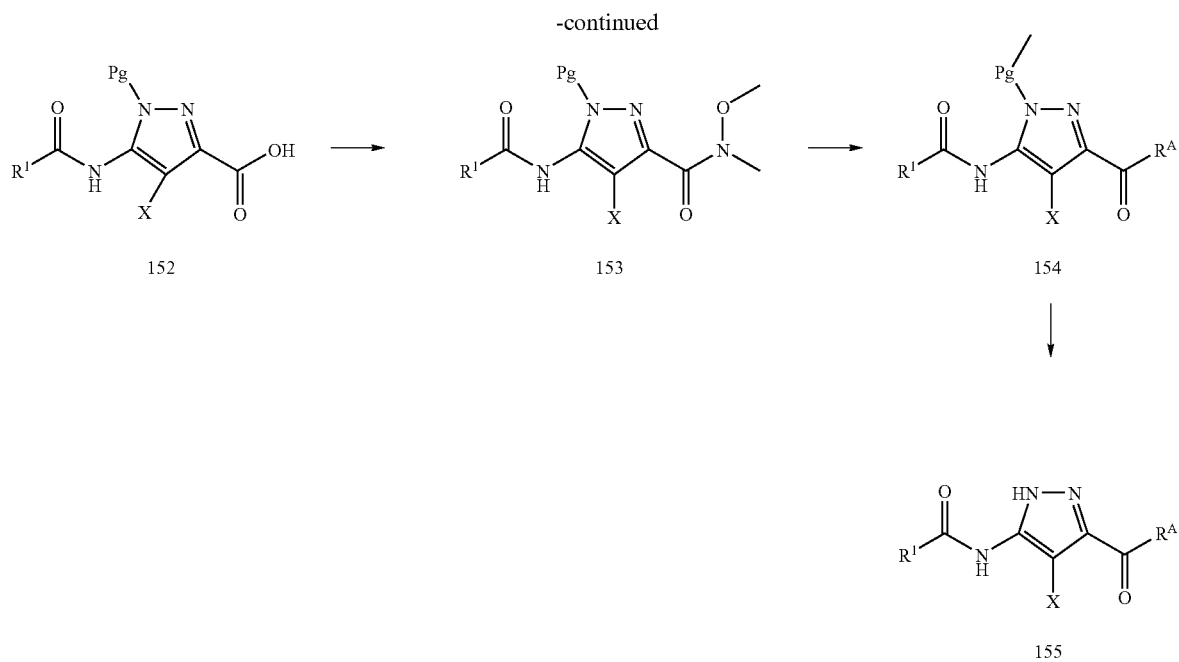

Specifically, in Scheme 2, wherein $R^1$ is defined above, commercially available oxalic acid diethyl ester, compound 145, is combined with at least a stoichiometric amount of an alkylnitrile, compound 146, in the presence of a suitable base such as potassium ethoxide in ethanol. The reaction is preferably maintained at a temperature of from about 60° C. to about 100° C. until the reaction is substantially complete, which is typically 12 to 24 hours. The resulting product, compound 147, can be recovered by conventional methods, such as chromatography, filtration, evaporation, crystallization, and the like or, alternatively, used in the next step without purification and/or isolation.

Compound 147 is then cyclized using a slight excess of t-butyl hydrazine hydrochloride (not shown) in ethanol. The reaction is preferably conducted at elevated temperatures and pressures such as a temperature of from about 75 to about 150° C. and a pressure of from about 1 to 10 atm until the reaction is substantially complete, which is typically 12 to 24 hours. The resulting product, compound 148, can be recovered by conventional methods, such as chromatography, filtration, crystallization, and the like or, alternatively, used in the next step without purification and/or isolation.

Reaction of compound 148 proceeds in the manner described above for compound 120 to provide for compounds of Formula (I) or Formula (II) where X is alkyl.

Scheme 2 further illustrates derivatization of the carboxyl group of the 2-(Pg)-3-(—NHC(O)$R^1$)-4-(X)-5-carboxyl pyrazole, compound 149. Specifically, conventional hydrolysis of the ester provides for compound 152 which is then converted to the methoxymethylamide by reaction with commercially available N—O-dimethyl-hydroxylamine hydrochloride under conventional coupling conditions in a suitable inert diluent such as tetrahydrofuran, dioxane, and the like optionally in the presence of an activating agent. The reaction is maintained under conditions sufficient to afford compound 153 including, for example, a temperature of from about 0 to about 40° C. for a period of from 12 to 24 hours. The resulting product, compound 153, can be recovered by conventional methods, such as chromatography, filtration, evaporation, crystallization, and the like or, alternatively, used in the next step without purification and/or isolation.

Compound 153 is then derivatized by contact with at least a stoichiometric amount, and preferably an excess, of $R^\wedge$—Li where $R^\wedge$ is selected from the group consisting of alkyl, substituted alkyl, cycloalkyl, substituted cycloalkyl, heterocyclic, substituted heterocyclic, aryl, substituted aryl, heteroaryl and substituted heteroaryl. The reaction is typically conducted in an inert solvent such as tetrahydrofuran, dioxane, and the like at a reduced temperature of from about 0° C. to about −78° C. for a period of time sufficient for substantial reaction completion which typically occurs in about 12 to 24 hours. The resulting product, compound 155, can be recovered by conventional methods, such as chromatography, filtration, evaporation, crystallization, and the like The starting materials employed in the reactions described above are either commercially available and/or can be prepared by methods well known in the art. For example, acid halides of the formula $R^1C(O)X$ are readily prepared from the corresponding carboxylic acid by reaction with, e.g., oxalyl halide, thionyl halide and the like. Acids of the formula $R^1C(O)OH$ are extremely well known and include aromatic acids (e.g., $R^1$ is aryl, substituted aryl, heteroaryl or substituted heteroaryl).

Alternatively, o-(Ar—S—$CH_2$—)benzoyl chloride, compound 143, can be prepared as illustrated in Scheme 3 below where Ar is an aryl, substituted aryl, heteroaryl, substituted heteroaryl, heterocyclic, and substituted heterocyclic:

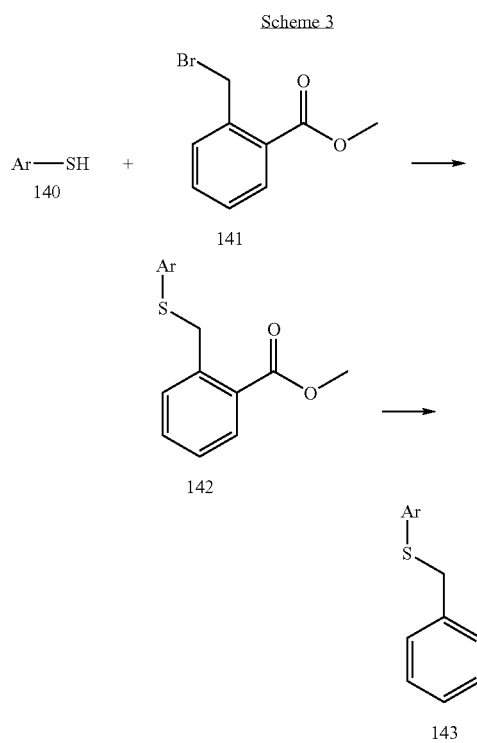

Scheme 3

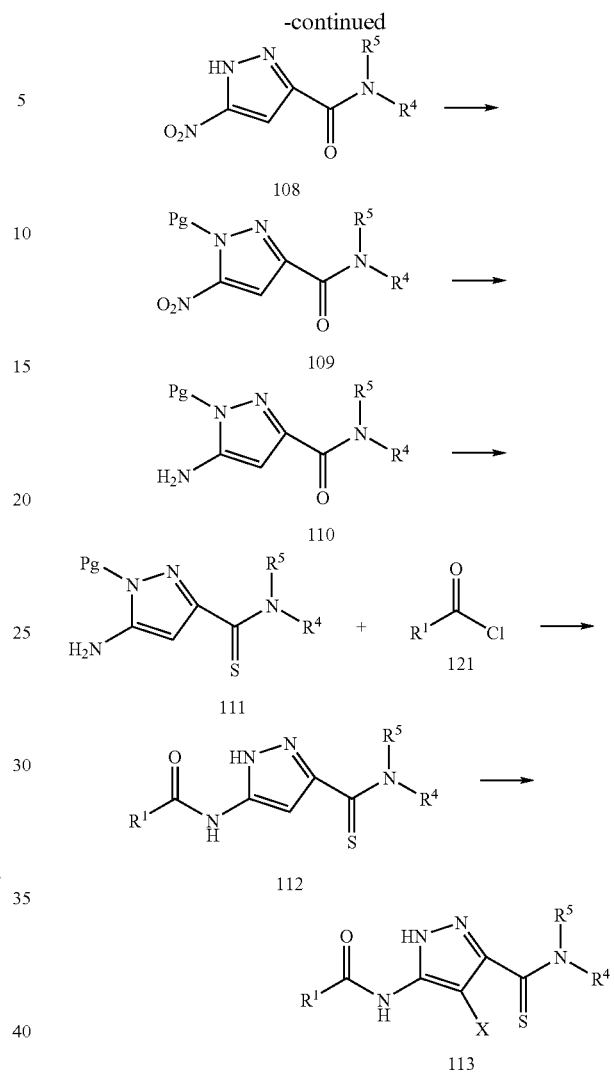

Specifically, compound 140 is coupled to o-bromomethyl-benzoic acid methyl ester, compound 141 (prepared as per Dvornikovs *J. Org. Chem,* 2002, 67, 2160), in the presence of about 30 equivalents potassium carbonate in DMF. This reaction is typically conducted at a temperature of from about 0 to about 30° C. until the reaction is substantially complete, which is typically 1 to 15 days. The resulting product, compound 142, can be recovered by conventional methods, such as chromatography, filtration, evaporation, crystallization, and the like or, alternatively, used in the next step without purification and/or isolation.

o-(Ar—S—CH$_2$—)benzoyl chloride, compound 143, is then prepared by conventional hydrolysis of the methyl ester in compound 142 followed by conventional conversion of the carboxyl group to the carboxyl halide using, e.g., oxalyl halide in the presence of a base to scavenge the acid generated. The reaction is typically conducted in an inert solvent such as dichloromethane. This reaction is typically run at a temperature of about −20 to about 10° C. until the reaction is substantially complete, which is typically 1 to 12 hours. The resulting product, compound 143, can be recovered by conventional methods, such as filtration, evaporation, crystallization, and the like or, alternatively, used in the next step without purification and/or isolation.

Scheme 4

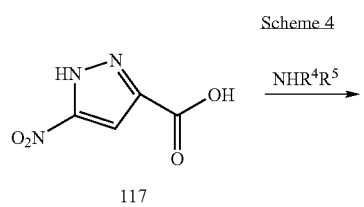

In one embodiment, Z' of the substituted pyrazoles of Formula 1 is sulfur. These substituted pyrazoles can be prepared as shown in Scheme 4, where Pg, X, R$^4$, R$^5$ and R$^1$ are as defined herein above.

Specifically, in Scheme 4, commercially available 3-nitro-5-carboxyl pyrazole, compound 117, is coupled to an amine using conventional conditions, for example, by using an activating agent such as HOBT, EDC.HCl, NMM and the like to effect coupling as described herein above. The resulting compound 108 can be recovered by conventional methods such as chromatography, filtration, evaporation, crystallization and the like.

The 3-nitro-5-carboxyl amide pyrazole, compound 108, is protected with a protecting group, Pg, under conventional conditions to afford compound 109. The selected protecting group is one that is removed under conditions other than hydrogenation. A preferred protecting group is the Boc group.

The nitro group of the protected 3-nitro-5-carboxyl amide pyrazole, compound 109, is reduced to an amine using standard reduction reactions. For example, compound 109 is reacted with hydrogen gas at about 10 to 60 psi, in the presence of a suitable catalyst such as palladium on carbon to afford the corresponding amine, compound 110.

The 3-amino-5-carboxyl amide pyrazole, compound 110, is converted to the thioamide, compound 111, under conventional conditions known in the art. Formation of thioamides from amides can be accomplished using a number of known methods including the use of $P_4S_{10}$ or Lawesson's reagent as well as other methods know in the art such as those illustrated by Ernst Schaumann in *Comprehensive Organic Synthesis* Barry M. Trost, Ed.; Pergamon Press: Oxford, 1991; Vol. 6, Chapter 2.4, which is incorporated herein by reference in its entirety.

The 3-amino-5-thiocarboxyl amide pyrazole, compound 111, is acylated under conventional conditions by reaction with a desired acyl chloride, compound 121. The reaction is preferably conducted in the presence of a conventional activating agent such as DMAP in the presence of a base such as pyridine that scavenges the acid generated. The reaction is preferably conducted in an inert solvent such as dichloromethane, chloroform and the like. Alternatively a liquid base such as pyridine can be employed as the solvent and to scavenge the acid generated. The reaction is typically conducted at a temperature of about −5 to about 35° C. until completion, usually about 2 to about 12 hours. The resulting product, compound 112, is obtained after a standard deprotection reaction, and can be recovered by conventional methods, such as chromatography, filtration, evaporation, crystallization, and the like or, alternatively, used in the next step without purification and/or isolation.

Compound 112, is functionalized at the 4-position of the pyrazole ring by conventional methods to provide for compound 113. For example, when X is halo, compound 112 is contacted with at least a stoichiometric amount of a suitable halogenation agent such as N-halo succinimide, $Br_2$, and the like. The reaction is conducted in an inert diluent such as dimethylformamide, dichloromethane and the like at a temperature sufficient to effect halogenation. Typically, the reaction is conducted at from about 0 to about 40° C. until reaction is substantially complete which typically occurs in about 0.1 to 10 hours. The resulting product, compound 113, can be recovered by conventional methods, such as chromatography, filtration, evaporation, crystallization, and the like or, alternatively, used in the next step without purification and/or isolation.

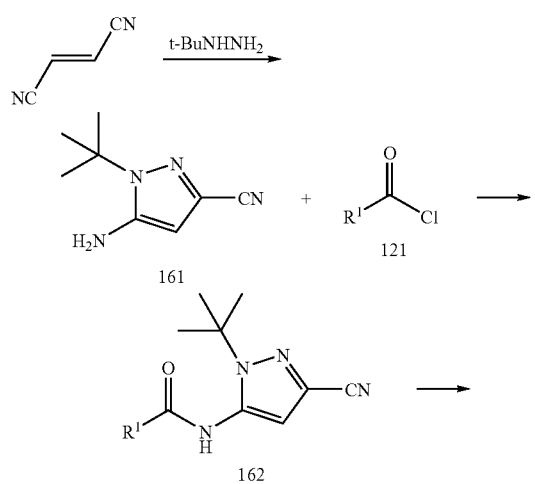

Scheme 5

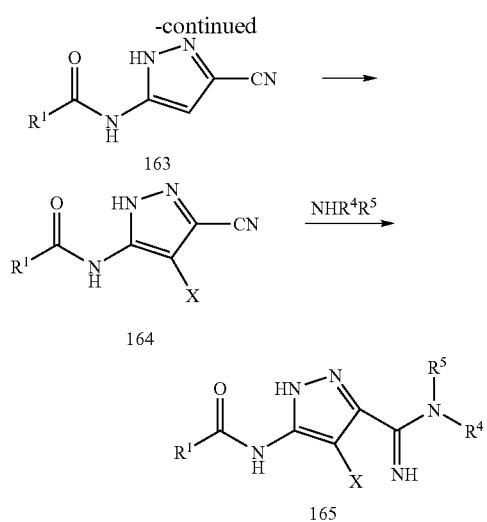

In one embodiment of this invention, Z' in the substituted pyrazoles of Formula 1 is NH. Such substituted pyrazoles can be prepared as shown in Scheme 5.

Specifically, in Scheme 5, 3-amino-5-cyano pyrazole, compound 161, is prepared by the addition of tert-butylhydrazine to fumaronitrile, compound 160. This reaction is typically run at a temperature of from about 0 to about 110° C. until substantially complete, usually about 1 to about 48 hours. The resulting product, compound 161 can be recovered by conventional methods, such as chromatography, filtration, evaporation, crystallization, and the like or, alternatively, used in the next step without purification and/or isolation.

The 3-amino-5-cyano pyrazole, compound 161, is acylated under conventional conditions by reaction with a desired acyl chloride, compound 121 to provide compound 162. The reaction is preferably conducted in the presence of a conventional activating agent such as DMAP in the presence of a base such as pyridine that scavenges the acid generated. The reaction is preferably conducted in an inert solvent such as dichloromethane, chloroform and the like although a liquid base such as pyridine can be employed as the solvent and to scavenge the acid generated. The resulting product, compound 163, is obtained after a standard deprotection of compound 162, and can be recovered by conventional methods, such as chromatography, filtration, evaporation, crystallization, and the like or, alternatively, used in the next step without purification and/or isolation.

Compound 163, is functionalized at the 4-position of the pyrazole ring by conventional methods to provide for compound 164. For example, when X is halo, compound 163 is contacted with at least a stoichiometric amount of a suitable halogenation agent such as N-halo succinimide, bromine, and the like. The reaction is conducted in an inert diluent such as dimethylformamide, dichloromethane and the like at a temperature sufficient to effect halogenation. Typically, the reaction is conducted at from about 0 to about 40° C. until reaction is substantially complete which typically occurs in about 0.1 to 10 hours. The resulting product, compound 164, can be recovered by conventional methods, such as chromatography, filtration, evaporation, crystallization, and the like or, alternatively, used in the next step without purification and/or isolation.

Compound 164 is converted to the amidine, compound 165, under conventional conditions known in the art. Formation of amidines from nitrites can be accomplished using a number of known methods including condensation with amines. Other methods of preparing amidines are illustrated by Willi Kantlehner in *Comprehensive Organic Synthesis* Barry M. Trost, Ed.; Pergamon Press: Oxford, 1991; Vol. 6, Chapter 2.7.

Suitable amines of the formula HNR⁴R⁵ are well known in the art and many are commercially available. In addition, methods for preparing suitable amines are well documented and the following schemes illustrate a sampling of suitable methods for preparing such amines.

Scheme 6

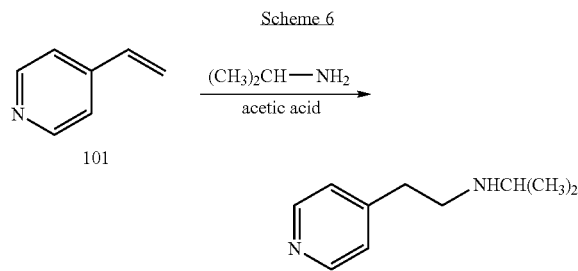

Scheme 6 above shows the conversion of a vinylpyridine group to a 2-aminoethylpyridine group by reacting 4-vinyl pyridine (1.6 mL; 15 mmol) dissolved in acetic acid (12.5 mmol; 0.72 mL) with isopropylamine (12.5 mmol; 1.06 mL). The reaction mixture is refluxed for 6 h. The solvent is evaporated under reduced pressure. To the resulting solid is added EtOAc as well as saturated NaHCO$_3$. The organic layer is isolated, dried over MgSO$_4$. The solvent is removed under reduced pressure. The desired material is isolated as a foam.

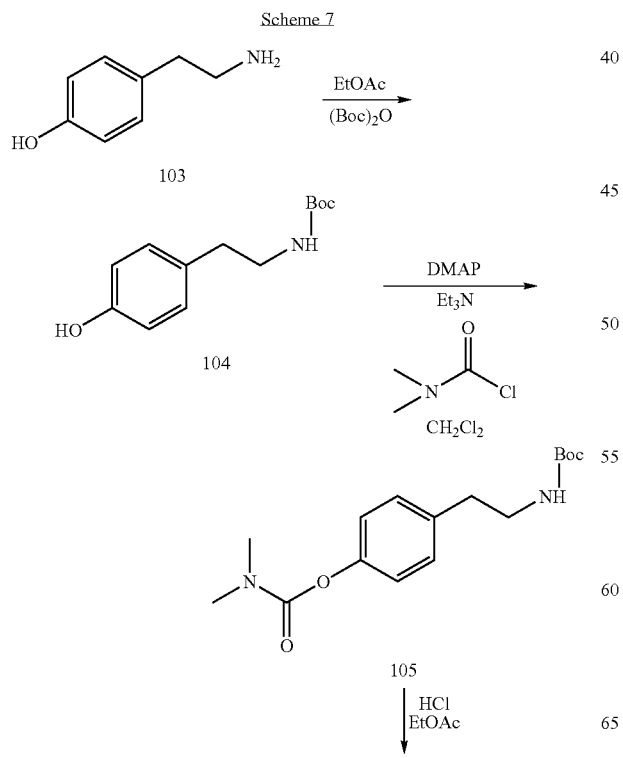

-continued

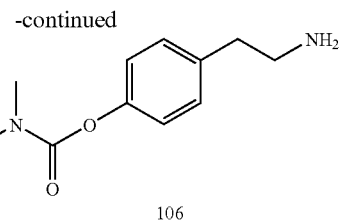

A procedure for the preparation of carbamoyloxy substituted phenylethyl amine compounds is shown in Scheme 7 above and detailed in the following reaction steps.

Step A: Synthesis of N-t-butoxycarbonyloxy 2-(4-hydroxyphenyl)ethylamine

The amine group of 2-(4-hydroxyphenyl)ethylamine can be protected with a Boc protecting group in a conventional manner to provide for N-t-butoxycarbonyloxy 2-(4-hydroxyphenyl)ethylamine.

Step B: Synthesis of N-t-butoxycarbonyloxy 2-[4-(N,N-dimethylaminocarbonyloxy)phenyl]ethylamine N-t-butoxycarbonyloxy 2-(4-hydroxyphenyl)ethylamine (2.53 g, 10.7 mmol), Et$_3$N (2.96 mL, 2 eq.), a catalytic amount of DMAP (131 mg) and dimethylcarbamyl chloride (2.0 mL, 2 eq) are mixed in CH$_2$Cl$_2$ at 0° C. The resulting mixture is stirred overnight. EtOAc is added to dilute the reaction mixture and then is washed with 1N HCl, sat.Na$_2$CO$_3$ and brine. Solvent is removed under reduced pressure to give pure t-butoxycarbonyloxy 2-[4-(N,N-dimethylaminocarbonyloxy) phenyl]ethylamine as a solid.

Step C: Synthesis of 2-[4-(N,N-dimethylaminocarbonyloxy)phenyl]ethylamine

The Boc protecting group on the t-butoxycarbonyloxy 2-[4-(N,N-dimethylaminocarbonyloxy)phenyl]ethylamine is removed using conventional techniques to provide for the title compound as a white solid.

Scheme 8

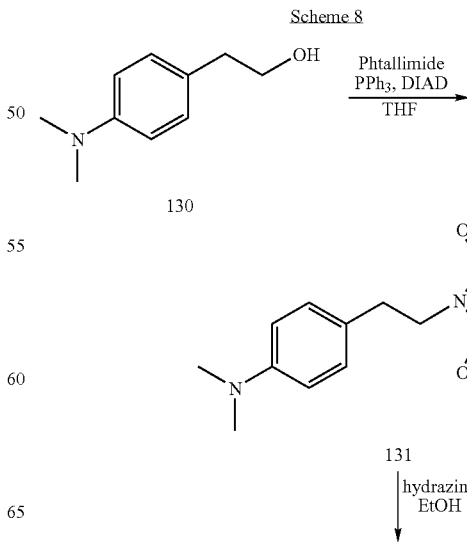

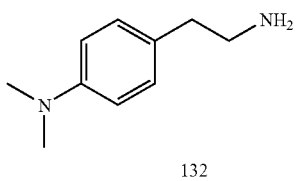

132

A procedure for converting 2-[4-(N,N-dimethylaminophenyl]ethanol to 2-[4-(N,N-dimethylaminophenyl]ethylamine is shown in Scheme 8 above and detailed in the following reaction steps.

Step A: Synthesis of 2-[2-(4-N,N-dimethylaminophenyl)-ethyl]-isoindole-1,3-dione 2-[4-(N,N-dimethylaminophenyl]ethanol (2.05 g, 17.4 mmol), phthalimide (2.19 g, 14.9 mmol) and PPh$_3$ (3.93 g, 14.9 mmol) (Aldrich) are mixed in 100 mL of THF maintained at 0° C. The mixture is then treated with DIAD (2.68 mL) (Aldrich) which is added dropwise. After stirring overnight, the solvent is removed under reduced pressure to give a pale yellow solid. The solid is triturated with EtOAc three times. The combined EtOAc layers are treated with gaseous HCl to precipitate the product, and the desired product is isolated through filtration.

Step B: Synthesis of 2-[4-(N,N-dimethylaminophenyl]ethylamine

2-[2-(4-N,N-dimethylaminophenyl)-ethyl]-isoindole-1,3-dione (606 mg, 1.84 mmol) and hydrazine hydrate (30%, 0.64 mL) in ethanol is heated at 65° C. for 5 h. The precipitate is removed via filtration. The filtrate is concentrated to give the title compound as a white solid.

Scheme 9

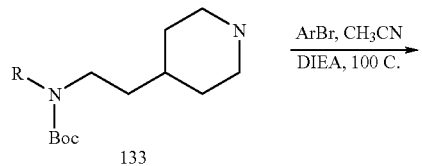

133

↓ ArBr, CH$_3$CN
DIEA, 100 C.

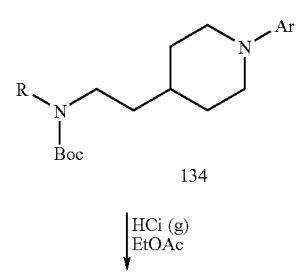

134

↓ HCl (g)
EtOAc

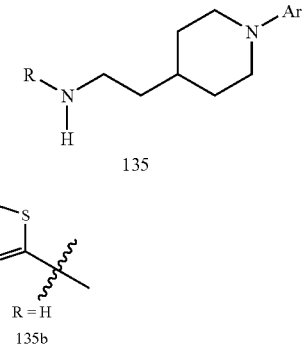

135

Ar = 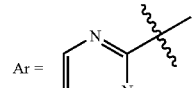   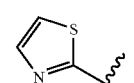

R = H            R = H
135a             135b

A procedure for preparing 2-[(1-pyrimidin-2-yl)piperidin-4-yl]-ethylamine compounds is shown in Scheme 9 above and detailed in the following reaction steps Step A: Synthesis of N-t-butoxycarbonyloxy 2-[1-(pyrimidin-2-yl)piperidin-4-yl]-ethylamine N-t-butoxycarbonyloxy 2-(piperidin-4-yl)-ethylamine, DIEA (0.75 mL) and 2-bromopyrimidine (204 mg) (Aldrich) in acetonitrile (5 mL) are heated under reflux overnight. The solvent is removed under reduced pressure and the black liquid is subjected to a column chromatography, eluted with 1:1 EtOAc/hexanes, to give pure N-t-butoxy-carbonyloxy 2-[1-(pyrimidin-2-yl)piperidin-4-yl]-ethylamine as a pale yellow oil.

Step B: Synthesis of 2-[(1-pyrimidin-2-yl)piperidin-4-yl]-ethylamine

The Boc protecting group on N-t-butoxy-carbonyloxy 2-[1-(pyrimidin-2-yl)piperidin-4-yl]-ethylamine is removed to afford the title compound.

A particularly preferred class of such amines includes the cyclic amines represented by the formula:

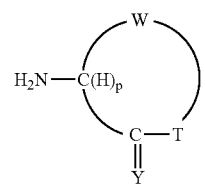 (IV)

where Y is oxygen, sulfur, [H and OH] and [H and H], T is preferably selected from the group consisting of —O—, —S—, >NR$^{16}$, and >CR$^{17}$R$^{18}$ where each of R$^{16}$, R$^{17}$ and R$^{18}$ are independently selected from the group consisting of hydrogen, alkyl, substituted alkyl, alkenyl, substituted alkenyl, alkynyl, substituted alkynyl, aryl, heteroaryl and heterocyclic with the proviso that if T is —O—, —S— or >NR$^{16}$, then Y is oxo or dihydro, and W together with T, C=Y and C(H)$_p$ forms an optionally fused lactone, thiolactone, locate, cyclic ketone, cyclic alcohol, a heterocycle, and the like. The synthesis of these rings is well known in the art and exhaustively described in U.S. Pat. No. 6,541,466, which is incorporated herein by reference in its entirety.

For the purposes of this application, it is understood that the term optionally fused lactone preferably refers to rings of the formula:

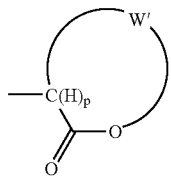

where W' is selected from alkylene, substituted alkylene, alkenylene, substituted alkenylene and —$R^{20}$-A-$R^{20}$— where each $R^{20}$ is independently alkylene, substituted alkylene, alkenylene, or substituted alkenylene, A is $NR^{16}$, O, S, S(O), S(O)$_2$, C(O), or C(S) and p is as defined above. Such structures optionally include fused ring systems such as those comprising from 1 to 3 rings fused thereto. Examples of such fused ring systems include the following:

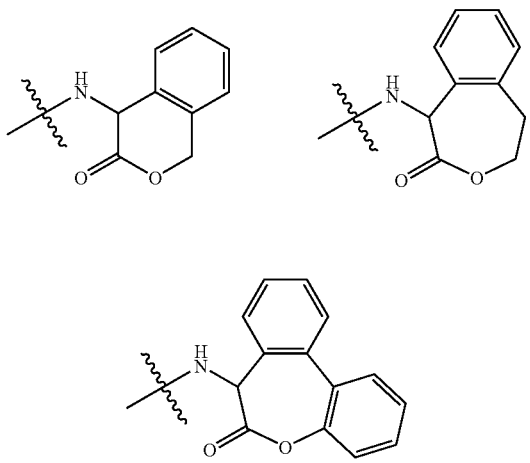

It is further understood that each of the rings can be optionally substituted with up to 3 substituents as defined for substituted aryl.

For the purposes of this application, it is understood that the term optionally fused thiolactone preferably refers to rings of the formula:

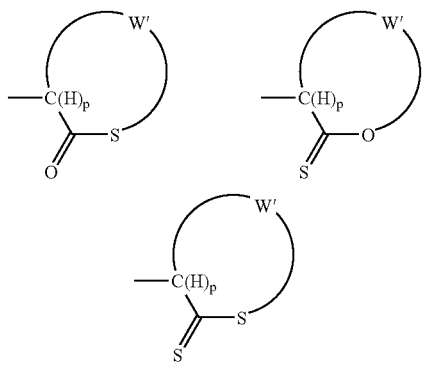

where W' and p are as defined above. Such structures optionally include fused ring systems such as those comprising from 1 to 3 rings fused thereto. Examples of such fused ring systems include the following:

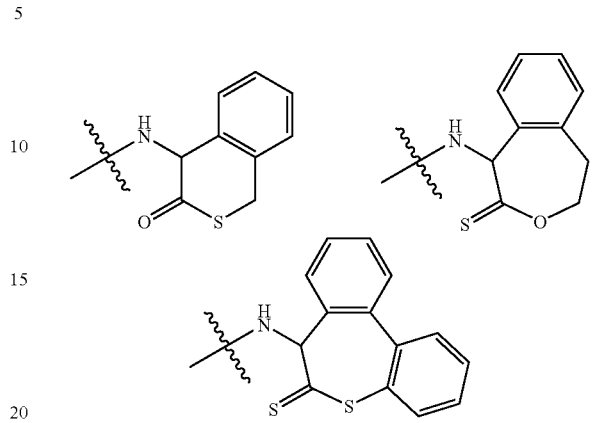

It is further understood that each of the rings can be optionally substituted with up to 3 substituents as defined for substituted aryl.

For the purposes of this application, it is understood that the term optionally fused lactam refers to rings of the formula:

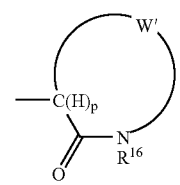

where W' and $R^{16}$ are as defined above and p are as defined above. Such structures optionally include fused ring systems such as those comprising from 1 to 3 rings fused thereto. Examples of such fused ring systems include the following:

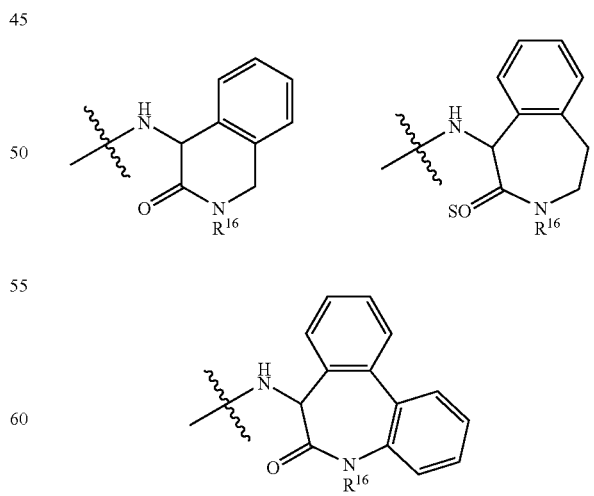

It is further understood that each of the rings can be optionally substituted with up to 3 substituents as defined for substituted aryl.

For the purposes of this application, it is understood that the term optionally fused ketones refers to rings of the formula:

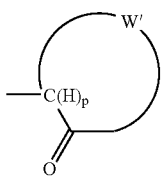

where W' and p are as defined above. Such structures optionally include fused ring systems such as those comprising from 1 to 3 rings fused thereto. Examples of such fused ring systems include the following:

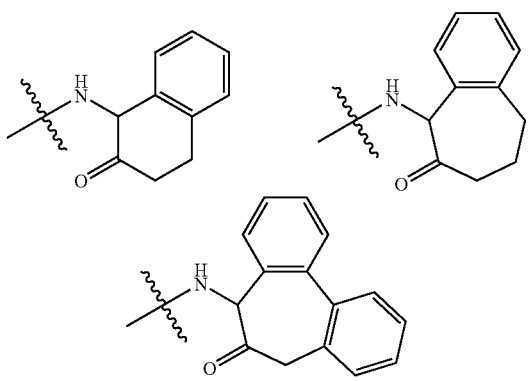

It is further understood that each of the rings can be optionally substituted with up to 3 substituents as defined for substituted aryl.

For the purposes of this application, it is understood that the term optionally fused alcohols refers to rings of the formula:

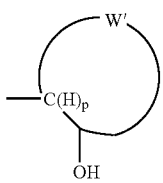

where W' and p are as defined above. Such structures optionally include fused ring systems such as those comprising from 1 to 3 rings fused thereto. Examples of such fused ring systems include the following:

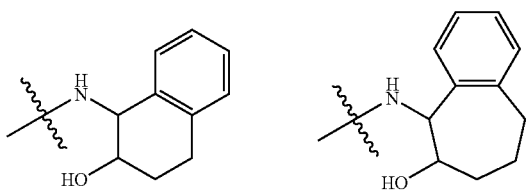

-continued

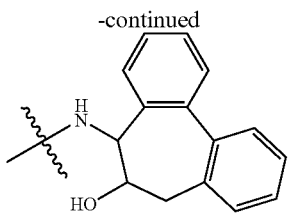

It is further understood that each of the rings can be optionally substituted with up to 3 substituents as defined for substituted aryl.

The aminolactams, aminolactones and aminothiolactones of the formula above are well known in the art and are described in detail in International Application WO 98/28268 which is incorporated herein by reference in its entirety.

For example, these compounds can be prepared by use or adaptation of known chemical syntheses which syntheses are well described in the literature. See, e.g., Ogliaruso and Wolfe, *Synthesis of Lactones and Lactams,* Patai, et al. Editor, J. Wiley & Sons, New York, N.Y., USA, pp. 1085 et seq. (1993).

The preparation of lactones can be similarly conducted using peracids in a Baeyer-Villiger reaction on ketones. Alternatively, thiolactones can be prepared by cyclization of an omega —SH group to a carboxylic acid and thiolactams can be prepared by conversion of the oxo group to the thiooxo group by $P_2S_5$ or by use of the commercially available Lawesson's Reagent, *Tetrahedron,* 35:2433 (1979).

Some of the lactams described above contain the requisite amino group alpha to the lactam carbonyl whereas others did not. However, the introduction of the required amino group can be achieved by any of several routes delineated below which merely catalogue several recent literature references for this synthesis.

For example, in a first general synthetic procedure, azide or amine displacement of a leaving group alpha to the carbonyl group of the lactam leads to the alpha-aminolactams. Such general synthetic procedures are exemplified by the introduction of a halogen atom followed by displacement with phthalimide anion or azide and subsequent conversion to the amine typically by hydrogenation for the azide as described in Rogriguez, et al., *Tetrahedron,* 52:7727-7736 (1996), Parsons, et al., *Biochem. Biophys. Res. Comm.,* 117:108-113 (1983) and Watthey, et al., *J. Med. Chem.,* 28:1511-1516 (1985). One particular method involves iodination and azide displacement on, for example, benzyllactams as described by Armstrong, et al., *Tetrahedron Lett.,* 35:3239 (1994) and by King, et al., *J. Org. Chem.,* 58:3384 (1993).

Another example of this first general procedure for the synthesis of alpha-aminolactams from the corresponding lactam involves displacement of a triflate group by an azido group as described by Hu, et al., *Tetrahedron Lett.,* 36(21): 3659-3662 (1995).

Still another example of this first general procedure uses a Mitsunobu reaction of an alcohol and a nitrogen equivalent (either —$NH_2$ or a phthalimido group) in the presence of an azodicarboxylate and a triarylphosphine as described in Wada, et al., *Bull. Chem. Soc. Japan,* 46:2833-2835 (1973) using an open chain reagent.

Yet another example of this first general procedure involves reaction of alpha-chlorolactams with anilines or alkyl amines in a neat mixture at 120 C to provide for 2-(N-aryl or N-alkyl) lactams as described by Gaetzi, Chem. Abs., 66:28690m.

In a second general synthetic procedure, reaction of an enolate with an alkyl nitrite ester to prepare the alpha oxime followed by reduction yields the alpha-aminolactam compound. This general synthetic procedure is exemplified by Wheeler, et al., *Organic Syntheses*, Coll. Vol. VI, p. 840 which describes the reaction of isoamyl nitrite with a ketone to prepare the desired oxime. The reduction of the oxime methyl ester (prepared from the oxime by reaction with methyl iodide) is described in the *J. Med. Chem.*, 28(12): 1886 (1985) and the reduction of alpha-oximino caprolactams by Raney-nickel and palladium catalysts is described by Brenner, et al., U.S. Pat. No. 2,938,029.

In a third general synthetic procedure, direct reaction of an enolate with an electrophilic nitrogen transfer agent can be used. The original reaction employed toluenesulfonyl azide but was improved as described by Evans, et al., *J. Am. Chem. Soc.*, 112:4011-4030 (1990). Specifically, direct introduction of an azido group which can be reduced to the amine by hydrogenation is described by Micouin, et al., *Tetrahedron*, 52:7719-7726 (1996). Likewise, the use of triisopropylbenzenesulfonyl azide as the azide transferring agent for reaction with an enolate is described by Evans, et al., supra. The use of triphenylphosphine to reduce the alpha-azidolactams to the corresponding aminolactams in the benzodiazepine series is disclosed by Butcher, et al., *Tetrahedron Lett.*, 37(37):6685-6688 (1996). Lastly, diazo transfer of beta-diketones and subsequent reduction of the diazo group to the amino group is exemplified by Hu, et al., *Tetrahedron Lett.*, 36(21):3659-3662 (1995) who used Raney-nickel and hydrogen in acetic acid and acetic anhydride as the solvent.

In a fourth general procedure, N-substituted lactams are first converted to the 3-alkoxycarbonyl derivatives by reaction with a dialkyl carbonate and a base such as sodium hydride. See, for example, M. L. Reupple, et al., *J. Am. Chem. Soc.*, 93:7021 et seq. (1971) The resulting esters serve as starting materials for conversion to the 3-amino derivatives.

Ring expansion methodology based on beta lactams to provide for larger ring lactams containing an aza group has twice been reported in Wasserman, et al., *J. Am. Chem. Soc.*, 103:461-2 (1981) and in Crombie, et al., *Tetrahedron Lett.*, 27(42):5151-5154 (1986).

Dieckmann methodology has been used to prepare aza caprolactams from unsymmetrical amines such as shown below by Yokoo, et al., *Bull, Chem. Soc. Jap.*, 29:631 (1956).

The synthesis of thialactams (generally oxalactams can be made by the same methodology) has been reported by Freidinger, et al., *J. Org. Chem.*, 47:104-109 (1982).

Similarly, various benzodiazepine derivatives suitable for use in this invention can be prepared using conventional procedures and reagents. For example, a 2-aminobenzophenone can be readily coupled to -(isopropylthio)-N-(benzyloxycarbonyl)glycine by first forming the acid chloride of the glycine derivative with oxalyl chloride, and then coupling the acid chloride with the 2-aminobenzophenone in the presence of a base, such as 4-methylmorpholine, to afford the 2-[-(isopropylthio)-N-(benzyloxycarbonyl)glycinyl]-aminobenzophenone. Treatment of this compound with ammonia gas in the presence of an excess, preferably about 1.1 to about 1.5 equivalents, of mercury (II) chloride then affords the 2-[N-(-amino)-N-(benzyloxycarbonyl) -glycinyl]aminobenzophenone. This intermediate can then be readily cyclized by treatment with glacial acetic acid and ammonium acetate to provide the 3-(benzyloxycarbonyl)amino-2,3-dihydro-5-phenyl-1H-1,4-benzodiazepin-2-one1. Subsequent removal of the Cbz group affords the 3-amino-2,3-dihydro-5-phenyl-1H-1,4-benzodiazepin-2-one.

Alternatively, 2,3-dihydro-5-phenyl-1H-1,4-benzodiazepin-2-ones can be readily animated at the 3-position using conventional azide transfer reactions followed by reduction of the resulting azido group to form the corresponding amino group. The conditions for these and related reactions are described in the examples set forth below. Additionally, 2,3-dihydro-5-phenyl-1H-1,4-benzodiazepin-2-ones are readily alkylated at the 1-position using conventional procedures and reagents. For example, this reaction is typically conducted by first treating the benzodiazepinone with about 1.1 to about 1.5 equivalents of a base, such as sodium hydride, potassium tert-butoxide, potassium 1,1,1,3,3,3-hexamethyldisilazane, cesium carbonate, in an inert diluent, such as DMF. This reaction is typically conducted at a temperature ranging from about −78 C. to about 80 C. for about 0.5 to about 6 hours. The resulting anion is then contacted with an excess, preferably about 1.1 to about 3.0 equivalents, of an alkyl halide, typically an alkyl chloride, bromide or iodide. Generally, this reaction is conducted at a temperature of about 0 C. to about 100 C. for about 1 to about 48 hours.

Additionally, the 3-amino-2,4-dioxo-2,3,4,5-tetrahydro-1H-1,5-benzo-diazepines employed in this invention are typically prepared by first coupling malonic acid with a 1,2-phenylenediamine. Conditions for this reaction are well known in the art. Subsequent alkylation and amination using conventional procedures and reagents affords various 3-amino-1,5-bis(alkyl)-2,4-dioxo-2,3,4,5-tetrahydro-1H-1,5-benzodiazepines. Such procedures are described in further detail in the example set forth below.

European Patent Application EP 0167919 B1 and references cited therein describes the synthesis of certain benzodiazepine derivatives which can also be used as intermediates in the preparation of the compounds herein described. Other references describing the synthesis of benzodiazepines which can be used as intermediates in the preparation of the compounds herein described include: Bock, M. G.; et al. *J. Org Chem.* 1987, 52, 3232; Showell, G. A.; et al. *J. Med. Chem.* 1994, 37, 719; Bock, M. G.; et al. *Bioorg Med. Chem.* 1994, 2, 987; Bock, M. G.; et al. *Tetrahedron Lett.* 1987, 28, 939; Bock, M. G.; et al. *J. Med. Chem.* 1990, 33, 450; Bourrain, S.; Showell, G. A. *Synthesis* 1994, 505; and International Patent Application WO 02/099388; each of which is incorporated herein by reference in its entirety.

Accordingly, a vast number of lactams, lactones and thiolactones are available by art recognized procedures. Similarly, the art is replete with examples of aminocycloalkyl compounds for use in the synthesis of compounds of Formula (I) or Formula (II) above.

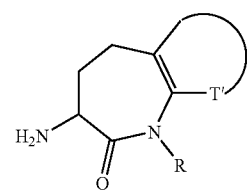

(V)

International Patent Application WO 95/16692 and International Patent Application WO 99/32453 describe the preparation of certain heterocyclic-fused lactams (as shown in Formula IV above, wherein T' together with the carbon atoms of the lactam comprises an optionally substituted cycloalkenyl, aryl, heteroaryl or heterocyclic group) and/or α-amino-ϵ-caprolactams, which can also be used as intermediates in the preparation of the compounds herein described.

$R^1$ may be a sulfonated aminoalkyl such as Formula (VI) below, wherein R is hydrogen or methyl, and $R^{20}$ is an amino acid side chain or where $R^{20}$ and $R^{21}$ and the atoms to which they are attached form a heterocyclic or heteroaryl group of from 4 to 12 ring atoms, and $R^{22}$ is alkyl, substituted alkyl, aryl or substituted aryl.

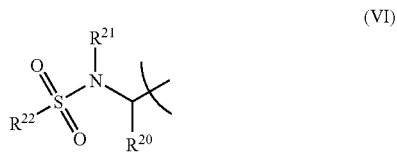

(VI)

Compounds of Formula (I) or Formula (II) wherein $R^1$ is such a sulfonated amino group may be prepared as shown in Scheme 10 below where X, Z', Q, $R^2$, $R^3$, $R^{20}$, $R^{21}$ and $R^{22}$ are as defined herein.

Scheme 10

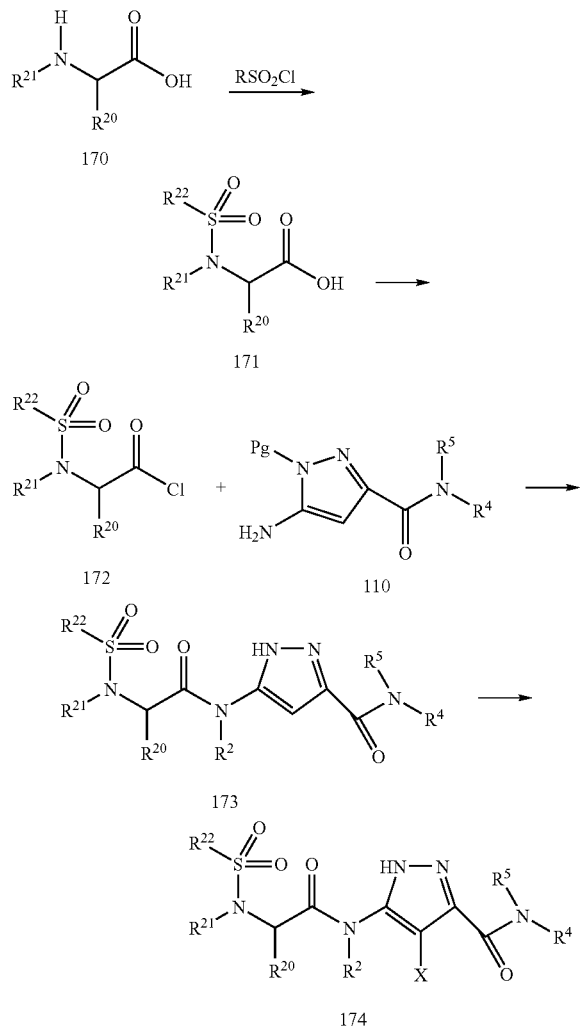

The amine group of compound 170 is converted to the sulfonamide using a suitable sulfonyl chloride, compound 175, and standard reactions conditions. For example, compound 170 may be reacted with an aryl sulfonyl chloride, compound 175, in the presence of a suitable base such as sodium carbonate an inert solvent such as water at a temperature of about 0° C. to about 100° C. until the reaction is substantially complete, typically 1 to about 24 hours. The product, compound 171, can be recovered by conventional methods, such as chromatography, filtration, crystallization, and the like or, alternatively, used in the next step without purification and/or isolation.

Compound 171 is then converted to the acyl chloride using standard conditions. For example, compound 171 may be reacted with $SOCl_2$ in an inert solvent such as dichloromethane at a temperature of about −10° C. to about 39° C. until the the reaction is substantially complete, typically 1 to about 24 hours. The product, compound 172, can be recovered by conventional methods, such as filtration, crystallization, and the like or, alternatively, used in the next step without purification and/or crystallization.

Compound 172 is then coupled to compound 110 to form compound 173, using well known methods which are described herein above for the amidation reactions in Scheme 1 (used to prepare compound 124 and/or compound 125). Compound 123 is functionalized at the 4-position of the pyrazole ring by conventional methods which are described herein above for the halogenation reactions in Scheme 1 (used to prepare compound 107 and/or 125) to afford compound 174.

The sulfonyl chlorides, compound 175, employed in the above reaction are either known compounds or compounds that can be prepared from known compounds by conventional synthetic procedures. Such compounds are typically prepared from the corresponding sulfonic acid, i.e., from compounds of the formula $R^{22}$—$SO_3H$ where $R^{22}$ is as defined above, using phosphorous trichloride and phosphorous pentachloride. This reaction is generally conducted by contacting the sulfonic acid with about 2 to 5 molar equivalents of phosphorous trichloride and phosphorous pentachloride, either neat or in an inert solvent, such as dichloromethane, at temperature in the range of about 0° C. to about 80° C. for about 1 to about 48 hours to afford the sulfonyl chloride. Alternatively, the sulfonyl chlorides can be prepared from the corresponding thiol compound, i.e., from compounds of the formula $R^{22}$—SH where $R^{22}$ is as defined herein, by treating the thiol with chlorine ($Cl_2$) and water under conventional reaction conditions. Examples of sulfonyl chlorides suitable for use in this invention include, but are not limited to, methanesulfonyl chloride, 2-propanesulfonyl chloride, 1-butanesulfonyl chloride, benzenesulfonyl chloride, 1-naphthalenesulfonyl chloride, 2-naphthalenesulfonyl chloride, p-toluenesulfonyl chloride, .2-methylphenylsulfonyl chloride, 4-acetamidobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamidobenzenesulfonyl chloride, 4-nitrobenzenesulfonyl chloride, 4-thioamidobenzenesulfonyl chloride, 4-trifluoromethyl-benzenesulfonyl chloride, 4-trifluoromethoxybenzenesulfonyl chloride, 2,4,6-trimethylbenzenesulfonyl chloride, 2-phenylethanesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfony chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reaction to form the N-sulfonyl amino acids.

Pharmaceutical Formulations

When employed as pharmaceuticals, the compounds of Formula (I) or Formula (II) are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions that contain, as the active ingredient, one or more of the compounds of Formula (I) or Formula (II) above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to 5.0 mL | |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

FORMULATION EXAMPLE 9

An intravenous formulation may be prepared as follows:

| Ingredient | Quantity |
| --- | --- |
| Active Ingredient | 250.0 mg |
| Isotonic saline | 1000 mL |

FORMULATION EXAMPLE 10

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, which is incorporated herein by reference in its entirety. Such patches may be constructed for continuous, pulsatile, or on demand delivery of pharmaceutical agents.

When it is desirable or necessary to introduce the pharmaceutical composition to the brain, either direct or indirect techniques may be employed. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is incorporated herein by reference in its entirety.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Utility

Bradykinin ("BK") is a kinin that plays an important role in the patho-physiological processes accompanying acute and chronic pain and inflammation. Bradykinins, like other related kinins, are autocoid peptides produced by the catalytic action of kallikrein enzymes on plasma and tissue precursors termed kininogens. Inhibition of bradykinin B1 receptors by compounds that are bradykinin B1 antagonists or inverse agonists would provide relief from maladies that mediate undesirable symptoms through a BK B1 receptor pathway.

The compounds of this invention are the bradykinin $B_1$ receptor antagonists and therefore are suitable for use in blocking or ameliorating pain as well as hyperalgesia in mammals. Such compounds would be effective in the treatment or prevention of pain including, for example, bone and joint pain (osteoarthritis), repetitive motion pain, dental pain, cancer pain, myofascial pain (muscular injury, fibromyalgia), perioperative pain (general surgery, gynecological) and chronic pain. In particular, inflammatory pain such as, for example, inflammatory airways disease (chronic obstructive pulmonary disease) would be effectively treated by bradykinin B1 antagonist compounds.

The compounds of this invention are also useful in the treatment of disease conditions in a mammal that are mediated, at least in part, by bradykinin $B_1$ receptor. Examples of such disease conditions include asthma, inflammatory bowel disease, rhinitis, pancreatitis, cystitis (interstitial cystitis), uveitis, inflammatory skin disorders, rheumatoid arthritis and edema resulting from trauma associated with burns, sprains or fracture. They may be used subsequent to surgical intervention (e.g. as post-operative analgesics) and to treat inflammatory pain of varied origins (e.g. osteoarthritis, rheumatoid arthritis, rheumatic disease, tenosynovitis and gout) as well as for the treatment of pain associated with angina, menstruation of cancer. They may be used to treat diabetic vasculopathy, post capillary resistance or diabetic symptoms associated with insulitis (e.g. hyperglycemia, diuresis, proteinuria and increased nitrite and kallikrein urinary excretion). They may be used as smooth muscle relaxants for the treatment of spasm of the gastrointestinal tract or uterus or in the therapy of Crohn's disease, ulcerative colitis or pancreatitis. Such compounds may be used therapeutically to treat hyperreactive airways and to treat inflammatory events associated with airways disease e.g. asthma, and to control, restrict or reverse airways hyperreactivity in asthma. They may be used to treat intrinsic and extrinsic asthma including allergic asthma (atopic or non-atopic) as well as exercise-induced asthma, occupational asthma, asthma post-bacterial infection, other non-allergic asthmas and "wheezy-infant syndrome". They may also be effective against pneumoconiosis, including aluminosis, anthracosis, asbestosis, chalicosis, ptilosis, siderosis, silicosis, tabacosis and byssinosis was well as adult respiratory distress syndrome, chronic obstructive pulmonary or airways disease, bronchitis, allergic rhinitis, and vasomotor rhinitis. Additionally, they may be effective against liver disease, multiple sclerosis, atherosclerosis, Alzheimer's disease, septic shock e.g. as anti-hypovolemic and/or anti-hypotensive agents, cerebral edema, headache, migraine, closed head trauma, irritable bowel syndrome and nephritis. Finally, such compounds are also useful as research tools (in vivo and in vitro).

As noted above, the compounds of this invention are typically administered to the mammal in the form of a pharmaceutical composition. Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985).

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount administered to the patient will vary depending upon what is being administered, the purpose of the administration, such as prophylaxis or therapy, the state of the patient, the manner of administration, and the like all of which are within the skill of the attending clinician. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 µg to about 500 µg per kilogram body weight, preferably about 100 mg to about 300 µg per kilogram body weight. Effective doses can be extrapolated from dose-response curves derived from in vitro or animal model test systems.

Alternatively, about 0.1 mg/day to about 1,000 mg/day of a compound, or mixture of compounds, of the present invention may be administered orally, preferably from about 1 mg/day to about 100 mg/day, and more preferably from 5 mg/day to about 50 mg/day. From about 0.5 to about 100 mg/day may be given to a patient for parenteral, sublingual, intranasal or intrathecal administration; for depo administration and implants, from about 0.5 mg/day to about 50 mg/day; for topical administration from about 0.5 mg/day to about 200 mg/day; for rectal administration from about 0.5 mg to about 500 mg; and more preferably for parenteral administration, from about 5 to about 50 mg daily.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| aq or aq. = | aqueous |
| AcOH = | acetic acid |
| $Ac_2O$ = | acetic anhydride |
| bd = | broad doublet |
| bm = | broad multiplet |
| bs = | broad singlet |
| Boc = | N-tert-butoxylcarbonyl |
| $Boc_2O$ = | di-tert-butyl dicarbonate |
| BOP = | benzotriazol-1-yloxy-tris(dimethylamino)phosphonium hexafluorophosphate |
| Cbz = | carbobenzyloxy |
| $CHCl_3$ = | chloroform |
| $CH_2Cl_2$ = | dichloromethane |
| $(COCl)_2$ = | oxalyl chloride |
| conc. = | concentrated |
| d = | doublet |
| dd = | doublet of doublets |
| dt = | doublet of triplets |
| DMAP = | 4-N,N-dimethylaminopyridine |
| DMF = | N,N-dimethylformamide |
| DMSO = | Dimethylsulfoxide |
| EDC = | 1-(3-dimethylaminopropyl)-3-ethylcarbodiimide hydrochloride |
| $Et_3N$ = | Triethylamine |
| $Et_2O$ = | diethyl ether |
| EtOAc = | ethyl acetate |
| EtOH = | Ethanol |
| eq or eq. = | Equivalent |
| g = | gram(s) |
| h or hr. = | hour(s) |
| HATU = | O-(7-azabenzotriazol-1-yl)-1,1,3-,3-tetramethyl-uronium hexafluorophosphate |
| $H_2O$ = | Water |
| HBr = | hydrobromic acid |
| HCl = | hydrochloric acid |
| HOBT = | 1-hydroxybenzotriazole hydrate |
| HPLC = | high performance liquid chromatography |
| $K_2CO_3$ = | potassium carbonate |
| L = | Liter |
| m = | multiplet |
| M = | Molar |
| MeOH = | methanol |
| mg = | milligram |
| $MgSO_4$ = | magnesium sulfate |
| min. = | Minute |
| mL = | milliliter |
| mm = | millimeter |
| mM = | millimolar |
| mmol = | millimol |
| mp = | melting point |
| MP carbonate = | meso porous carbonate |
| MS = | mass spectroscopy |
| N = | normal |
| NaCl = | sodium chloride |
| $Na_2CO_3$ = | sodium carbonate |
| $NaHCO_3$ = | sodium bicarbonate |
| NaOEt = | sodium ethoxide |
| NaOH = | sodium hydroxide |
| $NH_4Cl$ = | ammonium chloride |
| NBS = | N-bromosuccinimide |

| | |
|---|---|
| NCS = | N-chlorosuccinimide |
| NMM = | N-methylmorpholine |
| NMR = | nuclear magnetic resonance |
| psi = | pounds per square inch |
| $PtO_2$ = | platinum oxide |
| PS-trisamine resin = | polystyrene trisamine resin |
| q = | quartet |
| rt = | room temperature |
| s = | singlet |
| sat = | saturated |
| t = | triplet |
| TFA = | trifluoroacetic acid |
| THF = | tetrahydrofuran |
| TLC or tlc = | thin layer chromatography |
| Ts = | tosyl |
| TsCl = | tosyl chloride |
| TsOH = | toluene sulfonic acid |
| μL = | microliter |
| wt/wt = | weight to weight |

In the following examples and procedures, the term "Aldrich" indicates that the compound or reagent used in the procedure is commercially available from Aldrich Chemical Company, Inc., Milwaukee, Wis. 53233 USA; the term "Sigma" indicates that the compound or reagent is commercially available from Sigma, St. Louis Mo. 63178 USA; the term "TCI" indicates that the compound or reagent is commercially available from TCI America, Portland Oreg. 97203; the term "Frontier" or "Frontier Scientific" indicates that the compound or reagent is commercially available from Frontier Scientific, Utah, USA; the term "Bachem" indicates that the compound or reagent is commercially available from Bachem, Torrance, Calif., USA. The term "Matrix" indicates that the compound or reagent is commercially available from Matrix Scientific, Columbia, S.C., USA. The term "Ambinter" indicates that the compound or reagent is commercially available from Ambinter Paris, France.

The following general procedures illustrate general synthetic pathways for preparing 3-amido-5-substituted pyrazole derivatives of Formula (I) or Formula (II) and amine intermediates useful in preparing the same.

General Procedure 1

Preparation of tert-Butoxycarbonylaminoacetyl amides (3)

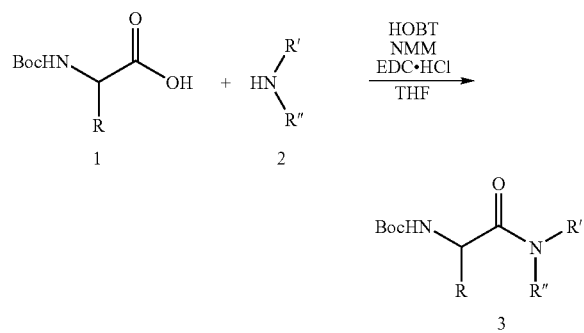

A mixture of 1.0 eq. of Boc-protected amino acid 1, 1.2 eq. of amine (2), 1.2 eq. of HOBT, 2.2 eq. of NMM, and 1.2 eq. of EDC.HCl in THF was stirred at rt. After a time sufficient for reaction completion, 1 M HCl was added to the reaction mixture. The acidified solution was extracted with EtOAc. The combined organic extracts were washed with saturated aqueous $NaHCO_3$ followed by drying over $MgSO_4$. The mixture was filtered. The filtrate was rotary evaporated and dried under vacuum to give amide 3.

GENERAL PROCEDURE 2

Preparation of tert-Butoxycarbonylaminoethyl amines (5).

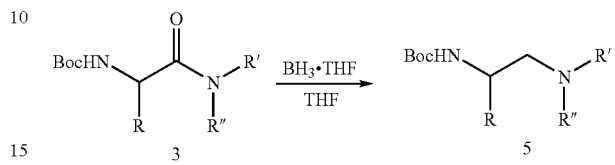

Amide 3 was prepared as described in General Procedure 1. Amine 5 was prepared as shown in General Procedure 2. A solution of 1.0 eq. of amide 3 in dry THF was cooled to 0° C. While stirring, 2.0 eq. of 1.0 M $BH_3$.THF was slowly added. The reaction mixture was allowed to warm to rt and stirred for a time sufficient for reaction completion. A solution of saturated aqueous $NaHSO_4$ was slowly added to the reaction mixture. The mixture was allowed to stir for 10 min and then enough solid NaOH was added to saturate the solution (vigorous bubbling occurred upon neutralization). The saturated solution was extracted with EtOAc. The combined organic extracts were either purified by extracting into 1 M HCl, followed by neutralization with solid $NaHCO_3$, extraction with EtOAC, drying the organic extracts after acidification over $MgSO_4$, filtering, and rotary evaporation; or by concentrating the crude material and flash chromatographing on silica gel using a mixture of EtOAc-hexanes as eluant to afford amine 5.

General Procedure 3

Preparation of 4-Bromo-5-(2-chlorobenzoylamino)-1H-pyrazole-3-carboxylic acid amides

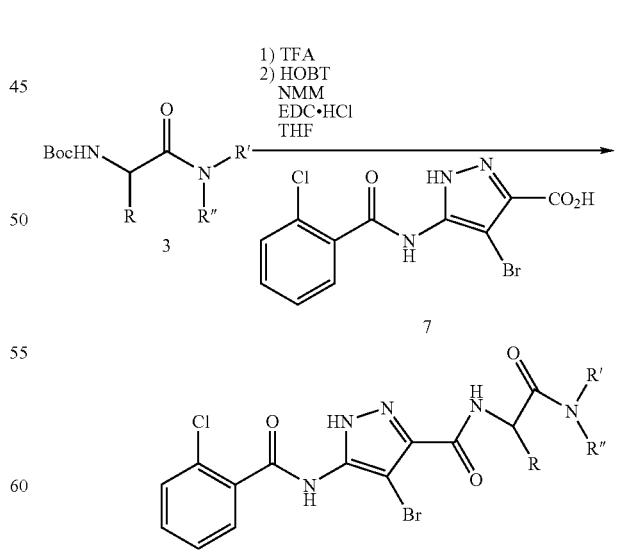

Amide 3 was prepared as described in General Procedure 1. Compound 8 was prepared as shown in General 3. A solution of 1.2 eq. of Boc-protected amide 6 in neat TFA was stirred at rt for 30 min. The reaction solution was rotary evaporated and dried under vacuum to afford the free amine. The deprotected amine was dissolved in THF. While stirring, 1.0 eq. of 7, 1.3 eq. of HOBT, 2.2 eq. of NMM, and 1.2 eq. of EDC.HCl were added in that order. After stirring the reaction mixture at rt for a time sufficient for reaction completion, the mixture was rotary evaporated. The crude material was dissolved in MeOH and flash chromatographed using a mixture of EtOAc-hexanes as eluant to afford product 8.

General Procedure 4

Preparation of [4-Bromo-5-(2-chlorobenzoylamino)-1H-pyrazole-3-carbonyl]aminoacetic acids (10)

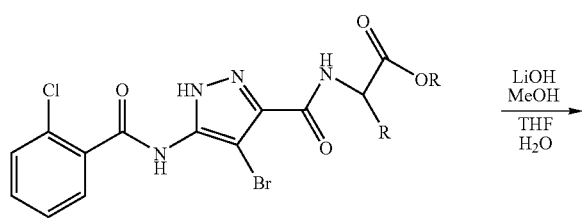

9

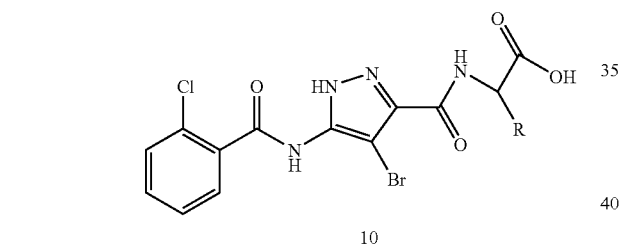

10

A solution of 1.0 eq. of ester 9, prepared as described in General Procedure 10, and 2.6 eq. of LiOH.H$_2$O in MeOH, THF, and H$_2$O (1:2:1) was stirred at rt. After a time sufficient for reaction completion, the reaction solution was rotary evaporated. The crude material was dissolved in water and 1 M HCl was added until the solution's pH was about 4. The acidified solution was extracted with EtOAc. The combined organic extracts were dried over MgSO$_4$ and filtered. The filtrate was rotary evaporated. The crude product was purified by crystallization from MeOH and hexanes to yield acid 10.

General Procedure 5

Preparation of 1-Benzenesulfonyl-4-tert-butoxycarbonylaminopiperidine (12)

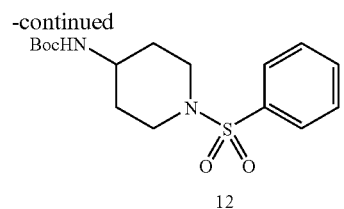

11

12

A solution of 1.0 eq. of 11 in pyridine was prepared. While stirring, 1.0 eq. of phenylsulfonyl chloride was added. After stirring at rt for a time sufficient for reaction completion, the reaction solution was rotary evaporated and 1 M HCl was added. The mixture was extracted with EtOAc. The combined organic extracts were dried over MgSO$_4$ and filtered. The filtrate was rotary evaporated and dried under vacuum to give sulfonamide 12.

General Procedure 6

Preparation of N-Acetyl-N-alkyl-N'-[1-(2-tert-butoxycarbonylamino)ethyl]amines (14)

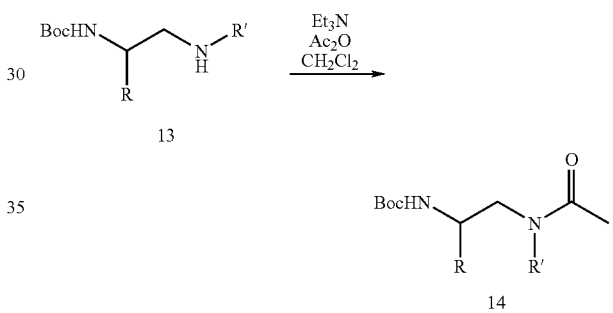

Amine 13 was prepared as described in General Procedure 2. Compound 14 was prepared as illustrated in General Procedure 6. A solution of 1.0 eq. of 13 in dry CH$_2$Cl$_2$ was cooled to 0° C. While stirring, 1.5 eq. of Et$_3$N and 1.5 eq. of acetic anhydride were added. The reaction mixture was allowed to warm to rt. After a time sufficient for reaction completion, the reaction mixture was rotary evaporated and redissolved in EtOAc. The solution was washed with 1 M HCl and saturated aqueous NaHCO$_3$, followed by drying with MgSO$_4$ and filtering. The filtrate was rotary evaporated and purified by flash chromatography on silica gel using a mixture of EtOAc/hexanes as eluant to give 14.

General Procedure 7

Preparation of (R)-tert-Butoxycarbonylalanine cyclopropylmethylamide (16)

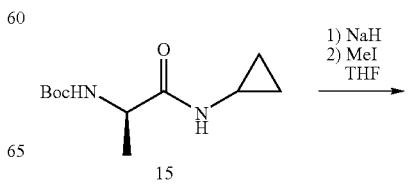

15

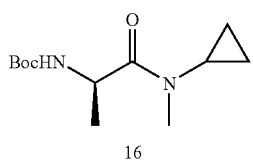

(R)-tert-butoxycarbonylalanine cyclopropylamide (15) was prepared as described in General Procedure 1 using (R)-tert-butoxycarbonylalanine and cyclopropyl amine. Intermediate 16 was prepared as illustrated in General Procedure 7. A solution of 1.0 eq. of 15 in THF was prepared. While stirring, 1.5 eq. of 60% NaH in mineral oil was added.

The reaction mixture was stirred for 10 min and 0.95 eq. of methyl iodide was slowly added. After stirring at rt for a time sufficient for reaction completion, saturated aqueous NH$_4$Cl was added. The mixture was extracted with EtOAc. The combined organic extracts were dried over MgSO$_4$ and filtered. The filtrate was rotary evaporated and purified by flash chromatography on silica gel using a mixture of EtOAc-hexanes as eluant to afford 16.

General Procedure 8

Preparation of 4-Bromo-5-(2-chlorobenzoylamino)-1H-pyrazole-3-carboxylic acid (7)

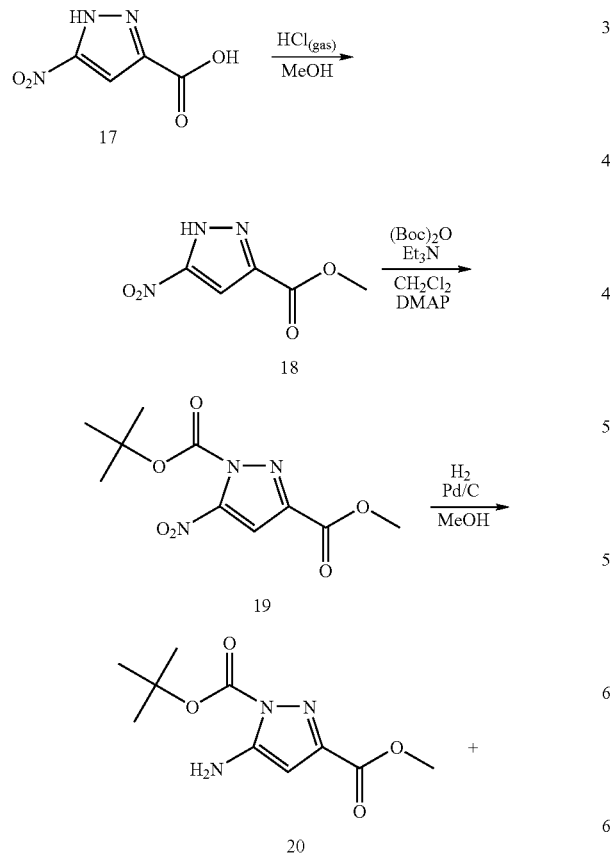

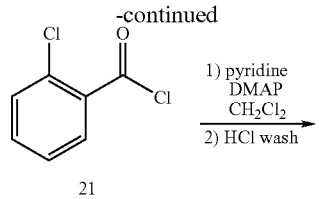

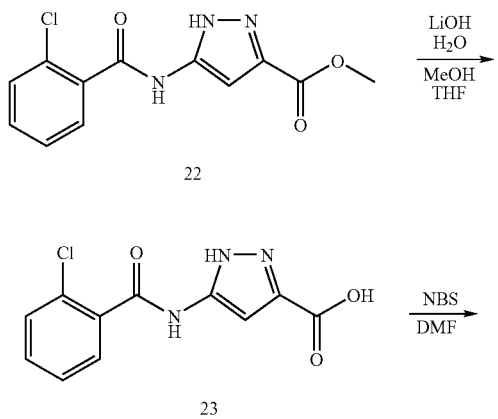

Preparation of 3-Methoxycarbonyl-5-nitropyrazole (18). A solution of 5-nitro-1H-pyrazole-3-carboxylic acid (17, Aldrich, cat. no. 41,483-2) in MeOH was prepared. While stirring, HCl was bubbled through the solution for 2 min. The reaction mixture was refluxed for a time sufficient for complete esterification and allowed to cool to rt. The solvent was removed by rotary evaporation. The crude material was basified by addition of saturated aqueous NaHCO$_3$ and extracting with EtOAc. The combined organic extracts were dried over MgSO$_4$ and filtered. The filtrate was rotary evaporated and dried under vacuum to yield 18.

Preparation of 1-tert-Butoxycarbonyl-3-methoxycarbonyl-5-nitropyrazole (19). A solution of 1.0 eq. of 18, 1.1 eq. of (Boc)$_2$O, 1.5 eq. of Et$_3$N, and 0.05 eq. of DMAP in CH$_2$Cl$_2$ was prepared. The reaction mixture was stirred at rt for a time sufficient for reaction completion and the solvent was removed by rotary evaporation. The crude material was dried under vacuum to afford product 19.

Preparation of 5-Amino-1-tert-butoxycarbonyl-3-methoxycarbonylpyrazole (20). A mixture of 1.0 eq. of 19 and 0.1 wt/wt eq. of 10% Pd on carbon was hydrogenated at 10-60 psi of hydrogen for a time sufficient for reaction completion. The reaction mixture was filtered through Celite. The filtrate was concentrated by rotary evaporation. The crude material was dried under vacuum to give product 20.

Preparation of 5-(2-Chlorobenzoylamino)-3-methoxycarbonylpyrazole (22). A solution of 1.0 eq. of 20, 1.5 eq. of pyridine, and 0.04 eq. of DMAP in CH$_2$Cl$_2$ was prepared. After cooling to 0° C., 1.1 eq. of 2-chlorobenzoyl chloride (Aldrich, cat. no. 10,391-8) was added. The reaction solution was allowed to warm to rt and after a time sufficient for reaction completion, the solvent was removed by rotary evaporation. The crude material was redissolved in 1 M HCl and extracted with EtOAc. The combined organic extracts were washed with saturated aqueous NaHCO₃, followed by drying over MgSO₄ and filtering. The filtrate was rotary evaporated and dried under vacuum to yield 22.

Preparation of 5-(2-Chlorobenzoylamino)-1H-pyrazole-3-carboxylic acid (23). A solution of 1.0 eq. of 22 and 5.0 eq. of LiOH.H₂O in THF, MeOH, and H₂O (2:1:1) was stirred at rt. After a time sufficient for reaction completion, the reaction mixture was rotary evaporated. The mixture was acidified with concentrated HCl. As the pH of the solution reached about 2, a precipitate formed. The solid was collected by filtration and after drying under vacuum, product 23 was obtained.

Preparation of the title compound (7). A solution of 1.0 eq. of 23 in DMF was prepared. While stirring, a solution of 1.2 eq. of N-bromosuccinamide in DMF was added. After stirring at rt for a time sufficient for reaction completion, H₂O was added. The mixture was extracted with EtOAc. The combined organic extracts were washed with 1 M HCl, followed by drying over MgSO₄ and filtering. The filtrate was rotary evaporated. The crude material was triturated with CH₂Cl₂ and dried under vacuum to yield 7.

General Procedure 9

Preparation of 4-Chloro-5-(2-chlorobenzoylamino)-1H-pyrazole-3-carboxylic acid (24)

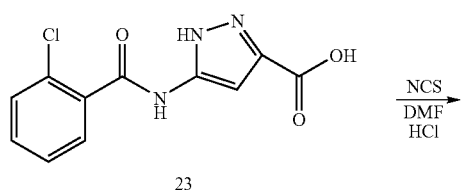

A solution of 1.0 eq. of 23 in DMF was prepared. While stirring, 1.3 eq. of N-chlorosuccinamide and a small amount of concentrated HCl were added. After stirring at rt for a time sufficient for reaction completion, H₂O was added. The quenched reaction solution was extracted with EtOAc. The combined organic extracts were dried over MgSO₄ and filtered. The filtrate was rotary evaporated. The crude material was triturated with CH₂Cl₂ and dried under vacuum to yield 24.

General Procedure 10

Preparation of (R)-4-Bromo-5-(2-chlorobenzoylamino)-1H-pyrazole-3-carboxylic acid amides (25)

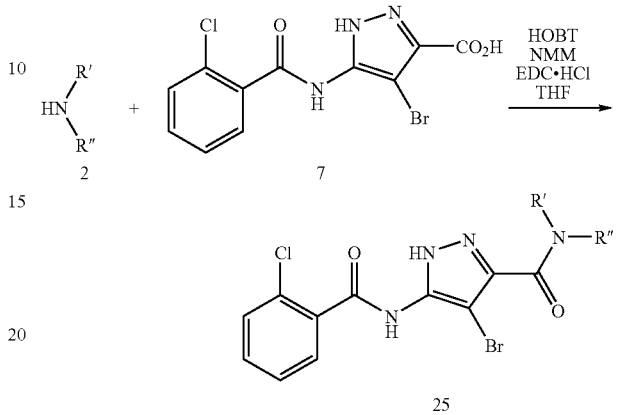

Compound 7 was prepared as shown in General Procedure 8. Compound 25 was prepared as shown in General Procedure 10. A mixture of 1.0 eq. of 7, 1.1 eq. of 2, 1.2 eq. of HOBT, 2.2 eq. of NMM, and 1.2 eq. of EDC. HCl in THF was stirred at rt. After a time sufficient for reaction completion, the reaction mixture was adsorbed onto silica gel and flash chromatographed using a mixture of EtOAc/hexanes as eluant to give product 25.

General Procedure 11

Preparation of 4-Bromo-5-(2-chlorobenzoylamino)-1H-pyrazole-3-carboxylic acid anilinoamides (27)

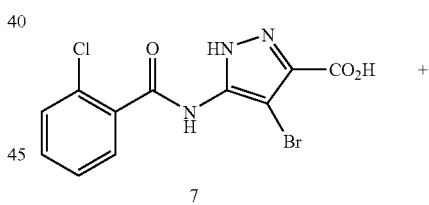

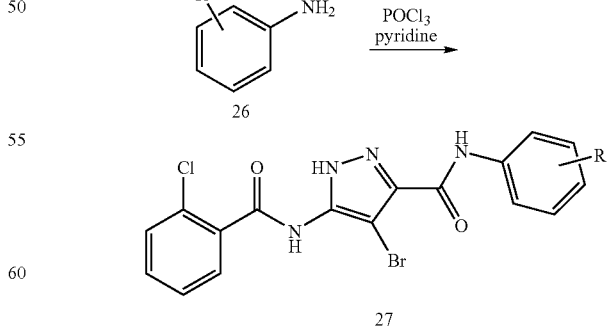

A solution of 1.0 eq. of 7 and 1.3 eq. of 26 in dry pyridine was cooled to −10° C. While stirring, 1.1 eq. of POCl₃ was added dropwise. The cooling bath was removed after 10 min and the mixture was stirred at rt. After 10 min, 1.0 M HCl was added. The mixture was extracted with EtOAc. The combined organic extracts were washed with saturated aqueous NaHCO₃, followed by drying over MgSO₄ and filtering. The filtrate was rotary evaporated. The crude material was flash chromatographed using a mixture of EtOAc -hexanes as eluant to yield 27.

General Procedure 12

Preparation of 5-[(2-Chloro-benzoyl)-methyl-amino]-1H-pyrazole-3-carboxylic acid methyl ester (29)

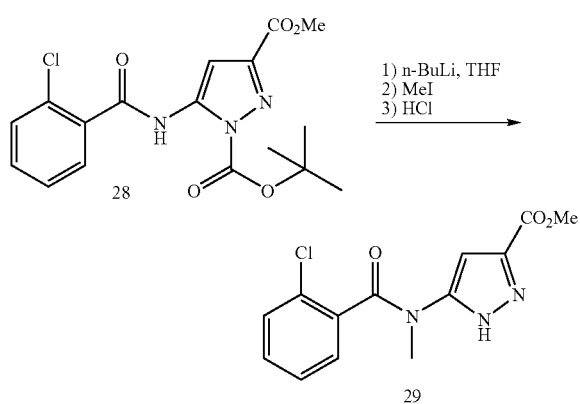

A suspension of 1.0 eq. of ester 28 in THF was stirred at −78° C. as 2.0 eq. of a 2.5 M solution of n-BuLi in THF was added. The cooling bath was removed and the reaction mixture was allowed to stir while warming for 10 min. The mixture was cooled back to −78° C. and 2.0 eq. of MeI was added. The bath was again removed and the reaction mixture was allowed to warm to rt. After a time sufficient for reaction completion, the reaction was quenched with 1 M HCl and extracted with EtOAc. The organic layer was washed with sat. aq. NaHCO₃, dried over MgSO₄, filtered and the solvent removed by rotary evaporation. The material was purified by flash chromatography on silica gel using a mixture of EtOAc-hexanes as eluant to afford 29.

General Procedure 13

Preparation of Aminoalkyl-N-(methyl)piperidines (33)

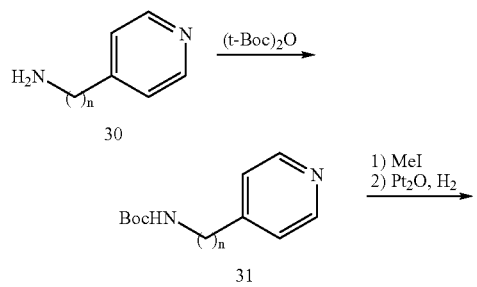

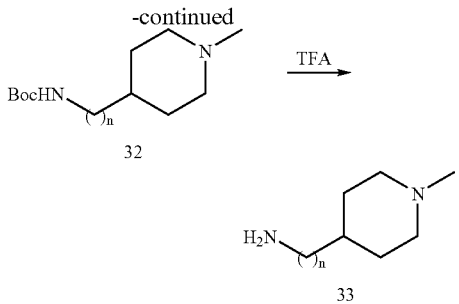

Preparation of tert-Butoxycarbonylaminoalkyl pyridines (31). A flask was charged with 1.1 eq. of (t-Boc)₂O and placed in an ice bath as 1.0 eq. of pyridine 30 was added dropwise (Caution: exotherm and vigorous gas evolution). After addition, the bath was removed and the reaction mixture was allowed to stir at rt for a time sufficient for reaction completion. The product was then vacuum distilled from the reaction mixture to afford 31.

Preparation of tert-Butoxycarbonylaminoalkyl-N-methylpiperidines (32). Pyridine 31 (1.0 eq.) was dissolved in MeOH/CH₂Cl₂ (2:1) to prepare a 2.5 M solution. To this was added 4 eq. of MeI and the mixture was heated in a sealed tube for a time sufficient for reaction completion. The solvent was removed under vacuum to afford the N-methylpyridium salt which can be used directly without further purification.

The N-methylpyridinium salt was dissolved in dry MeOH and cooled to 0° C. Excess NaBH₄ was added and the mixture was allowed to stir for 30 min. The solvent was then removed and water was added to the crude product and sonicated for 10 min. Upon filtration, the solvent was removed to afford the 1,2,3,6 tetrahydropyridine. The tetrahydropyridine was then hydrogenated with hydrogen/PtO₂ at about 10-60 psi to afford 32.

Preparation of the title compound (33). A solution of piperidine 32 in neat trifluoroacetic acid was stirred for 10-30 min. The trifluoroacetic acid was then removed by rotary evaporation to afford 33.

General Procedure 14

Preparation of Aminoalkyl-N-(pyrid-4-yl)piperidines (36)

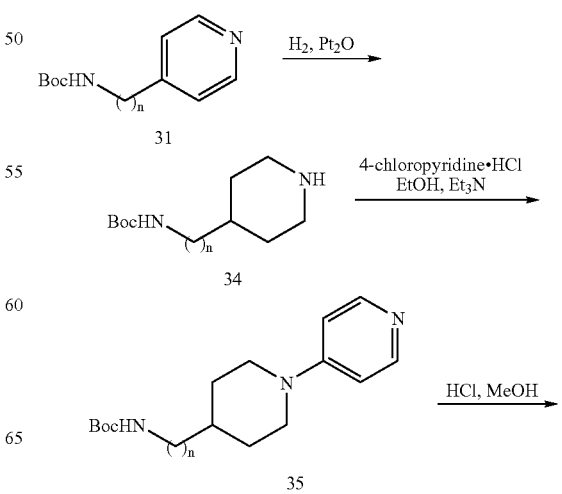

-continued

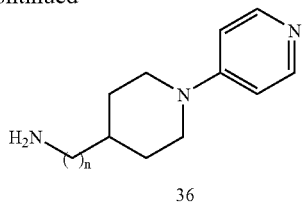

36

Preparation of tert-Butoxycarbonylaminoalkyl piperidines (34). A solution of 1.0 eq. of pyridine 31 (prepared as shown in General Procedure 14) in acetic acid was prepared and 0.1 eq. of $PtO_2$ was added. The mixture was hydrogenated at about 10-60 psi of hydrogen for a time sufficient for reaction completion. Filtration of the mixture through Celite and removal of the solvent afforded piperidine 34 of sufficient purity for further elaboration.

Preparation of tert-Butoxycarbonylaminoalkyl-N-(pyrid-4-yl)piperidines (35). A solution of 1.0 eq. of piperidine 34, 1.0 eq. of 4-chloropyridine hydrochloride and 2.2 eq. of triethylamine in ethanol was refluxed for a time sufficient for reaction completion. The product was isolated by column chromatography on silica gel using EtOAc as eluant to give 35.

Preparation of the title compound (36). Piperidine 35 was dissolved in a mixture of EtOAc and EtOH and HCl was bubbled through the solution. The reaction mixture was stirred for a time sufficient for reaction completion and concentrated. The crude material was triturated with EtOAc to afford 36 as its hydrochloride salt.

General Procedure 15

Preparation of Aminoalkyl-N-(phenyl)piperidines (38)

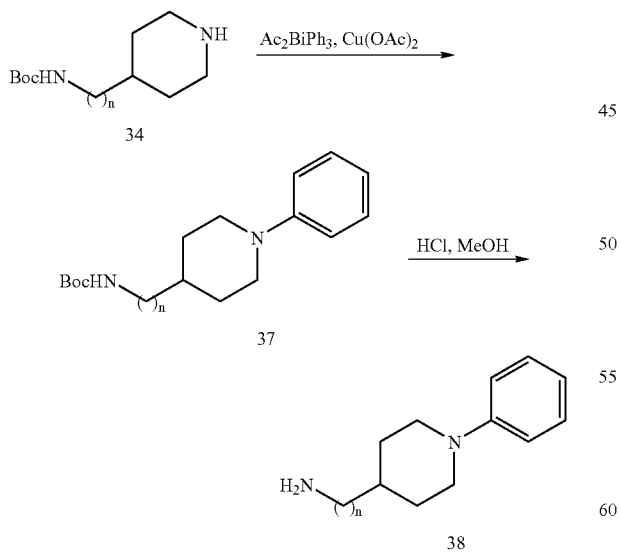

Preparation of tert-Butoxycarbonylaminoalkyl-N-(phenyl)piperidines (37). A solution of 1.0 eq. of piperidine 34 in $CH_2Cl_2$ was stirred at rt as 1.2 eq. of triphenylbismuth diacetate (Aldrich, cat. no. 48,572-1) and 0.12 eq. of $Cu(OAc)_2$ was added. The reaction mixture was stirred at rt for a time sufficient for reaction completion. The mixture was then partitioned between $CH_2Cl_2$ and water and stirred for 2 h. The organic layer was separated, dried and concentrated. The residue was chromatographed on silica gel to afford 37.

Preparation of the title compound (38). A solution of 4-(2-(tert-butoxycarbonyl-amino)ethyl)-N-(phenyl)piperidine in EtOAc was stirred at 0° C. and HCl gas was bubbled through the solution for 15 min. The reaction mixture was then stirred at rt for a time sufficient for reaction completion after which 38 was recovered by filtration as its hydrochloride salt.

General Procedure 16

Preparation of 4-Bromo-5-[2-(quinolin-8-ylsulfanyl-methyl)benzoylamino]-1H-pyrazole-3-carboxylic acid (43)

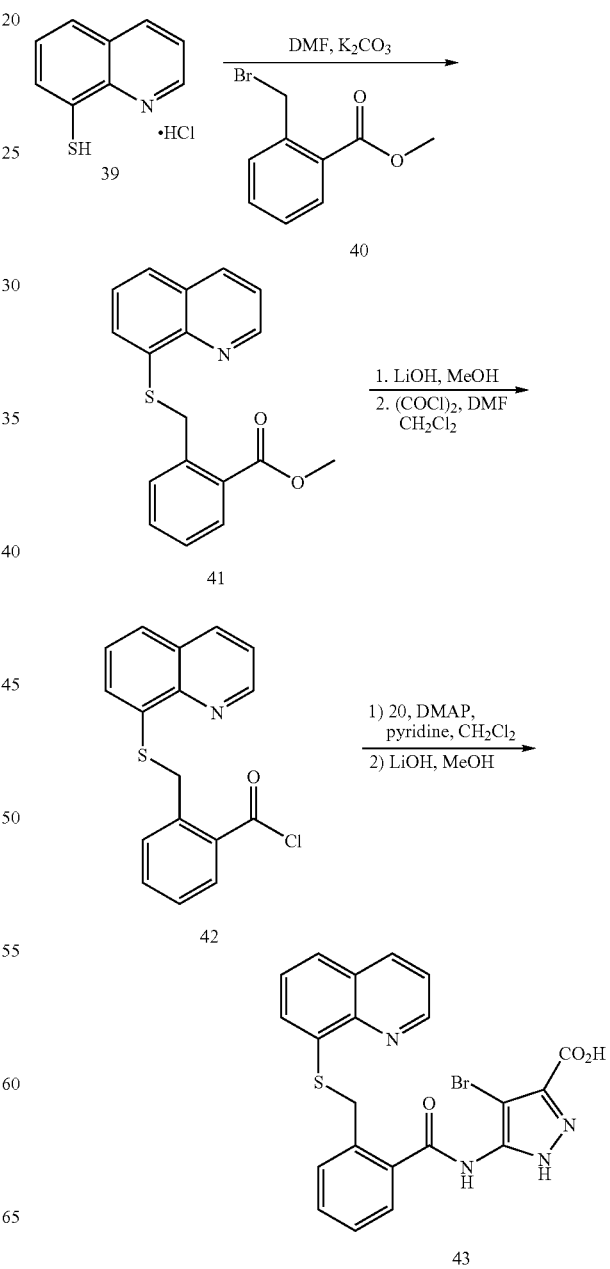

Preparation of 2-(Quinolin-8-ylsulfanylmethyl)benzoic acid methyl ester (41). A solution of 4.0 eq. of quinoline-8-thiol hydrochloride (39, Aldrich, cat. no. 35,978-5) was dissolved in DMF. To this was added 32.0 eq. of potassium carbonate. The mixture was stirred at room temperature for 20 minutes and 1.0 eq of 2-bromomethyl-benzoic acid methyl ester (40, J. Org. Chem, 2002, 67, 2160) was added. The mixture was stirred at room temperature for a time sufficient enough for reaction completion. The mixture was diluted with 0.1 M citric acid and extracted with EtOAc. The organic layer was washed with brine and dried with Na2SO4, filtered, and concentrated. The product was purified by flash chromatography on silica gel using a mixture of EtOAc-hexanes as eluant to give 41.

Preparation of 2-(Quinolin-8-ylsulfanylmethyl)benzoyl chloride (42). A solution of 1.0 eq of ester 41 and 3.0 eq. of LiOH in methanol and water was heated to 65° C. for a time sufficient for completion of the hydrolysis. The mixture was cooled to room temperature and concentrated, then diluted with $H_2O$. The pH of the aqueous mixture was adjusted to 4.5 and extracted with EtOAc. The organic layer was washed with brine and dried over $Na_2SO_4$, filtered, and concentrated to give the intermediate benzoic acid.

A solution of 1.0 eq. of 2-(quinolin-8-ylsulfanylmethyl) benzoic acid in $CH_2Cl_2$ was cooled to 0° C. To this was added 1.1 eq. of oxalyl chloride followed by one drop of DMF. The mixture was warmed to room temperature and stirred for a time sufficient for reaction completion. The mixture was concentrated to give 42 which was used directly.

Preparation of the title compound (43). The procedure described for compound 22 was employed using 2-(quinolin-8-ylsulfanylmethyl)benzoyl chloride (42). Hydrolysis of the methyl ester as described for compound 23 afforded acid 43.

General Procedure 17

Preparation of 4-Bromo-5-(2-chlorobenzoylamino)-1H-pyrazole-3-carboxylic acid amides (44)

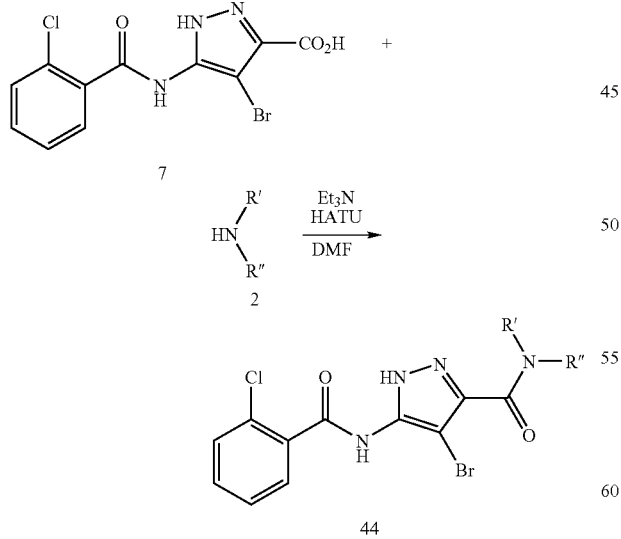

A solution of 1.0 eq. of acid 7, 1.0 eq. of amine 2, and 8.1 eq. of $Et_3N$ in DMF was prepared. While stirring, a solution of 1.0 eq. of HATU dissolved in DMF was added. After stirring at rt for a time sufficient for reaction completion, 6.0 eq. of MP-carbonate resin and 6.0 eq. of PS-trisamine resin (both from Argonaut Technologies, Inc.) were added. The mixture was stirred at rt for 16 hrs, filtered, and washed with DMF and MeOH. The crude material was purified by reverse-phase HPLC using a mixture of acetonitrile-water as eluant. The purified material was concentrated and dried to afford amide 44.

General Procedure 18

Preparation of 5-(2-Chloro-benzoylamino)-4-methyl-1H-pyrazole-3-carboxylic acid (51)

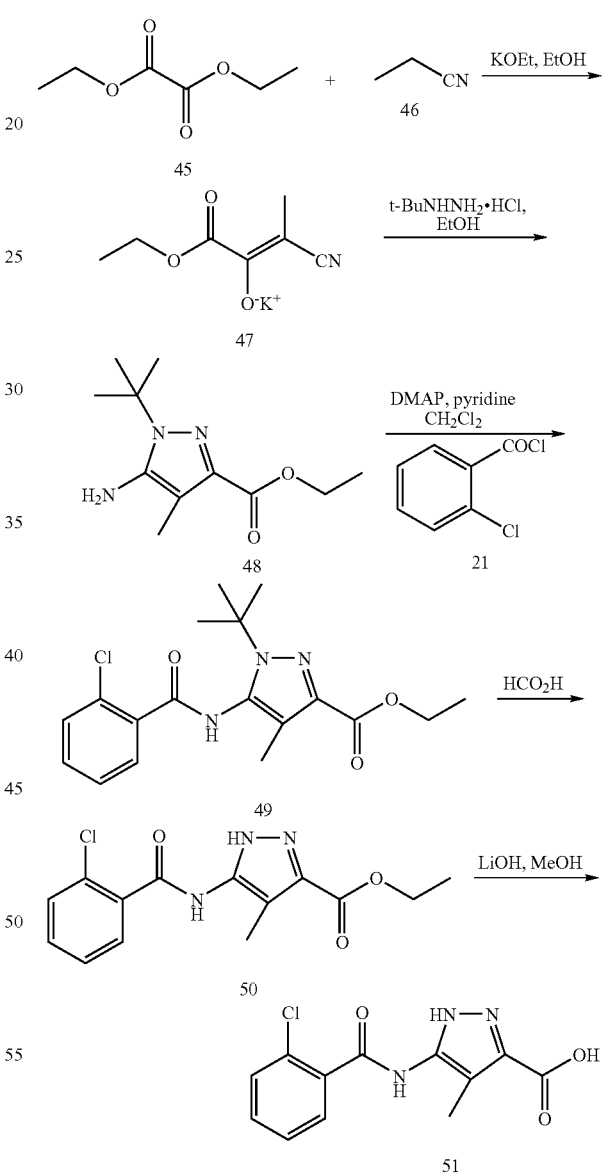

Preparation of Potassium 2-cyano-1-ethoxycarbonyl-2-methylethenolate (47). Placed potassium ethoxide (1.0 eq.) in a sealed tube with EtOH and shook until dissolved. A mixture of diethyl oxalate (1.0 eq.) and propionitrile (1.0 eq.) was added to the sealed tube and the mixture was capped and stirred at reflux. After a time sufficient for reaction completion, the reaction was cooled and the precipitate collected and washed with diethyl ether to afford 47.

Preparation of 5-Amino-1-tert-butyl-4-methyl-1H-pyrazole-3-carboxylic acid ethyl ester (48). Placed 47 (1.0 eq.) into a sealed pressure reaction flask. Added EtOH and t-butylhydrazine hydrochloride (1.1 eq.). The pressure flask was capped and heated to reflux. After a time sufficient for reaction completion, the mixture was evaporated to dryness and the solid obtained was dissolved in equal amounts of EtOAc and water. The organic layer was washed with saturated aqueous $NaHCO_3$, brine, dried with $MgSO_4$, and evaporated. This slightly yellow solid was triturated with hexanes and filtered to afford ester 48.

Preparation of 1-tert-Butyl-5-(2-chloro-benzoylamino)-4-methyl-1H-pyrazole-3-carboxylic acid ethyl ester (49). The procedure described for compound 22 was employed using 5-amino-1-tert-butyl-4-methyl-1H-pyrazole-3-carboxylic acid ethyl ester (49).

Preparation of 5-(2-Chloro-benzoylamino)-4-methyl-1H-pyrazole-3-carboxylic acid ethyl ester (50). Ester 48 was dissolved in a minimal amount of formic acid and heated to 80° C. for a time sufficient for reaction completion. Formic acid was removed via rotary evaporation to yield 50.

Preparation of the title compound (51). The procedure described for compound 23 was employed using 5-(2-chlorobenzoylamino)-4-methyl-1H-pyrazole-3-carboxylic acid ethyl ester (50).

General Procedure 19

Preparation of N-(5-Carboxyalkyl-4-methyl-2H-pyrazol-3-yl)-2-chloro-benzamide (55)

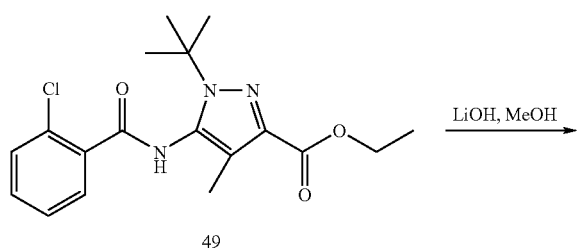
49

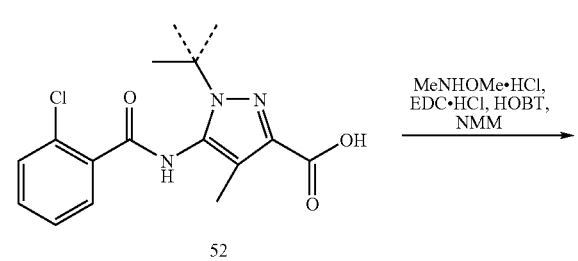
52

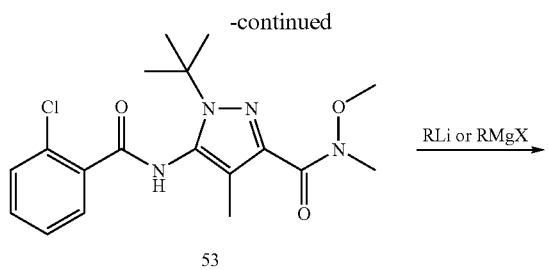
53

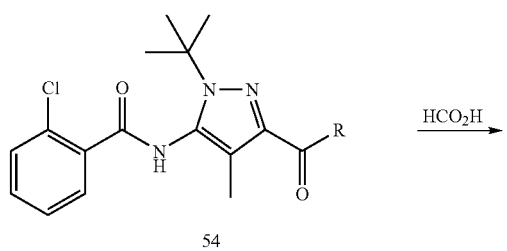
54

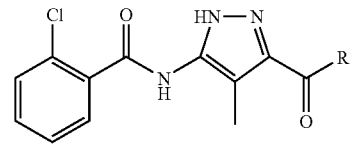
55

Preparation of 1-tert-Butyl-5-(2-chloro-benzoylamino)-4-methyl-1H-pyrazole-3-carboxylic acid (52). The procedure described for compound 23 was employed using 1-tert-butyl-5-(2-chlorobenzoylamino)-4-methyl-1H-pyrazole-3-carboxylic acid ethyl ester (49) to afford acid 52.

Preparation of 1-tert-Butyl-5-(2-chlorobenzoylamino)-4-methyl-1H-pyrazole-3-carboxylic acid methoxymethylamide (53). The procedure described for compound 3 was employed using 1-tert-butyl-5-(2-chloro-benzoylamino)-4-methyl-1H-pyrazole-3-carboxylic acid (52) and N,O-dimethylhydroxylamine hydrochloride (Aldrich, cat. no. D16,370-8).

Preparation of N-(5-Carboxyalkyl-2-tert-butyl-4-methyl-2H-pyrazol-3-yl)-2-chlorobenzamides (54). To a flask equipped with a stirbar was added 53 (1.0 eq.) dissolved in THF under a nitrogen atmosphere. The mixture was cooled to −10° C. and a 1.4 M solution of MeLi (6.0 eq.) in diethyl ether was added dropwise. The mixture was allowed to slowly warm to room temperature and stirred for a time sufficient for reaction completion. The reaction was poured into 0.1 N HCl and extracted with dichloromethane, dried over MgSO4, filtered and concentrated to a crude oil. The crude material was purified by column chromatography eluting with a mixture of EtOAc-hexanes to afford 54.

Preparation of the title compound (55). The procedure described for compound 50 was employed using benzamide 54.

General Procedure 20

Preparation of 3-Amino-5-phenyl-1,3-dihydro-benzo[e][1,4]diazepin-2-one (57)

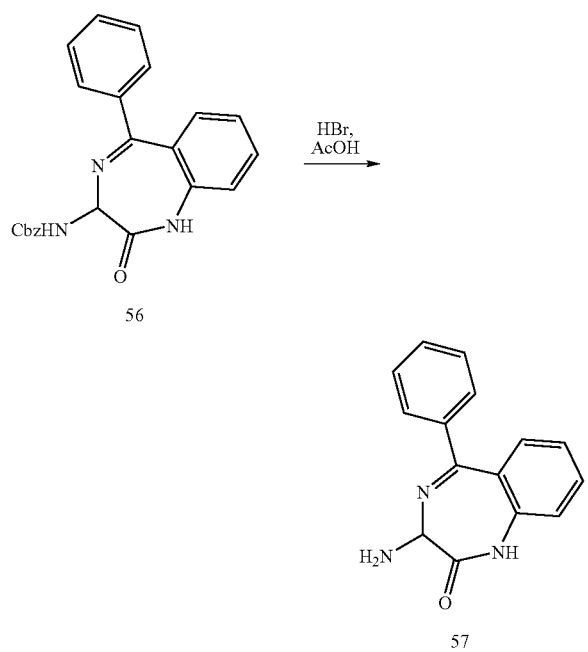

Carbamate 56 (1 mmol) was dissolved in 30% wt HBr in acetic acid, heated to 70° C. and stirred for 20 min. The temperature was raised to 80° C. and maintained for an additional 20 min. The reaction mixture was cooled to ambient temperature, the volatiles were removed under vacuum. The residue was triturated with saturated aqueous NaHCO3, and the solid was filtered and washed with water, followed by diethyl ether to yield the amine 57.

General Procedure 21

Preparation of 4-Bromo-5-(2-m-tolylsulfanylmethyl-benzoylamino)-1H-pyrazole-3-carboxylic acid (62)

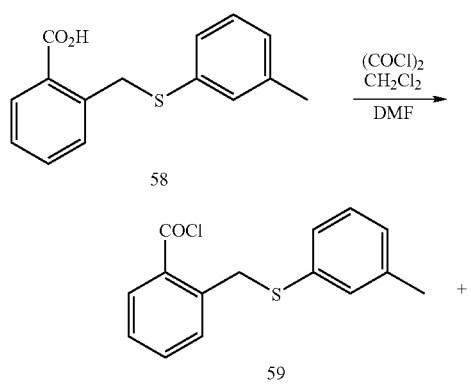

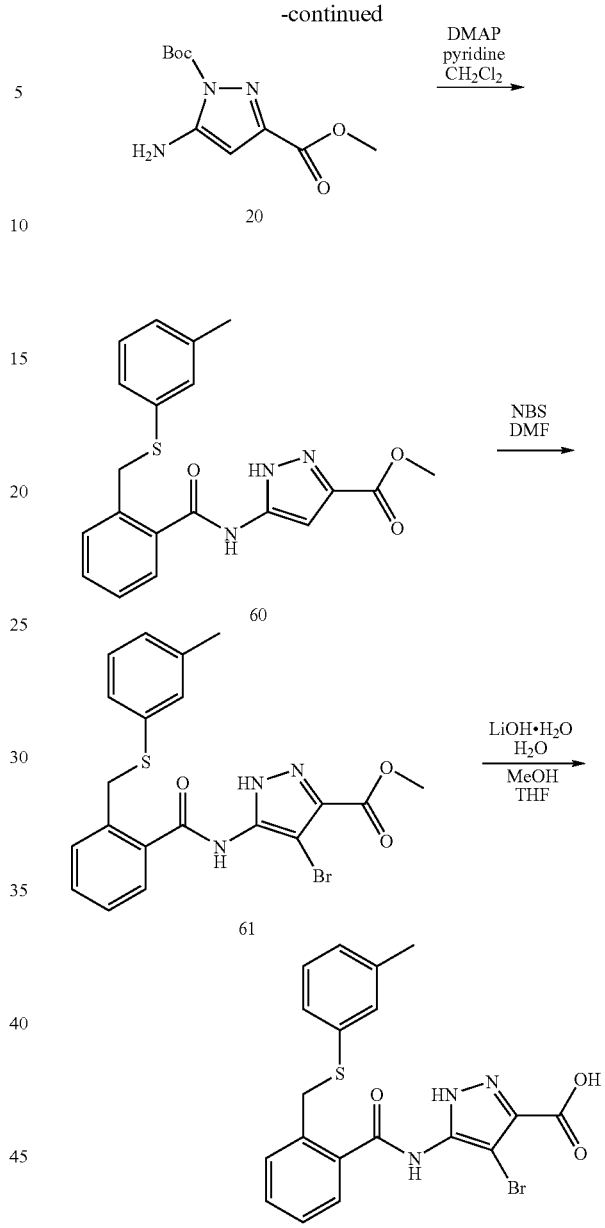

Preparation of 2-m-Tolylsulfanylmethyl-benzoyl chloride (59). A solution of 1.0 eq. of 58 (*Coll. Czech. Chem. Comm.* 1982, 47, 3094) in $CH_2Cl_2$ was prepared. While stirring, 1.1 eq. of oxalyl chloride and one drop of DMF was added. After stirring at rt for a time sufficient for reaction completion, the reaction mixture was rotary evaporated and dried under vacuum to produce 59.

Preparation of 5-(2-m-Tolylsulfanylmethybenzoylamino)-1H-pyrazole-3-carboxylic acid methyl ester (60). A solution of 1.1 eq. of 20, 1.1 eq. of pyridine, and 0.07 eq. of DMAP in $CH_2Cl_2$ was cooled to 0° C. While stirring, a solution of 1.0 eq. of 59 in $CH_2Cl_2$ was added. The reaction solution was allowed to warm to rt. After a time sufficient for reaction completion, the reaction solution was concentrated by rotary evaporation and 1.0 M HCl was added. The acidified solution was extracted with EtOAc. The combined organic extracts were washed with saturated aqueous $NaHCO_3$, followed by drying over MgSO₄ and filtering. The filtrate was rotary evaporated and the crude material was purified by flash chromatography on silica gel using a mixture of EtOAc-hexanes as eluant to give 60.

Preparation of 4-Bromo-5-(2-m-tolylsulfanylmethylbenzoylamino)-1H-pyrazole-3-carboxylic acid methyl ester (61). A solution of 1.0 eq. of 60 in DMF was prepared. While stirring, a solution of 1.1 eq. of NBS in DMF was added. After stirring at rt for a time sufficient for reaction completion, water was added. The solution was extracted with EtOAc. The combined organic extracts dried over MgSO₄ and vacuum filtered. The filtrate was rotary evaporated and the crude material was purified by flash chromatography on silica gel using a mixture of EtOAc-hexanes as eluant to give 61.

Preparation of the title compound (62). The procedure described for compound 23 was employed with methyl ester 61 to afford acid 62.

General Procedure 22

Preparation of 1-Methyl-2-(1-methyl-piperidin-4-yl)-ethylamine acetate (67)

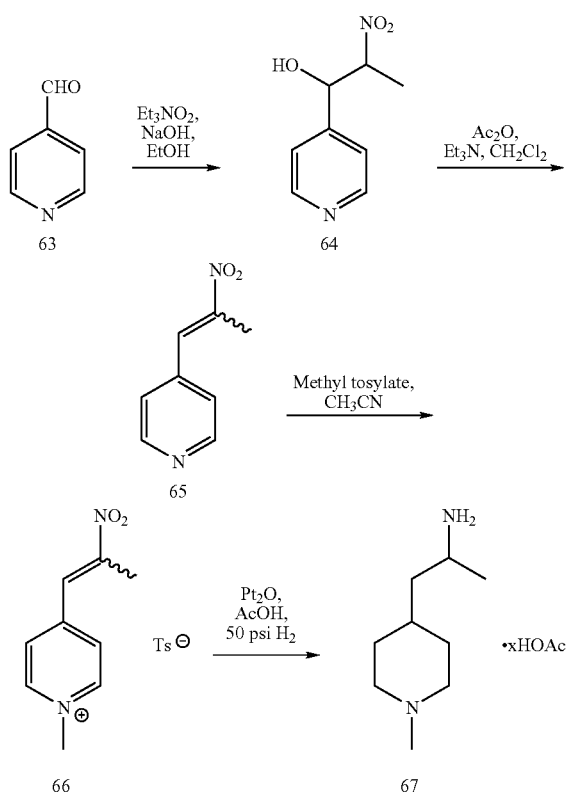

Preparation of 2-Nitro-1-pyridin-4-yl-propan-1-ol (64). A solution of 1.0 eq. of 4-pyridinecarboxaldehyde (63, Aldrich, cat. no. P6,240-2) and 1.5 eq of nitroethane (Aldrich, cat. no. 22,787-0) in absolute EtOH was stirred at 0° C. as a solution of 2.0 eq. of NaOH in water was added. After a time sufficient for reaction completion, the reaction mixture was concentrated by rotary evaporation and neutralized (pH 7-8) with conc. HCl. A white precipitate formed. The mixture was extracted with EtOAc. The organic layer was dried over MgSO4, filtered and the solvent removed by rotary evaporation. The material was purified by flash chromatography on silica gel using a mixture of MeOH—CH2Cl2 as eluant to afford 64 as a mixture of diastereomers.

Preparation of (E,Z)-4-(2-Nitro-propenyl)-pyridine (65). A solution of 1.0 eq. of 2-nitro-1-pyridin-4-yl-propan-1-ol (64) and 5.0 eq. of Et3N in CH2Cl2 was stirred at rt as 5.0 eq. of Ac2O was added. The reaction mixture was refluxed for 2 h and cooled to rt. The reaction mixture was adsorbed directly onto silica gel and flash chromatographed using a mixture of MeOH—CH2Cl2 as eluant to afford 65 as a mixture of E and Z isomers.

Preparation of 1-Methyl-4-(2-nitro-propenyl)-pyridinium tosylate (66). A solution of 1.0 eq. of (E,Z)-4-(2-nitro-propenyl)-pyridine (65) and 1.1 eq. of methyltosylate in CH3CN was stirred at rt for a time sufficient for reaction completion. The reaction mixture was then diluted with ether and filtered to afford 66 as a tan solid.

Preparation of the title compound (67). A mixture of 1-methyl-4-(2-nitro-propenyl)-pyridinium tosylate (66) and Pt2O (10 wt %) in AcOH was agitated under 50 psi of H2 (gas) for a time sufficient for reaction completion. The mixture was filtered through Celite and the solvent removed by rotary evaporation to afford compound 67.

General Procedure 23

Preparation of tert-Butoxycarbonylamino-1-methyl lactams (70)

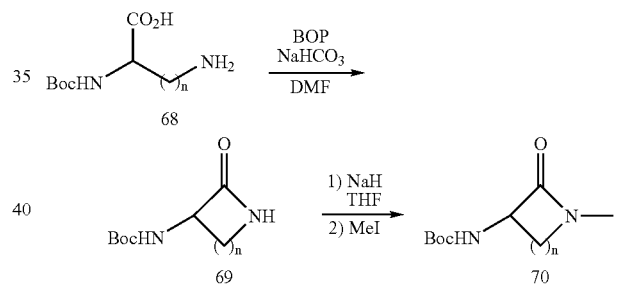

Preparation of tert-Butoxycarbonylamino lactams (69). A mixture of 1.0 eq. of 68 (n=1 to 5) and 5.2 eq. of solid NaHCO₃ in DMF was prepared. While stirring, 1.0 eq. of BOP (Aldrich, cat. no. 22,608-4) was added. After stirring at rt for a time sufficient for reaction completion, the DMF was stripped off by rotary evaporation and saturated aqueous NaHCO₃ was added. The mixture was extracted with EtOAc. The combined organic extracts were washed with saturated aqueous NaHCO₃ followed by drying over MgSO₄ and vacuum filtering. The filtrate was rotary evaporated and the crude material was purified by recrystallization with EtOAc and hexanes to give lactam 69.

Preparation of the title compound (70). A solution of 1.0 eq. of 69 in dry THF was prepared. While stirring, 1.5 eq of 60% NaH in mineral oil was added. The mixture was stirred at rt until the evolution of hydrogen ceased and 0.95 eq. of MeI was added. After stirring the mixture at rt for a time sufficient for reaction completion, saturated aqueous NH4Cl was slowly added. The mixture was extracted with EtOAc. The combined organic extracts were dried over MgSO₄ and vacuum filtered. The filtrate was rotary evaporated and dried under vacuum to produce product 70.

General Procedure 24

Preparation of tert-Butoxycarbonyl-3-amino-1-methyl-piperidin-2-one (75) and tert-Butoxycarbonyl-3-amino-3-methyl-piperidin-2-one (76)

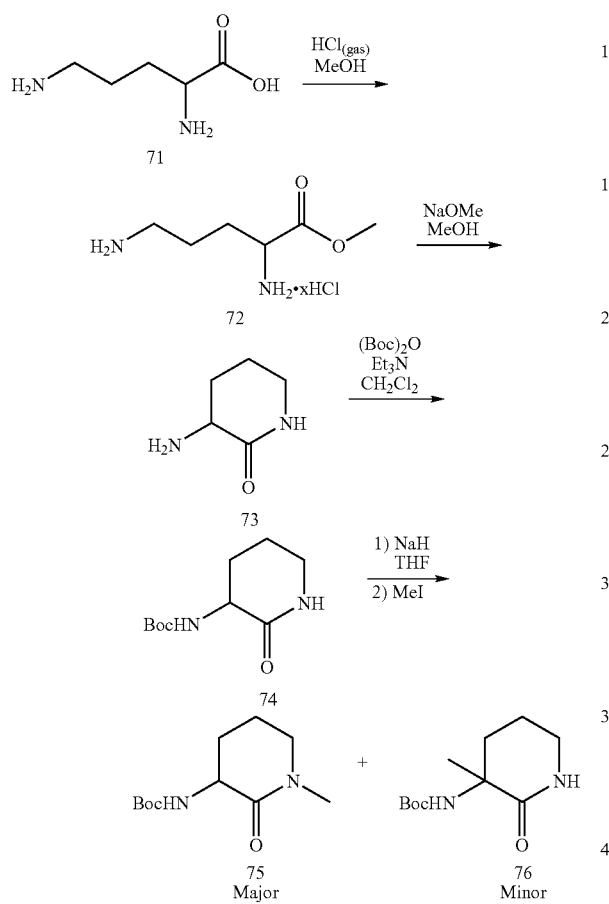

Preparation of 2,5-Diamino-pentanoic acid methyl ester (72). Hydrochloride gas was bubbled through a mixture of 71 in MeOH for 1-5 min. After refluxing the reaction solution for a time sufficient for complete esterification, the solution was concentrated by rotary evaporation and dried under vacuum to produce 72 as its hydrochloride salt.

Preparation of 3-Amino-piperidin-2-one (73). A mixture of 1.0 eq. of 72 in MeOH was prepared. While stirring, 3.0 eq. of NaOMe was added. After stirring the mixture at rt for 1-8 hrs, the mixture was rotary evaporated and dried under vacuum to afford product 73.

Preparation of tert-Butoxycarbonyl-3-amino-piperidin-2-one (74). A suspension of 1.0 eq. of 73 in CH$_2$Cl$_2$ was cooled to 0° C. and 1.2 eq. of (Boc)$_2$O and 1.2 eq. of Et$_3$N was added. The ice bath was removed 10 min later and the reaction mixture was stirred at rt for a time sufficient for reaction completion. The reaction mixture was concentrated by rotary evaporation. The crude material was flash chromatographed on silica gel using EtOAc as eluant to yield 74.

Preparation of the title compound (76). A solution of 1.0 eq. of 74 in THF was prepared. While stirring, 1.5 eq of 60% NaH in mineral oil was added. The mixture was stirred at rt until the evolution of hydrogen ceased and 0.95 eq. of MeI was added. After stirring the mixture at rt for a time sufficient for reaction completion, saturated aqueous NH$_4$Cl was slowly added. The mixture was extracted with EtOAc. The combined organic extracts were dried over MgSO$_4$ and vacuum filtered. The filtrate was rotary evaporated. The crude material was purified by flash chromatography using a mixture of EtOAc-hexanes as eluant to afford 75 as the major and 76 as the minor component.

General Procedure 25

Preparation of 3-Amino-2-oxo-1,2,3,4-tetrahydroquinoline (82)

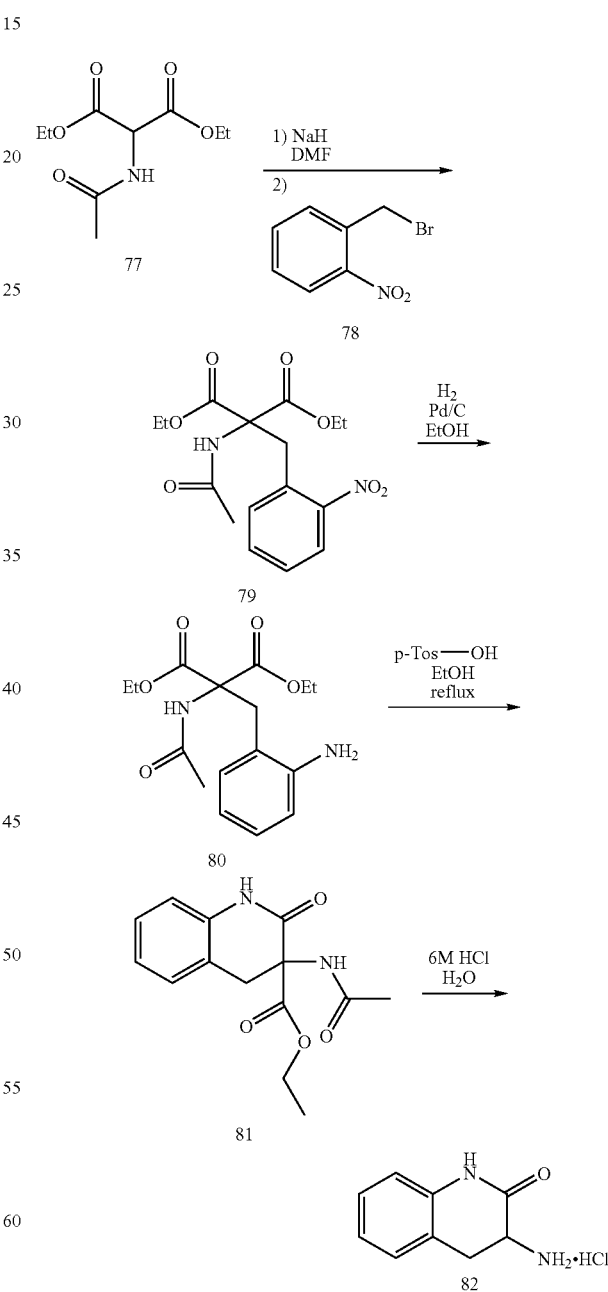

Preparation of 2-Acetylamino-2-(2-nitro-benzyl)-malonic acid diethyl ester (79). A solution of 1.0 eq. of 77 in dry DMF was prepared. While stirring, 1.0 eq. of 60% NaH in mineral oil was slowly added. After gas evolution ceased, a solution of 1.0 eq. of 78 in dry DMF was added. After stirring the reaction mixture at rt for a time sufficient for reaction completion, the solvent was removed by rotary evaporation and the crude material was flash chromatographed on silica gel using a mixture of EtOAc-hexanes as eluant to afford 79.

Preparation of 2-Acetylamino-2-(2-amino-benzyl)-malonic acid diethyl ester (80). A mixture of 1.0 eq. of 79 and 0.1 wt/wt eq. of 10% Pd on carbon in EtOH was hydrogenated at 10-60 psi of hydrogen for a time sufficient for reaction completion. The reaction mixture was filtered through Celite. The filtrate was concentrated by rotary evaporation. The crude material was dried under vacuum to give product 80.

Preparation of 3-Acetylamino-2-oxo-1,2,3,4-tetrahydroquinoline-3-carboxylic acid ethyl ester (81). A solution of 1.0 eq. of 80 and 0.3 eq of p-toluenesulfonic acid hydrate in EtOH was refluxed for 2 hrs. The mixture was then stirred at rt for a time sufficient for reaction completion. After rotary evaporation, 100 mL of saturated aqueous NaHCO₃ was added and the mixture was extracted with EtOAc. The combined organic extracts were dried over MgSO₄ and vacuum filtered. The filtrate was rotary evaporated and dried under vacuum to yield 81.

Preparation of the title compound (82). A mixture of 81 in 6 M HCl was refluxed for a time sufficient for reaction completion. After cooling to rt, the mixture was rotary evaporated and dried under vacuum to give 82 as its hydrochloride salt.

General Procedure 26

Preparation of 5-Amino-1-methyl-1H-pyrazole-3-carboxylic acid methyl ester (86) and 5-Amino-2-methyl-2H-pyrazole-3-carboxylic acid methyl ester (85)

pyrazole-3-carboxylic acid methyl ester (18) (18.6 g, 109 mmol) in anhydrous THF (200 mL) cooled under an ice-water bath. After stirring for 35 min, methyl iodide (20.4 mL, 327 mmol) was added, and the reaction mixture was stirred for 20 hr. The solvent was evaporated and the residue was taken up in EtOAc (200 mL), washed with water (60 mL), and stirred over anhydrous MgSO₄ for 20 min. After filtration and concentration, a colorless oil (22.2 g) was obtained, which was confirmed by HPLC/MS and NMR analyses as a mixture of 83 and 84 (see: Baraldi, Pier Giovanni, et al; *Molecules* [Electronic Publication], 1998, 3(2), M46) in a 1:2.27 ratio.

Preparation of 5-Amino-1-methyl-1H-pyrazole-3-carboxylic acid methyl ester (85) and 5-Amino-2-methyl-2H-pyrazole-3-carboxylic acid methyl ester (86). A solution of a mixture of methyl esters 83 and 84 was dissolved in ethanol (60 mL), 10% Pd/C (1.0 g) was added, and the mixture was hydrogenated at 30 psi of H₂ for 16 hr. The mixture was filtered through a layer of Celite and evaporated to afford a yellow solid (16.0 g), which was indicated by HPLC-MS analysis to be a mixture of 85 and 86. The two isomers were separated by flash chromatography (1:1 EtOAc/hexanes) to yield 86 (9.90 g, 63.9 mmol, 59%) (Ho H. Lee, et al; *J. Org Chem.* 1989, 54, 428-431) and 85 (4.14 g, 26.7 mmol, 24.5%) (Ho H. Lee, et al; *J. Org Chem.* 1989, 54, 428-431).

¹H-NMR (86) (CDCl₃) δ 6.13 (s, 1H), 4.00 (s, 3H), 3.85 (s, 3H),3.62 (br, 2H).

¹H-NMR (85) (CDCl₃) δ 6.06 (s, 1H), 3.86 (s, 3H), 3.72 (s, 3H),3.66 (br, 2H).

General Procedure 27

Preparation of 3-tert-Butoxycarbonylamino-1,5-dimethyl-1,3,4,5-tetrahydro-benzo[b][1,4]diazepin-2-one (92)

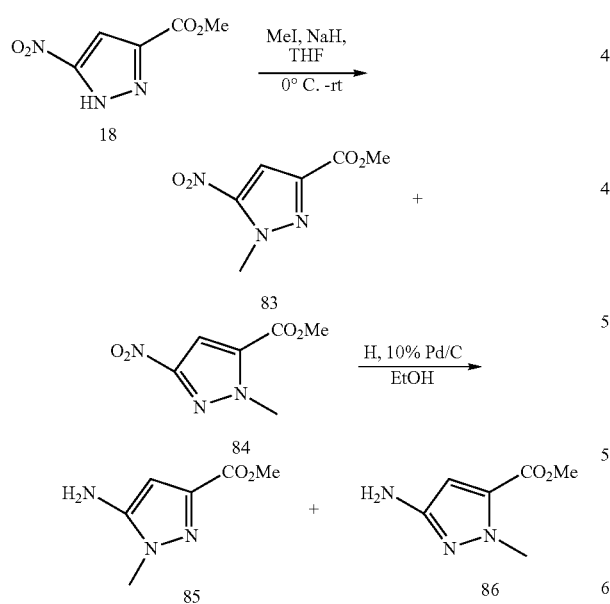

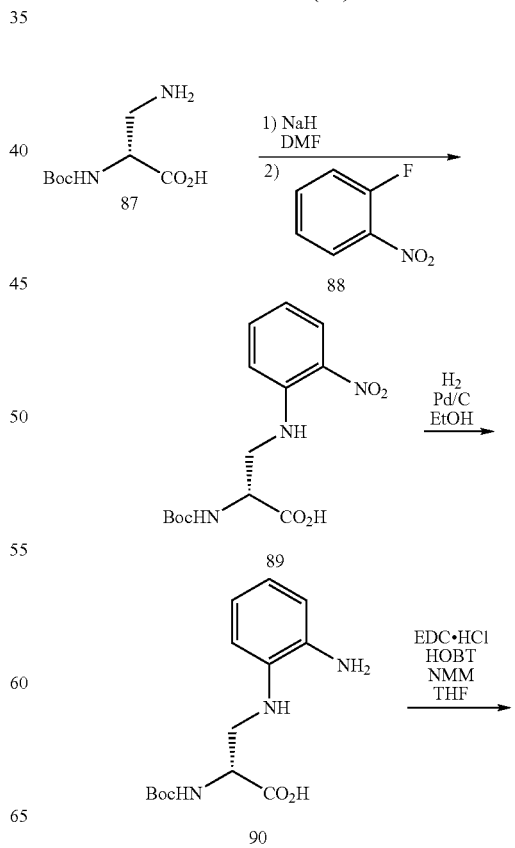

Preparation of 1-Methyl-5-nitro-1H-pyrazole-3-carboxylic acid methyl ester (83) and 2-Methyl-5-nitro-2H-pyrazole-3-carboxylic acid methyl ester (84). A suspension of 60% (weight) NaH dispersion in mineral oil (10.9 g, 273 mmol) was added in portions into a stirred solution of 5-nitro-1H-

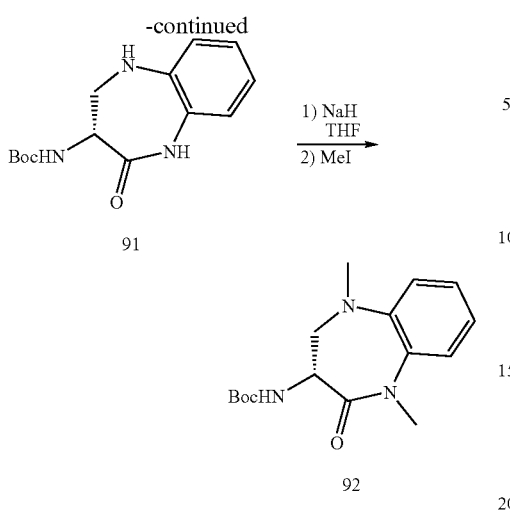

2-tert-Butoxycarbonylamino-3-(2-nitro-phenylamino) propionic acid (89). A solution of 1.0 eq of Boc-D-2,3-diaminopropionic acid (87) (Bachem, A-3590) in 100 mL of dry DMF was cooled to 0° C. While stirring, 2.2 eq of NaH (60% in mineral oil) was added. The mixture was stirred until bubbling ceased (about 30 min), at which time 1.1 eq of 88 was slowly added. The mixture was allowed to warm to rt and was then heated at 50° C. for 20 hrs. The orange colored solution was cooled to rt and the solution was rotary evaporated. The crude reaction mixture was flash chromatographed on silica using a step gradient of 10% and 20% MeOH/$CH_2Cl_2$ as eluents. Product-containing fractions were concentrated and dried to afford acid 89.

3-(2-Amino-phenylamino)-2-tert-butoxycarbonylaminopropionic acid (90). A suspension of 1.0 eq of 89 and 0.1 wt/wt eq of 10% Pd on carbon in 35 mL of EtOH was hydrogenated under 50 psi of $H_2$ for 30 min, until consumption of $H_2$ ceased. The reaction mixture was filtered through Celite. The filtrate was concentrated by rotary evaporation. The crude material was dried under vacuum to give acid 90.

3-tert-Butoxycarbonylamino-1,3,4,5-tetrahydro-benzo[b][1,4]diazepin-2-one (91). A solution of 1.0 eq of 90 in 40 mL of THF was prepared. While stirring, 1.1 eq of HOBT, 2.0 eq of NMM, and 1.1 eq of EDC.HCl was added. The reaction mixture was stirred at rt for 17 hrs. The crude reaction mixture was rotary evaporated and was then flash chromatographed on silica using 50% EtOAc/hexanes as eluant. After concentration and drying under vacuum of the fractions containing product, a yellowish solid as 91 was obtained.

3-tert-Butoxycarbonylamino-1,5-dimethyl-1,3,4,5-tetrahydro-benzo[b][1,4]diazepin-2-one (92). A solution of 1.0 eq of 91 in 10 mL of dry DMF was prepared. While stirring, 2.6 eq of NaH (60% in mineral oil) was added. After bubbling ceased (about 10 min), 2.0 eq of MeI was slowly added. After stirring at rt for 18 hrs, 25 mL of saturated $NH_4Cl$ was added to the reaction mixture. The mixture was extracted with EtOAc (3×50 mL). The combined organics were dried with $MgSO_4$ and filtered. The filtrate was rotary evaporated. The crude was flash chromatographed on silica using a step gradient of 50% and 75% EtOAc/hexanes. After concentration and drying under vacuum of the fractions containing product, a light yellowish solid was obtained as intermediate 92.

General Procedure 28

Preparation of 3-Amino-1,3,4,5-tetrahydro-1-methyl-2H-pyrido[3,2-b]azepin-2-one (99)

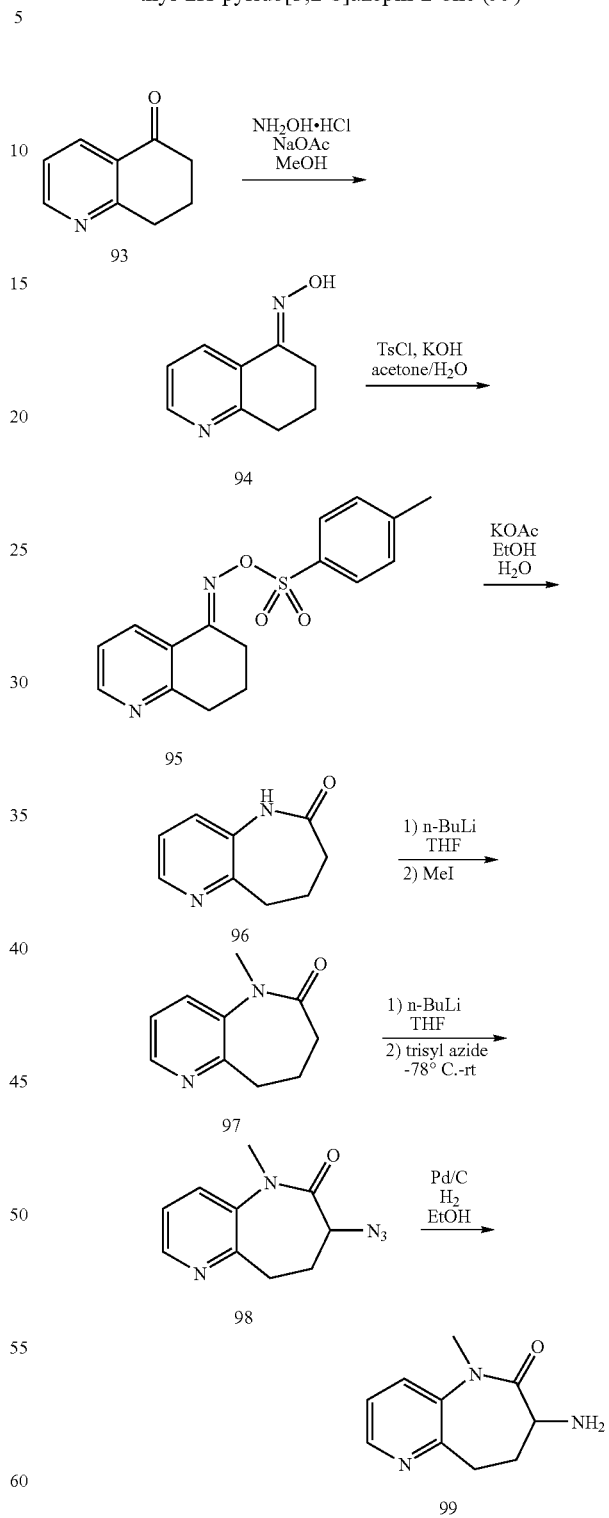

7,8-Dihydro-6H-quinolin-5-one oxime (94). A mixture of 1.0 eq of 5,6,7,8-tetrahydroquinolinone-5 (93) (Tyger Scientific, Ti 1850), 3.0 eq of hydroxylamine hydrochloride (Aldrich, 37,992-1), and 3.0 eq of sodium acetate in 50 mL of MeOH and 15 mL of H₂O was refluxed for 4 hrs. The mixture was allowed to cool to rt. After rotary evaporation of the MeOH, 100 mL of H₂O was added. The solid formed was collected by vacuum filtration. The solid collected was triturated with hexanes and dried under vacuum to give 94.

7,8-Dihydro-5(6H)-quinolinone O-[(4-methylphenyl)sulfonyl]oxime (95). A solution of 1.0 eq of 94 in 25 mL of acetone was prepared. While stirring, 1.5 eq of p-touenesulfonyl chloride (TsCl) (Aldrich, 24,087-7), 10 mL of H₂O, and 1.0 eq of KOH was added. After refluxing the mixture for 30 min, the reaction mixture was rotary evaporated and the remaining solid was washed with 50 mL of H₂0. The crude product was further triturated with diethyl ether and after drying under vacuum gave 95.

5,7,8,9-Tetrahydro-pyrido[3,2-b]azepin-6-one (96). A mixture of 1.0 eq of 95 and 2.3 eq of potassium acetate in 70 mL of EtOH and 140 mL of H₂O was refluxed for 17 hrs. After cooling to rt and rotary evaporation of the EtOH, the solution was made alkaline with 10 N NaOH. The mixture was extracted with chloroform (3×50 mL). The combined organic extracts were dried over MgSO₄ and vacuum filtered. The filtrate was rotary evaporated and dried under vacuum to yield 96.

5-Methyl-5,7,8,9-tetrahydro-pyrido[3,2-b]azepin-6-one (97). A solution of 1.0 eq of 96 in 30 mL of dry THF was cooled to −78° C. While stirring, 1.1 eq of n-BuLi (2.5 M in hexanes) was added dropwise. The reaction solution was warmed to 0° C. and stirred for 1 hr. The solution was then cooled to −78° C. and 1.2 eq of methyl iodide was slowly added. The mixture was stirred, as the solution warmed to rt. After 17 hrs, 50 mL of saturated NH₄Cl was added and extracted with EtOAc (3×50 mL). The combined organic extracts were dried over MgSO₄ and vacuum filtered. The filtrate was rotary evaporated and dried under vacuum to afford a dark orange colored solid as 97.

7-Azido-5-methyl-5,7,8,9-tetrahydro-pyrido[3,2-b] azepin-6-one (98). A solution of 2.5 eq of diisopropylamine in 50 mL of dry THF was cooled to −78° C. While stirring, 2.4 eq of n-BuLi (2.5 M in hexanes) was added dropwise. The reaction mixture was warmed to 0° C. After stirring for 30 min, the solution was cooled to −78° C. and 1.0 eq of 97 dissolved in 20 mL of dry THF was added. After stirring at −78° C. for 30 min, 1.5 eq of trisyl azide was added. The mixture was stirred, as it warmed to rt. After 17 hrs, 4.5 eq of 17 M glacial acetic acid was added and stirred at rt for 5 hrs. The reaction mixture was rotary evaporated and 30 mL of saturated NaHCO₃ was added. The mixture was extracted with EtOAc (3×50 mL). The combined organic extracts were dried over MgSO₄ and vacuum filtered. The filtrate was rotary evaporated and flash chromatographed on silica using EtOAc as eluent. After concentration and drying under vacuum of the fractions containing product, a brownish colored solid was obtained as 98.

3-Amino-1,3,4,5-tetrahydro-1-methyl-2H-pyrido[3,2-b] azepin-2-one (99). A suspension of 1.0 eq of 98 and 0.2 wt/wt eq of 10% Pd on carbon in 10 mL of EtOH was hydrogenated with hydrogen under atmospheric pressure for 18 hrs. The mixture was filtered through Celite. The filtrate was rotary evaporated and dried under vacuum to produce a yellowish colored oil as 99.

General Procedure 29

Preparation of (2-[1,4']Bipiperidin-1'-yl-ethyl)carbamic acid tert-butyl ester (182a) and (2-[1,4']Bipiperidin-1'-yl-2-cyanoethyl)carbamic acid tert-butyl ester (182b)

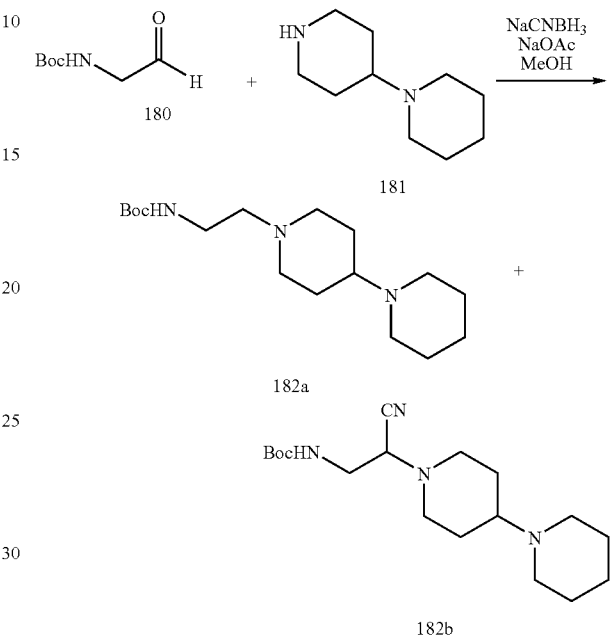

A solution of 1.0 eq of tert-butyl N-(2-oxoethyl)carbamate (180) (Aldrich, 47,265-4) in 50 mL of MeOH was prepared. While stirring, 1.0 eq of 4-piperidinopiperidine (181) (Aldrich, 53,449-8), 2.1 eq of sodium acetate, and 2.1 eq of sodium cyanoborohydride was added. After stirring at rt for 19 hrs, the reaction mixture was rotary evaporated, and flash chromatographed on silica using a step gradient of EtOAc and 2% Et₃N/MeOH as eluents. Concentration of product-containing fractions afforded a mixture of products 182a and 182b as a white solid.

General Procedure 30

Preparation of 4-tert-Butoxycarbonylaminopiperidine-1-carboxylic acid benzyl ester (185)

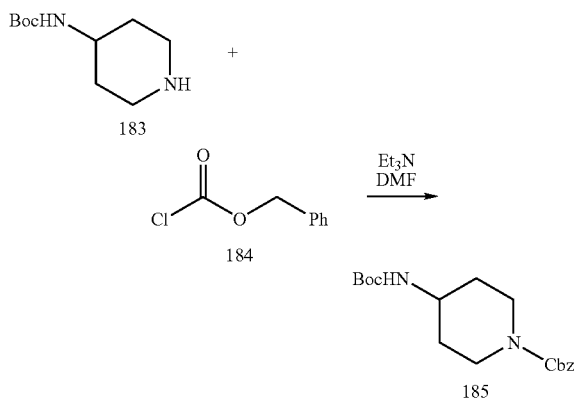

A suspension of 1.0 eq of 183 in 5 mL of dry DMF was prepared. While stirring, 1.2 eq of triethylamine was added followed by 1.2 eq of 184. The mixture was stirred at rt for 40 min and 30 mL of H₂O was added. The mixture was then extracted with EtOAc (3×50 mL). The combined organic extracts were dried over MgSO₄ and vacuum filtered. The filtrate was rotary evaporated and flash chromatographed on silica using 20% EtOAc/hexanes as eluent. After concentration and drying under vacuum of the fractions containing product, a white solid was obtained as 185.

General Procedure 31

Preparation of 2-(2-Phenyl-3H-benzoimidazol-5-yl)-ethylamine (193)

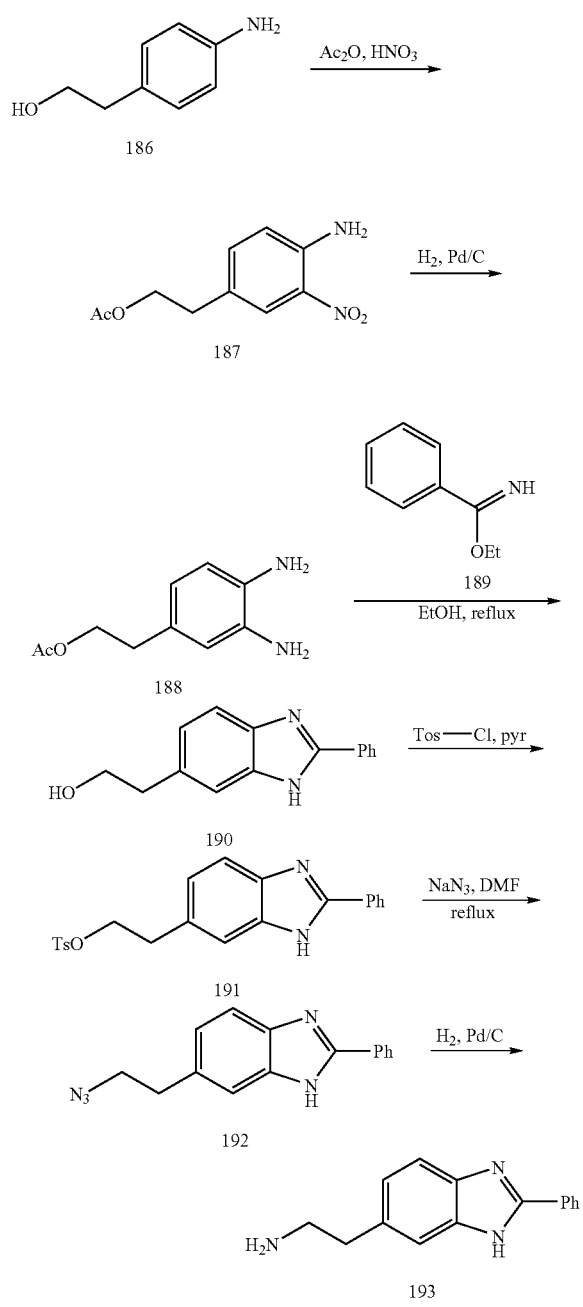

Preparation of 2-(4-Amino-3-nitro-phenyl)ethylacetate (187). 2-(4-Aminophenyl)ethanol (186) (Aldrich, 26,164-5) (2.4 g, 17.5 mmol) was dissolved in Ac₂O (12 mL) and chilled to 0° C. before addition of concentrated HNO3 (2.5 mL). The colorless solution turned red as it was stirred at 0° C. After stirring for 10 min, the reaction was quenched by addition of ice cold water (50 mL). The resulting biphasic mixture was stirred for 0.5 h to provide for 187 as a solid. The solid was recovered by filtration and recrystallized from methanol to give 187 (2.13 g) as a crystalline solid.

Preparation of 2-(3,4-Diamino-phenyl)ethylacetate (188). Aryl nitrate 187 was dissolved in neat ethanol (25 mL) and 10% Pd/C (50 mg) was added, followed by 3 drops of glacial acetic acid. H₂ gas was applied at 46 psi for 2 h with vigorous shaking, after which time TLC analysis indicated complete consumption of 187. The reaction mixture was filtered through a pad of Celite to remove the catalyst and the filtrate was concentrated under reduced pressure to give 188 as an oil. Column chromatography was employed with 10% MeOH/CH₂Cl₂ as eluent to give pure 188 as a white solid.

Preparation of 2-(2-Phenyl-3H-benzoimidazol-5-yl)ethanol (190). Diamine 188 (0.42 g) was added to an ethanolic suspension of 189 (0.41 g, see: Nelson, J. W.; McElvain, S. M. J. Am. Chem. Soc. 1942, 1827) and the mixture was heated to reflux for 16 h. Excess ethanol was removed under reduced pressure and the resulting solid was partitioned between EtOAc and sodium bicarbonate. The organic layer was separated, dried with Na₂SO₄, and concentrated under reduced pressure to give a brown oil. This oil was purified by column chromatography using a mobile phase of neat EtOAc to give compound 190.

Preparation of Toluene-4-sulfonic acid 2-(2-phenyl-3H-benzoimidazol-5-yl)ethyl ester (191). Benzimidazole 190 (50 mg) was dissolved in pyridine (5 mL) and tosyl chloride (40 mg) was added as a solid. The reaction was allowed to stir for 16 h under nitrogen at room temperature before being quenched by addition of a saturated, aqueous solution of NH₄Cl. This mixture was extracted with EtOAc which was in turn washed with dilute acid to ensure complete removal of pyridine. The organic layer was separated, dried over Na₂SO₄, and solvent removed under reduced pressure to give 191 which was used directly without further purification.

Preparation of 6-(2-Azido-ethyl)-2-phenyl-1H-benzoimidazole (192). Tosylate 191 (0.2 g) was dissolved in DMF (10 mL) and NaN₃ (99 mg) was added as a solid. A condenser was affixed under nitrogen, and the mixture was heated to 50° C. for 16 h. The reaction was cooled to rt before being extracted with EtOAc. The organic layer was rinsed several times with water to ensure complete removal of DMF. The organic layer was then separated and dried over Na₂SO₄ before the solvent was removed under reduced pressure to give 192.

Preparation of 2-(2-Phenyl-3H-benzoimidazol-5-yl)ethylamine (193). Azide 192 was dissolved in ethanol and 10% Pd/C (50 mg) was added. H₂ was applied at 40 psi with vigorous shaking. After 2 h, TLC analysis indicated complete consumption of starting material. The heterogeneous reaction mixture was filtered through Celite, and the filtrated was concentrated under reduced pressure to give 193.

General Procedure 33

Preparation of 4-Bromo-5-(2-chlorobenzoylamino)-2H-pyrazole-3-carboxylic acid {2-[4-(1H-benzoimidazol-2-yl)-phenyl]ethyl}amide (199)

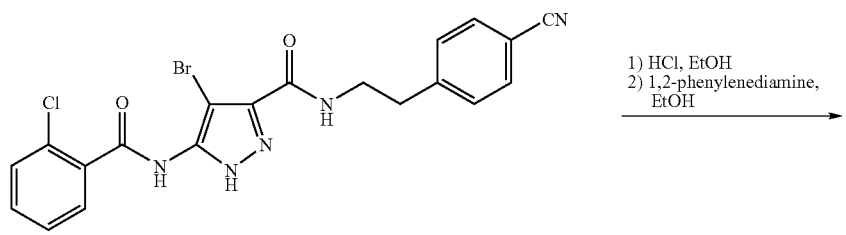

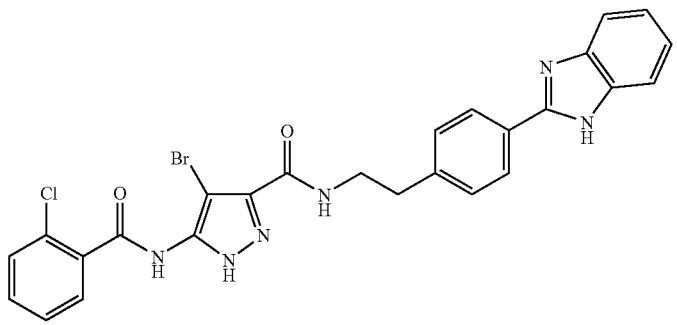

HCl gas was bubbled for 10 minutes into a solution of 198 (prepared as shown in General Procedure 10 using compound 169) in EtOH and cooled to 0° C. (1.0 eq.). After 30 minutes of stirring a white precipitate formed. The mixture was stirred for an additional 5 hours and then evaporated to dryness. The crude mixture was then dissolved in EtOH and ethylene diamine (10 eq.) was added. The reaction mixture was then refluxed under nitrogen overnight. The mixture was evaporated to dryness and purified by recrystallization in MeOH to afford compound 199.

General Procedure 34

Preparation of 4-(2-Aminoethyl)benzonitrile (169)

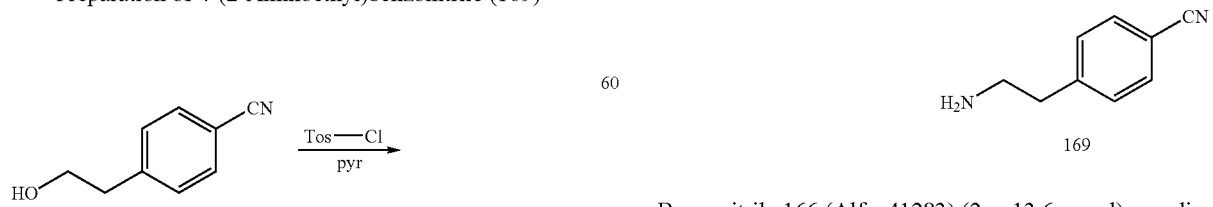

Benzonitrile 166 (Alfa, 41283) (2 g, 13.6 mmol) was dissolved in $CH_2Cl_2$ (30 mL), and $Et_3N$ (3.62 mL, 26 mmol) was added. The reaction mixture was chilled to 0° C. and tosyl chloride (3.89 g, 20 mmol) was added as a solid. The reaction was allowed to warm to rt overnight while being stirred under a positive pressure of nitrogen. After stirring for 17 h, reaction was quenched by addition of a saturated, aqueous solution of NH$_4$Cl, and the mixture was extracted with CH$_2$Cl$_2$. The organic solution was separated and rinsed with NaHCO$_3$ and brine before drying over Na$_2$SO$_4$. The drying agent was filtered off and the filtrate was concentrated under reduced pressure to give a yellow solid as the crude product. This solid was recrystallized from EtOAc/hexanes to give 167 (2.71 g, 66% yield) as a white solid.

Benzonitrile 167 (2.72 g, 9 mmol) was dissolved in DMF and sodium azide (0.88 g, 13.5 mmol) was added as a solid. The heterogeneous mixture was heated to 50° C. for 16 h, after which time starting material had been completely consumed. After cooling to rt, the reaction mixture was diluted with aqueous NH$_4$Cl and extracted with EtOAc. The organic layer was separated, dried over Na$_2$SO$_4$, and concentrated under reduced pressure to give azide 168 (1.4 g, 90% yield)

Azide 168 (1.4 g) was dissolved in EtOH (~15 mL) and a spatula tip of 10% of Pd/C was added. 50 psi of hydrogen gas was applied with shaking. After 5 h, the reaction was shown to be complete by TLC analysis using a 7% MeOH/CH$_2$Cl$_2$ mobile phase. The reaction was filtered through Celite to remove the catalyst and the resulting filtrate was concentrated under reduced pressure to give 169 (1.05 g, 89% yield) as an oil.

General Procedure 35

Preparation of (1'-Methyl-[1,4']bipiperidin-4-ylalkyl) carbamic acid tert-butyl esters (115)

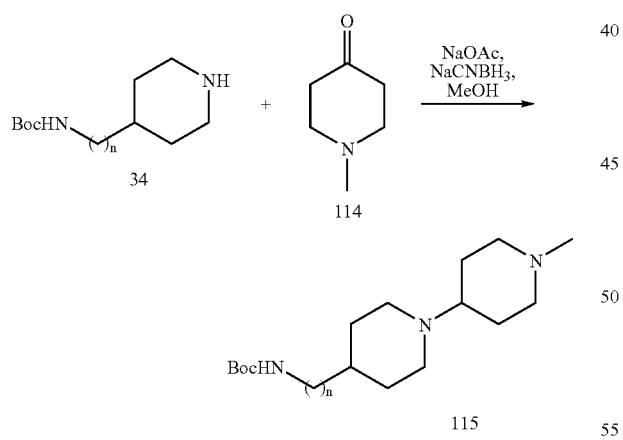

A solution of 1.0 eq. of piperidine 34 and 1.2 eq. of N-methyl-4-piperidinone (Aldrich, 13,003-6) in MeOH was stirred at rt as 3.0 eq. of NaOAc was added followed by 3.0 eq. of NaCNBH$_3$. The reaction mixture was stirred for a time sufficient for reaction completion. The reaction mixture was then absorbed onto silica gel and flash chromatographed using 10% isopropyl alcohol and 2% Et$_3$N in CHCl$_3$ as eluant to afford 115.

General Procedure 36

Preparation of 4-tert-Butoxycarbonylaminoalkyl-N-(2-(4-pyridyl)ethyl)piperidines (127)

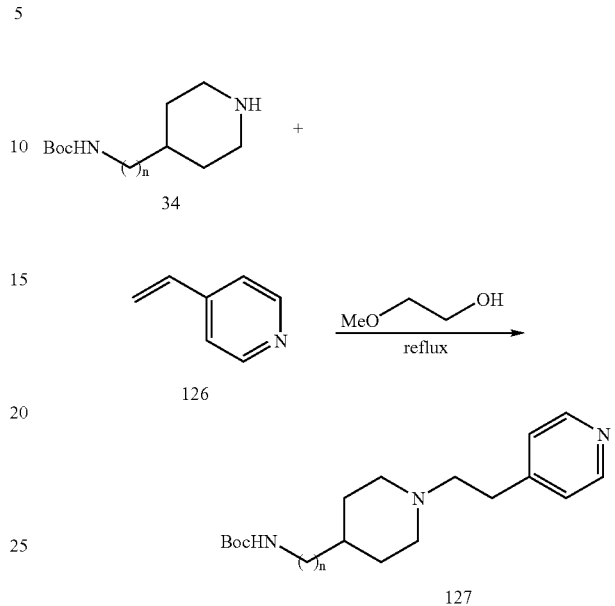

A solution of 1.0 eq. of piperidine 34 and 1.1 eq. of 4-vinylpyridine (Aldrich, V320-4) in 2-methoxyethanol (Aldrich, 27,048-2) was refluxed for a time sufficient for reaction completion. The reaction mixture was cooled to rt and the solvent removed by rotary evaporation to afford an amorphous solid. The solid was triturated with ether and filtered. The filtrate was concentrated to afford 127.

General Procedure 37

Preparation of (3,4,5,6-Tetrahydro-2H-[1,4']bipyridin-4-ylalkyl)carbamic acid tert-butyl esters (129)

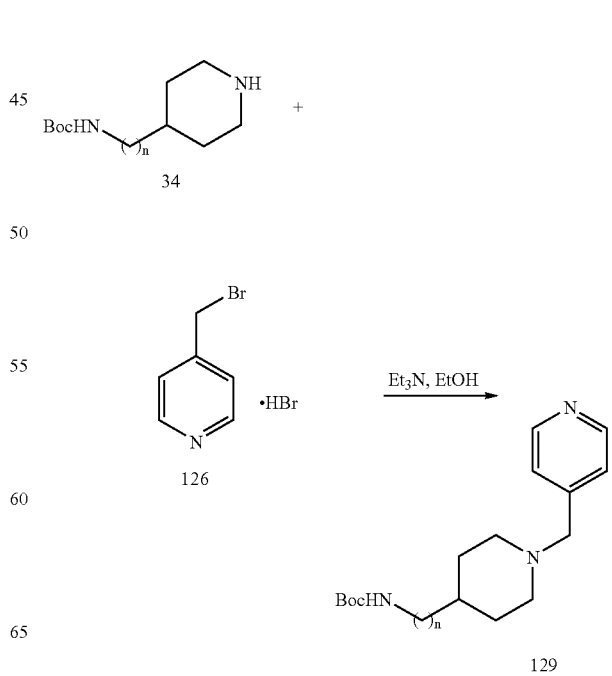

Preparation of (1-pyridin-4-ylmethylpiperidin-4-ylalkyl) carbamic acid tert-butyl esters (129). A mixture of 1.0 eq. of piperidine 34, 1.1 eq. of 4-(bromomethyl)pyridine hydrobromide (Aldrich, 49,174-8) and 3.0 eq. of Et$_3$N in absolute EtOH was stirred at 80° C. in a sealed tube for 64 h. The reaction mixture was filtered and the filtrate was concentrated and flash chromatographed on silica gel using 10% isopropyl alcohol and 2% Et$_3$N in CHCl$_3$ as eluant to afford 129.

General Procedure 38

Preparation of (1-Cyclopropylmethyl-5-methyl-2-oxo-2,3,4,5-tetrahydro-1H-benzo[b][1,4]diazepin-3-yl)carbamic acid tert-butyl ester (139)

(R)-2-tert-Butoxycarbonylamino-3-(2-nitrophenylamino) propionic acid (176). A solution of 1.0 eq of 175 in 100 mL of dry DMF was cooled to 0° C. While stirring, 2.2 eq of NaH (60% in mineral oil) was added. The mixture was stirred until bubbling ceased (about 30 min), at which time 1.1 eq of 116 (Aldrich, F1,080-1) was slowly added. The mixture was allowed to warm to rt and was then heated at 50° C. for 20 h.

The orange colored solution was cooled to rt and the solution was rotary evaporated. The crude reaction mixture was flash chromatographed on silica using a step gradient of 10% and 20% MeOH/CH$_2$Cl$_2$ as eluant. After concentration and drying under vacuum the fractions containing product afforded intermediate 176

(R)-2-tert-Butoxycarbonylamino-3-(2-nitrophenylamino) propionic acid methyl ester (177). A solution of 1.0 eq of 176 in 50 mL of benzene and 30 mL of MeOH was prepared. While stirring, 3.0 eq of a 2.0 M solution of trimethylsilyl diazomethane in hexanes (Aldrich, 36,283-2) was slowly added. After stirring the reaction solution for 1 h at rt, it was rotary evaporated. The crude material was flash chromatographed on silica using a step gradient of 20% and 30% EtOAc/hexanes as eluents. After concentration and drying under vacuum the fractions containing product afforded 177.

(R)-2-tert-Butoxycarbonylamino-3-[methyl-(2-nitrophenyl)amino]propionic acid methyl ester (178). A solution of 1.0 eq of 177 in 20 mL of dry DMF was stirred at rt as 1.3 eq of NaH (60% in mineral oil) was added. After bubbling ceased (about 10 min), 1.1 eq of MeI was slowly added. After 18 h, 50 mL of sat. aq. NH$_4$Cl was added to the reaction mixture. The mixture was extracted with EtOAc (3×50 mL). The combined organics were dried over MgSO$_4$ and filtered. The filtrate was rotary evaporated. The crude material was flash chromatographed on silica using 20% EtOAc/hexanes as eluant. After concentration and drying under vacuum the fractions containing product afforded intermediate 178.

(R)-2-tert-Butoxycarbonylamino-3-[methyl-(2-nitrophenyl)amino]propionic acid (179). A solution of 1.0 eq of 178 and 1.4 eq of LiOH.H$_2$O in 15 mL of THF, 10 mL of MeOH, and 10 mL of H$_2$O was prepared. After stirring at rt for 20 h, the reaction solution was rotary evaporated and 50 mL of 1 M HCl was added. The solution was extracted with CHCl$_3$ (3×50 mL). The combined organic extracts were dried over MgSO$_4$ and filtered. The filtrate was rotary evaporated and dried to afford 179 as an orange amorphous material.

(R)-3-[(2-Aminophenyl)methylamino]-2-tert-butoxycarbonylaminopropionic acid (136). A suspension of 1.0 eq of 179 and 0.1 wt/wt eq of 10% Pd/C in 20 mL of EtOH was hydrogenated under 50 psi of H$_2$ for 90 min, until consumption of H$_2$ ceased. The reaction mixture was filtered through Celite. The filtrate was concentrated by rotary evaporation and dried to give product 136.

(R)-3-tert-Butoxycarbonylamino-5-methyl-1,3,4,5-tetrahydro-benzo[b][1,4]diazepin-2-one (137). A solution of 1.0 eq of 136 in 40 mL of THF was prepared. While stirring, 1.2 eq of HOBT, 2.0 eq of NMM, and 1.2 eq of EDC.HCl was added. After stirring at rt for 17 h, the reaction mixture was rotary evaporated. The crude material was flash chromatographed on silica using 50% EtOAc/hexanes as eluant. After concentration and drying under vacuum the fractions containing product afforded intermediate 137.

(R)-3-tert-Butoxycarbonylamino-1-cyclopropylmethyl-5-methyl-2-oxo-2,3,4,5-tetrahydro-1H-benzo[b][1,4]diazepin-2-one (139). A solution of 1.0 eq of 137 in 5 mL of dry DMF was stirred at rt as 1.3 eq of NaH (60% in mineral oil) was added. After bubbling ceased (about 10 min), 1.1 eq of 138 (Aldrich, 24,240-3) was slowly added. After 16 h, the mixture was rotary evaporated. The crude material was flash chromatographed on silica using a step gradient of 30% and 50% EtOAc/hexanes as eluant. After concentration and drying under vacuum the fractions containing product afforded intermediate 139.

General Procedure 39

Preparation of N$^1$-Methyl-N$^1$-pyridin-4-yl-ethane-1,2-diamine (183)

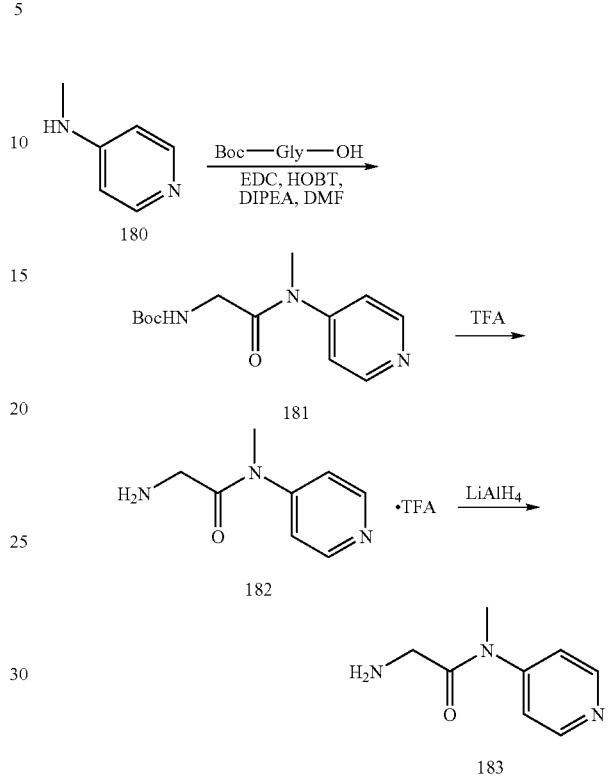

Preparation of [(Methyl-pyridin-4-yl-carbamoyl)-methyl]carbamic acid tert-butyl ester (181). A solution of 1.1 eq. of 4-(methylamino)pyridine (180, Aldrich, 19,551-0) in anhydrous DMF was stirred under an atmosphere of argon as 1.1 eq. of HOBT and 2.0 eq of DIPEA were added followed by 1.0 eq of N-(tert-butoxycarbonyl)glycine (Bachem, A-1730). The mixture was stirred for 1 hr, cooled in an ice-bath and 1.1 eq. of EDC.HCl was added. The reaction was stirred and allowed to reach rt overnight. Water was added to the reaction mixture and the solvents were evaporated under high vacuum. The residue was dissolved in ethyl acetate, washed with 0.15 M citric acid, sat. aq. NaHCO$_3$, brine and dried over anhydrous Na$_2$SO$_4$. To afford 181.

Preparation of 2-Amino-N-methyl-N-pyridin-4-yl-acetamide trifluoroacetate (182). [(Methyl-pyridin-4-yl-carbamoyl)-methyl]carbamic acid tert-butyl ester (181) (7 g, 28.1mmol) was dissolved in TFA (35mL) at rt. The reaction had to be cooled to prevent excessive heat being released. Once the reaction had settled, it was left for 1 hr. TFA was evaporated and the residue co-evaporated with toluene (3×1000 mL) and dried under vacuum to afford compound (182).

Preparation of N$^1$-Methyl-N$^1$-pyridin-4-yl-ethane-1,2-diamine (183). 2-Amino-N-methyl-N-pyridin-4-yl-acetamide trifluoroacetate (182, 1.0 eq.) was dissolved in anhydrous THF (50 mL) under argon. A 1 M solution of LiAlH$_4$ in THF (6.1 eq.) was added dropwise at rt and the reaction vessel was placed in an oil bath. The temperature was raised to 70° C. and the mixture stirred for 15 hr. The reaction mixture was cooled and quenched by the slow addition of water (5 mL). Solvents were evaporated to give a white solid which was titurated several times with ethyl acetate to give compound 183 as a colourless oil.

General Procedure 40

Preparation of (6'-Amino-3,4,5,6-tetrahydro-2H-[1,2']bipyridin-4-ylmethyl)carbamic acid tert-butyl ester (186)

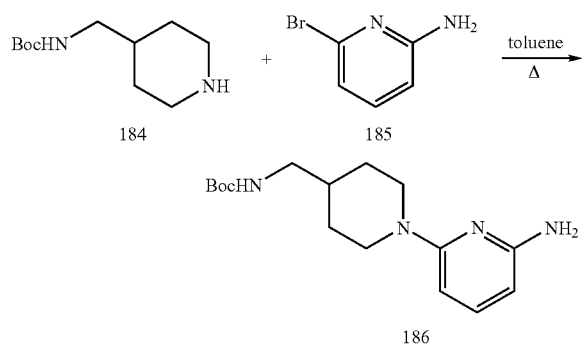

A solution of 1.0 eq. of 4-N-Boc-aminomethyl piperidine (184, Astatech, B56683) and 3.0 eq. of 2-amino-6-bromopyridine (185, Aldrich, 52,174-4) in toluene was stirred an heated at 100° C. in a sealed tube for 16 h. The temperature was then raised to 150° C. for 3 days. The reaction mixture was cooled to rt and diluted with EtOAc. The mixture was extracted with sat. aq. $NH_4Cl$. The organic layer was dried over $MgSO_4$, filtered, and the solvent removed by rotary evaporation. Purification of the material on silica gel using 3% MeOH—$CH_2Cl_2$ as eluant afforded compound 186.

General Procedure 41

Preparation of 5-Amino-1-phenyl-1H-pyrazole-3-carboxylic acid ethyl ester (188)

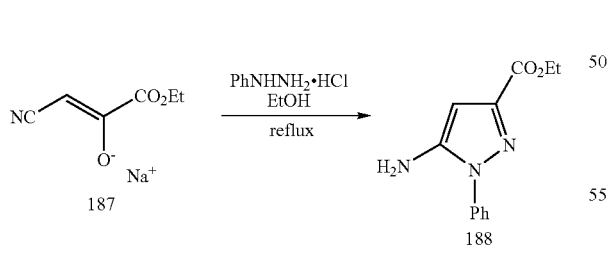

A suspension of 1.0 eq. of 3-cyano-2-oxopropanoic acid ethyl ester (187) (Degussa, NACOPE) and 1.2 eq. of phenylhydrazine hydrochloride in absolute EtOH was stirred at reflux for 3 days. The reaction mixture was cooled to rt and filtered through Celite. The solvent was removed by rotary evaporation. Purification of the material on silica gel using 50% EtOAc-hexanes as eluant afforded compound 188.

General Procedure 42

Preparation of 5-Amino-1-phenyl-1H-pyrazole-3-carboxylic acid ethyl ester (190)

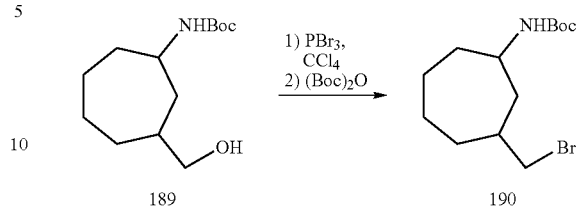

A solution of 1.0 eq of 189 in 16 mL of $CCl_4$ was prepared. While stirring, 5.1 eq of $PBr_3$ was added. After stirring the mixture at rt for 5 hr, 30 mL of water and enough 1 M NaOH was added to adjust pH to about 12. While stirring, 1.2 eq of $(Boc)_2O$ was added to the mixture. After 15 min, the mixture was extracted with $CH_2Cl_2$ (3×50 mL). The combined organic extracts were dried over $MgSO_4$ and vacuum filtered. The filtrate was rotary evaporated. The material was purified by flash chromatographed on silica using 10% EtOAc/hexanes as eluant to afford compound 190 as a clear, colorless oil.

Example 1
Preparation of 4-Bromo-5-(2-chloro-benzoylamino)-1H-pyrazole-3-carboxylic acid [2-(1-methyl-piperidin-4-yl)-ethyl]-amide

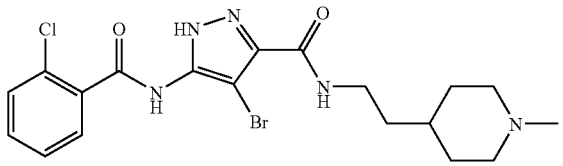

The pyrazole acid, prepared as described in Procedure 8, was coupled with 4-(2-aminoethyl)-1-methylpiperidine (prepared as described in Procedure 13) using the method described in Procedure 10.

MS+=468.0

$^1$H-NMR (CDCl$_3$) δ 7.98 (d, J=7.7 Hz, 1H), 7.54 (m, 2H), 7.50-7.43 (m, 1H), 7.22 (m, 1H), 3.49 (m, 3H), 2.81 (d, J=11.6 Hz, 2H), 2.24 (s, 3H), 1.89 (m, 2H), 1.69 (m, 2H), 1.57 (m, 2H), 1.29 (m, 4H).

Example 2
Preparation of 4-Bromo-5-(2-chloro-benzoylamino)-1H-pyrazole-3-carboxylic acid (2-pyrrolidin-1-yl-prop-1-yl)-amide

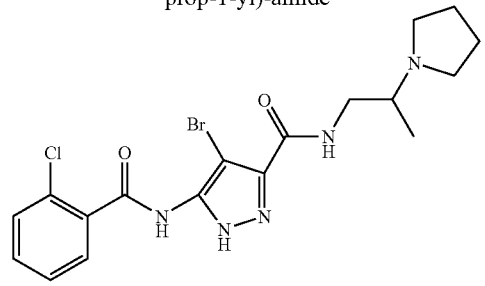

The pyrazole acid, prepared as described in Procedure 8, was coupled with β-methyl-1-pyrrolidineethanamine (MicroChemistry Building Blocks, mch-bb 1222) using the method described in Procedure 10.

MS+=454.1

$^1$H-NMR (CDCl$_3$) δ 7.95 (d, J=7.17 Hz), 7.64 (m, 1 H), 7.51-7.40 (m, 3H), 3.48 (m, 1H), 2.73 (m, 3H), 1.78 (m, 2H), 1.25 (m, 4H), 1.15 (d, J=6.2 Hz, 3H), 0.90-0.70 (m, 1H).

Example 3

Preparation of (R)-4-Bromo-5-(2-chloro-benzoylamino)-1-phenyl-pyrazole-3-carboxylic acid (2-oxo-azepan-3-yl)-amide

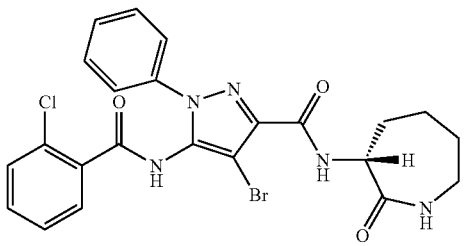

The pyrazole acid, prepared as described in Procedure 8 using compound 188 (Procedure 41) in place of compound 20, was coupled to (2-oxo-azepan-3-yl)carbamic acid tert-butyl ester (prepared as described in Martin G. Banwell and Kenneth J. McRae; *J. Org. Chem.* 2001, 66, 6768, which is incorporated herein by reference in its entirety) using the method of Procedure 3.

MS+=530.0
$^1$H-NMR (CD$_3$OD) δ 8.43 (m, 1H), 7.60 (m, 2H), 7.44 (m, 7H), 4.66 (m, 1H), 3.26 (m, 2H), 2.04 (m, 2H), 1.84 (m, 2H), 1.57 (m, 1H), 1.37 (m, 1H).

Example 4

Preparation of (R)-4-Bromo-5-(2-chloro-benzoylamino)-1H-pyrazole-3-carboxylic acid (1-aza-bicyclo[2.2.2]oct-3-yl)-amide

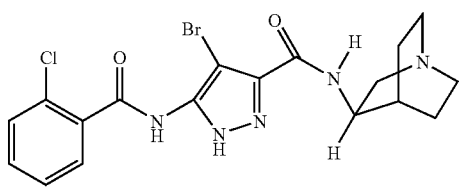

The pyrazole acid, prepared as described in Procedure 8, was coupled with (R)-(+)-3-aminoquinuclidine dihydrochloride (Aldrich, 41,571-5) using the method described in Procedure 10.

MS+=452.0
$^1$H-NMR (CDCl) δ 7.94 (d, J=7.4 Hz, 1H), 7.52-7.41 (m, 3H), 7.25 (m, 2H), 4.15 (m, 1H), 3.41 (dd, J=12.5, 10.5 Hz, 1H), 2.97-2.84 (m, 4H), 2.74 (dd, J=14.0, 4.3 Hz, 1H), 2.08 (m, 1H), 1.83-1.69 (m, 3H), 1.51 (m, 1H).

Example 5

Preparation of (S)-4-Bromo-5-(2-chloro-benzoylamino)-1H-pyrazole-3-carboxylic acid (1-aza-bicyclo[2.2.2]oct-3-yl)-amide

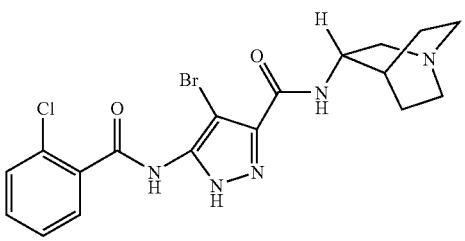

The pyrazole acid, prepared as described in Procedure 8, was coupled with (S)-(−)-3-aminoquinuclidine dihydrochloride (Aldrich, 41,572-3) using the method described in Procedure 10.

MS+=451.9
$^1$H-NMR (CDCl$_3$) δ 8.35 (br, 1H), 7.89 (d, J=7.0 Hz, 1H), 7.51-7.38 (m, 3H), 7.22 (d, J=7.3 Hz, 2H), 4.12 (m, 1H), 3.37 (dd, J=14.1, 9.7 Hz, 1H), 2.84 (m, 4H), 2.67 (dd, J=14.0, 4.5 Hz, 1H), 2.03 (m, 1H), 1.79-1.66 (m, 3H), 1.50-1.45 (m, 1H).

Example 6

Preparation of 4-Bromo-5-(2-chloro-benzoylamino)-1H-pyrazole-3-carboxylic acid benzhydryl-amide

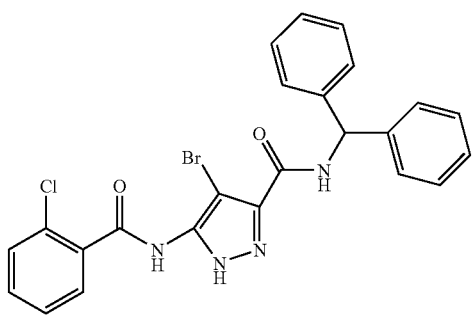

The pyrazole acid, prepared as described in Procedure 8, was coupled with α-aminodiphenylmethane (Fluka, 07940) using the method described in Procedure 10.

MS+=508.9
$^1$H-NMR (DMSO-d6) δ 8.87 (d, J=8.5 Hz, 1H), 7.58-7.23 (m, 16H), 6.28 (m, 1H).

Example 7

Preparation of 4-Bromo-5-(2-chloro-benzoylamino)-1H-pyrazole-3-carboxylic acid [2-(1-phenyl-piperidin-4-yl)-ethyl]-amide

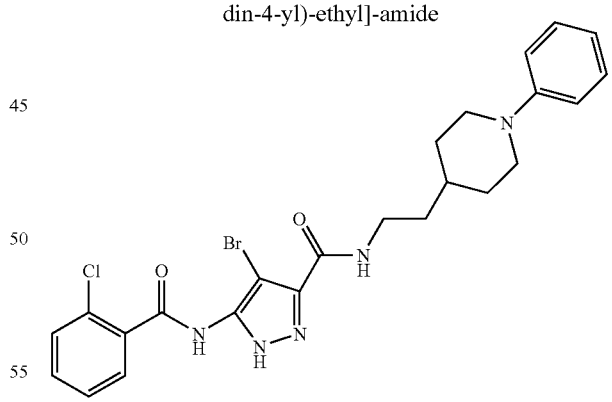

The pyrazole acid, prepared as described in Procedure 8, was coupled with 1-phenyl-4-(2-aminoethyl)piperidine (prepared as described in Procedure 15) using the method described in Procedure 10.

MS+=530.0
$^1$H-NMR (DMSO-d$_6$) δ 13.85 (br, 1H), 10.77, 10.34 (two br, 1H), 8.25, 8.08 (two br, 1H), 7.58-7.49 (m, 4H), 7.19 (dd (app. t), J=7.9 Hz, 2H), 6.93 (d, J=8.3 Hz, 2H), 6.73 (dd (app. t), J=7.2 Hz, 1H), 3.68 (d, J=11.8 Hz, 2H), 3.33 (m, 2H), 2.62 (m, 2H), 1.81 (m, 2H), 1.50 (m, 3H), 1.25 (m, 2H).

Example 8
Preparation of 4-Bromo-5-[2-(quinolin-8-ylthiom-ethyl)-benzoylamino]-1H-pyrazole-3-carboxylic acid (2-morpholin-4-yl-ethyl)-amide

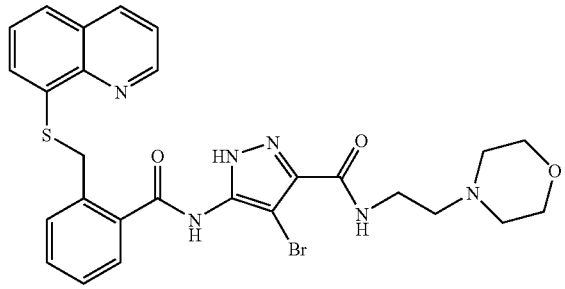

The pyrazole acid, prepared as described in Procedure 16, was coupled to 4-(2-aminoethyl)morpholine (Acros Organics, 40075) using the method described in Procedure 10.
MS+=596.0

Example 9
Preparation of 5-(2-Chloro-benzoylamino)-4-methyl-2H-pyrazole-3-carboxylic acid (2-piperidin-1-yl-ethyl)-amide

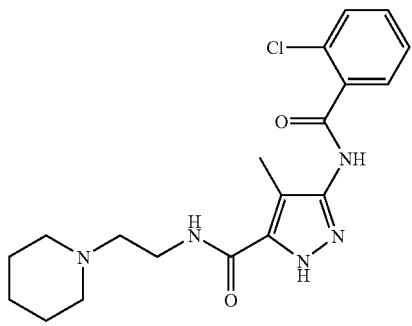

The pyrazole acid prepared as described in Procedure 18 was coupled to 1-(2-aminoethyl)piperidine (Lancaster Synthesis, 10084) using the method described in Procedure 10.
MS+=390.0
$^1$H-NMR (DMSO-d6) δ 7.57-7.45 (m, 4H), 3.34 (t, J=6.3 Hz, 2H), 2.42 (t, J=6.7 Hz, 2H), 2.50 (bs, 4H), 2.12 (s, 3H), 1.54-1.14 (m, 6H).

Example 10
Preparation of 5-(2-Chloro-benzoylamino)-4-methyl-1H-pyrazole-3-carboxylic acid isopropylamide

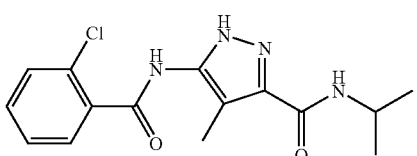

The pyrazole acid prepared as described in Procedure 18 was coupled to isopropylamine (Aldrich, 10,906-1) using the method described in Procedure 10.
MS+=321.0
$^1$H-NMR (CD$_3$OD) δ 7.64-7.14 (m, 4H), 4.14 (m, 1H), 2.23 (s, 3H), 1.25 (d, J=6.6 Hz, 6H).

Example 11
Preparation of 5-(2-Chloro-benzoylamino)-4-methyl-1H-pyrazole-3-carboxylic acid cyclohexylamide

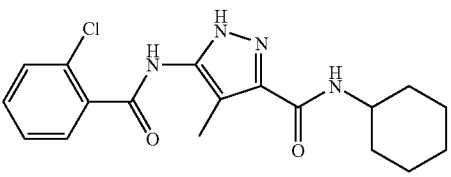

The pyrazole acid, prepared as described in Procedure 18, was coupled to cyclohexylamine (Fluka, 29310) using the method described in Procedure 10.
MS+=361.0
$^1$H-NMR (CD$_3$OD) δ 7.64-7.44 (m, 4H), 3.85 (m, 1H), 2.25 (s, 3H), 1.99-1.27 (m, 10H).

Example 12
Preparation of 5-(2-Chloro-benzoylamino)-4-methyl-1H-pyrazole-3-carboxylic acid methoxy-methyl-amide

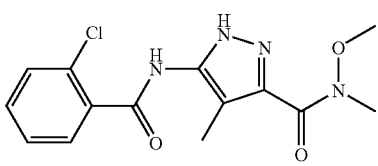

The title compound was prepared as described in Procedure 19 using N,O-dimethylhydroxylamine hydrochloride (Fluka, 40706).
MS+=323.0
$^1$H-NMR (DMSO-d6) δ 7.58-7.46 (m, 4H), 3.68 (s, 3H), 3.32 (s, 3H), 2.03 (s, 3H).

Example 13
Preparation of 3-benzoyl-5-(2-chloro-benzoylamino) 4-methyl-1H-pyrazole

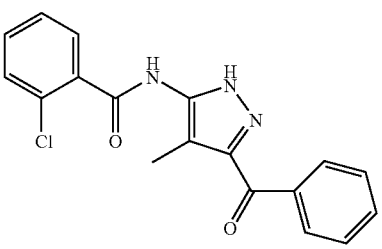

The title compound was prepared as described in Procedure 19 using phenyl magnesium chloride (Aldrich).
MS+=340.0 $^1$H-NMR (CDCl$_3$) δ 8.91 (s, 1H), 8.04 (d, J=7.3 Hz, 2H), 7.84 (d, J=7.4 Hz, 1H), 7.61-7.32 (m, 7H).

Example 14
Preparation of 4-methyl-5-(2-chloro-benzoylamino)-1-(pyridine-2-yl)-pyrazole-3-carboxylic acid (2-oxo-5-phenyl-2,3-dihydro-1H-benzo[e][1,4]diazepin-2-yl)amide

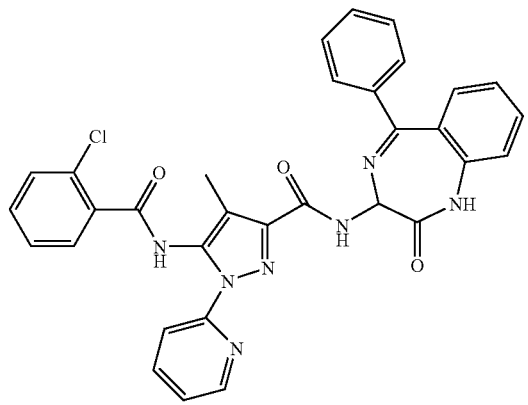

The pyrazole acid, prepared as described in Procedure 8 using 5-amino-4-methyl-1-pyridin-2-yl-1H-pyrazole-3-carboxylic acid ethyl ester (prepared as described in Procedure 41 using 3-cyano-3-methyl-2-oxopropanoic acid ethyl ester (U.S. Pat. No. 4,652,669) and 2-hydrazinopyridine dihydrochloride (Aldrich, H1,710-4)) in place of compound 20, was coupled to 3-amino-5-phenyl-1,3-dihydro-benzo[e][1,4]diazepin-2-one (prepared as described in Procedure 20) using the method of Procedure 10.

MS+=590.1

$^1$H-NMR (DMSO-d6) δ 11.03 (s, 1H), 10.61 (s, 1H), 8.73 (d, J=7.8 Hz, 1H), 8.59 (d, J=3.9 Hz, 1H), 8.08 (m, 1H), 7.97 (m, 1H), 7.26-7.69 (m, 13H), 5.44 (d, J=7.8 Hz, 1H), 2.22 (s, 3H).

Example 15
Preparation of 5-(2-Chloro-benzoylamino)-4-methyl-1H-pyrazole-3-carboxylic acid (1-benzyl-piperidin-4-yl)-amide

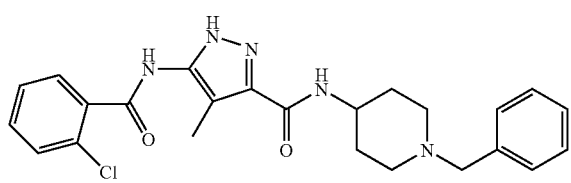

The pyrazole acid, prepared as described in Procedure 18, was coupled to 4-Amino-1-benzylpiperidine (Fluka, 07100) using the method described in Procedure 10.

MS+=452.2

$^1$H-NMR (CD$_3$OD) δ 7.64-7.35 (m, 9H), 3.85 (m, 1H), 3.57 (s, 2H), 2.93 (m, 2H), 2.24 (s, 3H), 2.23 (m, 2H), 1.97 (m, 2H), 1.63 (m, 2H).

Example 16
Preparation of (S)-5-(2-Chloro-benzoylamino)-4-methyl-1H-pyrazole-3-carboxylic acid (1-phenyl-ethyl)-amide

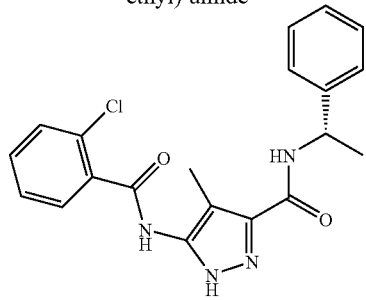

The title compound was prepared using the methods described in Procedure 10 using, pyrazole acid 51 and (S)-(−)-α-methylbenzylamine, (Aldrich, 77869).

MS+=383.0

$^1$H-NMR (CD$_3$OD) δ 7.64-7.25 (m, 9H), 5.17 (m, 1H), 2.22 (s, 3H), 1.57 (d, J=6.6 Hz, 3H).

Example 17
Preparation of 4-Benzyl-5-(2-chloro-benzoylamino)-1H-pyrazole-3-carboxylic acid (2-piperidin-1-yl-ethyl)-amide

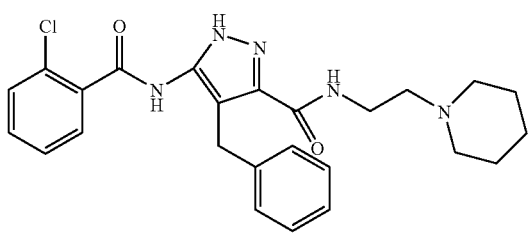

The pyrazole acid prepared as described in Procedure 18 was coupled to 1-(2-Aminoethyl)piperidine (Lancaster Synthesis, 10084) using the method described in Procedure 10.

MS+=466.0

$^1$H-NMR (CDCl$_3$) δ 8.16 (m, 1H), 8.05 (s, 1H), 7.55 (d, J=5.5 Hz, 1H), 7.43-7.16 (m, 7H), 4.29 (s, 2H), 3.85 (q, J=6.0 Hz, 2H), 3.68 (m, 2H), 3.27 (t, J=6.1 Hz, 2H), 2.68 (m, 2H), 2.01-1.85 (m, 6H).

Example 18
Preparation of 4-Bromo-5-(2-m-tolylthiomethyl-benzoylamino)-1H-pyrazole-3-carboxylic acid methyl ester

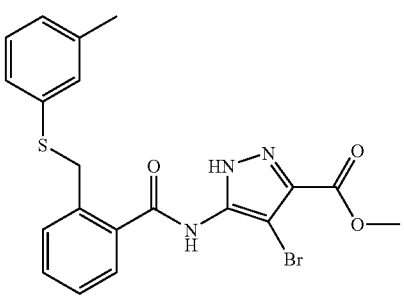

The amino pyrazole compound 20 prepared as in Procedure 8, was coupled to 2-meta-tolylsulfanylmethylbenzoyl chloride which was prepared as described in Procedure 16, using 3-methyl benzene thiol (Aldrich, T2,851-7).

MS+=460.0

$^1$H-NMR (CDCl$_3$) δ 8.57 (s, 1H), 7.58 (d, J=7.7 Hz), 7.36 (m, 3H), 7.04 (m, 4H), 4.35 (s, 2H), 3.94 (s, 3H), 2.21 (s, 3H).

Example 19

Preparation of 4-Bromo-5-(2-chloro-benzoylamino)-1H-pyrazole-3-carboxylic acid methyl ester

The pyrazole ester compound 22, was brominated as described in Procedure 8,

MS+=357.9

$^1$H-NMR (CDCl$_3$) δ 9.09 (s, 1H), 7.99 (d, J=7.1 Hz, 1H), 7.48 (m, 4H), 3.96 (s, 3H).

Example 20

Preparation of 4-Bromo-5-(2-chloro-benzoylamino)-1H-pyrazole-3-carboxylic acid benzylamide

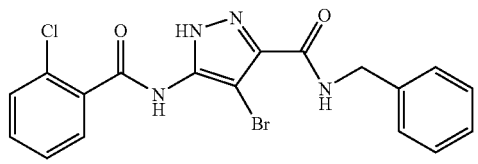

The pyrazole acid, prepared as described in Procedure 8, was coupled with benzylamine (Aldrich, 40,771-2) using the method described in Procedure 10.

MS+=432.9

$^1$H-NMR (CD$_3$OD) δ 7.63 (d, J=7.0 Hz, 1H), 7.39 (m, 8H), 4.87 (s, 2H).

Example 21

Preparation of 4-Bromo-5-(2-chloro-benzoylamino)-1H-pyrazole-3-carboxylic acid methylamide

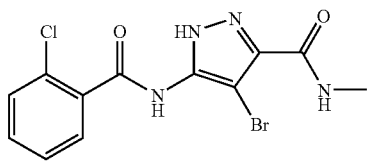

The pyrazole acid, prepared as described in Procedure 8, was coupled with methylamine (Aldrich, 39,505-6) using the method described in Procedure 10.

MS+=356.9

$^1$H-NMR (CD$_3$OD) δ 7.63 (d, J=7.0 Hz, 1H), 7.48 (m, 3H), 2.91 (s, 3H).

Example 22

Preparation of (R)-4-Bromo-5-(2-chloro-benzoylamino)-1H-pyrazole-3-carboxylic acid (1-phenyl-ethyl)-amide

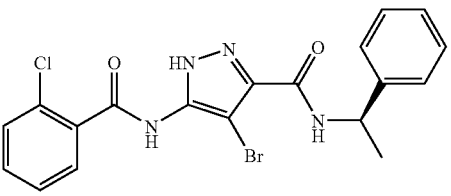

The pyrazole acid, prepared as described in Procedure 8, was coupled with (R)-(+)-α-methylbenzylamine (Aldrich, 11,554-1) using the method described in Procedure 10.

MS+=447.0

$^1$H-NMR (CD$_3$OD) δ 7.61 (d, J=7.1 Hz, 1H), 7.37 (m, 8H), 5.19 (q, J=7.1 Hz, 1H), 1.55 (d, J=7.1 Hz, 1H).

Example 23

Preparation of 4-Bromo-5-(2-chloro-benzoylamino)-1H-pyrazole-3-carboxylic acid (2-pyridin-4-yl-ethyl)-amide

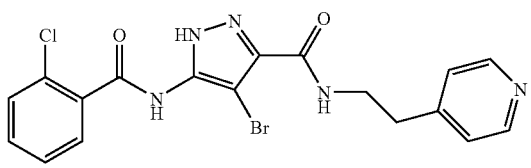

The pyrazole acid, prepared as described in Procedure 8, was coupled with 4-(2-Aminoethyl)pyridine (TCI America, A1264) using the method described in Procedure 10.

MS+=447.9

$^1$H-NMR (CD$_3$OD) δ 8.45 (d, J=4.5 Hz, 2H), 7.65 (d, J=7.2 Hz, 1H), 7.47 (m, 5H), 3.69 (t, J=6.9 Hz, 2H), 3.01 (t, 6.9 Hz, 2H).

Example 24

Preparation of 4-Bromo-5-(2-chloro-benzoylamino)-1H-pyrazole-3-carboxylic acid (1-methyl-1-phenyl-ethyl)-amide

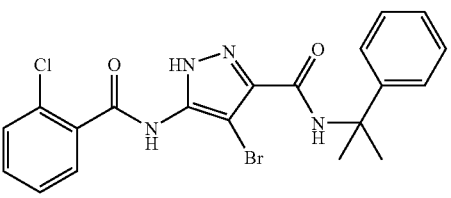

The pyrazole acid, prepared as described in Procedure 8, was coupled with cumylamine (TCI America, C1293) using the method described in Procedure 10.

MS+=461.0
¹H-NMR (CD₃OD) δ 7.63 (d, J=7.1 Hz, 1H), 7.48 (m, 5H), 7.31 (m, 2H), 7.20 (m, 1H), 1.77 (s, 6H).

Example 25

Preparation of (S)-4-Bromo-5-(2-chloro-benzoylamino)-1H-pyrazole-3-carboxylic acid (2-hydroxy-1-phenyl-ethyl)-amide

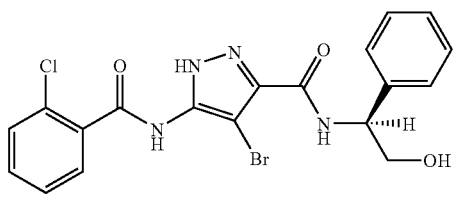

The pyrazole acid, prepared as described in Procedure 8, was coupled with (S)-(+)-2-phenylglycinol (Aldrich, 28,269-3) using the method described in Procedure 10.
MS+=462.9
¹H-NMR (CD₃OD) δ 7.62 (m, 1H), 7.38 (m, 8H), 5.16 (t, J=6.0 Hz, 1H), 3.84 (m, 2H).

Example 26

Preparation of (R)-4-Bromo-5-(2-chloro-benzoylamino)-1H-pyrazole-3-carboxylic acid methyl-(1-phenyl-ethyl)-amide

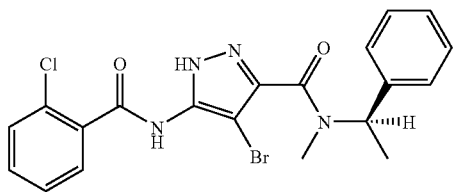

The pyrazole acid, prepared as described in Procedure 8, was coupled with (R)-(+)-N-α-dimethylbenzylamine (Aldrich, 39,400-9) using the method described in Procedure 10.
MS+=461.0
¹H-NMR (CDCl₃) δ 12.39 (br, 1H), 9.52 (d, J=6.5 Hz, 1H), 7.89 (d, J=7.7 Hz, 1H), 7.33 (m, 8H), 6.07 and 5.38 (two multiplets, 1H), 2.69 (d, J=9.3 Hz, 3H), 1.58 (t, J=7.1 Hz, 3H).

Example 27

Preparation of 4-Bromo-5-(2-chloro-benzoylamino)-1H-pyrazole-3-carboxylic acid (2-pyrrolidin-1-yl-ethyl)-amide

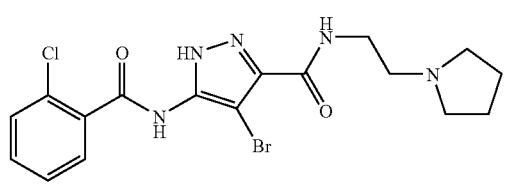

The pyrazole acid, prepared as described in Procedure 8, was coupled with N-(2-Aminoethyl)pyrrolidine (Acros, 10370) using the method described in Procedure 10.
MS+=440.0

Example 28

Preparation of (S)-4-Bromo-5-(2-chloro-benzoylamino)-1H-pyrazole-3-carboxylic acid (1-phenyl-ethyl)-amide

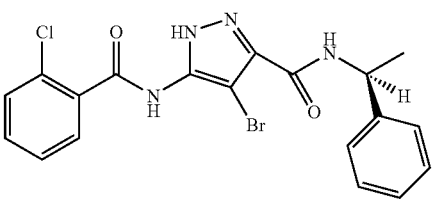

The pyrazole acid, prepared as described in Procedure 8, was coupled with (S)-(−)-α-methylbenzylamine (Aldrich, 77869) using the method described in Procedure 10.
MS+=447.0

Example 29

Preparation of 4-Bromo-5-(2-chloro-benzoylamino)-1H-pyrazole-3-carboxylic acid (2-morpholin-4-yl-ethyl)-amide

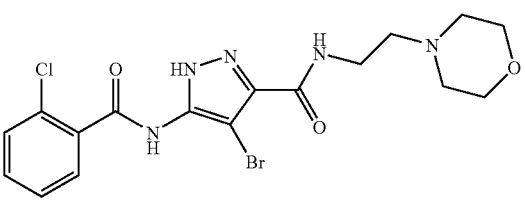

The pyrazole acid, prepared as described in Procedure 8, was coupled with 4-(2-Aminoethyl)morpholine (Acros Organics, 40075) using the method described in Procedure 10.
MS+=456.0

Example 30

Preparation of 4-Bromo-5-(2-chloro-benzoylamino)-1H-pyrazole-3-carboxylic acid (3-morpholin-4-yl-propyl)-amide

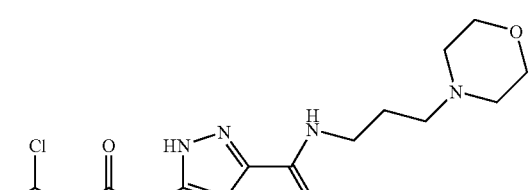

The pyrazole acid, prepared as described in Procedure 8, was coupled with 3-morpholinopropylamine (Fluka, 09312) using the method described in Procedure 10.
MS+=470.0

Example 31

Preparation of 4-Bromo-5-(2-chloro-benzoylamino)-1H-pyrazole-3-carboxylic acid (2-dimethylamino-ethyl)-amide

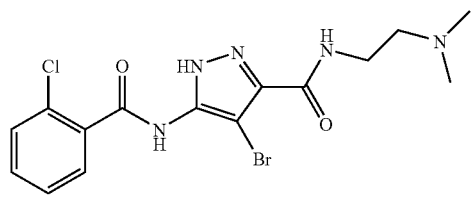

The pyrazole acid, prepared as described in Procedure 8, was coupled with N,N-dimethylethylenediamine (Fluka, 39030) using the method described in Procedure 10.
MS+=414.0

Example 32

Preparation of 4-Bromo-5-(2-chloro-benzoylamino)-1H-pyrazole-3-carboxylic acid (3-dimethylamino-propyl)-amide

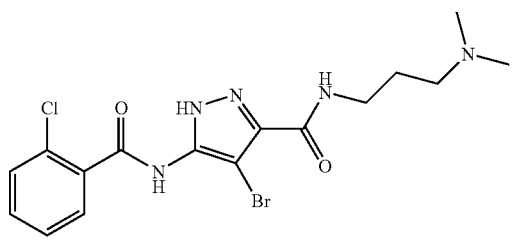

The pyrazole acid, prepared as described in Procedure 8, was coupled with 3-dimethylamino-1-propylamine (Fluka, 39380) using the method described in Procedure 10.
MS+=428.0

Example 33

Preparation of 4-bromo-5-(2-chloro-benzoylamino) 1H-pyrazole-3-carboxylic acid 4-methyl-piperazin-1-yl amide

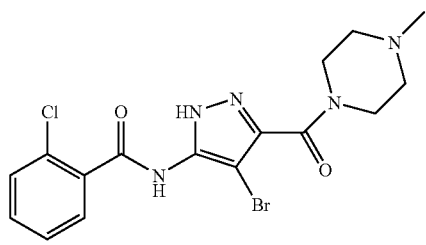

The pyrazole acid, prepared as described in Procedure 8, was coupled with 1-methylpiperazine (Fluka, 68810) using the method described in Procedure 10.
MS+=425.9

Example 34

Preparation of 4-bromo-5-(2-chloro-benzoylamino)-1H-pyrazole-3-carboxylic acid morpholino-4-yl-amide

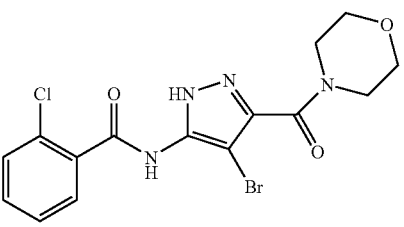

The pyrazole acid, prepared as described in Procedure 8, was coupled with morpholine (Aldrich, 39,446-7) using the method described in Procedure 10.
MS+=414.9

Example 35

Preparation of 4-Bromo-5-(2-chloro-benzoylamino)-1H-pyrazole-3-carboxylic acid cyclohexylamide

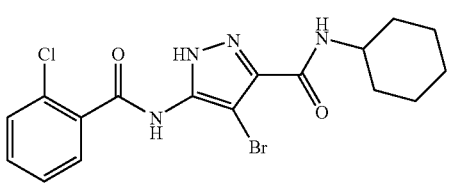

The pyrazole acid, prepared as described in Procedure 8, was coupled with cyclohexylamine (Aldrich, 24,064-8) using the method described in Procedure 10.
MS+=425.0

Example 36

Preparation of 4-Bromo-5-(2-chloro-benzoylamino)-1H-pyrazole-3-carboxylic acid phenethyl-amide

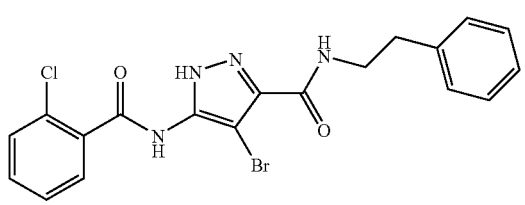

The pyrazole acid, prepared as described in Procedure 8, was coupled with phenethylamine (Aldrich, 12,894-5) using the method described in Procedure 10.
MS+=446.9

Example 37

Preparation of (S)-4-Bromo-5-(2-chloro-benzoylamino)-1H-pyrazole-3-carboxylic acid (1-hydroxymethyl-2-methyl-propyl)-amide

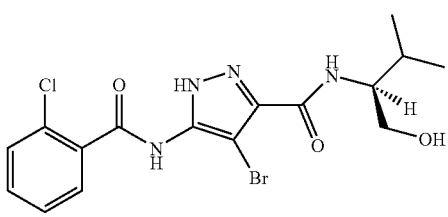

The pyrazole acid, prepared as described in Procedure 8, was coupled with D-valinol (Fluka, 94674) using the method described in Procedure 10.
MS+=429.0

Example 38

Preparation of 4-Bromo-5-(2-chloro-benzoylamino)-1H-pyrazole-3-carboxylic acid (1-benzyl-piperidin-4-yl)-amide

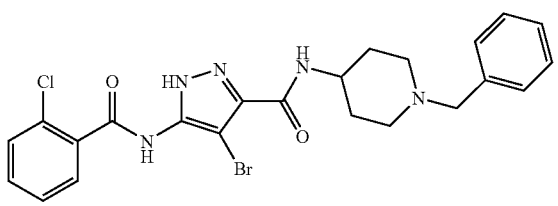

The pyrazole acid, prepared as described in Procedure 8, was coupled with 4-Amino-1-benzylpiperidine (Fluka, 07100) using the method described in Procedure 10.
MS+=516.0
$^1$H-NMR (CDCl$_3$) δ 9.07 (br, 1H), 8.00 (d, J=8.2 Hz, 1H), 7.44 (m, 3H), 7.30 (m, 5H), 7.01 (d, J=8.2 Hz, 1H), 4.00 (m, 1H), 3.51 (s, 2H), 2.84 (m, 2H), 2.16 (m, 2H), 1.99 (m, 2H), 1.63 (m, 2H).

Example 39

Preparation of 4-Bromo-5-(2-chloro-benzoylamino)-1H-pyrazole-3-carboxylic acid (2-hydroxy-ethyl)-amide

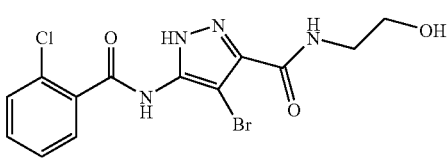

The pyrazole acid, prepared as described in Procedure 8, was coupled with ethanolamine (Fluka, 02410) using the method described in Procedure 10.
MS+=386.9

Example 40

Preparation of 4-Bromo-5-(2-chloro-benzoylamino)-1H-pyrazole-3-carboxylic acid (trans-4-hydroxy-cyclohexyl)-amide

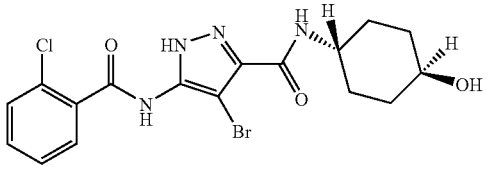

The pyrazole acid, prepared as described in Procedure 8, was coupled with trans-4-Aminocyclohexanol (Acros Organics, 34668) using the method described in Procedure 10.
MS+=441.0

Example 41

Preparation of 4-Bromo-5-(2-chloro-benzoylamino)-1H-pyrazole-3-carboxylic acid (2-methyl-cyclohexyl)-amide

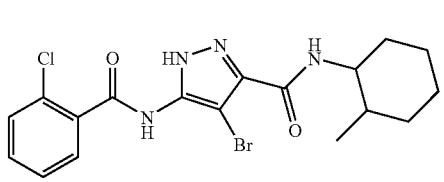

The pyrazole acid, prepared as described in Procedure 8, was coupled with 2-methylcyclohexylamine (Fluka, 66461) using the method described in Procedure 10.
MS+=439.0

Example 42

Preparation of 4-Bromo-5-(2-chloro-benzoylamino)-1H-pyrazole-3-carboxylic acid [2-(4-hydroxy-phenyl)-ethyl]-amide

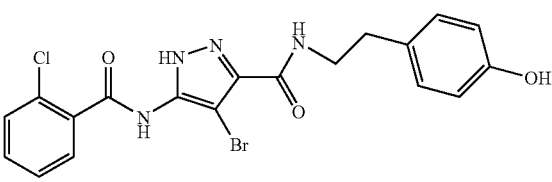

The pyrazole acid, prepared as described in Procedure 8, was coupled with tyramine (Fluka, 93810) using the method described in Procedure 10.
MS+=462.9

Example 43

Preparation of 4-Bromo-5-(2-chloro-benzoylamino)-1H-pyrazole-3-carboxylic acid (1S,2S)-(2-benzyloxy-cyclopentyl)-amide

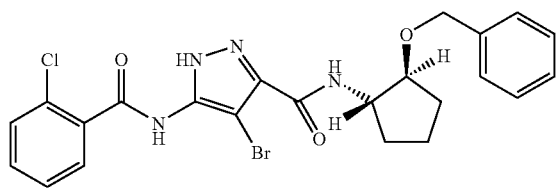

The pyrazole acid, prepared as described in Procedure 8, was coupled with (1S,2S)-2-Benzyloxycyclopentylamine (Lancaster Synthesis, 17018) using the method described in Procedure 10.

MS+=517.0

Example 44

Preparation of 4-Bromo-5-(2-chloro-benzoylamino)-1H-pyrazole-3-carboxylic acid [2-(1H-indol-3-yl)-ethyl]-amide

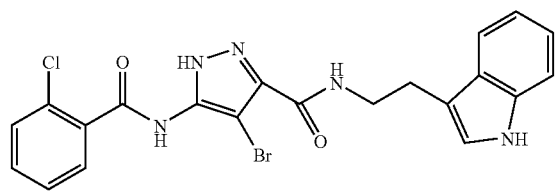

The pyrazole acid, prepared as described in Procedure 8, was coupled with tryptamine (Fluka, 93639) using the method described in Procedure 10.

MS+=486.0

Example 45

Preparation of 4-Bromo-5-(2-chloro-benzoylamino)-1H-pyrazole-3-carboxylic acid [2-(1H-imidazol-4-yl)-ethyl]-amide

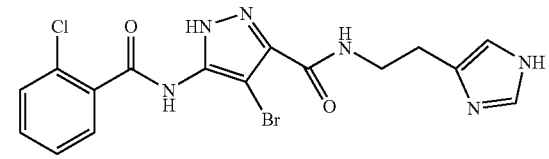

The pyrazole acid, prepared as described in Procedure 8, was coupled with histamine (Aldrich, 27,165-9) using the method described in Procedure 10.

MS+=437.0

Example 46

Preparation of 4-Bromo-5-(2-chloro-benzoylamino)-1H-pyrazole-3-carboxylic acid (1S,2R)-(2-hydroxy-indan-1-yl)-amide

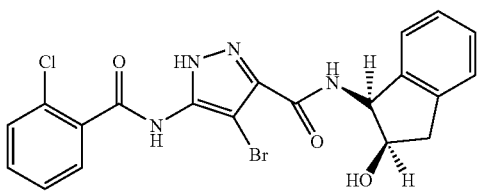

The pyrazole acid, prepared as described in Procedure 8, was coupled with (1S,2R)-(−)-cis-1-Amino-2-indanol (Fluka, 08243) using the method described in Procedure 10.

MS+=474.9

Example 47

Preparation of 4-Bromo-5-(2-chloro-benzoylamino)-1H-pyrazole-3-carboxylic acid (3-hydroxy-butyl)-amide

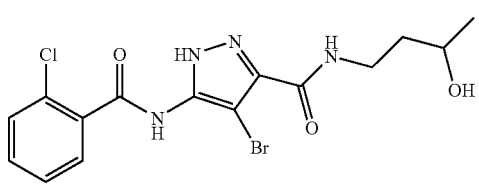

The pyrazole acid, prepared as described in Procedure 8, was coupled with 4-Amino-2-butanol (Fluka, 07195) using the method described in Procedure 10.

MS+=415.0

Example 48

Preparation of 4-Bromo-5-(2-chloro-benzoylamino)-1H-pyrazole-3-carboxylic acid (2-dimethylamino-1-methyl-ethyl)-amide

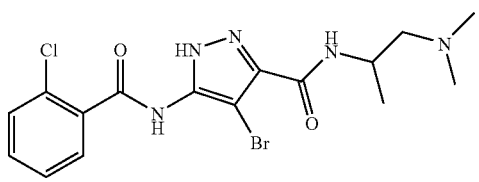

The pyrazole acid, prepared as described in Procedure 8, was coupled with 1-dimethylamino-2-propylamine (Fluka, 39370) using the method described in Procedure 10.

MS+=428.0

Example 49

Preparation of 4-Bromo-5-(2-chloro-benzoylamino)-1H-pyrazole-3-carboxylic acid (trans-2-hydroxy-cyclohexyl)-amide

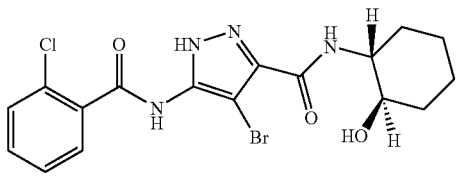

The pyrazole acid, prepared as described in Procedure 8, was coupled with trans-2-aminocyclohexanol hydrochloride (Aldrich, 22,257-7) using the method described in Procedure 10.
MS+=440.9

Example 50

Preparation of (R)-4-Chloro-5-(2-chloro-benzoylamino)-1H-pyrazole-3-carboxylic acid (1-phenyl-ethyl)-amide

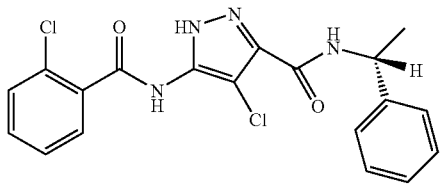

The pyrazole acid, prepared as described in Procedure 9, was coupled with (R)-(+)-α-methylbenzylamine (Aldrich, 11,554-1) using the method described in Procedure 10.
MS+=403.0
$^1$H-NMR (CD$_3$OD) δ 7.53 (m, 9H), 5.20 (q, J=7.1 Hz, 1H), 1.53 (d, J=7.1 Hz, 3H).

Example 51

Preparation of (S)-4-Bromo-5-(2-chloro-benzoylamino)-1H-pyrazole-3-carboxylic acid (1-methyl-2-piperidin-1-yl-ethyl)-amide

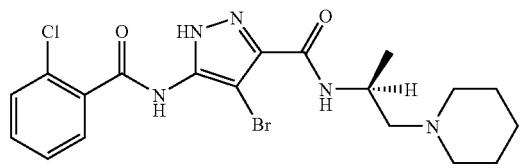

The pyrazole acid, prepared as described in Procedure 8, was coupled (using the methods described in Procedure 3) with the amine (S)-tert-butyl 1-(piperidin-1-yl)propan-2-ylcarbamate prepared as described in Procedure 2.

MS+=468.1
$^1$H-NMR (CDCl$_3$) δ 7.93 (d, J=7.2 Hz, 1H), 7.45 (m, 4H), 4.13 (m, 1H), 2.43 (m, 4H), 1.56 (m, 3H), 1.42 (m, 1H), 1.28 (d, J=9.9 Hz, 3H).

Example 52

Preparation of 4-Bromo-5-(2-chloro-benzoylamino)-1H-pyrazole-3-carboxylic acid (1-methyl-2-pyrrolidin-1-yl-ethyl)-amide

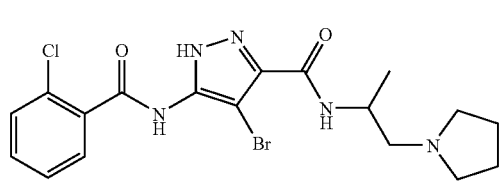

The pyrazole acid, prepared as described in Procedure 8, was coupled (using the methods described in Procedure 3) with the amine tert-butyl 1-(pyrrolidin-1-yl)propan-2-ylcarbamate prepared as shown in Procedure 2.
MS+=454.0
$^1$H-NMR (CDCl$_3$) δ 7.88 (d, J=7.1 Hz, 1H), 7.41 (m, 4H), 7.21 (m, 1H), 4.36 (m, 1H), 3.02 (m, 1H), 2.79 (m, 2H), 2.64 (m, 2H), 2.42 (m, 1H), 1.76 (m, 4H), 1.25 (d, J=6.0 Hz, 3H).

Example 53

Preparation of 4-Bromo-5-(2-chloro-benzoylamino)-1H-pyrazole-3-carboxylic acid (1-methyl-2-morpholin-4-yl-ethyl)-amide

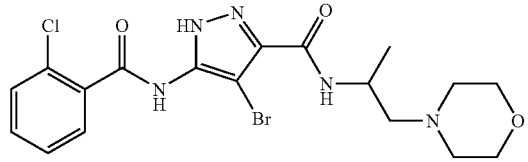

The pyrazole acid, prepared as described in Procedure 8, was coupled with α-methyl-4-morpholineethanamine (TimTec, Inc., TBB015574) using the method described in Procedure 10.
MS+=470.0
$^1$H-NMR (CDCl$_3$) δ 9.08 (br, 1H), 7.90 (d, J=7.7 Hz, 1H), 7.41 (m, 4H), 4.25 (m, 1H), 3.66 (m, 4H), 2.46 (m, 6H), 1.24 (d, J=6.6 Hz, 3H).

Example 54

Preparation of (S)-4-Bromo-5-(2-chloro-benzoylamino)-1H-pyrazole-3-carboxylic acid (2-hydroxy-1-methyl-ethyl)-amide

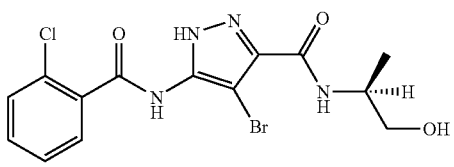

The pyrazole acid, prepared as described in Procedure 8, was coupled with L-alaninol (Fluka, 05230) using the method described in Procedure 10.
MS+=401.0
$^1$H-NMR (CD$_3$OD) δ 7.62 (m, 1H), 7.47 (m, 3H), 4.14 (m, 1H), 3.60 (d, J=4.9 Hz, 2H), 1.25 (d, J=6.6 Hz, 3H).

Example 55

Preparation of 4-Bromo-5-(2-chloro-benzoylamino)-1H-pyrazole-3-carboxylic acid [2-(1-methyl-piperidin-4-yl)-ethyl]-amide

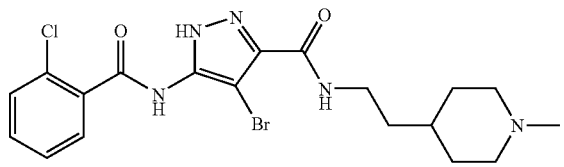

The pyrazole acid, prepared as described in Procedure 8, was coupled with 1-methyl-4-piperidineethanamine (prepared as shown in Procedure 13) using the method described in Procedure 10.

MS+=468.0

$^1$H-NMR (CDCl3) δ 7.93 (d, J=7.6 Hz, 1H), 7.63 (m, 1H), 7.52 (m, 2H), 7.46 (m, 1H), 3.47 (m, 2H), 2.88 (m, 2H), 2.30 (s, 3H), 1.98 (m, 2H), 1.68 (m, 2H), 1.31 (m, 3H).

Example 56

Preparation of 4-Bromo-5-(2-chloro-benzoylamino)-1H-pyrazole-3-carboxylic acid (1-benzenesulfonyl-piperidin-4-yl)-amide

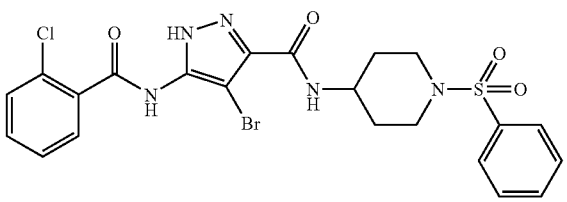

The pyrazole acid, prepared as described in Procedure 8, was coupled with 1-phenylsulfonyl-4-pieridineamine prepared as shown in Procedure 5, using the method of Procedure 3.

MS+=566.0

$^1$H-NMR (CD$_3$OD) δ 7.75 (m, 2H), 7.64 (m, 4H), 7.48 (m, 3H), 3.70 (m, 3H), 2.56 (m, 2H), 2.00(m, 2H), 1.72 (m, 2H).

Example 57

Preparation of 4-Bromo-5-(2-chloro-benzoylamino)-1H-pyrazole-3-carboxylic acid (1-methyl-piperidin-4-yl)-amide

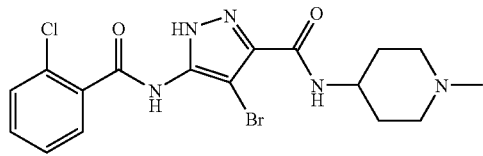

The pyrazole acid, prepared as described in Procedure 8, was coupled with 1-methyl-4-piperidineamine (Matrix 7267), using the method of Procedure 3.

MS+=440.0

$^1$H-NMR (CD$_3$OD) δ 7.53 (m, 4H), 3.88 (m, 1H), 2.88 (m, 2H), 2.27 (m, 5H), 1.98 (m, 2H), 1.68 (m, 2H).

Example 58

Preparation of (R)-4-Bromo-5-(2-chloro-benzoylamino)-1H-pyrazole-3-carboxylic acid (1-methyl-2-piperidin-1-yl-ethyl)-amide

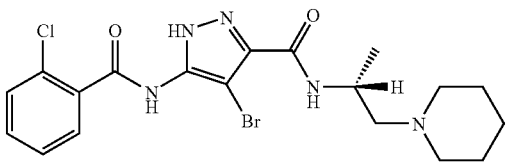

The pyrazole acid, prepared as described in Procedure 8, was coupled with 1-alpha-methyl-piperidineethanamine, (TimTec, Inc., TBB015577) using the method described in Procedure 10.

MS+=468.1

$^1$H-NMR (CDCl$_3$) δ 7.88 (d, J=7.1 Hz, 1H), 7.55 (m, 1H), 7.39 (m, 3H), 4.18 (m, 1H), 2.50 (m, 6H), 1.57 (m, 4H), 1.41 (m, 2H), 1.22 (d, J=6.0 Hz, 3H).

Example 59

Preparation of (R)-4-Bromo-5-(2-chloro-benzoylamino)-1H-pyrazole-3-carboxylic acid (1-methyl-2-morpholin-4-yl-ethyl)-amide

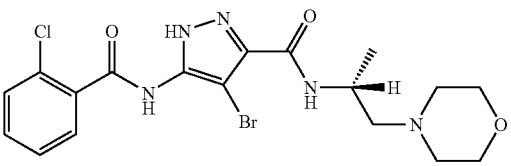

The pyrazole acid, prepared as described in Procedure 8, was coupled with (R)-alpha-methyl-4-morpholinethanamine (prepared as shown in Procedure 2) using the method of Procedure 3.

MS+=469.8

$^1$H-NMR (CDCl$_3$) δ 9.14 (br, 1H), 7.91 (m, 1H), 7.44 (m, 4H), 4.23 (m, 1H), 3.67 (m, 4H), 2.46 (m, 6H), 1.25 (d, J=6.0 Hz, 3H).

Example 60

Preparation of (R)-4-Bromo-5-(2-chloro-benzoylamino)-1H-pyrazole-3-carboxylic acid (1-phenyl-2-piperidin-1-yl-ethyl)-amide

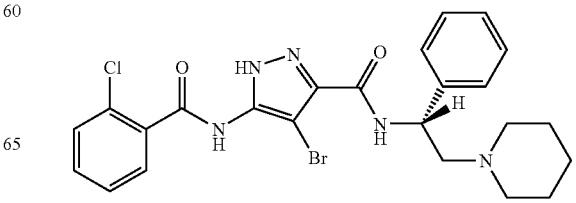

The pyrazole acid, prepared as described in Procedure 8, was coupled with (R)-alpha-phenyl-1-piperidineethanamine (prepared as shown in Procedure 2) using the method of Procedure 3.

MS+=530.3

¹H-NMR (CDCl₃) δ 8.95 (br, 1H), 8.15 (m, 1H), 7.91 (d, J=7.7 Hz, 1H), 7.38 (m, 8H), 5.21 (m, 1H), 2.98 (m, 1H), 2.63 (m, 3H), 2.55 (m, 2H), 1.61 (m, 4H), 1.44 (m, 2H).

Example 61

Preparation of (S)-4-Bromo-5-(2-chloro-benzoylamino)-1H-pyrazole-3-carboxylic acid (1-phenyl-2-piperidin-1-yl-ethyl)-amide

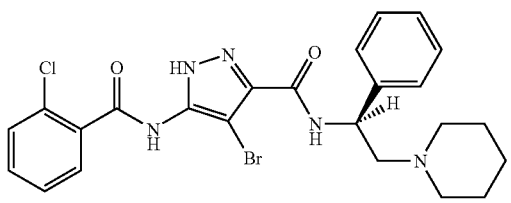

The pyrazole acid, prepared as described in Procedure 8, was coupled with (S)-alpha-phenyl-1-piperidineethanamine (prepared as shown in Procedure 2) using the method of Procedure 3.

MS+=530.3

¹H-NMR (CDCl₃) δ 8.93 (br, 1H), 8.09 (m, 1H), 7.81 (d, J=7.7 Hz, 1H), 7.32 (m, 8H), 5.17 (m, 1H), 2.88 (m, 1H), 2.55 (m, 3H), 2.39 (m, 2H), 1.55 (m, 4H), 1.40 (m, 2H).

Example 62

Preparation of (R)-4-Bromo-5-(2-chloro-benzoylamino)-1H-pyrazole-3-carboxylic acid (2-hydroxy-1-methyl-ethyl)-amide

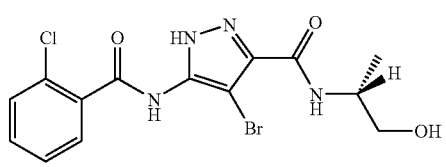

The pyrazole acid, prepared as described in Procedure 8, was coupled with D-alaninol (Fluka, 05225) using the method described in Procedure 10.

MS+=401.2

¹H-NMR (CD₃OD) δ 7.62 (m, 1H), 7.46 (m, 3H), 4.15 (m, 1H), 3.60 (d, J=4.9 Hz, 2H), 1.25 (d, J=6.6 Hz, 3H).

Example 63

Preparation of (R)-4-Bromo-5-(2-chloro-benzoylamino)-1H-pyrazole-3-carboxylic acid (2-dimethylamino-1-methyl-ethyl)-amide

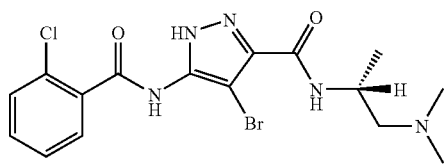

The pyrazole acid, prepared as described in Procedure 8, was coupled with (R)—N,N dimethyl-1,2-propanediamine (prepared as shown in Procedure 2) using the method of Procedure 3.

MS+=428.2

¹H-NMR (CDCl₃) δ 7.87 (d, J=7.1 Hz, 1H), 7.41 (m, 4H), 4.32 (m, 1H), 2.79 (m, 1H), 2.35 (m, 7H), 1.25 (d, J=6.6 Hz, 3H).

Example 64

Preparation of (R)-5-(2-Chloro-benzoylamino)-1H-pyrazole-3-carboxylic acid (1-phenyl-ethyl)-amide

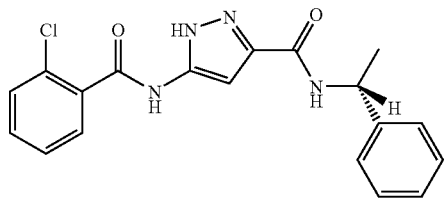

The pyrazole acid, prepared as described in Procedure 8, was coupled with (R)-(+)-alpha-Methylbenzylamine (Fluka, 77880) using the method described in Procedure 10.

MS+=369.1

¹H-NMR (CDCl₃) δ 7.63 (m, 1H), 7.31 (m, 6H), 7.11 (m, 1H), 6.62 (m, 1H), 4.57 (m, 1H), 1.33 (d, J=7.1 Hz, 3H).

Example 65

Preparation of (S)-4-Bromo-5-(2-chloro-benzoylamino)-1H-pyrazole-3-carboxylic acid (2-dimethylamino-1-methyl-ethyl)-amide

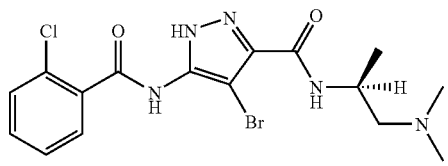

The pyrazole acid, prepared as described in Procedure 8, was coupled with (S)—N,N dimethyl-1,2-propanediamine (prepared as shown in Procedure 2) using the method of Procedure 3.

MS+=428.0

¹H-NMR (CDCl₃) δ 8.95 (br, 1H), 7.92 (m, 1H), 7.39 (m, 4H), 4.41 (m, 1H), 2.83 (m, 1H), 2.29 (m, 7H), 1.25 (d, J=1.25 Hz, 3H).

Example 66

Preparation of (R)-4-Bromo-5-(2-chloro-benzoylamino)-1H-pyrazole-3-carboxylic acid (1-dimethylaminomethyl-propyl)-amide

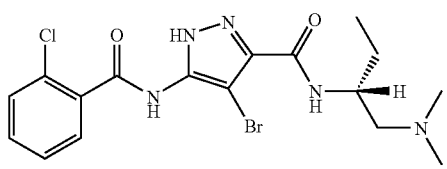

The pyrazole acid, prepared as described in Procedure 8, was coupled with (R)—N,N-dimethyl-1,2-butanediamine (prepared as shown in Procedure 2) using the method of Procedure 3.

MS+=442.0

¹H-NMR (CDCl₃) δ 8.77 (br, 1H), 7.89 (d, J=7.2 Hz, 1H), 7.44 (m, 3H), 4.31 (m, 1H), 2.83 (m, 1H), 2.38 (m, 7H), 1.63 (m, 2H), 1.00 (t, J=7.2 Hz, 3H).

Example 67

Preparation of (R)-4-Bromo-5-(2-chloro-benzoylamino)-1H-pyrazole-3-carboxylic acid (2-diethylamino-1-methyl-ethyl)-amide

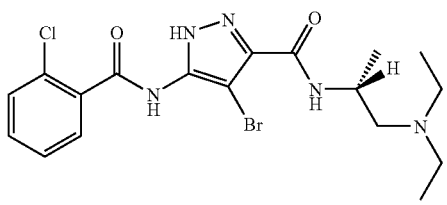

The pyrazole acid, prepared as described in Procedure 8, was coupled with (R)—N,N-diethyl-1,2-propanediamine (prepared as shown in Procedure 2) using the method of Procedure 3.

MS+=456.1

¹H-NMR (CDCl₃) δ 7.96 (d, J=7.1 Hz, 1H), 7.44 (m, 3H), 4.12 (m, 1H), 2.54 (m, 6H), 1.27 (d, J=6.6 Hz, 3H), 1.00 (t, J=7.1 Hz, 6H).

Example 68

Preparation of (R)-4-Bromo-5-(2-chloro-benzoylamino)-1H-pyrazole-3-carboxylic acid [2-(ethyl-methyl-amino)-1-methyl-ethyl]-amide

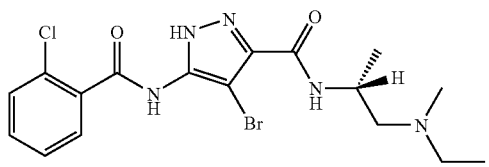

The pyrazole acid, prepared as described in Procedure 8, was coupled with (R)—N-ethyl-N-methyl-1,2-propanediamine (prepared as shown in Procedure 2) using the method of Procedure 3.

MS+=442.0

¹H-NMR (CDCl₃) δ 9.06 (br, 1H), 7.87 (d, J=7.7 Hz, 1H), 7.41 (m, 3H), 2.67 (m, 1H), 2.53 (m, 2H), 2.33 (m, 4H), 1.24 (d, J=6.6 Hz, 3H), 1.02 (t, J=7.1 Hz, 3H).

Example 69

Preparation of 4-Bromo-5-(2-chloro-benzoylamino)-1H-pyrazole-3-carboxylic acid (2-acetylamino-ethyl)-amide

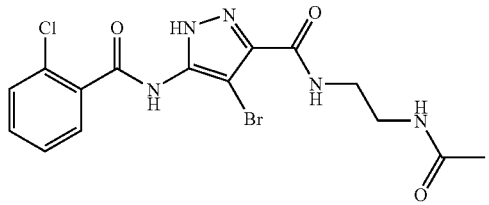

The pyrazole acid, prepared as described in Procedure 8, was coupled with N-(2-aminoethyl)acetamide (Fluka, 00911) using the method described in Procedure 10.

MS+=428.0

¹H-NMR (CD₃OD) δ 7.63 (m, 1H), 7.46 (m, 3H), 3.48 (m, 2H), 3.38 (m, 2H), 1.95 (s, 3H).

Example 70

Preparation of (R)-4-Bromo-5-(2-chloro-benzoylamino)-1H-pyrazole-3-carboxylic acid (1-dimethylaminomethyl-3-phenyl-propyl)-amide

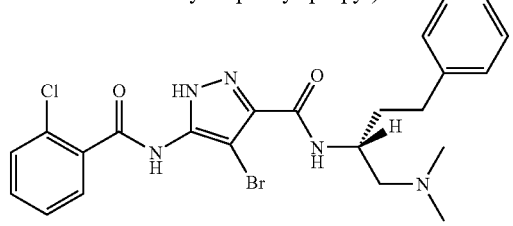

The pyrazole acid, prepared as described in Procedure 8, was coupled with (R)—N,N-dimethyl-4-phenyl-1,2-butanediamine (prepared as shown in Procedure 2) using the method of Procedure 3.

MS+=518.1

¹H-NMR (CDCl₃) δ 8.81 (br, 1H), 7.87 (d, J=7.1 Hz, 1H), 7.38 (m, 3H), 7.17 (m, 5H), 4.40 (m, 1H), 2.70 (m, 3H), 2.34 (m, 7H), 1.92 (m, 2H).

Example 71

Preparation of (R)-4-Bromo-5-(2-chloro-benzoylamino)-1H-pyrazole-3-carboxylic acid [2-(acetyl-methyl-amino)-1-methyl-ethyl]-amide

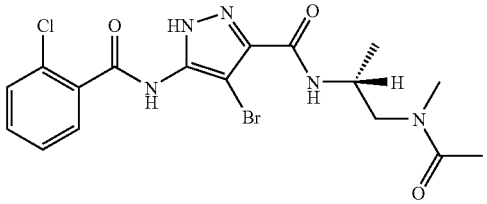

The pyrazole acid, prepared as described in Procedure 8, was coupled with (R)—N-acetyl-N-methyl-1,2-propanediamine (prepared as shown in Procedure 6) using the method of Procedure 3.
MS+=456.0
$^1$H-NMR (CDCl$_3$) δ 9.08 (s, 1H), 7.96 (m, 2H), 7.50 (m, 3H), 4.45 (m, 1H), 4.00 (m, 1H), 2.99 (m, 4H), 2.07 (s, 3H), 1.25 (t, J=6.0 Hz, 3H).

Example 72

Preparation of 4-Bromo-5-(2-chloro-benzoylamino)-1H-pyrazole-3-carboxylic acid [2-(methyl-phenyl-amino)-ethyl]-amide

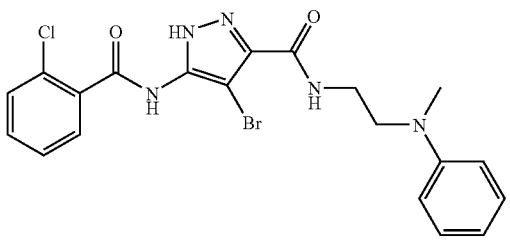

The pyrazole acid, prepared as described in Procedure 8, was coupled with N-mehtyl-N-phenyl-1,2-ethanediamine (prepared as shown in Procedure 2) using the method of Procedure 3.
MS+=476.0
$^1$H-NMR (DMSO-d6) δ 8.38 (br, 1H), 7.55 (m, 4H), 7.18 (t, J=8.1 Hz, 2H), 6.79 (d, J=8.1 Hz, 2H), 6.61 (t, J=6.9 Hz, 1H), 3.39 (m, 4H), 2.94 (s, 3H).

Example 73

Preparation of 4-Bromo-5-(2-chloro-benzoylamino)-1H-pyrazole-3-carboxylic acid ((3S)-1-benzyl-pyrrolidin-3-yl)-amide

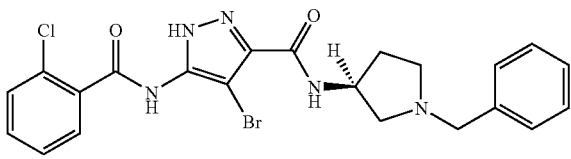

The pyrazole acid, prepared as described in Procedure 8, was coupled with (3S)-(+)-1-Benzyl-3-aminopyrrolidine (Aldrich, 53,659-8) using the method described in Procedure 10.
MS+=502.0
$^1$H-NMR (CDCl$_3$) δ 9.14 (br, 1H), 7.92 (d, J=7.8 Hz, 1H), 7.33 (m, 8H), 4.62 (m, 1H), 3.61 (s, 2H), 2.75 (m, 3H), 2.35 (m, 2H), 1.79 (m, 1H).

Example 74

Preparation of 4-Bromo-5-(2-chloro-benzoylamino)-1H-pyrazole-3-carboxylic acid ((3R)-1-benzyl-pyrrolidin-3-yl)-amide

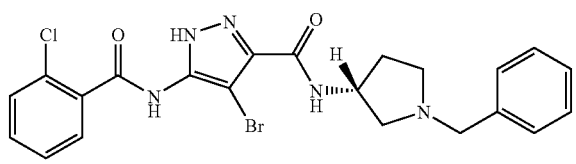

The pyrazole acid, prepared as described in Procedure 8, was coupled with (3R)-(−)-1-Benzyl-3-aminopyrrolidine (Lancaster Synthesis, 10302) using the method described in Procedure 10.
MS+=502.0
$^1$H-NMR (CDCl$_3$) δ 9.07 (br, 1H), 7.96 (d, J=7.5 Hz, 1H), 7.46 (m, 4H), 7.27 (m, 4H), 4.64 (m, 1H), 3.64 (s, 2H), 2.83 (m, 3H), 2.37 (m, 2H), 1.81 (m, 1H).

Example 75

Preparation of (R)-4-Bromo-5-(2-chloro-benzoylamino)-1H-pyrazole-3-carboxylic acid [2-(cyclopropyl-methyl-amino)-1-methyl-ethyl]-amide

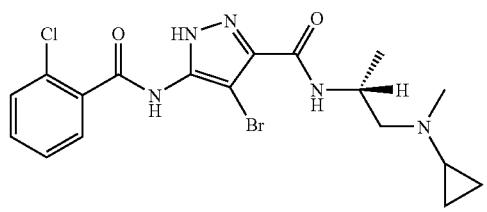

The pyrazole acid, prepared as described in Procedure 8, was coupled with (R)—N-cyclopropyl-N-methyl-1,2-propanediamine (prepared from compound 16 using the method of Procedure 2) using the method of Procedure 3.
MS+=454.0
$^1$H-NMR (CDCl$_3$) δ 9.08 (br, 1H), 7.93 (d, J=7.1 Hz, 1H), 7.42 (m, 3H), 4.20 (m, 1H), 2.78 (m, 1H), 2.57 (m, 1H), 2.37 (s, 3H), 1.76 (m, 1H), 1.23 (d, J=6.6 Hz, 3H), 0.46 (m, 4H).

Example 76

Preparation of 4-Bromo-5-(2-chloro-benzoylamino)-1H-pyrazole-3-carboxylic acid (4-phenyl-morpholin-2-ylmethyl)-amide

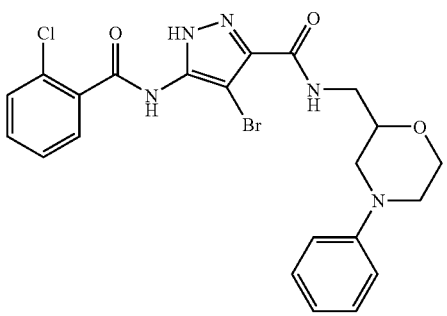

The pyrazole acid, prepared as described in Procedure 8, was coupled with C-(4-Phenyl-morpholin-2-yl)-methylamine (prepared as described in *Chem. Pharm. Bull.* 1992, 40, 652, which is incorporated herein by reference in its entirety.) using the method described in Procedure 10.

MS+=518.0

$^1$H-NMR (CDCl$_3$) δ 9.23 (s, 1H), 8.09 (m, 2H), 7.47 (m, 3H), 7.26 (m, 2H), 6.88 (m, 3H), 4.06 (m, 1H), 3.92 (m, 1H), 3.79 (m, 2H), 3.49 (m, 2H), 2.87 (m, 1H), 2.62 (m, 1H).

Example 77

Preparation of 4-Bromo-5-(2-chloro-benzoylamino)-1H-pyrazole-3-carboxylic acid [2-(3,4-dihydro-2H-quinolin-1-yl)-ethyl]-amide

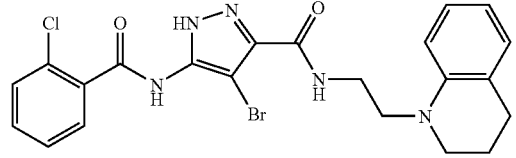

The pyrazole acid, prepared as described in Procedure 8, was coupled with 3,4-dihydro-1-(2H)-quinolineethanamine (prepared as shown in Procedure 2) using the method of Procedure 3.

MS+=502.0

$^1$H-NMR (DMSO-d6) δ 13.90 (br, 1H), 8.35 (br, 1H), 7.54 (m, 4H), 6.98 (t, J=6.0 Hz, 1H), 6.86 (d, J=9.0 Hz, 1H), 6.77 (d, J=9.0 Hz, 1H), 6.47 (m, 1H), 3.35 (m, 4H), 2.67 (m, 2H), 1.85 (m, 2H).

Example 78

Preparation of 4-Bromo-5-(2-chloro-benzoylamino)-1H-pyrazole-3-carboxylic acid [2-(1-methyl-pyrrolidin-2-yl)-ethyl]-amide

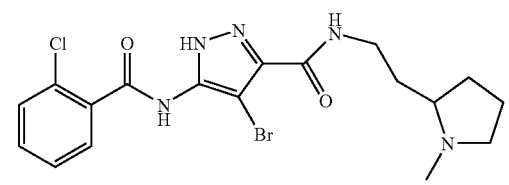

The pyrazole acid, prepared as described in Procedure 8, was coupled with 2-(2-aminoethyl)-1-methylpyrrolidine (Aldrich, 13,950-5) using the method of Procedure 17.

MS+=454.2

Example 79

Preparation of 4-Bromo-5-(2-chloro-benzoylamino)-1H-pyrazole-3-carboxylic acid (pyridin-2-ylmethyl)-amide

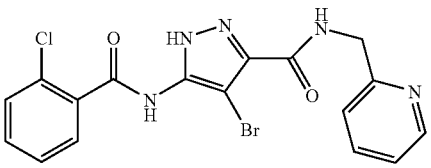

The pyrazole acid, prepared as described in Procedure 8, was coupled with 2-picolylamine (Fluka, 80350) using the method of Procedure 17.

MS+=434.1

Example 80

Preparation of 4-Bromo-5-(2-chloro-benzoylamino)-1H-pyrazole-3-carboxylic acid (pyridin-3-ylmethyl)-amide

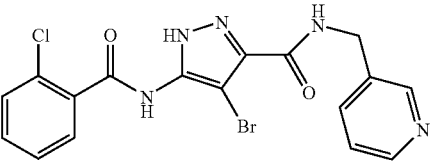

The pyrazole acid, prepared as described in Procedure 8, was coupled with 3-picolylamine (Fluka, 80360) using the method of Procedure 17.

MS+=434.1

Example 81

Preparation of 4-Bromo-5-(2-chloro-benzoylamino)-1H-pyrazole-3-carboxylic acid (pyridin-4-ylmethyl)-amide

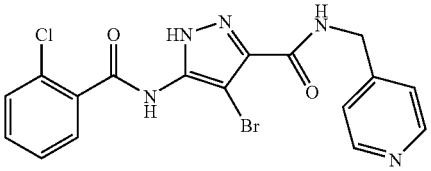

The pyrazole acid, prepared as described in Procedure 8, was coupled with 4-Picolylamine (Fluka, 80370) using the method of Procedure 17.

MS+=434.2

Example 82

Preparation of 4-Bromo-5-(2-chloro-benzoylamino)-1H-pyrazole-3-carboxylic acid (2-piperidin-1-yl-ethyl)-amide

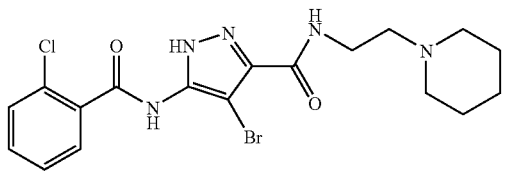

The pyrazole acid, prepared as described in Procedure 8, was coupled with 1-(2-Aminoethyl)piperidine (Lancaster Synthesis, 10084) using the method of Procedure 17.
MS+=454.1

Example 83

Preparation of 4-Bromo-5-(2-chloro-benzoylamino)-1H-pyrazole-3-carboxylic acid [1-(4-hydroxy-phenyl)-ethyl]-amide

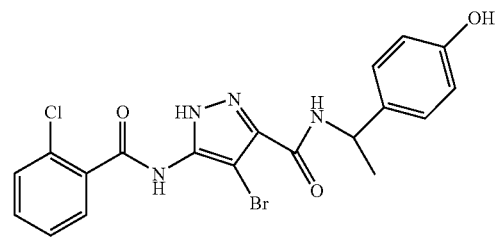

The pyrazole acid, prepared as described in Procedure 8, was coupled with 4-(1-Aminoethyl)phenol (Frinton Laboratories, Inc., FR-2083) using the method of Procedure 17.
MS+=462.9

Example 84

Preparation of 4-Bromo-5-(2-chloro-benzoylamino)-1H-pyrazole-3-carboxylic acid (2-pyrrolidin-1-yl-ethyl)-amide

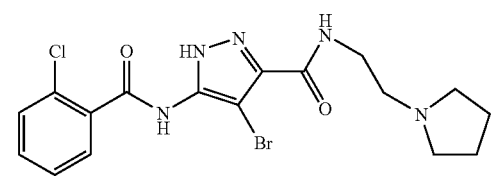

The pyrazole acid, prepared as described in Procedure 8, was coupled with N-(2-Aminoethyl)pyrrolidine (Acros, 10370) using the method of Procedure 17.
MS+=440.1

Example 85

Preparation of 4-Bromo-5-(2-chloro-benzoylamino)-1H-pyrazole-3-carboxylic acid (5-methyl-pyrazin-2-ylmethyl)-amide

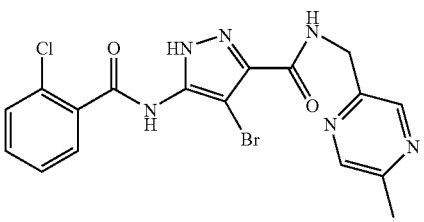

The pyrazole acid, prepared as described in Procedure 8, was coupled with 2-(Aminomethyl)-5-methylpyrazine (TCI America, A1154) using the method of Procedure 17.
MS+=449.1

Example 86

Preparation of 4-Bromo-5-(2-chloro-benzoylamino)-1H-pyrazole-3-carboxylic acid (2-hydroxy-propyl)-amide

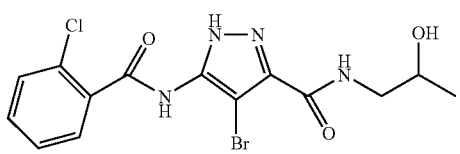

The pyrazole acid, prepared as described in Procedure 8, was coupled with (α)-1-Amino-2-propanol (Fluka, 09280) using the method of Procedure 17.
MS+=401.0

Example 87

Preparation of 4-Bromo-5-(2-chloro-benzoylamino)-1H-pyrazole-3-carboxylic acid piperidin-1-ylamide

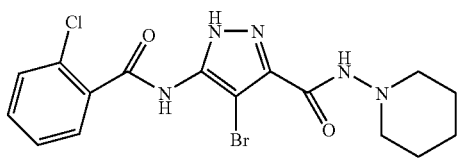

The pyrazole acid, prepared as described in Procedure 8, was coupled with 1-Aminopiperidine (Lancaster Synthesis, 14078) using the method of Procedure 17.
MS+=426.1

Example 88

Preparation of (R)-4-Bromo-5-(2-chloro-benzoylamino)-1H-pyrazole-3-carboxylic acid (1-p-tolylethyl)-amide

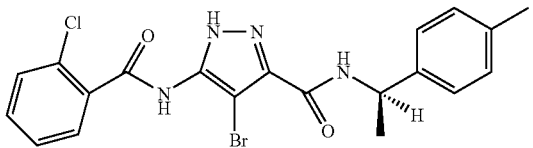

The pyrazole acid, prepared as described in Procedure 8, was coupled with (R)-(+)-α,4-Dimethylbenzylamine (Aldrich, 40,524-8) using the method of Procedure 17.
MS+=460.9

Example 89

Preparation of 4-Bromo-5-(2-chloro-benzoylamino)-1H-pyrazole-3-carboxylic acid (2-aminocarbonylethyl)-amide

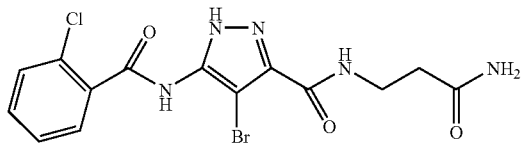

The pyrazole acid, prepared as described in Procedure 8, was coupled with β-alaninamide hydrochloride (TCI America, A1391) using the method of Procedure 17.
MS+=414.0

Example 90

Preparation of 4-Bromo-5-(2-chloro-benzoylamino)-1H-pyrazole-3-carboxylic acid (2-(tert-butoxycarbonyl)eth-1-yl)-amide

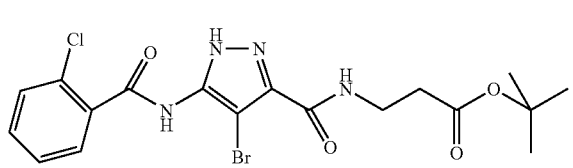

The pyrazole acid, prepared as described in Procedure 8, was coupled with beta-alanine t-butyl ester hydrochloride (Sigma, A3041) using the method of Procedure 17.
MS+=470.6

Example 91

Preparation of (R)-4-Bromo-5-(2-chloro-benzoylamino)-1H-pyrazole-3-carboxylic acid [1-(4-chlorophenyl)-ethyl]-amide

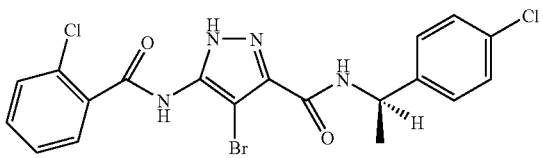

The pyrazole acid, prepared as described in Procedure 8, was coupled with (R)-1-(4-Chlorophenyl)ethylamine (Lancaster Synthesis, 19119) using the method of Procedure 17.
MS+=480.9

Example 92

Preparation of (R)-4-Bromo-5-(2-chloro-benzoylamino)-1H-pyrazole-3-carboxylic acid [1-(4-methoxy-phenyl)-ethyl]-amide

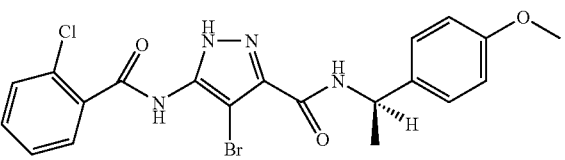

The pyrazole acid, prepared as described in Procedure 8, was coupled with (R)-(+)-1-(4-Methoxyphenyl)ethylamine (Lancaster Synthesis, 16321) using the method of Procedure 17.
MS+=476.8

Example 93

Preparation of 4-Bromo-5-(2-chloro-benzoylamino)-1H-pyrazole-3-carboxylic acid [1-(4-methanesulfonyl-phenyl)-ethyl]-amide

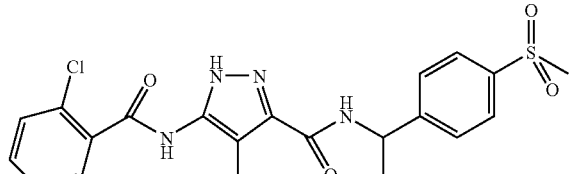

The pyrazole acid, prepared as described in Procedure 8, was coupled with alpha-methyl-4-(methylsulfonyl)-benzenemethanamine (Peakdale Molecular 3000851) using the method of Procedure 17.
MS+=524.9

Example 94

Preparation of 4-Bromo-5-(2-chloro-benzoylamino)-1H-pyrazole-3-carboxylic acid (2-dimethylamino-ethyl)-methyl-amide

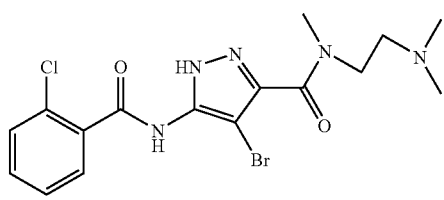

The pyrazole acid, prepared as described in Procedure 8, was coupled with N,N,N'-Trimethylethylenediamine (Fluka, 92240) using the method of Procedure 17.
MS+=428.1

Example 95

Preparation of 4-bromo-5-(2-chlorobenzoylamino)-1H-pyrazole-3-carboxylic acid [2-(pyrrolidin-1-ylm-ethyl)-pyrrolidin-1-yl]amide

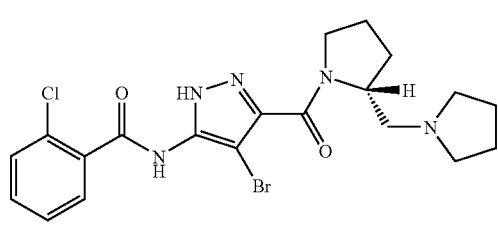

The pyrazole acid, prepared as described in Procedure 8, was coupled with 1-[(2R)-2-pyrrolidinylmethyl]-pyrrolidine (prepared using the method of De Costa, B. R.; et al. J. Med Chem. 1992, Vol 35 page 4334, which is incorporated herein by reference in its entirety) using the method of Procedure 17.
MS+=480.1

Example 96

Preparation of 4-Bromo-5-(2-chloro-benzoylamino)-2H-pyrazole-3-carboxylic acid (2-oxo-azepan-3-yl)-amide

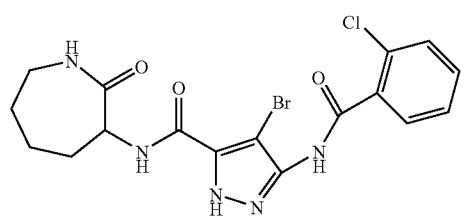

The pyrazole acid, prepared as described in Procedure 8, was coupled with DL-a-amino-e-caprolactam (TCI America, A1003) ) using the method of Procedure 17.
MS+=454.1

No Example 97

Example 98

Preparation 4-bromo-5-(2-chloro-benzoylamino) 1H-pyrazole-3-carboxylic acid (4-phenylpiperzin-1-yl)amide

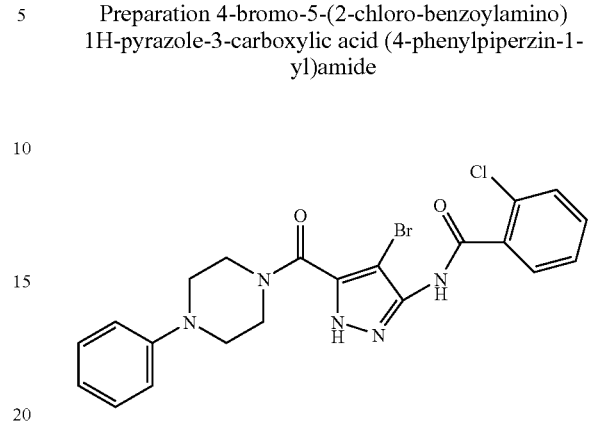

The pyrazole acid, prepared as described in Procedure 8, was coupled with 1-Phenylpiperazine (Fluka, 78919) using the method of Procedure 17.
MS+=488.1

Example 99

Preparation of 4-Bromo-3-(2-chloro-benzoylamino)-1H-pyrazole-4-carboxylic acid (1-ethyl-pyrrolidin-2-ylmethyl)-amide

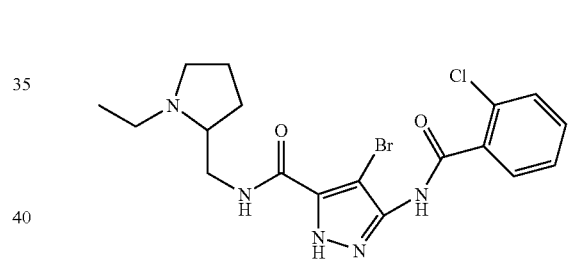

The pyrazole acid, prepared as described in Procedure 8, was coupled with 2-(aminomethyl)-1-ethylpyrrolidine (Acros Organics, 17948) using the method of Procedure 17.
MS+=454.2

Example 100

Preparation of (R)-4-Bromo-5-(2-chloro-benzoy-lamino)-1H-pyrazole-3-carboxylic acid [1-(4-fluoro-phenyl)-ethyl]-amide

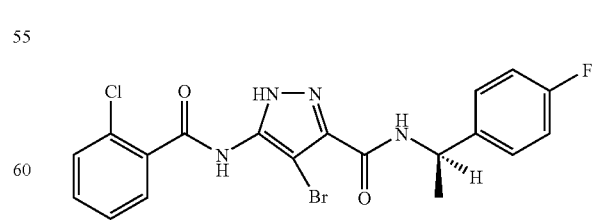

The pyrazole acid, prepared as described in Procedure 8, was coupled with (R)-1-(4-fluorophenyl)ethylamine (Lancaster Synthesis, 19120) using the method of Procedure 17.
MS+=464.9

Example 101

Preparation of (S)-4-Bromo-5-(2-chloro-benzoylamino)-1H-pyrazole-3-carboxylic acid (2-oxo-azepan-3-yl)-amide

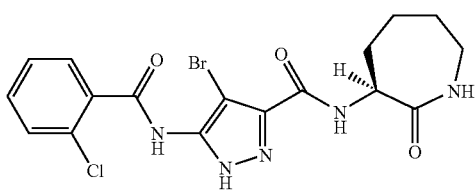

The pyrazole acid, prepared as described in Procedure 8, was coupled with L(−)-alpha-amino-epsilon-caprolactam hydrochloride (Fluka, cat: 21612) using the method described in Procedure 10.

MS+=454.0
$^1$H-NMR (CD$_3$OD) δ 7.65 (m, 1H), 7.40-7.52 (m, 3H), 5.48 (s, 3H), 4.72 (d, J=9.9 Hz, 1H), 3.31 (m, 2H), 2.25-1.95 (m, 2H), 1.82-1.95 (m, 2H), 1.60 (m, 1H), 1.45 (m, 1H).

Example 102

Preparation of (R)-4-Bromo-5-(2-chloro-benzoylamino)-1H-pyrazole-3-carboxylic acid (2-oxo-azepan-3-yl)-amide

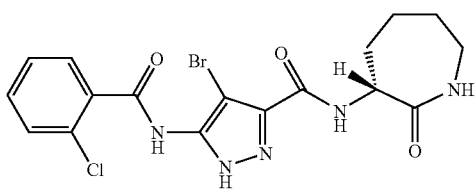

The pyrazole acid, prepared as described in Procedure 8, was coupled with (2-Oxo-azepan-3-yl)-carbamic acid tert-butyl ester (prepared as described in Martin G. Banwell and Kenneth J. McRae; *J. Org. Chem.* 2001, 66, 6768, which is incorporated herein by reference in its entirety) using the method of Procedure 3.

MS+=454.0
$^1$H-NMR (CD$_3$OD) δ 7.65 (m, 1H), 7.40-7.52 (m, 3H), 5.48 (s, 3H), 4.72 (d, J=9.9 Hz, 1H), 3.31 (m, 2H), 2.25-1.95 (m, 2H), 1.82-1.95 (m, 2H), 1.60 (m, 1H), 1.45 (m, 1H).

Example 103

Preparation of (S)-4-Bromo-5-(2-chloro-benzoylamino)-1H-pyrazole-3-carboxylic acid (1-methyl-2-oxo-azepan-3-yl)-amide

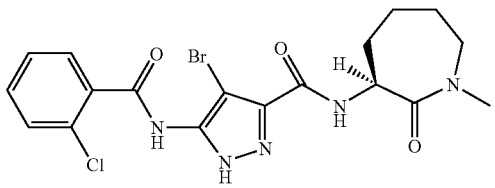

The pyrazole acid, prepared as described in Procedure 8, was coupled with (S)-alpha-amine-epsilon-N-methyl-caprolactam (Astatech, Inc., cat: 66077-1) using the method described in Procedure 10.

MS+=468.2
$^1$H-NMR (CD$_3$OD) δ 7.65 (m, 1H), 7.40-7.58 (m, 3H), 3.73 (dd, J=11.4, 15.3 Hz, 1H), 3.34 (m, 2H), 3.05 (s, 3H), 2.12 (m, 1H), 2.06-1.79 (m, 3H), 1.52 (m, 2H).

Example 104

Preparation of (R)-4-Bromo-5-(2-chloro-benzoylamino)-1H-pyrazole-3-carboxylic acid (1-methyl-2-oxo-azepan-3-yl)-amide

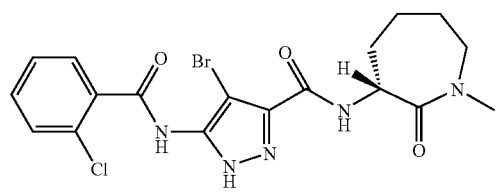

The pyrazole acid, prepared as described in Procedure 8, was coupled with (1-Methyl-2-oxo-azepan-3-yl)-carbamic acid tert-butyl ester (prepared as described in Muriel Amblard et al; *J. Med. Chem.* 1999, 42, 4193, which is incorporated herein by reference in it entirety) using the method of Procedure 3.

MS+=468.2
$^1$H-NMR (CD$_3$OD) δ 7.65 (m, 1H), 7.40-7.58 (m, 3H), 3.73 (dd, J=11.4, 15.3 Hz, 1H), 3.34 (m, 2H), 3.05 (s, 3H), 2.12 (m, 1H), 2.06-1.79 (m, 3H), 1.52 (m, 2H).

Example 105

Preparation of 4-Bromo-5-(2-chloro-benzoylamino)-1H-pyrazole-3-carboxylic acid (2-oxo-5-phenyl-2,3-dihydro-1H-benzo[e][1,4]diazepin-3-yl)-amide

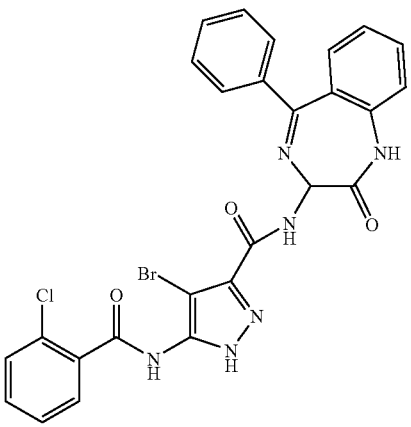

The pyrazole acid, prepared as described in Procedure 8, was coupled with 3-amino-1-methyl-5-phenyl-1,3-dihydro-benzo[e][1,4]diazepin-2-one (Ronald G. Sherrill and Elizabeth E. Sugg; *J. Org. Chem.* 1995, 60, 730.) using the method described in Procedure 10.

MS+=579.0
$^1$H-NMR (CD$_3$OD) δ 7.64 (m, 2H), 7.21-7.66 (m, 11H), 5.54 (s, 1H).

Example 106

Preparation of (R)-4-Bromo-5-(2-chloro-benzoylamino)-1H-pyrazole-3-carboxylic acid (1-methyl-azepan-3-yl)-amide

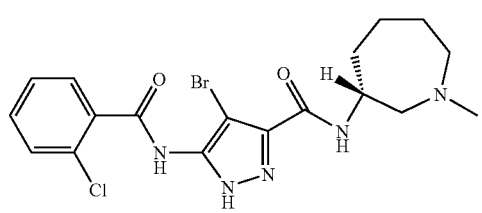

The pyrazole acid, prepared as described in Procedure 8, was coupled with Azepan-3-ylamine (prepared using procedures described in Procedure 23 followed by Procedure 2) using the method described in Procedure 10.

MS+=454.1

$^1$H-NMR (D$_2$O) δ 7.52 (d, J=7.5 Hz, 1H), 7.42 (m, 2H), 7.34 (m, 1H), 4.25 (m, 1H), 3.33-3.50 (m, 3H), 3.13 (m, 1H), 2.85 (s, 3H), 1.50-2.10 (m, 6H).

Example 107

Preparation of 4-Bromo-5-(2-chloro-benzoylamino)-1H-pyrazole-3-carboxylic acid (1-methyl-2-oxo-5-phenyl-2,3-dihydro-1H-benzo[e][1,4]diazepin-3-yl)-amide

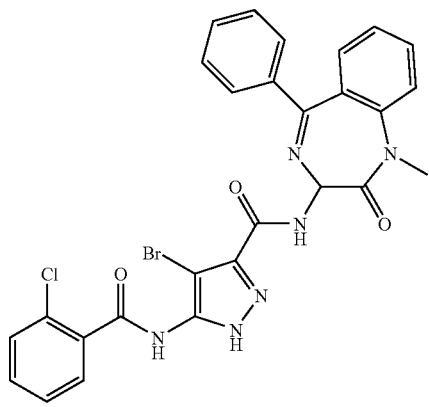

The pyrazole acid, prepared as described in Procedure 8, was coupled with 3-amino-1-methyl-5-phenyl-1,3-dihydro-benzo[e][1,4]diazepin-2-one (prepared as described by Ronald G. Sherrill and Elizabeth E. Sugg; *J. Org. Chem.* 1995, 60, 730, which is incorporated herein by reference in its entirety) using the method described in Procedure 10.

MS+=591.1

$^1$H-NMR (CDCl$_3$) δ 9.25 (bs, 1H), 8.71 (d, J=8.10 Hz, 1H), 8.03 (d, J=7.2 Hz, 1H), 7.63 (m, 3H), 7.52-7.35 (m, 8H), 7.26 (m, 2H), 5.72 (d, J=7.5 Hz, 1H), 3.50 (s, 3H).

Example 108

Preparation of 5-(2-Chloro-benzoylamino)-1H-pyrazole-3-carboxylic acid (2-oxo-5-phenyl-2,3-dihydro-1H-benzo[e][1,4]diazepin-3-yl)-amide

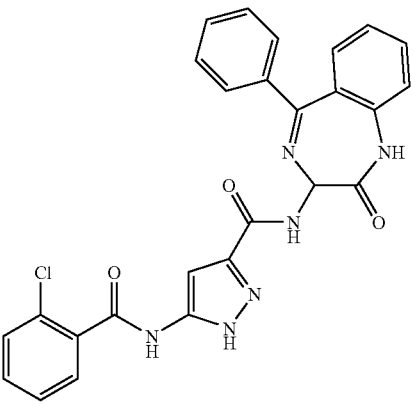

The pyrazole acid, prepared as described in Procedure 8, was coupled with the amine prepared in Procedure 20, using the method described in Procedure 10.

MS+=499.1

$^1$H-NMR (CD$_3$OD) δ 7.59-7.32 (m, 14H), 5.55 (s, 1H).

Example 109

Preparation of 4-Bromo-5-(2-chloro-benzoylamino)-1H-pyrazole-3-carboxylic acid (2-oxo-2,3,4,5-tetrahydro-1H-benzo[b]azepin-3-yl)-amide

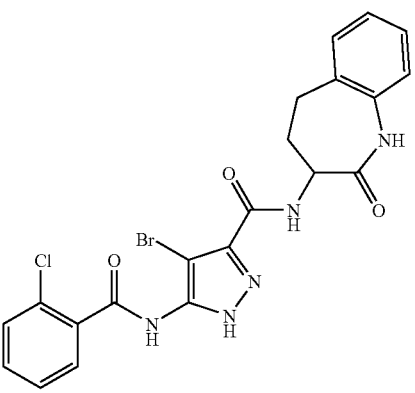

The pyrazole acid, prepared as described in Procedure 8, was coupled with 3-amino-1,3,4,5-tetrahydro-2H-1-benzazepin-2-one (Tyger Scientific Product List; A18401) using the method described in Procedure 10.

MS+=502.0

$^1$H-NMR (DMSO-d6) δ 13.86 (br, 1H), 10.61 (br, 1H), 10.04 (s, 1H), 8.08 (m, 1H), 7.56 (m, 4H), 7.32 (m, 2H), 7.17 (m, 1H), 7.04 (m, 1H), 4.34 (m, 1H), 2.73 (m, 3H), 2.18 (m, 1H).

Example 110

Preparation of 4-Chloro-5-(2-chloro-benzoylamino)-1H-pyrazole-3-carboxylic acid (2-oxo-5-phenyl-2,3-dihydro-1H-benzo[e][1,4]diazepin-3-yl)-amide

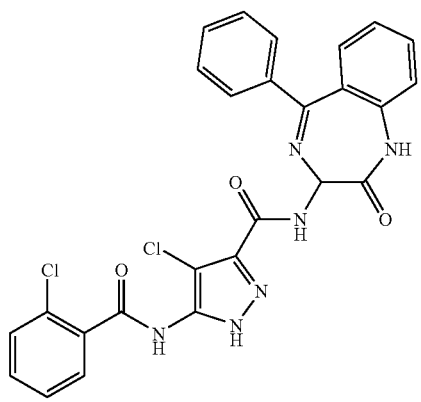

The title compound was prepared using the methods of Procedure 9 followed by coupling to the amine prepared in Procedure 20, using the method described in Procedure 10.

MS+=532.9

$^1$H-NMR (CD$_3$OD) δ 7.62 (m, 2H), 7.55-7.24 (m, 11H), 5.54 (s, 1H).

Example 111

Preparation of 4-Bromo-5-(2-chloro-benzoylamino)-1H-pyrazole-3-carboxylic acid (5-methyl-6-oxo-6,7-dihydro-5H-dibenzo[b,d]azepin-7-yl)-amide

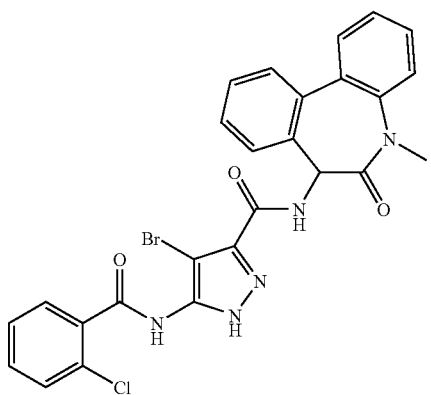

The pyrazole acid, prepared as described in Procedure 8, was coupled with 7-amino-5-methyl-5H,7H-dibenzo[b,d]azepin-6-one (prepared as described in International Patent Application WO 99/32453, which is incorporated herein by reference in its entirety) using the method described in Procedure 10.

MS+=564.0

$^1$H-NMR (DMSO-d6) δ 14.14 (s, 1H), 10.40-10.10 (br, 1H), 8.80-8.40 (br, 1H), 7.75 (m, 2H), 7.62-7.47 (m, 9H), 7.38 (m, 1H), 5.25 (m, 1H), 3.30 (s, 1H).

Example 112

Preparation of 4-Bromo-5-(2-chloro-benzoylamino)-1H-pyrazole-3-carboxylic acid (5-cyclohexyl-2-oxo-2,3-dihydro-1-H-benzo[e][1,4]diazepin-3-yl)-amide

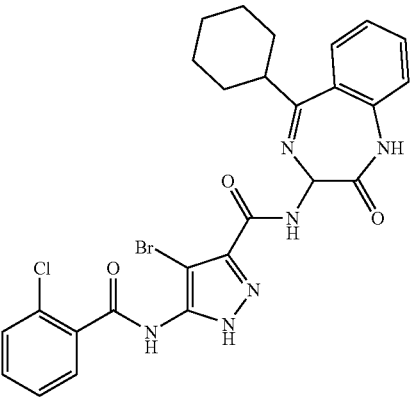

The pyrazole acid, prepared as described in Procedure 8, was coupled with 3-amino-5-cyclohexyl-1,3-dihydro-benzo[e][1,4]diazepin-2-one (D. Beher, et al. *J. Biol. Chem.* 2001, 276(48), 45394), using the method described in Procedure 10.

MS+=583.0

$^1$H-NMR (DMSO-d6) δ 14.09 (s, 1H), 10.85 (s, 1H), 10.85+10.42 (2s, 1H), 8.67+8.35 (2s, 1H), 7.80 (d, J=6.0 Hz, 1H), 7.54 (m, 5H), 7.30 (m, 1H), 7.21 (m, 1H), 5.18 (m, 1H), 2.97 (m, 1H), 1.93 (m, 1H), 1.77 (m, 1H), 1.59 (m, 3H), 1.50-1.00 (m, 4H), 0.91 (m, 1H).

Example 113

Preparation of 4-Bromo-5-(2-chloro-benzoylamino)-1H-pyrazole-3-carboxylic acid (1-methyl-2-oxo-5-phenyl-2,3-dihydro-1H-benzo[e][1,4]diazepin-3-yl)-amide

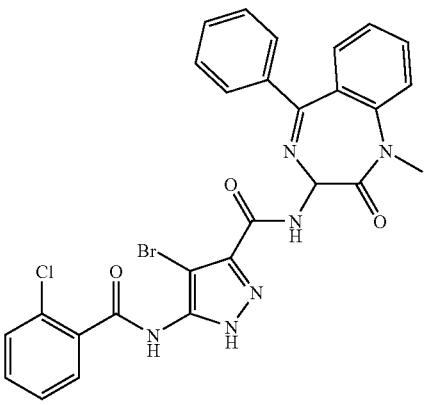

The pyrazole acid, prepared as described in Procedure 8, was coupled with (1-methyl-2-oxo-5-phenyl-2,3-dihydro-1H-benzo[e][1,4]diazepin-3-yl)-carbamic acid benzyl ester (Ronald G. Sherrill and Elizabeth E. Sugg; *J. Org. Chem.* 1995, 60, 730) using the method described in Procedure 10.

MS+=591.0

¹H-NMR (CDCl₃) δ 9.06 (s, 1H), 8.71 (d, J=8.10 Hz, 1H), 8.03 (d, J=6.9 Hz, 1H), 7.63 (m, 3H), 7.52-7.35 (m, 8H), 7.26 (m, 2H), 5.72 (d, J=8.1 Hz, 1H), 3.50 (s, 3H).

Example 114

Preparation of 4-methyl-5-(2-chlorobenzoylamino)-1 (2,6-dimethylpyrimidin-4-yl)-pyrazole-3-carboxylic acid [2-(3,4,5,6-tetrahydro-2H-[1,4'bipyridin-4-yl) ethyl]amide

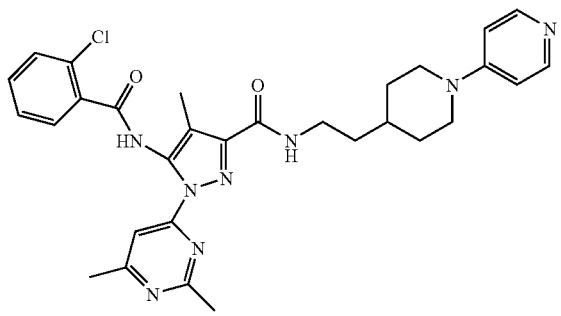

The pyrazole acid, prepared as described in Procedure 8 using 5-amino-1-(2,6-dimethylpyrimidin-4-yl)-4-methyl-1H-pyrazole-3-carboxylic acid ethyl ester (prepared as described in Procedure 41 using 3-cyano-3-methyl-2-oxo-propanoic acid ethyl ester (U.S. Pat. No. 4,652,669) and 4-hydrazino-2,6-dimethylpyrimidine (Ryan Scientific, BTB 10371)) in place of compound 20, was coupled to 2-(3,4,5,6-tetrahydro-2H-[1,4']bipyridin-4-yl)ethylamine (prepared as described in Procedure 14) using the method of Procedure 10.

MS+=573.2

¹H-NMR (DMSO-d6) δ 13.18 (s, 1H), 10.66 (s, 1H), 8.41 (m, 1H), 8.17 (d, J=9.0 Hz, 2H), 7.69 (m, 2H), 7.54 (m, 3H), 7.17 (d, J=9.0 Hz, 2H), 5.05 (broad, 2H), 4.22 (m, 2H), 3.34 (m, 2H), 3.15 (m, 2H), 2.57 (s, 3H), 2.51 (s, 3H), 2.18 (s, 3H), 1.90 (m, 2H), 1.72 (m, 1H), 1.52 (m, 2H), 1.15 (m, 2H).

Example 115

Preparation of 4-Bromo-5-(2-chloro-benzoylamino)-1H-pyrazole-3-carboxylic acid {2-[(2-benzyl-phenyl)-methyl-amino]-ethyl}-amide

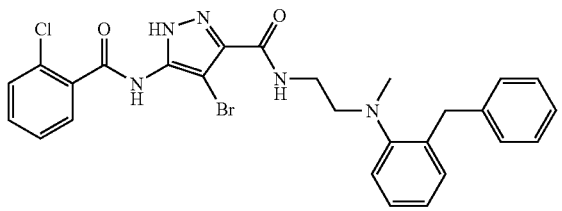

The pyrazole acid was prepared using the methods described in Procedure 8 followed by coupling to {2-[(2-benzylphenyl)methylamino]ethyl}carbamic acid tert-butyl ester using the method of Procedure 3. {2-[(2-Benzylphenyl) methyl-amino]ethyl}carbamic acid tert-butyl ester is prepared from N-(tert-butoxycarbonyl)glycine (Aldrich, 13,453-8) and 2-benzylaniline (Aldrich, 23,535-0) using the method of Procedure 11 followed by reduction using the method of Procedure 2 and methylation with formaldehyde using the method of Procedure 35.

MS+566.0

¹H-NMR (DMSO-d6) δ 7.52 (m, 4H), 7.18 (m, 7H), 6.97 (m, 2H), 4.01 (s, 2H), 3.34 (m, 2H), 3.03 (m, 2H), 2.60 (s, 3H).

Example 116

Preparation of 4-Chloro-5-(2-chloro-benzoylamino)-1H-pyrazole-3-carboxylic acid [7-chloro-5-(2-chloro-phenyl)-2-oxo-2,3-dihydro-1H-benzo[e][1,4] diazepin-3-yl]-amide

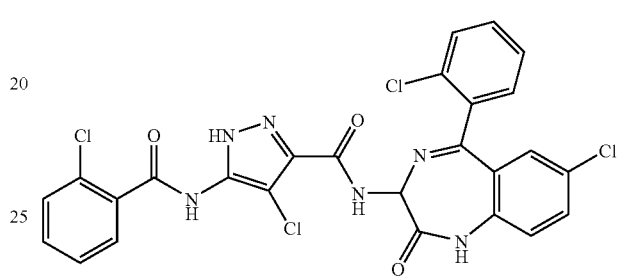

The pyrazole acid was prepared using the methods described in Procedure 9 followed by coupling to [7-chloro-5-(2-chlorophenyl)-2,3-dihydro-2-oxo-1H-1,4-benzodiazepin-3-yl]carbamic acid, phenylmethyl ester (Rare Chemicals GmbH, EM WB 0238) using the method of Procedure 3.

MS+602.9

¹H-NMR (CD₃OD) δ 7.56 (m, 8H), 7.29 (m, 1H), 7.07 (m, 1H), 5.61 (s, 1H).

Example 117

Preparation of 4-Chloro-5-(2-chloro-benzoylamino)-1H-pyrazole-3-carboxylic acid (7-chloro-2-oxo-5-phenyl-2,3-dihydro-1H-benzo[e][1,4diazepin-3-yl) amide

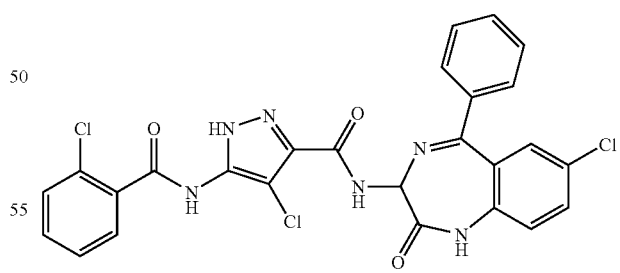

The pyrazole acid was prepared using the methods described in Procedure 9 followed by coupling to (7-chloro-2,3-dihydro-2-oxo-5-phenyl-1H-1,4-benzodiazepin-3-yl) carbamic acid, phenylmethyl ester (Rare Chemicals GmbH, EM WB 0239) using the method of Procedure 3

MS+567.0

¹H-NMR (DMSO-d6) δ 7.73 (m, 1H), 7.46 (m, 11H), 5.43 (br, 1H).

Example 118

Preparation of (R)-4-Bromo-5-(2-chloro-benzoylamino)-1H-pyrazole-3-carboxylic acid (3-phenyl-1-piperidin-1-ylmethyl-propyl)amide

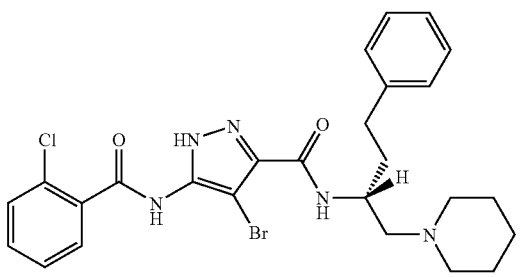

The pyrazole acid was prepared using the methods described in Procedure 8 followed by coupling to 2-Amino-4-phenyl-1-piperidin-1-ylbutane (prepared by Procedure 2) using the method of Procedure 3.
MS+558.0
$^1$H-NMR (CDCl$_3$) δ 8.94 (br, 1H), 7.92 (m, 1H), 7.45 (m, 4H), 7.20 (m, 4H), 4.29 (m, 1H), 2.71 (m, 3H), 2.47 (m, 5H), 1.94 (m, 2H), 1.57 (m, 4H), 1.41 (m, 2H).

Example 119

Preparation of 4-Bromo-5-(2-chloro-benzoylamino)-1H-pyrazole-3-carboxylic acid (1,5-dimethyl-1H-pyrazol-3-ylmethyl)amide

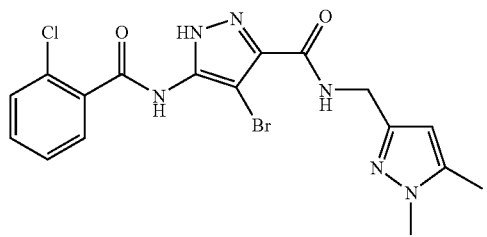

The pyrazole acid was prepared using the methods described in Procedure 8 followed by coupling to 1,5-dimethyl-1H-pyrazole-3-methanamine (TimTec, Inc., TBB019539) using the method of Procedure 10.
MS+451.0
$^1$H-NMR (DMSO-d6) δ 8.33 (br, 1H), 7.51 (m, 4H), 5.93 (br, 1H), 4.28 (m, 1H), 3.64 (s, 3H), 2.18 (s, 3H).

Example 120

Preparation of 4-Bromo-5-(2-chloro-benzoylamino)-1pyrazole-3-carboxylic acid (1-methyl-1H-pyrrol-2-ylmethyl)amide

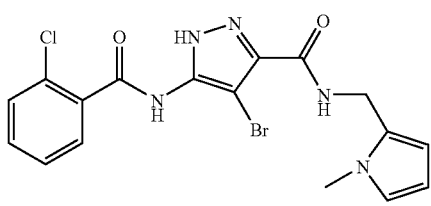

The pyrazole acid was prepared using the methods described in Procedure 8 followed by coupling to 1-methyl-1H-pyrrole-2-methanamine (Maybridge, CC02713) using the method of Procedure 10.

MS+436.0

$^1$H-NMR (DMSO-d6) δ 13.92 (s, 1H), 10.67 (br, 1H), 8.46 (br, 1H), 7.58 (m, 4H), 6.72 (s, 1), 6.04 (s, 1H), 5.95 (s, 1H), 4.47 (m, 2H), 3.65 (s, 3H).

Example 121

Preparation of 4-Bromo-5-(2-chloro-benzoylamino)-1H-pyrazole-3-carboxylic acid (benzo[b]thiophen-3-ylmethyl)amide

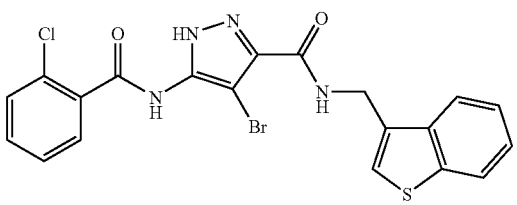

The pyrazole acid was prepared using the methods described in Procedure 8 followed by coupling to 3-aminomethylbenzothiophene (Maybridge, CC12313) using the method of Procedure 10.
MS+488.9
$^1$H-NMR (DMSO-d6) δ 8.74 (br, 1H), 7.97 (m, 2H), 7.45 (m, 7H), 4.68 (s, 2H).

Example 122

Preparation of 4-Bromo-5-(2-chloro-benzoylamino)-1H-pyrazole-3-carboxylic acid (5-methyl-isoxazol-3-ylmethyl)amide

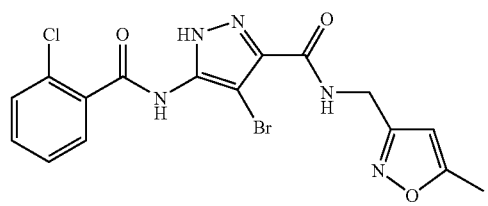

The pyrazole acid was prepared using the methods described in Procedure 8 followed by coupling to 5-methyl-3-isoxazolemethanamine (Maybridge, CC10413) using the method of Procedure 10.

MS+438.0
$^1$H-NMR (DMSO-d6) δ 8.89 (br, 1H), 7.53 (m, 4H), 6.13 (s, 1H), 4.39 (br, 2H), 2.35 (s, 3H).

Example 123

Preparation of 4-Bromo-5-(2-chloro-benzoylamino)-1H-pyrazole-3-carboxylic acid (3-methyl-2-oxo-piperidin-3-yl)amide

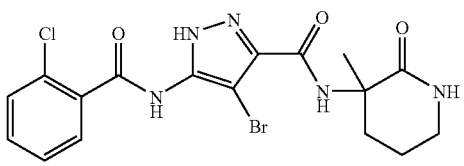

The pyrazole acid was prepared using the methods described in Procedure 8 followed by coupling to 3-amino-3-methyl-2-piperidone (prepared by Procedure 24) using the method of Procedure 3.

MS+454.0

$^1$H-NMR (CDCl$_3$) δ 9.16 (br, 1H), 7.97 (d, J=7.7 Hz, 1H), 7.76 (s, 1H), 7.44 (m, 3H), 3.51 (m, 1H), 3.29 (m, 1H), 2.50 (m, 1H), 2.21 (m, 1H), 1.88 (m, 2H), 1.63 (s, 3H).

Example 124

Preparation of 4-Bromo-5-(2-chloro-benzoylamino)-1H-pyrazole-3-carboxylic acid (1-methyl-2-oxo-piperidin-3-yl)amide

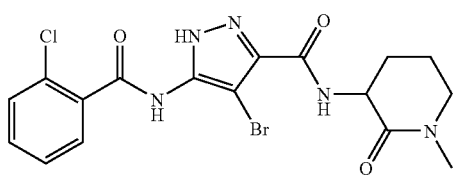

The pyrazole acid was prepared using the methods described in Procedure 8 followed by coupling to 3-amino-1-methyl-2-piperidinone (prepared by Procedure 24) using the method of Procedure 3.

MS+454.0

$^1$H-NMR (DMSO-d6) δ 8.16 (br, 1H), 7.51 (m, 4H), 4.30 (m, 1H), 3.31 (m, 2H), 2.83 (s, 3H), 2.11 (m, 1H), 1.85 (m, 3H).

Example 125

Preparation of 4-Bromo-5-(2-chloro-benzoylamino)-1H-pyrazole-3-carboxylic acid (1-methyl-piperidin-3-yl)-amide

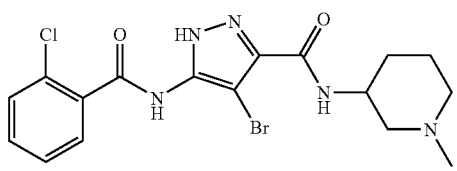

The pyrazole acid was prepared using the methods described in Procedure 8 followed by coupling to 1-methyl-3-piperidinamine (prepared by Procedure 2) using the method of Procedure 3.

MS+440.0

$^1$H-NMR (CDCl$_3$) δ 9.18 (br, 1H), 7.91 (d, J=7.1 Hz, 1H), 7.43 (m, 3H), 4.19 (m, 1H), 2.37 (m, 7H), 1.67 (m, 4H).

Example 126

Preparation of 4-Bromo-5-(2-chloro-benzoylamino)-1H-pyrazole-3-carboxylic acid (2-oxo-1,2,3,4-tetrahydro-quinolin-3-yl)amide

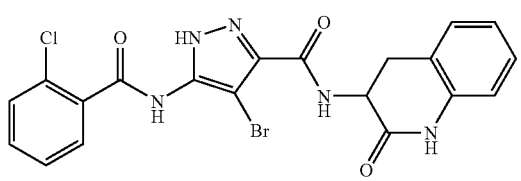

The pyrazole acid was prepared using the methods described in Procedure 8 followed by coupling to 3-amino-2-oxo-1,2,3,4-tetrahydroquinoline (prepared by Procedure 25) using the method of Procedure 10.

MS+488.0

$^1$H-NMR (DMSO-d6) δ 7.53 (m, 4H), 7.19 (m, 2H), 6.92 (m, 2H), 4.61 (m, 1H), 3.13 (m, 2H).

Example 127

Preparation of (R)-4-Chloro-5-(2-chlorobenzoylamino)-1H-pyrazole-3-carboxylic acid (1-methylazepin-3-yl)amide

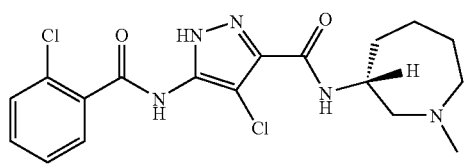

The pyrazole acid was prepared using the methods described in Procedure 9 followed by coupling to (R)-hexahydro-1-methyl-1H-azepin-3-amine (prepared by Procedure 2) using the method of Procedure 3.

MS+410.0

$^1$H-NMR (CDCl$_3$) δ 9.72 (br, 1H), 8.17 (m, 1H), 7.82 (d, J=7.1 Hz, 1H), 7.42 (m, 3H), 3.97 (m, 1H), 2.76 (m, 2H), 2.43 (m, 5H), 1.65 (m, 6H).

Example 128

Preparation of (R)-4-Bromo-5-(2-chlorobenzoylamino)-1H-pyrazole-3-carboxylic acid (1-benzyl-2-oxo-azepin-3-yl)amide

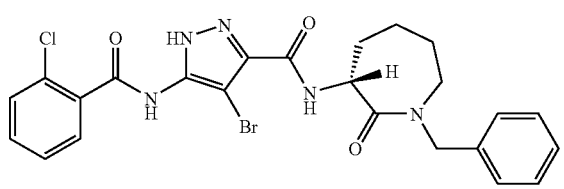

The pyrazole acid was prepared using the methods described in Procedure 8 followed by coupling to (R)-3-aminohexahydro-1-(phenylmethyl)-2H-azepin-2-one (prepared by Procedure 23) using the method of Procedure 3.

MS+544.0

$^1$H-NMR (CDCl$_3$) δ 9.21 (br, 1H), 8.48 (m, 1H), 7.97 (m, 1H), 7.42 (m, 3H), 7.25 (m, 5H), 4.82 (m, 2H), 4.49 (m, 1H), 3.47 (m, 1H), 3.24 (m, 1H), 2.17 (m, 1H), 1.72 (m, 4H), 1.22 (m, 1H).

Example 129

Preparation of (R)-4-Bromo-5-(2-chlorobenzoylamino)-1H-pyrazole-3-carboxylic acid (1-ethyl-2-oxo-azepin-3-yl)amide

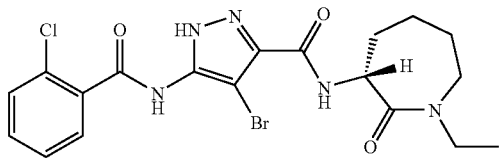

The pyrazole acid was prepared using the methods described in Procedure 8 followed by coupling to (R)-3-amino-1-ethylhexahydro-2H-azepin-2-one (prepared by Procedure 23) using the method of Procedure 3.

MS+482.0

$^1$H-NMR (CDCl$_3$) δ 9.31 (br, 1H), 8.42 (br, 1H), 7.83 (d, J=6.0 Hz, 1H), 7.36 (m, 3H), 4.66 (m, 1H), 3.42 (m, 3H), 3.20 (m, 1H), 2.05 (m, 1H), 1.85 (m, 3H), 1.39 (m, 2H), 1.08 (t, J=7.1 Hz, 3H).

Example 130

Preparation of 4-Bromo-5-[(2-chloro-benzoyl)-methyl-amino]-1H-pyrazole-3-carboxylic acid [2-(1-methyl-piperidin-4-yl)-ethyl]amide

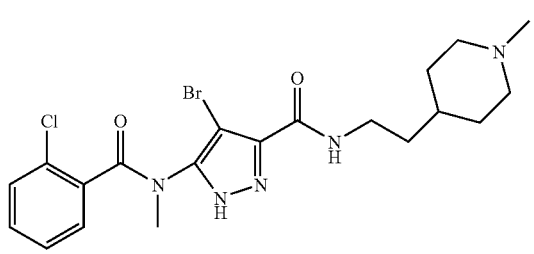

The pyrazole acid was prepared using the methods described in Procedure 8 followed by coupling to 1-methyl-4-piperidineethanamine (prepared by Procedure 13) using the method of Procedure 10.

MS+482.0

$^1$H-NMR (CDCl3) δ 8.16 (br, 1H), 7.84 (d, J=6.8 Hz, 1H), 7.45-7.38 (m, 3H), 6.63 (br, 1H), 4.15 (s, 3H), 3.48 (dt (app. q), J=6.7 Hz, 2H), 2.83 (d, J=11.7 Hz, 2H), 2.23 (s, 3H), 1.94-1.83 (m, 2H), 1.72 (d, J=9.8 Hz, 2H), 1.57 (dt(app. q), J=6.6 Hz, 2H), 1.34-1.24 (m, 3H).

Example 131

Preparation of 4-Bromo-5-(2-chlorobenzoylamino)-1H-pyrazole-3-carboxylic acid [2-(3,4,5,6-tetrahydro-2H-[1,4']bipyridin-4-yl)ethyl]amide

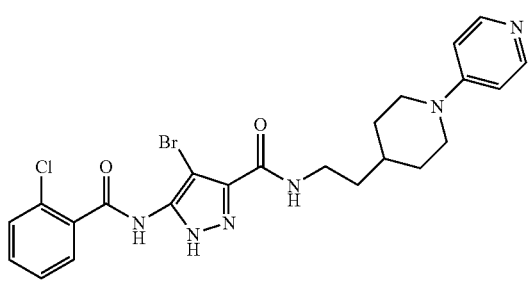

The pyrazole acid, prepared as described in Procedure 8, was coupled to 1-(4-pyridyl)-4-piperidineethanamine (prepared as described in Procedure 14) using the method of Procedure 10.

MS+=531.0

$^1$H-NMR (DMSO-d6) δ 8.07 (m, 3H), 7.48-7.37 (m, 4H), 7.08 (d, J=6.2 Hz, 2H), 4.12 (d, J=13.6 Hz, 2H), 3.19 (s, 2H), 3.02 (dd(app. t), J=12.6 Hz, 2H), 1.77 (d, J=12.4 Hz, 2H), 1.63 (s, 1H), 1.37 (d, J=6.1 Hz, 2H), 1.03 (m, 2H).

Example 132

Preparation of 4-Bromo-5-(2-chloro-benzoylamino)-1H-pyrazole-3-carboxylic acid [2-(4-benzyl-piperazin-1-yl)ethyl]amide

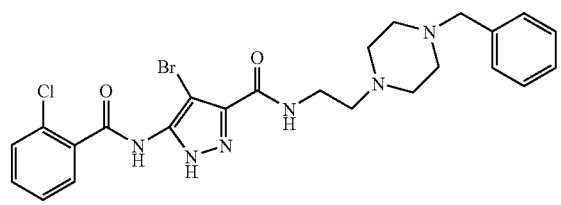

The pyrazole acid, prepared as described in Procedure 8, was coupled to 2-(4-benzylpiperazin-1-yl)ethylamine (Maybridge, KM10049) using the method of Procedure 10.

MS+=545.0

$^1$H-NMR (CDCl$_3$) δ 9.16 (br, 1H), 7.79 (d, J=7.3 Hz, 1H), 7.58 (m, 1H), 7.39-7.26 (m, 3H), 7.20-7.10 (m, 5H), 3.38 (m, 4H), 2.51-2.38 (m, 8H).

Example 133

Preparation of 4-Bromo-5-(2-chloro-benzoylamino)-1H-pyrazole-3-carboxylic acid [2-(4-methyl-piperazin-1-yl)ethyl]amide

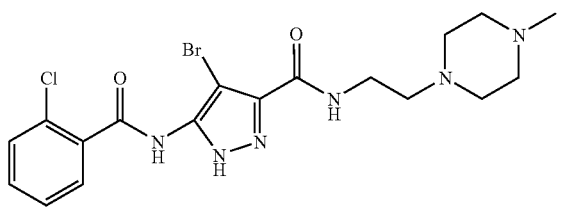

The pyrazole acid, prepared as described in Procedure 8, was coupled to 2-(4-Methylpiperazin-1-yl)ethylamine (ChemPacific, 33298) using the method of Procedure 10.

MS+=469.0

$^1$H-NMR (CDCl$_3$) δ 9.04 (br, 1H), 8.00 (d, J=7.6 Hz, 1H), 7.54-7.43 (m, 4H), 3.55 (m, 2H), 2.64-2.49 (m, 10H), 2.31 (s, 3H).

Example 134

Preparation of 4-Bromo-5-(2-chloro-benzoylamino)-1H-pyrazole-3-carboxylic acid 3-pyrrol-1-yl-benzylamide

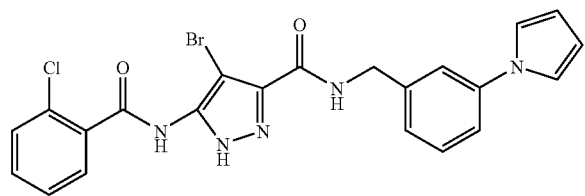

The pyrazole acid, prepared as described in Procedure 8, was coupled to 3-(1H-pyrrol-1-yl)-benzenemethanamine (Maybridge, CC21913) using the method of Procedure 10.

MS+=498.0

$^1$H-NMR (DMSO-d6) δ 7.61-7.19 (m, 12H), 6.27 (s, 2H).

Example 135

Preparation of 4-Chloro-5-(2-chloro-benzoylamino)-1H-pyrazole-3-carboxylic acid [2-(3,4,5,6-tetrahydro-2H-[1,4']bipyridin-4-yl)-ethyl]amide

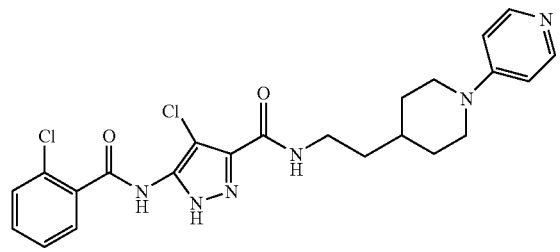

The pyrazole acid, prepared as described in Procedure 8, was coupled to 1-(4-Pyridyl)-4-piperidineethanamine (prepared as described in Procedure 14) using the method of Procedure 10.

MS+=487.1

$^1$H-NMR (DMSO-d6) δ 8.19 (d, J=7.5 Hz, 2H), 7.60-7.46 (m, 4H), 7.19 (d, J=7.6 Hz, 2H), 4.23 (m, 2H), 3.13 (m, 2H), 1.88 (m, 2H), 1.74 (br, 1H), 1.48 (m, 2H), 1.15 (m, 2H).

Example 136

Preparation of endo-4-Bromo-5-(2-chloro-benzoylamino)-1H-pyrazole-3-carboxylic acid (8-methyl-8-aza-bicyclo[3.2.1]oct-3-yl)amide

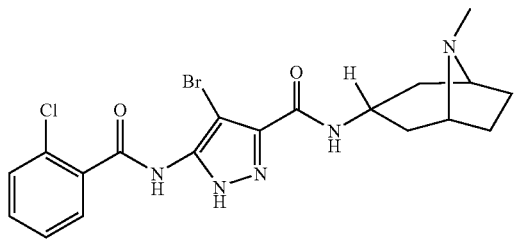

The pyrazole acid, prepared as described in Procedure 8, was coupled to endo-8-methyl-8-azabicyclo[3.2.1]octan-3-amine (Boehringer Ingelheim, 000314) using the method of Procedure 10.

MS+=466.0

$^1$H-NMR (DMSO-d6) δ 13.92 (br, 1H), 10.54 (br, 1H), 8.23 (m, 1H), 7.60-7.45 (m, 4H), 4.07-3.76 (m, 5H), 2.69 (m, 2H), 2.39-2.17 (m, 7H).

Example 137

Preparation of 4-Bromo-5-(2-chloro-benzoylamino)-1H-pyrazole-3-carboxylic acid [1-methyl-2-(1-methyl-piperidin-4-yl)ethyl]amide

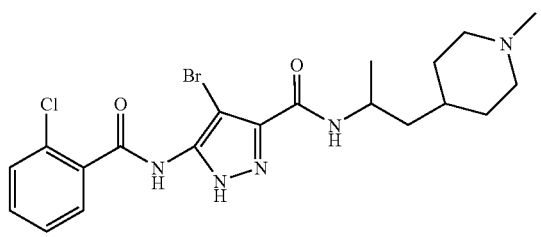

The pyrazole acid, prepared as described in Procedure 8, was coupled to 1-(4-methyl)-4-piperidinepropan-2-amine (prepared as described in Procedure 22) using the method of Procedure 10.

MS+=482.1

$^1$H-NMR (DMSO-d6) δ 9.21 (br,1H), 8.01 (m, 1H), 7.57 (m, 4H), 4.10 (br, 1H), 3.36 (s, 3H), 2.87 (m, 2H), 2.72 (s, 3H), 1.99 (m, 1H), 1.59 (m, 2H), 1.34-1.15 (m, 6H).

Example 138

Preparation of 4-Bromo-5-(2-chlorobenzoylamino)-1H-pyrazole-3-carboxylic acid (3,4,5,6-tetrahydro-2H-[1,4']bipyridin-4-yl)amide

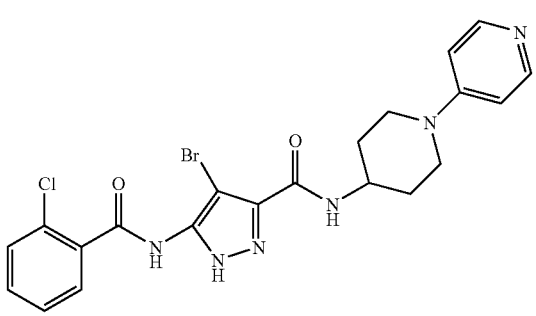

The pyrazole acid, prepared as described in Procedure 8, was coupled to 1-(4-pyridinyl)-4-piperidinamine (prepared as described in Procedure 14) using the method of Procedure 10.

MS+=503.0

$^1$H-NMR (CD$_3$OD) δ 8.12 (d, J=7.7 Hz, 2H), 7.65 (m, 1H), 7.56-7.43 (m, 3H), 7.20 (d, J=7.7 Hz, 2H), 4.29 (m, 3H), 3.42 (m, 2H), 2.17 (m, 2H), 1.74 (m, 2H).

Example 139

Preparation of 4-Bromo-5-(2-chlorobenzoylamino)-1H-pyrazole-3-carboxylic acid [2-(3,4,5,6-tetrahydro-2H-[1,2']bipyridin-4-yl)-ethyl]amide

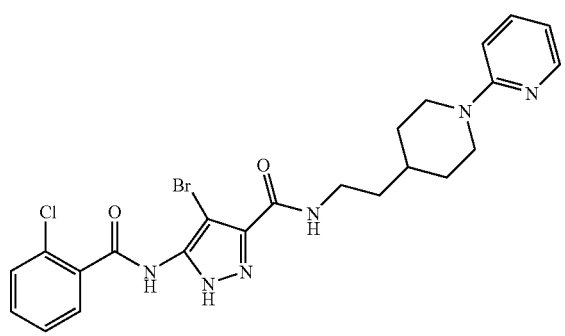

The pyrazole acid, prepared as described in Procedure 8, was coupled to 1-(2-pyridinyl)-4-piperidinamine (prepared as described in Procedure 14) using the method of Procedure 10.

MS+=531.0

$^1$H-NMR (CD$_3$OD) δ 8.00 (m, 1H), 7.89 (d, J=6.3 Hz, 1H), 7.65 (m, 1H), 7.57-7.38 (m, 5H), 6.94 (dd(app. t), J=6.6 Hz, 1H), 4.18 (m, 2H), 3.49 (m, 2H), 3.30 (m, 2H), 2.04 (m, 2H), 1.85 (m, 1H), 1.65 (m, 2H), 1.39 (m, 2H).

Example 140

Preparation of 5-(2-Chloro-benzoylamino)-1H-pyrazole-3-carboxylic acid (2-oxo-2,3,4,5-tetrahydro-1H-benzo[b]azepin-3-yl)amide

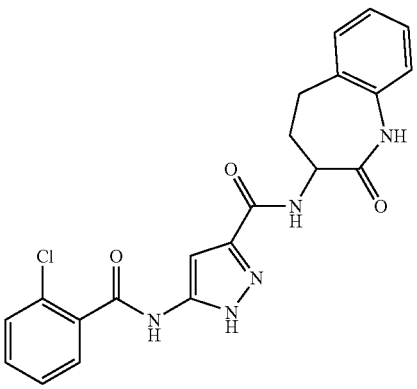

The pyrazole acid, prepared as described in Procedure 8, was coupled to 3-amino-1,3,4,5-tetrahydro-benzo[b]azepin-2-one (Tetrahedron Letters 1994, 35(20), 3239-42) using the method of Procedure 10.

MS+=424.0

$^1$H-NMR (DMSO-d6) δ 13.15 (br, 1H), 11.08 (br, 1H), 9.90 (s, 1H), 8.70 (br, 1H), 7.55-7.32 (m, 4H), 7.30 (m, 2H), 7.04 (d, J=6.00 Hz, 2H), 7.38 (m, 1H), 2.73 (m, 2H), 2.20 (m, 1H).

Example 141

Preparation of 4-Chloro-5-(2-chloro-benzoylamino)-1H-pyrazole-3-carboxylic acid (2-oxo-2,3,4,5-tetrahydro-1H-benzo[b]azepin-3-yl)amide

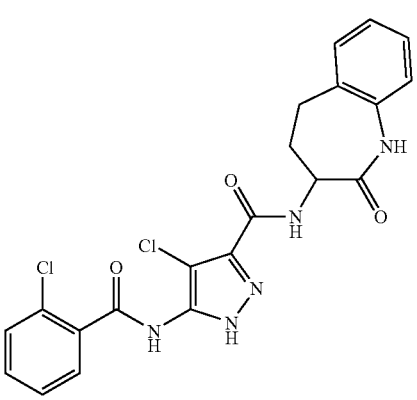

The pyrazole acid, prepared as described in Procedure 9, was coupled to 3-amino-1,3,4,5-tetrahydro-benzo[b]azepin-2-one (Tetrahedron Letters 1994, 35(20), 3239-42) using the method of Procedure 10.

MS+=458.0

$^1$H-NMR (DMSO-d6) δ 13.91 (br, 1H), 10.92 (br, 1H), 10.40 (br, 1H), 10.03 (br, 1H), 8.05 (d, J=6.00 Hz, 1H), 7.59-7.44 (m, 3H), 7.30 (m, 2H), 7.16 (t, J=6.00 Hz, 1H), 7.04 (d, J=6.00 Hz, 1H), 7.35 (m, 1H), 2.75 (m, 2H), 2.19 (m, 1H).

Example 142

Preparation of (R)-4-Bromo-5-(2-chloro-benzoylamino)-1H-pyrazole-3-carboxylic acid (1-methyl-2-oxo-5-phenyl-2,3-dihydro-1H-benzo[e][1,4]diazepin-3-yl)amide

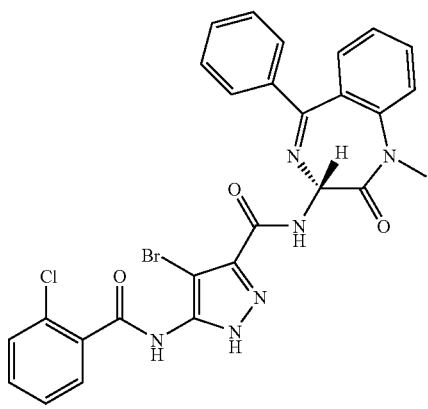

The pyrazole acid, prepared as described in Procedure 8, was coupled to (R)-3-amino-1-methyl-5-phenyl-1,3-dihydro-benzo[e][1,4]diazepin-2-one (prepared as described by Ronald G. Sherrill and Elizabeth E. Sugg; J. Org. Chem. 1995, 60, 730, which is incorporated herein by reference in its entirety) using the method of Procedure 10.
MS+=591.0
$^1$H-NMR (CDCl$_3$) δ 9.07 (s, 1H), 8.74 (d, J=6.00 Hz, 1H), 8.03 (d, J=9.00 Hz, 1H), 7.62 (m, 3H), 7.57-7.35 (m, 8H), 7.28 (m, 2H), 5.73 (d, J=6.00 Hz, 1H), 3.51 (s, 3H).

Example 143

Preparation of (S)-4-Chloro-5-(2-chloro-benzoylamino)-1H-pyrazole-3-carboxylic acid (2-oxo-5-phenyl-2,3-dihydro-1H-benzo[e][1,4]diazepin-3-yl) amide

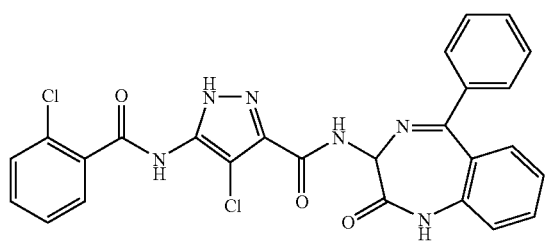

The pyrazole acid, prepared as described in Procedure 9, was coupled to (S)-3-amino-5-phenyl-1,3-dihydro-benzo[e][1,4]diazepin-2-one (prepared as described by Ronald G. Sherrill and Elizabeth E. Sugg; J. Org. Chem. 1995, 60, 730, which is incorporated herein by reference in its entirety) using the method of Procedure 10.
MS+=533.0
$^1$H-NMR (CD$_3$OD) δ 7.68-7.60 (m, 2H), 7.55-7.23 (m, 11H), 5.55 (s, 1H).

Example 144

Preparation of (R)-4-Chloro-5-(2-chloro-benzoylamino)-1H-pyrazole-3-carboxylic acid (2-oxo-5-phenyl-2,3-dihydro-1H-benzo[e][1,4]diazepin-3-yl) amide

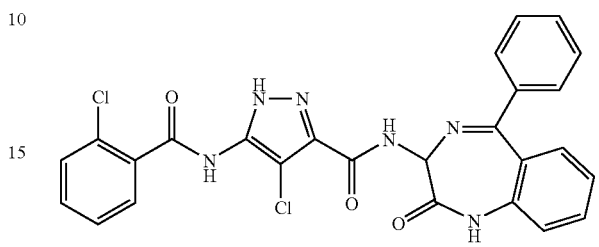

The pyrazole acid, prepared as described in Procedure 9, was coupled to (R)-3-amino-5-phenyl-1,3-dihydro-benzo[e][1,4]diazepin-2-one (prepared as described by Ronald G. Sherrill and Elizabeth E. Sugg; J. Org. Chem. 1995, 60, 730, which is incorporated herein by reference in its entirety) using the method of Procedure 10.
MS+=533.0
$^1$H-NMR (CD$_3$OD) δ 7.68-7.60 (m, 2H), 7.55-7.23 (m, 11H), 5.55 (s, 1H).

Example 145

Preparation of 4-Chloro-5-(2-chloro-benzoylamino)-1H-pyrazole-3-carboxylic acid (1-methyl-2-oxo-5-phenyl-2,3-dihydro-1H-benzo[e][1,4]diazepin-3-yl) amide

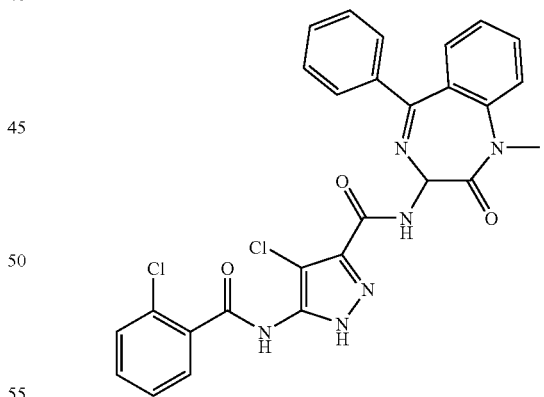

The pyrazole acid, prepared as described in Procedure 9, was coupled to (R)-3-amino-1-methyl-5-phenyl-1,3-dihydro-benzo[e][1,4]diazepin-2-one (prepared as described by Ronald G. Sherrill and Elizabeth E. Sugg; J. Org. Chem. 1995, 60, 730, which is incorporated herein by reference in its entirety) using the method of Procedure 10.
MS+=547.1
$^1$H-NMR (CDCl$_3$) δ 9.01(s, 1H), 8.72 (d, J=7.5 Hz, 1H), 7.98 (d, J=7.5 Hz, 1H), 7.61 (m, 3H), 7.53-7.36 (m, 8H), 7.26 (m, 2H), 5.71 (d, J=7.8 hZ, 1H), 3.51 (s, 3H).

Example 146

Preparation of (R)-4-Bromo-5-(2-chlorobenzoylamino)-1H-pyrazole-3-carboxylic acid (9-methyl-8-oxo-6,7,8,9-tetrahydro-5-oxo-9-aza-benzocyclohepten-7-yl)amide

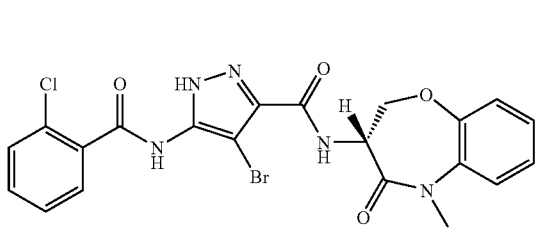

The pyrazole acid, prepared as described in Procedure 8, was coupled to (R)-7-Amino-9-methyl-6,7-dihydro-9H-5-oxa-9-aza-benzocyclohepten-8-one (prepared as described by Itoh, K.; et al. Chem. Pharm. Bull. 1986, 34(3), 1128. which is incorporated herein by reference in its entirety) using the method of Procedure 10.

MS+=518.0
$^1$H-NMR (DMSO-d6) δ 8.25 (d, J=7.7 Hz, 1H), 7.53 (m, 5H), 7.28 (m, 3H), 4.84 (m, 1H), 4.49 (m, 2H), 3.32 (s, 3H).

Example 147

Preparation of (R)-4-Bromo-5-(2-chlorobenzoylamino)-1H-pyrazole-3-carboxylic acid (2-oxo-1-phenethyl-azepan-3-yl)amide

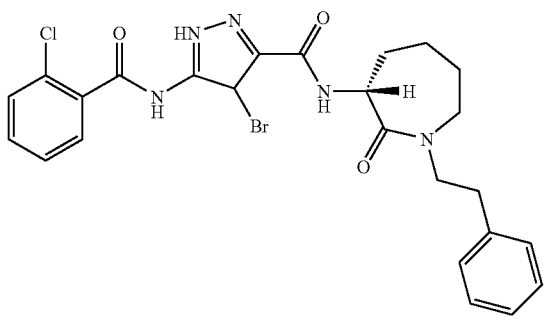

The pyrazole acid, prepared as described in Procedure 8, was coupled to (R)-3-amino-1-phenethyl-azepan-2-one (prepared using the method of Procedure 23) using the method of Procedure 10.

MS+=558.0

$^1$H-NMR (DMSO-d6) δ 7.51 (m, 4H), 7.26 (m, 5H), 4.68 (m, 1H), 3.58 (m, 2H), 3.39 (m, 3H), 2.77 (m, 1H), 1.84 (m, 4H), 1.30 (m, 2H).

Example 148

Preparation of 4-Bromo-5-(2-chlorobenzoylamino)-1H-pyrazole-3-carboxylic acid (1,5-dimethyl-2-oxo-2,3,4,5-tetrahydro-1H-benzo[b]azepin-3-yl)amide

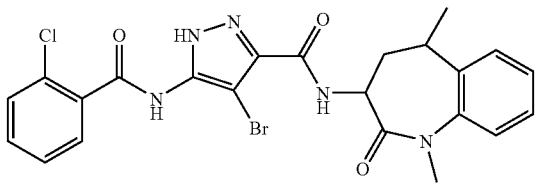

The pyrazole acid, prepared as described in Procedure 8, was coupled to 3-amino-1,5-dimethyl-1,3,4,5-tetrahydro-benzo[b]azepin-2-one (prepared as described in U.S. Pat. No. 6,528,505) using the method of Procedure 10.

MS+=529.9
$^1$H-NMR (CDCl$_3$) δ 9.06 (s, 1H), 7.99 (m, 2H), 7.46 (m, 3H), 7.29 (m, 3H), 7.18 (m, 1H), 4.59 (m, 1H), 3.42 (s, 3H), 2.29 (m, 2H), 1.33 (d, J=7.1 Hz, 3H).

Example 149

Preparation of (R)-4-Bromo-5-(2-chlorobenzoylamino)-1H-pyrazole-3-carboxylic acid (1-ethyl-azepan-3-yl)amide

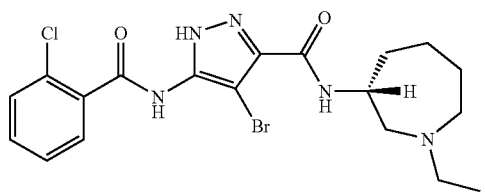

The pyrazole acid, prepared as described in Procedure 8, was coupled to 1-ethyl-azepan-3-ylamine (prepared as described in Procedure 23 followed by reduction as described in Procedure 2) using the method of Procedure 3.

MS+=468.0
$^1$H-NMR (CDCl$_3$) δ 9.06 (s, 1H), 7.99 (m, 2H), 7.46 (m, 3H), 7.29 (m, 3H), 7.18 (m, 1H), 4.59 (m, 1H), 3.42 (s, 3H), 2.29 (m, 2H), 1.33 (d, J=7.1 Hz, 3H).

Example 150

Preparation of (R)-4-Bromo-5-(2-chlorobenzoylamino)-1H-pyrazole-3-carboxylic acid (9-ethyl-8-oxo-6,7,8,9-tetrahydro-5-oxa-9-aza-benzocyclohepten-7-yl)amide

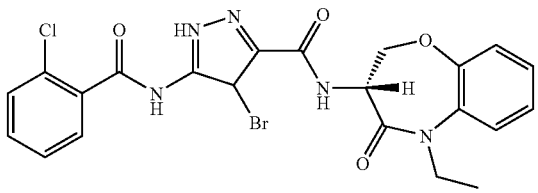

The pyrazole acid, prepared as described in Procedure 8, was coupled to (R)-7-Amino-9-ethyl-6,7-dihydro-9H-5-oxa-9-aza-benzocyclohepten-8-one (prepared as described by Itoh, K.; et al. Chem. Pharm. Bull. 1986, 34(3), 1128. which is incorporated herein by reference in its entirety) using the method of Procedure 10.

MS+=532.0

$^1$H-NMR (CDCl$_3$) δ 9.94 (br, 1H), 8.21 (d, J=8.2 Hz, 1H), 7.77 (d, J=7.7 Hz, 1H), 7.38 (m, 3H), 3.92 (m, 1H), 2.81 (m, 1H), 2.54 (m, 5H), 1.80 (m, 1H), 1.56 (m, 5H), 1.01 (t, J=7.1 Hz, 3H).

Example 151

Preparation of 4-Bromo-5-(2-chlorobenzoylamino)-1H-pyrazole-3-carboxylic acid (3-methyl-2-oxo-2,3,4,5-tetrahydro-1H-benzo[d]azepin-1-yl)amide

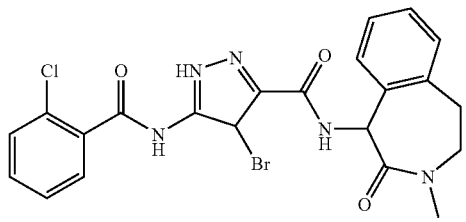

The pyrazole acid, prepared as described in Procedure 8, was coupled to 1-amino-3-methyl-1,3,4,5-tetrahydro-benzo[d]azepin-2-one (WO 02/40508) using the method of Procedure 10.

MS+=516.0

$^1$H-NMR (DMSO-d6) δ 8.21 (d, J=7.7 Hz, 1H), 7.51 (m, 4H), 7.30 (m, 3H), 4.80 (m, 1H), 4.46 (m, 2H), 4.09 (m, 1H), 3.63 (m, 1H), 1.03 (t, J=7.1 Hz, 3H).

Example 152

Preparation of (R)-5-(2-Chlorobenzoylamino)-1H-pyrazole-3-carboxylic acid (9-ethyl-8-oxo-6,7,8,9-tetrahydro-5-oxa-9-aza-benzocyclohepten-7-yl)amide

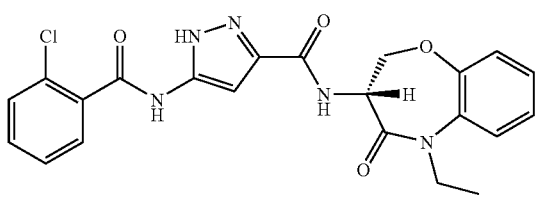

The pyrazole acid, prepared as described in Procedure 8, was coupled to (R)-7-amino-9-ethyl-6,7-dihydro-9H-5-oxa-9-aza-benzocyclohepten-8-one (prepared as described by Itoh, K.; et al. Chem. Pharm. Bull. 1986, 34(3), 1128. which is incorporated herein by reference in its entirety) using the method of Procedure 10.

MS+=454.1

$^1$H-NMR (CDCl$_3$) δ 11.07 (br, 1H), 9.44 (br, 1H), 7.31 (m, 6H), 6.97 (m, 2H), 6.75 (br, 1H), 4.51 (m, 3H), 4.08 (m, 1H), 3.74 (m, 1H), 1.18 (t, J=7.1 Hz, 3H).

Example 153

Preparation of (R)-4-Bromo-5-(2-chlorobenzoylamino)-1H-pyrazole-3-carboxylic acid (1-benzoyl-azepan-3-yl)amide

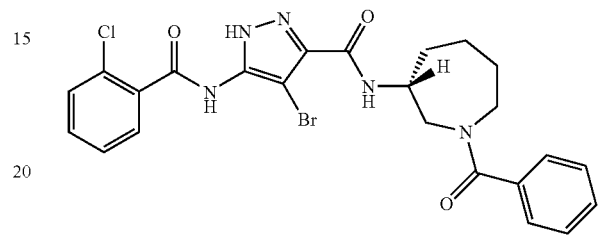

The pyrazole acid, prepared as described in Procedure 8, was coupled to (1-benzoylazepan-3-yl)carbamic acid tert-butyl ester (prepared as described in Procedure 23 followed by reduction as described in Procedure 2 and coupling to benzoic acid as described in Procedure 1) using the method of Procedure 3.

MS+=544.0

$^1$H-NMR (CDCl$_3$) δ 9.30 (two br, 1H), 8.46 (m, 1H), 7.85 (m, 1H), 7.32 (m, 8H), 4.40 (m, 1H), 4.13 (m, 1H), 3.59 (m, 2H), 3.34 (m, 1H), 3.05 (m, 1H), 2.30 (m, 1H), 1.58 (m, 4H).

Example 154

Preparation of (R)-4-Bromo-5-(2-chlorobenzoylamino)-1H-pyrazole-3-carboxylic acid (1-acetyl-azepan-3-yl)amide

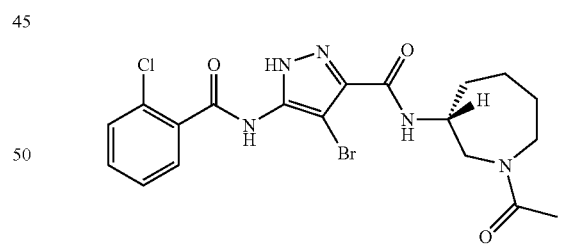

The pyrazole acid, prepared as described in Procedure 8, was coupled to (1-acetylazepan-3-yl)carbamic acid tert-butyl ester (prepared as described in Procedure 23 followed by reduction as described in Procedure 2 and coupling to acetic acid as described in Procedure 1) using the method of Procedure 3.

MS+=482.0

$^1$H-NMR (CDCl$_3$) δ 7.91 (m, 1H), 7.43 (m, 3H), 4.22 (m, 1H), 3.84 (m, 2H), 3.12 (m, 2H), 2.16 (two s, 3H), 1.94 (m, 4H), 1.48 (m, 2H).

Example 155

Preparation of 4-Bromo-5-(2-chlorobenzoylamino)-1H-pyrazole-3-carboxylic acid (1,5,5-trimethyl-2-oxo-2,3,4,5-tetrahydro-1H-benzo[b]azepin-3-yl)amide

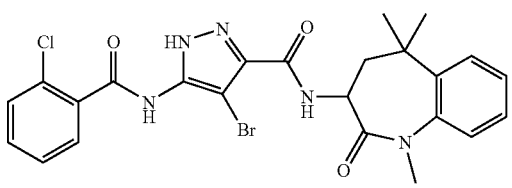

The pyrazole acid, prepared as described in Procedure 8, was coupled to 3-amino-1,5,5-trimethyl-1,3,4,5-tetrahydrobenzo[b]azepin-2-one (WO 9828268) using the method of Procedure 10.

MS+=544.0

$^1$H-NMR (DMSO-d6) δ 8.04 (m, 1H), 7.44 (m, 8H), 4.36 (m, 1H), 3.29 (two s, 3H), 2.26 (m, 1H), 2.02 (m, 1H), 1.39 (s, 3H), 1.19 (s, 3H).

Example 156

Preparation of 4-Bromo-5-(2-chlorobenzoylamino)-1H-pyrazole-3-carboxylic acid [2-(1-pyrimidin-2-yl-piperidin-4-yl)-ethyl]amide

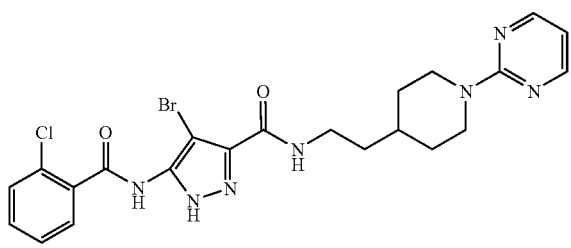

The pyrazole acid, prepared as described in Procedure 8, was coupled to 2-(1-Pyrimidin-2-yl-piperidin-4-yl)ethylamine (WO 2003093245) using the method of Procedure 10.

MS+=532.0

$^1$H NMR (CDCl$_3$) δ 13.17 (br, 1H), 9.14 (s, 1H), 8.28 (d, J=4.8 Hz, 2H), 7.93 (m, 1H), 7.69 (m, 1H), 7.54-7.41 (m, 3H), 6.43 (dd (app. t), J=4.7 Hz, 1H), 4.67 (m, 2H), 3.52 (m, 2H), 2.81 (m, 2H), 1.72 (m, 2H), 1.59 (m, 3H), 1.18-1.06 (m, 2H).

Example 157

Preparation of 5-(2-Chlorobenzoylamino)-1H-pyrazole-3-carboxylic acid [2-(1-methyl-piperidin-4-yl)-ethyl]amide

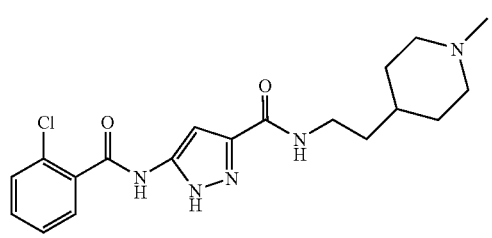

The pyrazole acid, prepared as described in Procedure 8, was coupled to 2-(1-methyl-piperidin-4-yl)-ethylamine (prepared as described in Procedure 13) using the method of Procedure 10.

MS+=390.1

$^1$H NMR (CDCl$_3$) δ 7.58-7.40 (m, 4H), 3.52-3.41 (m, 4H), 2.97 (m, 2H), 2.84 (s, 3H), 2.08 (bd, J=14.1 Hz, 2H), 1.62 (m, 3H), 1.43 (m, 2H).

Example 158

Preparation of 4-Bromo-5-isobutyrylamino-1H-pyrazole-3-carboxylic acid (2-oxo-5-phenyl-2,3-dihydro-1H-benzo[e][1,4]diazepin-3-yl)amide

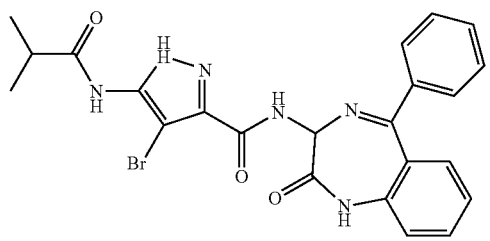

The pyrazole acid, prepared as described in Procedure 8 using isobutyryl chloride (Aldrich, 13,912-2) instead of compound 21, was coupled to 3-amino-5-phenyl-1,3-dihydro-benzo[e][1,4]diazepin-2-one (prepared as described in Procedure 20) using the method of Procedure 10.

MS+=511.0

$^1$H-NMR (DMSO-d6) δ 11.10 (br, 1H), 7.69 (m, 1H), 7.50 (m, 5H), 7.33 (m, 3H), 5.39 (m, 1H), 1.15 (d, J=7.1 Hz, 6H).

Example 159

Preparation of 4-Bromo-5-(2-fluorobenzoylamino)-1H-pyrazole-3-carboxylic acid (2-oxo-5-phenyl-2,3-dihydro-1H-benzo[e][1,4]diazepin-3-yl)amide

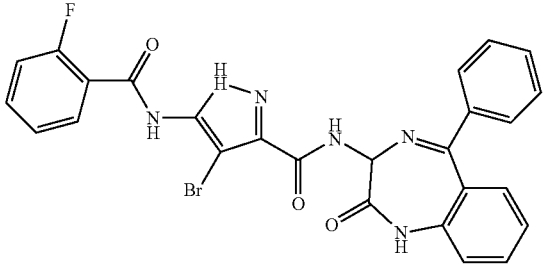

The pyrazole acid, prepared as described in Procedure 8 using 2-fluorobenzoyl chloride (Aldrich, 12,084-7) instead of compound 21, was coupled to 3-amino-5-phenyl-1,3-dihydro-benzo[e][1,4]diazepin-2-one (prepared as described in Procedure 20) using the method of Procedure 10.

MS+=561.0

$^1$H-NMR (DMSO-d6) δ 11.11 (br, 1H), 7.68 (m, 3H), 7.51 (m, 5H), 7.35 (m, 5H), 5.40 (m, 1H).

Example 160

Preparation of 5-Acetylamino-4-bromo-1H-pyrazole-3-carboxylic acid (2-oxo-5-phenyl-2,3-dihydro-1H-benzo[e][1,4]diazepin-3-yl)amide

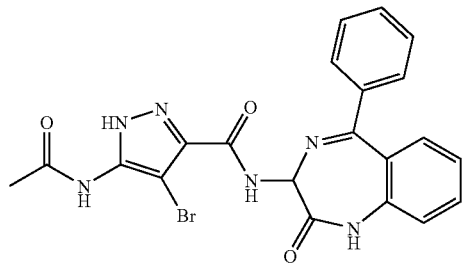

The pyrazole acid, prepared as described in Procedure 8 using acetyl chloride (Aldrich, 23,957-7) instead of compound 21, was coupled to 3-amino-5-phenyl-1,3-dihydrobenzo[e][1,4]diazepin-2-one (prepared as described in Procedure 20) using the method of Procedure 10.

MS+=481.0

$^1$H-NMR (DMSO-d6) δ 13.85 (br, 1H), 11.08 (br, 1H), 10.22 (br, 1H), 8.53 (br, 1H), 7.69 (m, 1H), 7.51 (m, 5H), 7.33 (m, 3H), 5.39 (d, J=4.5 Hz, 1H), 2.13 (s, 3H).

Example 161

Preparation of 5-Benzoylamino-4-bromo-1H-pyrazole-3-carboxylic acid (2-oxo-5-phenyl-2,3-dihydro-1H-benzo[e][1,4]diazepin-3-yl)amide

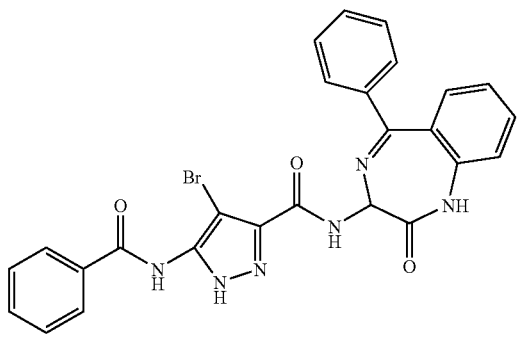

The pyrazole acid, prepared as described in Procedure 8 using benzoyl chloride (Aldrich, 24,054-0) instead of compound 21, was coupled to 3-amino-5-phenyl-1,3-dihydrobenzo[e][1,4]diazepin-2-one (prepared as described in Procedure 20) using the method of Procedure 10.

MS+=543.0

$^1$H-NMR (DMSO-d6) δ 11.37(br, 1H), 8.68 (d, J=7.4 Hz, 1H), 8.02 (d, J=8.2 Hz, 2H), 7.70-7.27 (m, 15H), 5.41 (d, J=7. Hz, 1H).

Example 162

Preparation of 4-Bromo-5-(2-chloro-benzoylamino)-1H-pyrazole-3-carboxylic acid (2-oxo-1-propyl-azepan-3-yl)amide

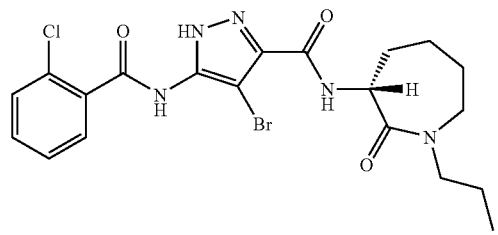

General Procedure 8 was used to synthesize the pyrazole acid for the title compound. The amine was synthesized using methods well known in the art, and described in Hirokawa, Yoshimi; Morie, Toshiya; Yamazaki, Hiroshi; Yoshida, Naoyuki; Kato, Shiro. *Bioorganic & Medicinal Chemistry Letters* 1998, 8(6), 619-624. The final coupling was accomplished using General Procedure 10.

MS+=496.0

$^1$H-NMR (CDCl$_3$) δ 8.97 (s, 1H), 8.41 (d, J=6.0 Hz, 1H), 8.01 (d, J=7.7 Hz, 1H), 7.48 (m, 3H), 4.78 (m, 1H), 3.53 (m, 2H), 3.30 (m, 2H), 2.21 (m, 1H), 1.94 (m, 3H), 1.50 (m, 4H), 0.92 (t, J=7.7 Hz, 3H).

Example 163

Preparation of 5-Benzoylamino-4-chloro-1H-pyrazole-3-carboxylic acid (2-oxo-5-phenyl-2,3-dihydro-1H-benzo[e][1,4]diazepin-3-yl)amide

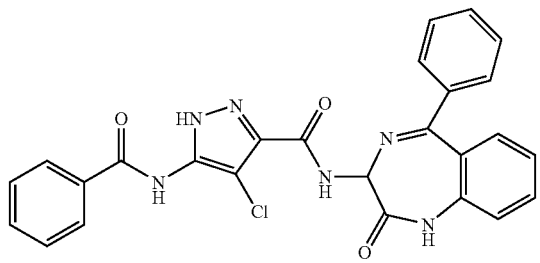

The pyrazole acid was prepared as described for compound 22 using compound 20 and benzoyl chloride (Aldrich 24,054-0) followed by chlorination as shown in General Procedure 9. The diazepinone amine was prepared as describe in General Procedure 20. The final coupling was accomplished using General Procedure 10.

MS+=499.1

$^1$H-NMR (DMSO-d6) δ 8.67 (m, 1H), 8.04 (m, 2H), 7.66 (m, 1H), 7.52 (m, 7H), 7.38 (m, 2H), 7.32 (m, 1H), 5.43 (d, J=5.7 Hz, 1H).

Example 164

Preparation of 4-Chloro-5-(2-methyl-benzoylamino)-1H-pyrazole-3-carboxylic acid (2-oxo-5-phenyl-2,3-dihydro-1H-benzo[e][1,4]diazepin-3-yl)amide

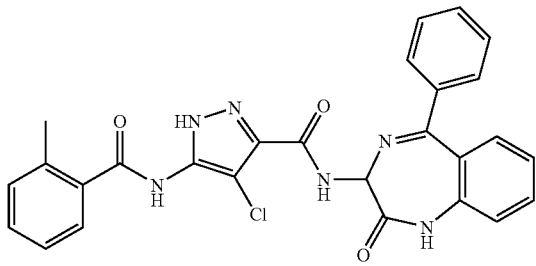

The pyrazole acid was prepared as described for compound 22 using compound 20 and 2-methylbenzoyl chloride (Aldrich 12,201-7) followed by chlorination as shown in General Procedure 9. The diazepinone amine was prepared as describe in General Procedure 20. The final coupling was accomplished using General Procedure 10.

MS+=513.1
$^1$H-NMR (DMSO-d6) δ 8.67 (m, 1H), 7.68 (m, 1H), 7.49 (m, 7H), 7.35 (m, 5H), 5.42 (d, J=5.6 Hz, 1H), 2.48 (s, 3H).

Example 165

Preparation of 4-Bromo-5-(3,5-dichloro-benzoylamino)-1H-pyrazole-3-carboxylic acid (2-oxo-5-phenyl-2,3-dihydro-1H-benzo[e][1,4]diazepin-3-yl)amide

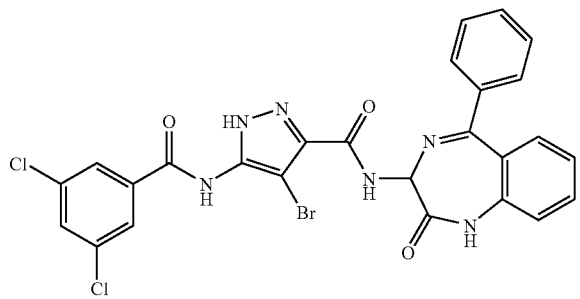

The pyrazole acid was prepared as described for compound 22 using compound 20 and 3,5-dichlorobenzoyl chloride (Aldrich 29,628-7) followed by bromination as shown in General Procedure 8. The diazepinone amine was prepared as describe in General Procedure 20. The final coupling was accomplished using General Procedure 10.

MS+=611.0
$^1$H-NMR (DMSO-d6) δ 7.82 (m, 1H), 7.68 (m, 2H), 7.49 (m, 7H), 7.36 (m, 2H), 5.41 (d, J=5.6 Hz, 1H).

Example 166

Preparation of 4-Bromo-5-(4-chloro-benzoylamino)-1H-pyrazole-3-carboxylic acid (2-oxo-5-phenyl-2,3-dihydro-1H-benzo[e][1,4]diazepin-3-yl)amide

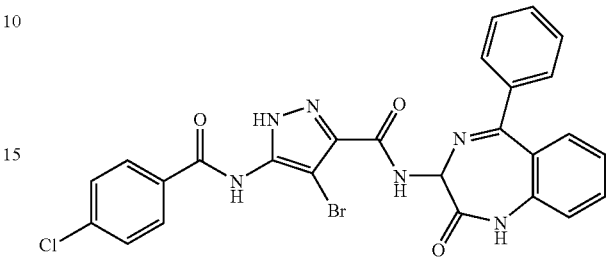

The pyrazole acid was prepared as described for compound 22 using compound 20 and 4-chlorobenzoyl chloride (Aldrich 37,428-8) followed by bromination as shown in General Procedure 8. The diazepinone amine was prepared as describe in General Procedure 20. The final coupling was accomplished using General Procedure 10.

MS+=577.0
$^1$H-NMR (DMSO-d6) δ 8.04 (m, 2H), 7.68 (m, 3H), 7.50 (m, 5H), 7.38 (m, 2H), 7.31 (m, 1H), 5.43 (m, J=5.5 Hz, 1H).

Example 167

Preparation of 4-Bromo-5-(2-chloro-benzoylamino)-1H-pyrazole-3-carboxylic acid (1-ethyl-2-oxo-5-phenyl-2,3-dihydro-1H-benzo[e [1,4]diazepin-3-yl) amide

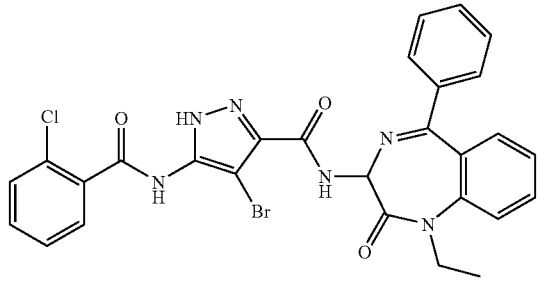

General Procedure 8 was used to synthesize the pyrazole acid for the title compound. The amine was prepared using methods well known in the art, and described in International Patent Application Publication Number WO 99/20281. The final coupling was accomplished using General Procedure 10.

MS+=605.1
$^1$H-NMR (CDCl$_3$) δ 9.07 (br, 1H), 8.75 (m, 1H), 8.03 (m, 1H), 7.60 (m, 3H), 7.36 (m, 9H), 5.72 (d, J=8.2 Hz, 1H), 4.35 (m, 1H), 3.82 (m, 1H), 1.16 (t, J=7.1 Hz, 3H).

Example 168
Preparation of 4-Bromo-5-(3-chloro-benzoylamino)-1H-pyrazole-3-carboxylic acid (2-oxo-5-phenyl-2,3-dihydro-1H-benzo[e][1,4]diazepin-3-yl)amide

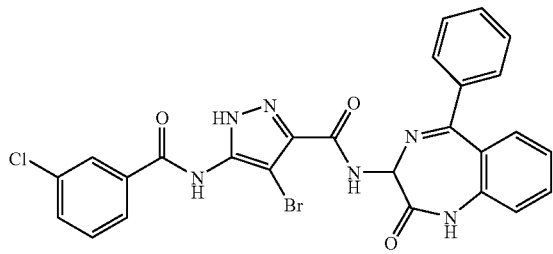

The pyrazole acid was prepared as described for compound 22 using compound 20 and 3-chlorobenzoyl chloride (Aldrich C2,680-1) followed by bromination as shown in General Procedure 8. The diazepinone amine was prepared as describe in General Procedure 20. The final coupling was accomplished using General Procedure 10.

MS+=577.1
$^1$H-NMR (CDCl$_3$) δ 7.79 (m, 1H), 7.38 (m, 12H), 5.75 (d, J=8.2 Hz, 1H).

Example 169
Preparation of 4-Bromo-5-(2-chloro-benzoylamino)-1H-pyrazole-3-carboxylic acid (1.5-dimethyl-2-oxo-2,3,4,5-tetrahydro-1H-benzo[b][1,4]diazepin-3-yl) amide

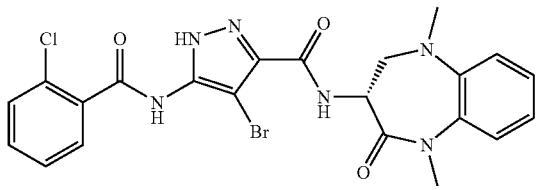

General Procedure 8 was used to synthesize the pyrazole acid for the title compound. The amine was prepared using methods well known in the art, and described in U.S. Pat. No. 6,528,505. The final coupling was accomplished using General Procedure 10.

MS+=531.1
$^1$H-NMR (CDCl$_3$) δ 8.99 (m, 1H), 7.97 (m, 1H), 7.45 (m, 3H), 7.20 (m, 1H), 7.07 (m, 2H), 6.88 (m, 1H), 5.46 (m, 1H), 4.06 (m, 1H), 3.84 (m, 1H), 7.36 (two s, 6H).

Example 170
Preparation of 4-Chloro-5-(3-chloro-benzoylamino)-1H-pyrazole-3-carboxylic acid (2-oxo-5-phenyl-2,3-dihydro-1H-benzo[e][1,4]diazepin-3-yl)amide

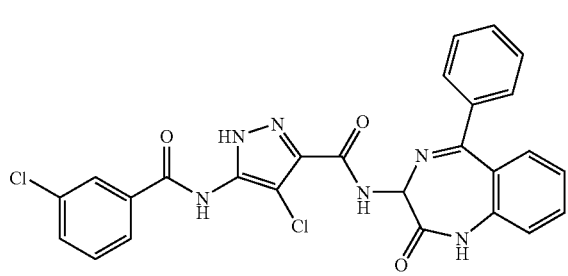

The pyrazole acid was prepared as described for compound 22 using compound 20 and 3-chlorobenzoyl chloride (Aldrich C2,680-1) followed by chlorination as shown in General Procedure 9. The diazepinone amine was prepared as describe in General Procedure 20. The final coupling was accomplished using General Procedure 10.

MS+=533.1
$^1$H-NMR (CDCl$_3$) δ 7.79 (m, 1H), 7.50 (m, 3H), 7.36 (m, 3H), 7.19 m, 5H), 5.56 (s, 1H).

Example 171
Preparation of 4-Bromo-5-(2-chloro-benzoylamino)-1H-pyrazole-3-carboxylic acid (1-cyclopropylmethyl-2-oxo-azepan-3-yl)amide

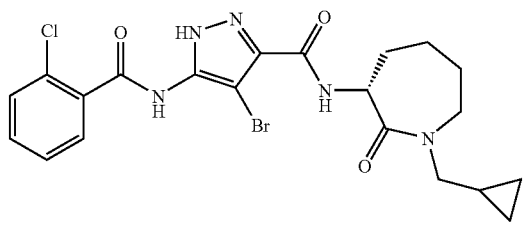

General Procedure 8 was used to synthesize the pyrazole acid for the title compound. The amine was prepared using methods well known in the art, and described in International Patent Application Publication Number WO 00/07995. The final coupling was accomplished using General Procedure 10.

MS+=508.1
$^1$H-NMR (CDCl$_3$) δ 9.22 (m, 1H), 8.42 (m, 1H), 7.92 (m, 1H), 7.41 (m, 3H), 4.74 (m, 1H), 3.46 (m, 3H), 3.18 (m, 1H), 2.12 (m, 1H), 1.86 (m, 3H), 1.51 (m, 2H), 0.98 (m, 1H), 0.50 (m, 2H), 0.24 (m, 2H).

Example 172
Preparation of 5-(2-Chloro-benzoylamino)-4-fluoro-1H-pyrazole-3-carboxylic acid (2-oxo-5-phenyl-2,3-dihydro-1H-benzo[e][1,4]diazepin-3-yl)amide

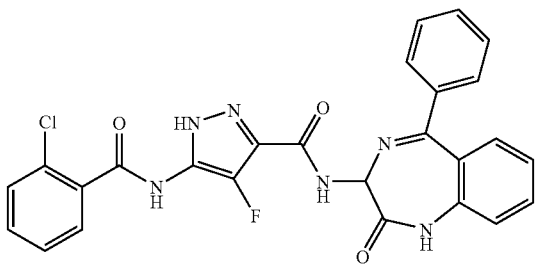

The pyrazole acid was prepared using compound 23 and SELECTFLUOR™ (Aldrich, 43,947-9) using a procedure similar to that described in Katoch-Rouse, R. et al., *J. Med. Chem.* (2003) 46, 642. The amine was prepared as described in General Procedure 20. The final coupling was accomplished using General Procedure 10.

MS+=517.1

$^1$H-NMR (DMSO-d6) δ 7.60 (m, 10H), 7.33 (m, 3H), 5.40 (m, 1H).

Example 173

Preparation of Chloro-5-(2-fluoro-benzoylamino)-1H-pyrazole-3-carboxylic acid (2-oxo-5-phenyl-2,3-dihydro-1H-benzo[e][1,4]diazepin-3-yl)amide

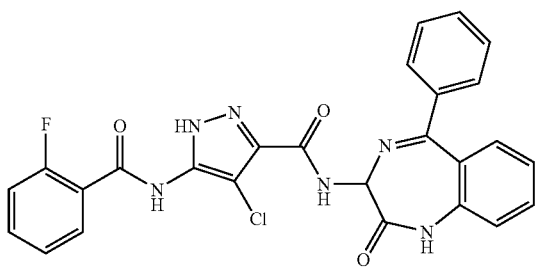

The pyrazole acid was prepared as described for compound 22 using compound 20 and 2-fluorobenzoyl chloride (Aldrich, 12,084-7) followed by chlorination as shown in General Procedure 9. The amine was prepared as describe in General Procedure 20. The final coupling was accomplished using General Procedure 10.

MS+=517.1

$^1$H-NMR (DMSO-d6) δ 7.49 (m, 13H), 5.40 (m, 1H).

Example 174

Preparation of 4-Chloro-5-(2-chloro-benzoylamino)-1H-pyrazole-3-carboxylic acid methyl-(1-methyl-2-oxo-5-phenyl-2,3-dihydro-1H-benzo[e][1,4]diazepin-3-yl)amide

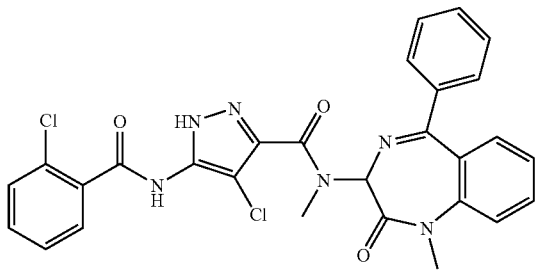

The pyrazole acid, prepared as described in Procedure 9, was coupled to 1-methyl-3-methylamino-5-phenyl-1,3-dihydro-benzo[e][1,4]diazepin-2-one (prepared by alkylation of compound 56 using the method of Procedure 7 followed by treatment with HBr/AcOH as shown in Procedure 20) using the method of Procedure 10.

MS+=561.1

$^1$H-NMR (DMSO-d6) δ 7.71 (m, 2H), 7.52 (m, 8H), 7.34 (m, 2H), 7.22 (m, 1H), 5.82 (s, 1H), 3.44 (s, 3H), 3.38 (s, 3H).

Example 175

Preparation of 4-Bromo-5-(2-chloro-benzoylamino)-1H-pyrazole-3-carboxylic acid (1-cyclopropylmethyl-azepan-3-yl)amide

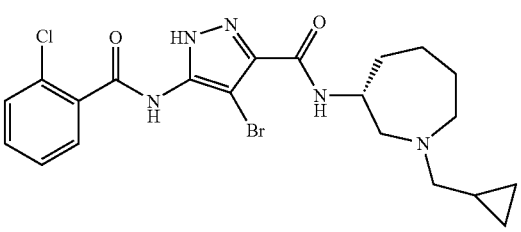

General Procedure 8 was used to synthesize the pyrazole acid for the title compound. The amine was prepared as shown for compound 70 starting from D-Lysine (Aldrich 28,170-0) and alkylating with cyclopropylmethyl bromide (Aldrich 24,240-3) followed by reduction of the lactam as shown for compound 5 in General Procedure 2. Coupling of the pyrazole acid and the amine was accomplished using General Procedure 3.

MS+=494.1

$^1$H-NMR (CD$_3$OD) δ 7.65 (m, 1H), 7.51 (m, 3H), 4.35 (m, 1H), 3.69 (m, 2H), 3.27 (m, 4H), 2.03 (m, 6H), 1.19 (m, 1H), 0.80 (m, 2H), 0.51 (m, 2H).

Example 176

Preparation of 4-Bromo-5-(2-chloro-benzoylamino)-1H-pyrazole-3-carboxylic acid [2-(N-methyl-N-pyridin-4-yl)eth-1-yl]amide

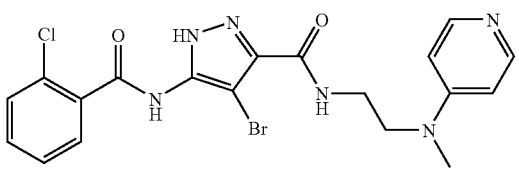

The pyrazole acid, prepared as described in Procedure 8, was coupled to N1-methyl-N1-pyridin-4-yl-ethane-1,2-diamine (prepared as described in Procedure 39) using the method of Procedure 10.

MS+=477.0

$^1$H-NMR (DMSO-d6) δ 13.21 (br, 1H), 8.67 (m, 1H), 8.09 (m, 2H), 7.54 (m, 4H), 6.84 (m, 2H), 3.64 (m, 4H), 3.07 (m, 3H).

Example 177

Preparation of 4-Bromo-5-(2-chloro-benzoylamino)-1H-pyrazole-3-carboxylic acid (1-methyl-piperidin-4-ylmethyl)amide

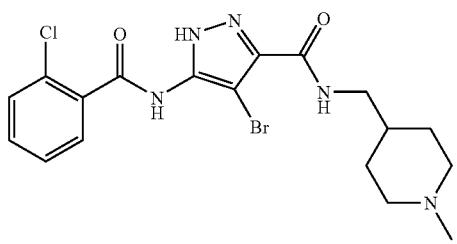

General Procedure 8 was used to synthesize the pyrazole acid for the title compound. General Procedure 13 was used to prepare the appropriate amine. The final coupling was accomplished using General Procedure 10.

MS+=454.0

¹H-NMR (DMSO-d6) δ 8.10 (m, 1H), 7.48 (m, 4H), 3.08 (m, 2H), 2.68 (m, 2H), 2.09 (s, 3H), 1.76 (m, 2H), 1.59 (m, 2H), 1.45 (m, 1H), 1.11 (m, 2H).

Example 178

Preparation of 4-Bromo-5-(2-chloro-benzoylamino)-1H-pyrazole-3-carboxylic acid [1-(2-dimethylamino-ethyl)-2-oxo-azepan-3-yl]amide

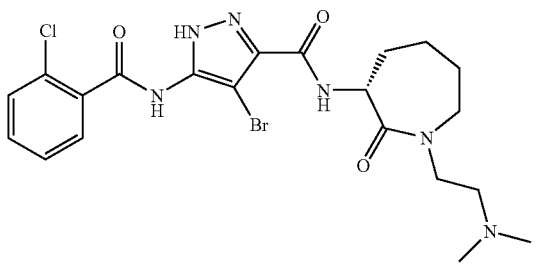

General Procedure 8 was used to synthesize the pyrazole acid for the title compound. The amine was prepared as described for compound 70 using R-(2-Oxo-azepan-3-yl)-carbamic acid tert-butyl ester and 2-(dimethylamino)ethyl chloride hydrochloride (Aldrich, D14,120-8) as shown in General Procedure 23. Coupling of the pyrazole acid and the amine was accomplished using General Procedure 3.

MS+=525.0

¹H-NMR (CD₃OD) δ 7.63 (m, 1H), 7.48 (m, 3H), 4.26 (m, 1H), 3.67 (m, 1H), 3.44 (m, 3H), 3.29 (m, 2H), 3.00 (s, 3H), 2.96 (s, 3H), 1.99 (m, 4H), 1.57 (m, 2H).

Example 179

Preparation of 4-Bromo-5-(2-chloro-benzoylamino)-1H-pyrazole-3-carboxylic acid (5-methyl-6-oxo-6,7,8,9-tetrahydro-5H-pyrido[3,2-b]azepin-7-yl)amide

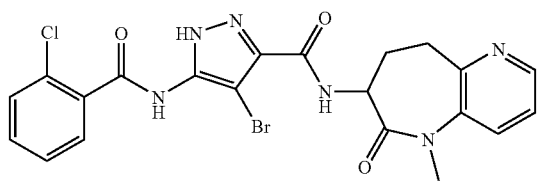

General Procedure 8 was used to synthesize the pyrazole acid for the title compound. General Procedure 28 was used to prepare the appropriate amine. The final coupling was accomplished using General Procedure 10.

MS+=517.0

¹H-NMR (DMSO-d6) δ 13.98 (br, 1H), 10.80 (br, 1H), 8.41 (m, 1H), 8.20 (br, 1H), 7.85 (m, 1H), 7.52 (m, 5H), 4.36 (m, 1H), 3.35 (s, 3H), 3.04 (m, 1H), 2.83 (m, 1H), 2.28 (m, 2H).

Example 180

Preparation of 5-(3-Chloro-benzoylamino)-1H-pyrazole-3-carboxylic acid [2-(3,4,5,6-tetrahydro-2H-[1,4']bipyridin-4-yl)-ethyl]amide

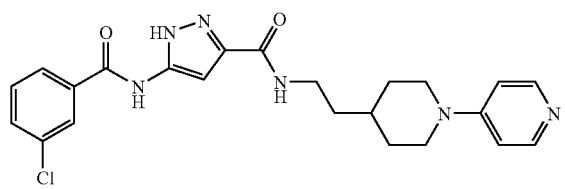

The pyrazole acid was prepared as described for compound 22 using compound 20 and 3-chlorobenzoyl chloride (Aldrich C2,680-1). General Procedure 14 was used to prepare the appropriate amine. Coupling of the pyrazole acid and the amine was accomplished using General Procedure 3.

MS+=453.1

¹H-NMR (DMSO-d6) δ 13.20 (br, 1H), 11.09 (br, 1H), 8.51 (br, 1H), 8.15 (m, 2H), 8.01 (s, 1H), 7.92 (m, 1H), 7.62 (m, 1H), 7.51 (m, 1H), 7.15 (m, 2H), 4.20 (m, 2H), 3.27 (m, 2H), 3.10 (m, 2H), 1.84 (m, 2H), 1.70 (m, 1H), 1.44 (m, 2H), 1.10 (m, 2H).

Example 181

Preparation of 4-Bromo-5-(2-methyl-benzoylamino)-1H-pyrazole-3-carboxylic acid [2-(3,4,5,6-tetrahydro-2H-[1,4']bipyridin-4-yl)-ethyl]amide

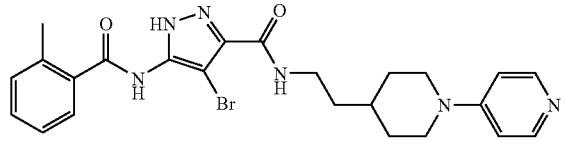

The pyrazole acid was prepared as described for compound 22 using compound 20 and 2-methylbenzoyl chloride (Aldrich 12,201-7) followed by hydrolysis and bromination as shown in General Procedure 8. General Procedure 14 was used to prepare the appropriate amine. Coupling of the pyrazole acid, 7, and the amine was accomplished using General Procedure 3.

MS+=511.1

¹H-NMR (DMSO-d6) δ 8.10 (d, J=6.3 Hz, 2H), 7.50 (d, J=6.9 Hz, 1H), 7.40 (m, 1H), 7.30 (m, 2H), 6.69 (d, J=6.6 Hz, 2H), 3.91 (d, J=12.9 Hz, 2H), 3.30 (m, 2H), 2.79 (t, J=11.7 Hz, 2H), 1.78 (d, J=12.0 Hz, 2H), 1.60 (m, 1H), 1.46 (m, 2H), 1.14 (m, 2H).

Example 182

Preparation of 4-Bromo-5-(2-fluoro-benzoylamino)-1H-pyrazole-3-carboxylic acid [2-(3,4,5,6-tetrahydro-2H-[1,4']bipyridin-4-yl)-ethyl]amide

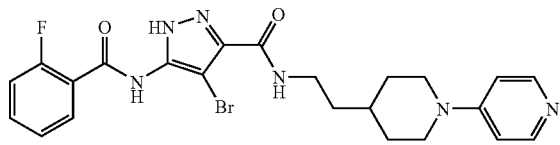

The pyrazole acid was prepared as described for compound 22 using compound 20 and 2-fluorobenzoyl chloride (Aldrich, 12,084-7) followed by hydrolysis and bromination as shown in General Procedure 8. General Procedure 14 was used to prepare the appropriate amine. Coupling of the pyrazole acid and the amine was accomplished using General Procedure 3.

MS+=515.0

¹H-NMR (DMSO-d6) δ 13.87 (br, 1H), 13.23 (br, 1H), 10.45 (br, 1H), 8.19 (m, 2H), 7.69 (m, 2H), 7.39 (m, 2H), 7.19 (m, 2H), 4.24 (m, 2H), 3.34 (m, 2H), 3.13 (m, 2H), 1.89 (m, 2H), 1.74 (m, 1H), 1.49 (m, 2H), 1.19 (m, 2H).

Example 183

Preparation of 4-Bromo-5-(2-chloro-benzoylamino)-1H-pyrazole-3-carboxylic acid (2-(N-(N,N-dimethylaminocarbonyl)piperidin-4-yl)eth-1-yl)amide

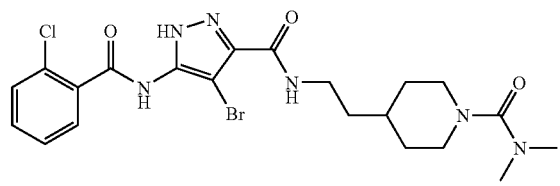

General Procedure 8 was used to synthesize the pyrazole acid for the title compound. The amine was prepared as shown for compound 22 in General Procedure 8 using (2-Piperidin-4-yl-ethyl)carbamic acid tert-butyl ester (see compound 34 in General Procedure 14) and dimethylcarbamyl chloride (Aldrich, D15,280-3). Coupling of the pyrazole acid and the amine was accomplished using General Procedure 3.

MS+=525.0

¹H-NMR (DMSO-d6) δ 13.84 (m, 1H), 10.55 (m, 1H), 8.15 (m, 1H), 7.58 (m, 4H), 3.52 (m, 2H), 3.33 (m, 2H), 2.71 (s, 6H), 2.63 (m, 2H), 1.69 (m, 2H), 1.46 (m, 2H).

Example 184

Preparation of 4-Bromo-5-(2-chloro-benzoylamino)-1H-pyrazole-3-carboxylic acid {2-[1-(pyridine-4-carbonyl)-piperidin-4-yl]-ethyl}amide

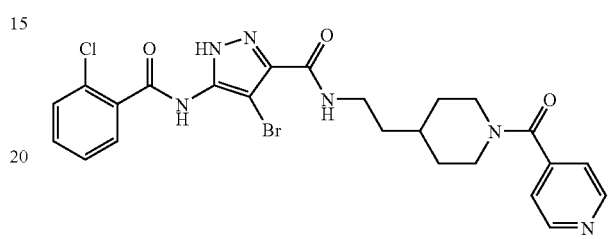

General Procedure 8 was used to synthesize the pyrazole acid for the title compound. The amine was prepared as shown for compound 22 in General Procedure 8 using (2-Piperidin-4-yl-ethyl)carbamic acid tert-butyl ester (see compound 34 in General Procedure 4) and isonicotinoyl chloride hydrochloride (Aldrich, 22,875-3). Coupling of the pyrazole acid, 7, and the amine was accomplished using General Procedure 3.

MS+=559.0

¹H-NMR (DMSO-d6) δ 13.80 (br, 1H), 8.61 (m, 2H), 8.15 (br, 1H), 7.49 (m, 4H), 7.33 (m, 2H), 3.32 (m, 4H), 2.96 (m, 1H), 2.72 (m, 1H), 1.78 (m, 1H), 1.61 (m, 2H), 1.45 (m, 2H), 1.10 (m, 2H).

Example 185

Preparation of 4-Bromo-5-(2-chloro-benzoylamino)-1H-pyrazole-3-carboxylic acid [2-(4-pyridin-4-yl-piperazin-1-yl)-ethyl]amide

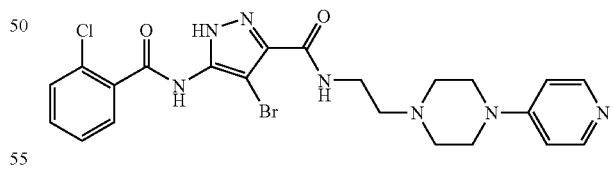

General Procedure 8 was used to synthesize the pyrazole acid for the title compound. The amine was prepared using methods well known in the art and described in Canadian Patent number CA 985683. Coupling of the pyrazole acid and the amine was accomplished using General Procedure 10.

MS+=532.1

¹H-NMR (CD₃OD) δ 8.25 (d, J=7.7 Hz, 2H), 7.63 (d, J=8.2 Hz, 1H), 7.49 (m, 3H), 7.28 (d, J=7.7 Hz, 2H), 4.03 (m, 4H), 3.79 (m, 2H), 3.51 (m, 4H), 3.37 (m, 2H).

Example 186

Preparation of 4-Bromo-5-(2-chloro-benzoylamino)-1H-pyrazole-3-carboxylic acid (1-pyridin-4-ylm-ethyl-piperidin-4-yl)amide

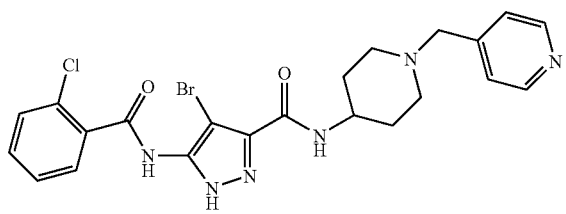

General Procedure 8 was used to synthesize the pyrazole acid for the title compound. General Procedure 14 was used to prepare the appropriate amine. Coupling of the pyrazole acid and the amine was accomplished using General Procedure 3.

MS+=517.0

$^1$H-NMR (CD$_3$OD/HCl) δ 9.02 (d, J=6.6 Hz, 2H), 8.47 (d, J=6.6 Hz, 2H), 7.63 (d, J=6.6 Hz, 1H), 7.53-7.43 (m, 3H), 4.76 (bs, 2H), 4.21 (m, 1H), 3.65 (m, 2H), 3.37 (m, 2H), 2.27-2.06 (m, 4H).

Example 187

Preparation of 4-methyl-5-(2-chlorobenzoylamino)-1-(pyrimidin-2-yl)-pyrazole-3-carboxylic acid[2-(3,4,5,6-tetrahydro-2H-[1,4']bipyridin-4-ethyl]amide

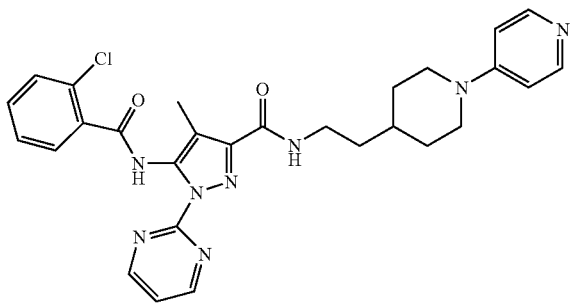

The pyrazole acid, prepared as described in Procedure 8 using 5-amino-4-methyl-1-pyrimidin-2-yl-1H-pyrazole-3-carboxylic acid ethyl ester (prepared as described in Procedure 41 using 3-cyano-3-methyl-2-oxopropanoic acid ethyl ester (U.S. Pat. No. 4,652,669) and 2(1H)-pyrimidinone, hydrazone (Ambinter, PFR-114431)) in place of compound 20, was coupled to 2-(3,4,5,6-tetrahydro-2H-[1,4']bipyridin-4-yl)ethylamine (prepared as described in Procedure 14) using the method of Procedure 10.

MS+=544.8

$^1$H-NMR (DMSO-d6) δ 8.95 (d, J=4.8 Hz, 2H), 8.26 (m, 1H), 8.10 (dd, J=1.2, 4.8 Hz, 2H), 7.53 (m, 4H), 6.77 (dd, J=1.5, 5.1 Hz, 2H), 3.89 (m, 2H), 3.29 (m, 4H), 2.78 (m, 2H), 2.20 (s, 3H), 1.79 (m, 2H), 1.50 (m, 3H), 1.13 (m, 2H).

Example 188

Preparation of 4-Bromo-5-(2-chloro-benzoylamino)-1H-pyrazole-3-carboxylic acid [2-(1-pyridin-4-ylm-ethyl-piperidin-4-yl)-ethyl]amide

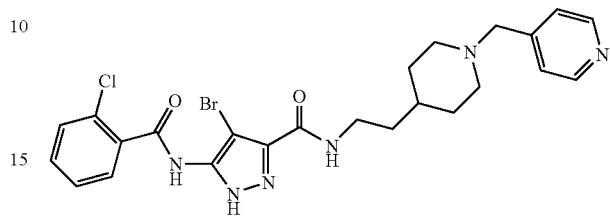

General Procedure 8 was used to synthesize the pyrazole acid for the title compound. The amine was prepared using methods well known in the art and described in General Procedure 37. Coupling of the pyrazole acid and the amine was accomplished using General Procedure 3.

MS+=545.0

$^1$H-NMR (CD$_3$OD/HCl) δ 9.00 (d, J=6.3 Hz, 2H), 8.40 (d, J=6.3 Hz, 2H), 7.64 (m, 1H), 7.55-7.44 (m, 3H), 4.69 (s, 2H), 3.56 (m, 2H), 3.45 (m, 2H), 3.1 (m, 2H), 2.07 (m, 2H), 1.65 (m, 5H).

Example 189

Preparation of 4-Bromo-5-(2-chloro-benzoylamino)-1H-pyrazole-3-carboxylic acid {2-[1-(2-pyridin-4-yl-ethyl)-piperidin-4-yl]-ethyl}amide

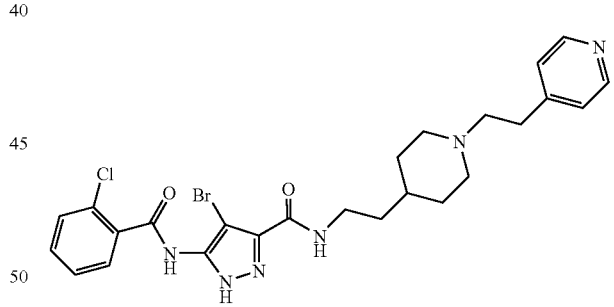

General Procedure 8 was used to synthesize the pyrazole acid for the title compound. The amine was prepared using methods well known in the art and described in General Procedure 36. Coupling of the pyrazole acid and the amine was accomplished using General Procedure 3.

MS+=559.0

$^1$H-NMR (CD$_3$OD) δ 8.42 (d, J=5.8 Hz, 2H), 7.64 (m, 1H), 7.55-7.43 (m, 3H), 7.33 (d, J=5.8 Hz, 2H), 3.44 (dd(app. t), J=7.0 Hz, 2H), 3.04 (m, 2H), 2.89 (m, 2H), 2.64 (m, 2H), 2.12 (dd(app. t), J=10.9 Hz, 2H), 1.83 (m, 2H), 1.59 (m, 2H), 1.50-1.26 (m, 3H).

Example 190
Preparation of 4-Bromo-5-(2-chloro-benzoylamino)-1H-pyrazole-3-carboxylic acid (1-pyridin-4-ylm-ethyl-piperidin-4-ylmethyl)amide

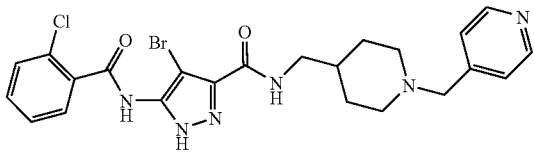

General Procedure 8 was used to synthesize the pyrazole acid for the title compound. The amine was prepared using methods well known in the art and described in General Procedure 37. Coupling of the pyrazole acid and the amine was accomplished using General Procedure 3.

MS+=531.0

$^1$H-NMR (CD$_3$OD/HCl) δ 8.81 (d, J=5.7 Hz, 2H), 7.94 (d, J=5.7 Hz, 2H), 7.64 (d, J=6.7 Hz, 1H), 7.55-7.43 (m, 3H), 4.53 (s, 2H), 3.55 (m, 2H), 3.35 (m, 2H), 3.14 (m, 2H), 2.04 (m, 3H), 1.68 (m, 2H).

Example 191
Preparation of 4-Bromo-5-(2-chloro-benzoylamino)-1H-pyrazole-3-carboxylic acid [1-(2-pyridin-4-yl-ethyl)-piperidin-4-yl]amide

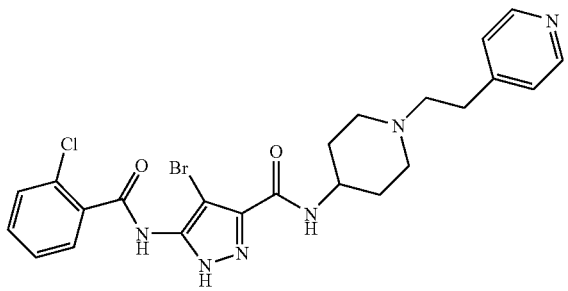

General Procedure 8 was used to synthesize the pyrazole acid for the title compound. The amine was prepared using methods well known in the art and described in General Procedure 36. Coupling of the pyrazole acid and the amine was accomplished using General Procedure 3.

MS+=531.0

$^1$H-NMR (CD$_3$OD) δ 8.45 (d, J=5.8 Hz, 2H0, 7.64 (m, 1H), 7.56-7.42 (m, 3H), 7.37 (d, J=5.8 Hz, 2H), 3.97 (m, 1H), 3.17 (m, 2H), 2,91 (m, 4H), 2.50 (m, 2H), 2.07 (m, 2H), 1.76 (m, 2H).

Example 192
Preparation of 4-Bromo-5-(2-chloro-benzoylamino)-1H-pyrazole-3-carboxylic acid [1-(2-pyridin-4-yl-ethyl)-piperidin-4-ylmethyl]amide

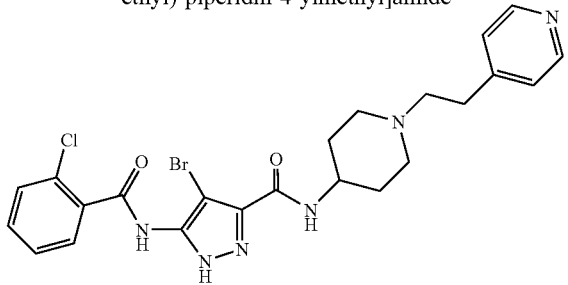

General Procedure 8 was used to synthesize the pyrazole acid for the title compound. The amine was prepared using methods well known in the art and described in General Procedure 36. Coupling of the pyrazole acid and the amine was accomplished using General Procedure 3.

MS+=545.0

$^1$H-NMR (CD$_3$OD) δ 8.48 (d, J=4.5 Hz, 2H), 7.65-7.39 (m, 6H), 3.59 (m, 2H), 3.35 (m, 4H), 3.13 (m, 2H), 2.95 (m, 2H), 2.01 (m, 3H), 1.60 (m, 2H).

Example 193
Preparation of 4-Bromo-5-(2-chloro-benzoylamino)-1H-pyrazole-3-carboxylic acid [2-(1'-methyl-[1,4']bipiperidin-4-yl)-ethyl]amide

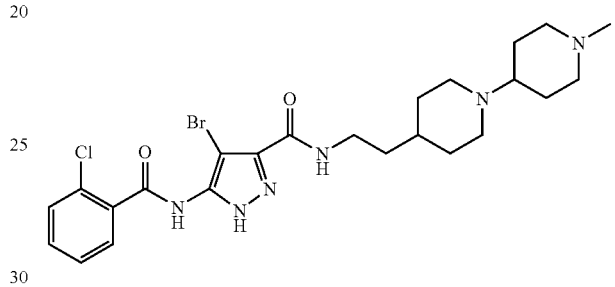

General Procedure 8 was used to synthesize the pyrazole acid for the title compound. The amine was prepared using methods well known in the art and described in General Procedure 35. Coupling of the pyrazole acid and the amine was accomplished using General Procedure 3.

MS+=551.1

$^1$H-NMR (CD$_3$OD) δ 7.64 (d, J=7.1 Hz, 1H), 7.56-7.42 (m, 3H), 3.71-3.56 (m, 5H), 3.46 (m, 2H), 3.11 (m, 4H), 2.90 (s, 3H), 2.42 (m, 2H), 2.11 (m, 4H), 1.74 (b, 1H), 1.59 (m, 4H).

Example 194
Preparation of 4-Chloro-5-(2-chloro-benzoylamino)-1H-pyrazole-3-carboxylic acid [5-(3-aza-bicyclo[3.2.2]non-3-yl)-1-methyl-2-oxo-2,3-dihydro-1H-benzo[e][1,4]diazepin-3-yl]amide

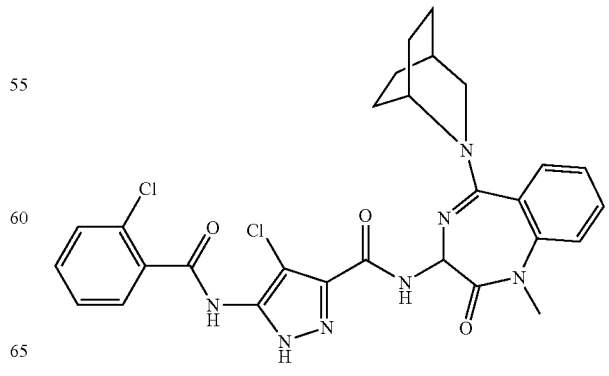

General Procedure 9 was used to synthesize the pyrazole acid for the title compound. The amine was prepared using methods well known in the art and described in Showell, G. A., et. al. *J. Med. Chem.* 1994, 37, 719. Coupling of the pyrazole acid and the amine was accomplished using General Procedure 10.

MS+=594.1

$^1$H-NMR (CD$_3$OD) δ 7.40-7.68 (m, 8H), 5.32 (s, 1H), 3.69 (m, 2H), 3.45 (s, 3H), 3.36 (m, 2H), 1.83-2.03 (m, 4H), 1.67-1.8 (m, 6H).

Example 195

Preparation of 4-Bromo-5-(2-chloro-benzoylamino)-1H-pyrazole-3-carboxylic acid [5-(3-aza-bicyclo[3.2.2]non-3-yl)-1-methyl-2-oxo-2,3-dihydro-1H-benzo[c][1,4]diazepin-3-yl]amide

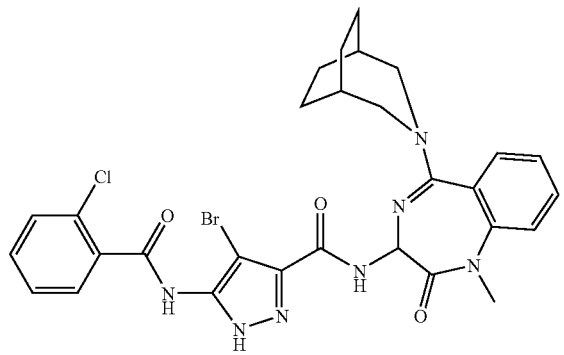

General Procedure 8 was used to synthesize the pyrazole acid for the title compound. The amine was prepared using methods well known in the art and described in Showell, G. A., et. al. *J. Med. Chem.* 1994, 37, 719. Coupling of the pyrazole acid and the amine was accomplished using General Procedure 10.

MS+=638.1

$^1$H-NMR (CDCl$_3$) δ 9.02 (s, 1H), 8.37 (m, 1H), 7.50 (m, 8H), 5.44 (m, 1H), 3.55 (m, 2H), 3.32 (m, 2H), 1.55-2.00 (m, 10H).

Example 196

Preparation of 4-Chloro-5-(2-chloro-benzoylamino)-1H-pyrazole-3-carboxylic acid (2-oxo-5-phenethyl-1-propyl-2,3-dihydro-1H-benzo[e][1,4]diazepin-3-yl)amide

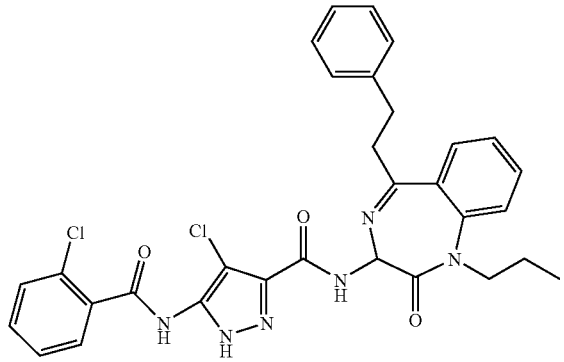

General Procedure 9 was used to synthesize the pyrazole acid for the title compound. The amine was prepared using methods well known in the art and described in International Patent Application Publication Number WO 02/099388. Coupling of the pyrazole acid and the amine was accomplished using General Procedure 10.

MS+=603.2

$^1$H-NMR (CDCl$_3$) δ 7.75 (d, J=6.6 Hz, 1H), 7.39-7.70 (m, 7H), 7.20-7.28 (m, 2H), 7.15 (m, 3H), 5.40 (s, 1H), 4.10 (m, 1H), 3.71 (m, 1H), 3.03-3.30 (m, 2H), 2.86 (m, 2H), 1.30-1.55 (m, 2H), 0.81 (t, J=7.2 Hz, 3H).

Example 197

Preparation of 4-Chloro-5-(2-chloro-benzoylamino)-1H-pyrazole-3-carboxylic acid [5-(3-aza-bicyclo[3.2.2]non-3-yl)-1-methyl-2-oxo-2,3-dihydro-1H-benzo[e][1,4]diazepin-3-yl]amide

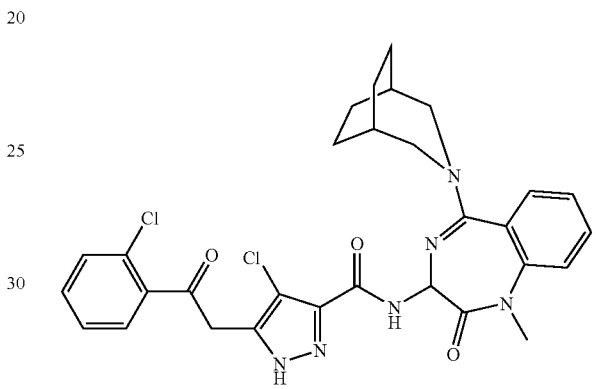

General Procedure 9 was used to synthesize the pyrazole acid for the title compound. The amine was prepared using methods well known in the art and described in Showell, G. A., et. al. *J. Med. Chem.* 1994, 37, 719. Coupling of the pyrazole acid and the amine was accomplished using General Procedure 10.

MS+=594.1

$^1$H-NMR (CD$_3$OD) δ 7.37-7.68 (m, 8H), 5.31 (s, 1H), 3.73 (m, 2H), 3.44 (s, 3H), 3.35 (m, 2H), 1.84-2.03 (m, 4H), 1.65-1.80 (m, 6H).

Example 198

Preparation of 4-Chloro-5-(2-chloro-benzoylamino)-1H-pyrazole-3-carboxylic acid [5-(3-aza-bicyclo[3.2.2]non-3-yl)-1-methyl-2-oxo-2,3-dihydro-1H-benzo[e][1,4]diazepin-3-yl]amide

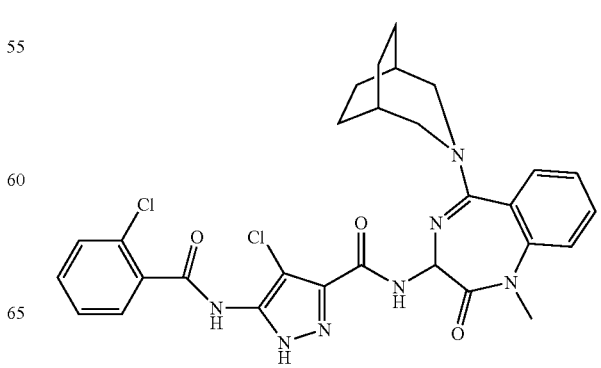

General Procedure 9 was used to synthesize the pyrazole acid for the title compound. The amine was prepared using methods well known in the art and described in Showell, Graham A., et. al. *J. Med. Chem.* 1994, 37, 719. Coupling of the pyrazole acid and the amine was accomplished using General Procedure 10.

MS+=594.1

$^1$H-NMR (CD$_3$OD) δ 7.37-7.68 (m, 8H), 5.31 (s, 1H), 3.73 (m, 2H), 3.44 (s, 3H), 3.35 (m, 2H), 1.84-2.03 (m, 4H), 1.65-1.80 (m, 6H).

Example 199

Preparation of 4-Bromo-5-(2-chloro-benzoylamino)-1H-pyrazole-3-carboxylic acid (1-ethyl-2-oxo-5-phenyl-2,3-dihydro-1H-benzo[e][1,4]diazepin-3-yl) amide

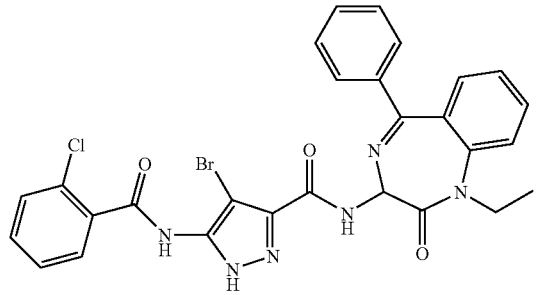

General Procedure 8 was used to synthesize the pyrazole acid for the title compound. The amine was prepared using methods well known in the art and described in International Patent Application Publication Number WO 00/0038618. Coupling of the pyrazole acid and the amine was accomplished using General Procedure 10.

MS+=605.0

$^1$H-NMR (CD$_3$OD) δ 7.34-7.78 (m, 13H), 5.57 (s, 1H), 4.39 (m, 1H), 3.91 (m, 1H), 1.14 (m, 3H).

Example 200

Preparation of 4-Bromo-5-(2-chloro-benzoylamino)-1H-pyrazole-3-carboxylic acid (1-ethyl-2-oxo-5-phenyl-2,3-dihydro-1H-benzo[e][1,4]diazelpin-3-yl) amide

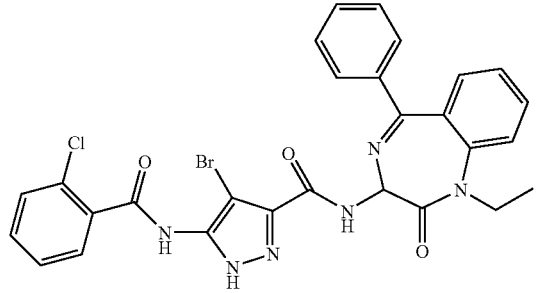

General Procedure 8 was used to synthesize the pyrazole acid for the title compound. The amine was prepared using methods well known in the art and described in International Patent Application Publication Number WO 00/38618. Coupling of the pyrazole acid and the amine was accomplished using General Procedure 10.

MS+=605.0

$^1$H-NMR (CD$_3$OD) δ 7.34-7.78 (m, 13H), 5.57 (s, 1H), 4.39 (m, 1H), 3.91 (m, 1H), 1.14 (m, 3H).

Example 201

Preparation of 4-Bromo-3-(2-chloro-benzoylamino)-1-methyl-pyrazole-5-carboxylic acid [2-(3,4,5,6-tetrahydro-2H-[1,4']bipyridin-4-yl)-ethyl]amide

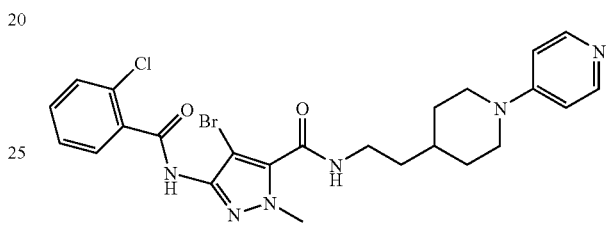

The pyrazole acid was prepared by coupling methyl ester 85 (General Procedure 26) with 2-chlorobenzoyl chloride (21), followed by hydrolysis and bromination as shown in General Procedure 8. General Procedure 14 was used to prepare the appropriate amine. Coupling of the pyrazole acid and the amine was accomplished using General Procedure 3.

MS+=545.1

$^1$H-NMR (CD$_3$OD) δ 7.96 (d, J=9.0 Hz, 2H), 7.52 (d, J=9.0 Hz, 1H), 7.31-7.46 (m, 3H), 7.04 (d, J=6.0, Hz, 2H), 4.18 (d, J=15 Hz, 2H), 3.89 (s, 3H), 3.41 (m, 2H), 3.12 (t, J=12 Hz, 2H), 1.72-1.98 (m, 3H), 1.56 (m, 2H), 1.25 (m, 2H).

Example 202

Preparation of 4-Bromo-5-(2-chlorobenzoylamino)-1H-pyrazole-3-carboxylic acid [2-(4-cyano-phenyl) ethyl]amide

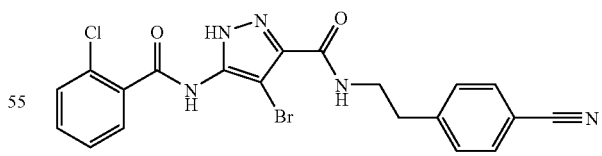

General Procedure 8 was used to synthesize the pyrazole acid for the title compound. The amine was prepared using methods well known in the art and described in General Procedure 34. Coupling of the pyrazole acid and the amine was accomplished using General Procedure 10.

MS+=472.0

$^1$H-NMR (DMSO-d6) δ 7.77 (m, 2H), 7.44 (m, 6H), 3.48 (m, 2H), 2.95 (m, 2H).

Example 203

Preparation of 4-Bromo-5-(2-chlorobenzoylamino)-1H-pyrazole-3-carboxylic acid {2-[4-(4,5-dihydro-1H-imidazol-2-yl)-phenyl]ethyl}amide

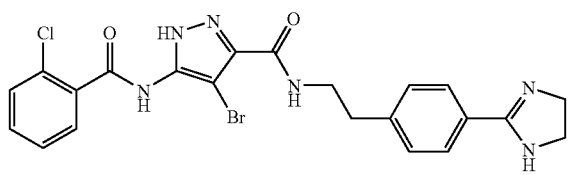

The title compound was prepared as shown in General Procedure 10 using pyrazole acid 7 and amine 169 (shown in General Procedure 34) followed by formation of the amidine using ethylene diamine as shown in General Procedure 33.
MS+=515.0
$^1$H-NMR (DMSO-d6) δ 13.89 (br, 1H), 10.43 (br, 1H), 7.85 (m, 2H), 7.43 (m, 6H), 4.03 (m, 4H), 3.54 (m, 2H), 2.98 (m, 2H).

Example 204

Preparation of 4-Bromo-5-(2-chlorobenzoylamino)-1H-pyrazole-3-carboxylic acid [1-(2-pyridin-4-yl-acetyl)-piperidin-4-yl]amide

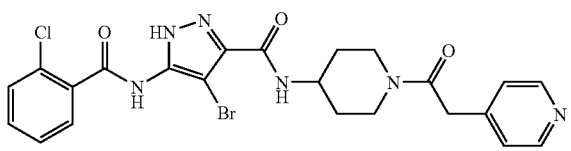

General Procedure 8 was used to synthesize the pyrazole acid for the title compound. The amine was prepared as shown for compound 22 in General Procedure 8 using compound 183 (shown in General Procedure 30) and 4-pyridylacetic acid hydrochloride (Aldrich, P6,585-1). Coupling of the pyrazole acid and the amine was accomplished using General Procedure 3.
MS+=545.0
$^1$H-NMR (DMSO-d6) δ 8.76 (d, J=5.1 Hz, 2H), 8.13 (d, J=7.5 Hz, 2H), 7.53 (m, 4H), 4.30 (m, 1H), 4.07 (s, 2H), 3.97 (m, 2H), 3.23 (m, 1H), 2.82 (m, 1H), 1.85 (m, 2H), 1.52 (m, 2H).

Example 205

Preparation of 4-Bromo-5-(2-chlorobenzoylamino)-1H-pyrazole-3-carboxylic acid [1-(pyridine-4-carbonyl)-piperidin-4-ylmethyl]amide

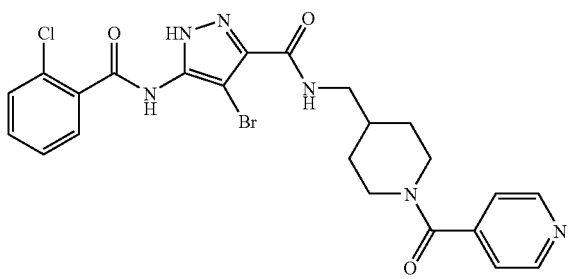

General Procedure 8 was used to synthesize the pyrazole acid for the title compound. The amine was prepared as shown for compound 22 in General Procedure 8 using piperidin-4-ylmethylcarbamic acid tert-butyl ester (see compound 34 in General Procedure 14) and isonicotinoyl chloride hydrochloride (Aldrich, 22,875-3). Coupling of the pyrazole acid and the amine was accomplished using General Procedure 3.
MS+=545.0

$^1$H-NMR (DMSO-d6) δ 10.58 (br, 1H), 8.74 (m, 2H), 8.25 (br, 1H), 7.52 (m, 6H), 4.46 (m, 2H), 3.42 (m, 1H), 3.18 (m, 1H), 2.99 (m, 1H), 2.80 (m, 1H), 1.83 (m, 2H), 1.63 (m, 1H), 1.18 (m, 2H).

Example 206

Preparation of 4-Bromo-5-(2-chlorobenzoylamino)-1H-pyrazole-3-carboxylic acid (2-[1,4']bipiperidin-1'-yl-ethyl)amide

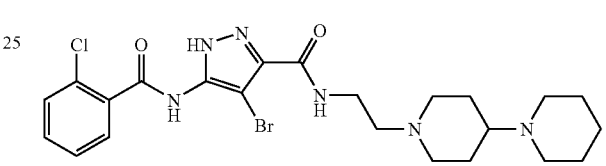

General Procedure 8 was used to synthesize the pyrazole acid for the title compound. General Procedure 29 was used to prepare the appropriate amine. Coupling of the pyrazole acid and the amine was accomplished using General Procedure 3.
MS+=537.1
$^1$H-NMR (CD$_3$OD) δ 7.60 (m, 1H), 7.46 (m, 3H), 3.88 (m, 2H), 3.75 (m, 2H), 3.59 (m, 3H), 3.37 (m, 2H), 3.27 (m, 1H), 3.03 (m, 4H), 2.38 (m, 2H), 2.11 (m, 2H), 1.89 (m, 4H), 1.49 (m, 1H).

Example 207

Preparation of 4-Bromo-5-(2-chlorobenzoylamino)-1H-pyrazole-3-carboxylic acid (2-[1,4']bipiperidin-1'-yl-2-cyanoethyl)amide

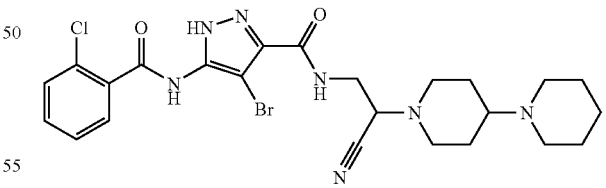

General Procedure 8 was used to synthesize the pyrazole acid for the title compound. The amine was prepared using methods well known in the art and described in General Procedure 29. Coupling of the pyrazole acid and the amine was accomplished using General Procedure 3.
MS+=562.1
$^1$H-NMR (CD$_3$OD) δ 7.63 (m, 1H), 7.53 (m, 3H), 4.11 (m, 1H), 3.70 (m, 3H), 3.51 (m, 2H), 3.19 (m, 2H), 2.98 (m, 2H), 2.53 (m, 1H), 2.30 (m, 3H), 1.97 (m, 2H), 1.78 (m, 4H), 1.50 (m, 1H).

Example 208

Preparation of 4-Bromo-5-(2-chlorobenzoylamino)-1H-pyrazole-3-carboxylic acid {2-[1-(2-pyridin-4-yl-acetyl)-piperidin-4-yl]ethyl}amide

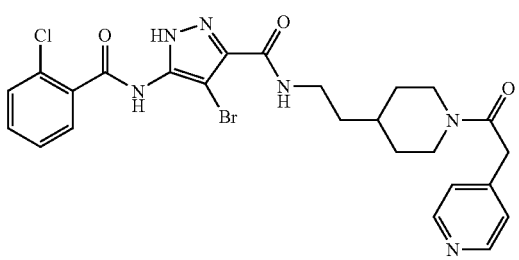

General Procedure 8 was used to synthesize the pyrazole acid for the title compound. The amine was prepared as shown for compound 3 in General Procedure 1 using (2-Piperidin-4-yl-ethyl)carbamic acid tert-butyl ester (see compound 34 in General Procedure 14) and 4-pyridylacetic acid hydrochloride (Aldrich, P6,585-1). Coupling of the pyrazole acid and the amine was accomplished using General Procedure 3.

MS+=573.1

$^1$H-NMR (DMSO-d6) δ 13.85 (br, 1H), 8.48 (m, 2H), 7.53 (m, 4H), 7.24 (m, 2H), 4.37 (m, 1H), 3.92 (m, 1H), 3.76 (s, 2H), 3.30 (m, 2H), 2.97 (m, 1H), 2.58 (m, 1H), 1.71 (m, 2H), 1.36 (m, 3H), 0.95 (m, 2H).

Example 209

Preparation of 4-Bromo-5-(2-chlorobenzoylamino)-1H-pyrazole-3-carboxylic acid (1,5-dimethyl-2,3,4,5-tetrahydro-1H-benzo[b][1,4]diazepin-3-yl)amide

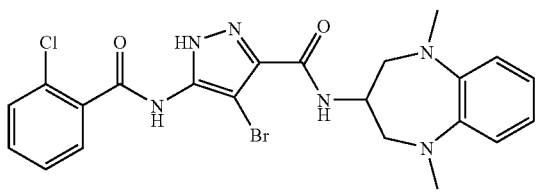

General Procedure 8 was used to synthesize the pyrazole acid for the title compound. The amine was prepared as described for compound 5, General Procedure 2, using compound 92, General Procedure 27. Coupling of the pyrazole acid and the amine was accomplished using General Procedure 3.

MS+=517.0

$^1$H-NMR (CDCl$_3$) δ 9.17 (m, 1H), 7.98 (m, 1H), 7.46 (m, 3H), 6.65 (m, 4H), 4.72 (2 br, 1H), 3.57 (m, 4H), 3.21 (m, 3H), 2.88 (br, 3H).

Example 210

Preparation of 4-Bromo-5-(2-chlorobenzoylamino)-1H-pyrazole-3-carboxylic acid [2-(3,4,5,6-tetrahydro-2H-[4,4']bipyridin-1-yl)ethyl]amide

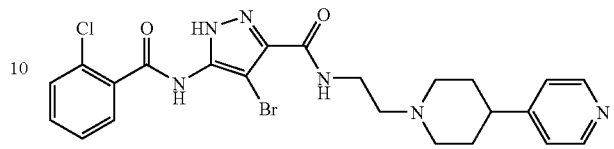

General Procedure 8 was used to synthesize the pyrazole acid for the title compound. The amine was prepared by reductive amination of tert-butyl N-(2-oxoethyl)carbamate (Aldrich, 47,265-4) with 4-(4-piperidinyl)pyridine (see: *Tetrahedron Letters* 2001, 42(29), 4915) as shown in General Procedure 29. Coupling of the pyrazole acid and the amine was accomplished using General Procedure 3.

MS+=531.0

$^1$H-NMR (CD$_3$OD) δ 8.72 (d, J=6.6 Hz, 2H), 7.87 (d, J=6.0 Hz, 2H), 7.59 (d, J=8.2 Hz, 1H), 7.45 (m, 3H), 3.83 (m, 2H), 3.77 (m, 2H), 3.41 (m, 2H), 3.25 (m, 2H), 2.24 (m, 2H), 2.06 (m, 3H).

Example 211

Preparation of 4-Bromo-5-(2-chlorobenzoylamino)-1H-pyrazole-3-carboxylic acid [N-benzyloxycarbonyl)piperidin-4-yl]amide

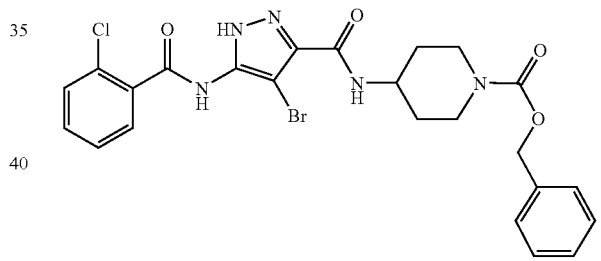

General Procedure 8 was used to synthesize the pyrazole acid for the title compound. The amine was prepared as shown for compound 22 in General Procedure 8 using 4-(N-BOC amino)-piperidine (Aldrich, 54,093-5) and benzyl chloroformate (Aldrich, 11,993-8). Coupling of the pyrazole acid and the amine was accomplished using General Procedure 3.

MS+=560.0

$^1$H-NMR (CDCl$_3$) δ 13.18 (br, 1H), 9.14 (s, 1H), 7.83 (m, 1H), 7.53 (m, 1H), 7.43 (m, 7H), 5.09 (s, 2H), 4.10 (m, 3H), 2.87 (m, 2H), 1.93 (m, 2H), 1.49 (m, 2H).

Example 212

Preparation of 4-Bromo-5-(2-chlorobenzoylamino)-1H-pyrazole-3-carboxylic acid piperidin-4-ylamide

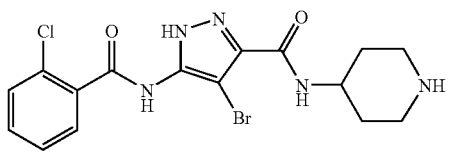

General Procedure 8 was used to synthesize the pyrazole acid for the title compound. The Boc-amine was prepared as described in Procedure 30. Coupling of the amine and the pyrazole acid was accomplished using Procedure 3. Deprotection of the piperidine amine using the method of Procedure 20 afforded the title compound.

MS+=426.0

$^1$H-NMR (CD$_3$OD) δ 7.63 (m, 1H), 7.52 (m, 3H), 4.14 (m, 1H), 3.42 (m, 2H), 3.16 (m, 2H), 2.19 (m, 2H), 1.86 (m, 2H).

Example 213

Preparation of 1-(pyridin-4-yl)-4-methyl-5-(2-chloro-benzoylamino)-1H-pyrazole-3-carboxylic acid [2-(3,4,5,6-tetrahydro-2H-[1,4']bipyridin-4-yl)-ethyl]amide

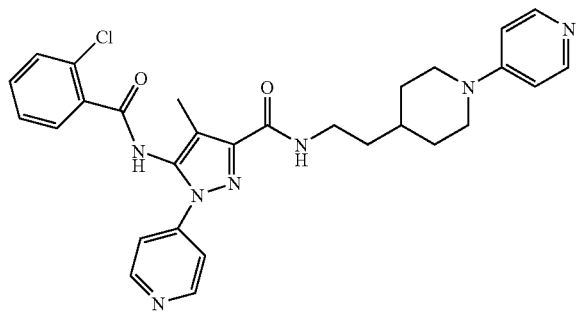

The pyrazole acid, prepared as described in Procedure 8 using 5-Amino-4-methyl-1-pyridin-4-yl-1H-pyrazole-3-carboxylic acid ethyl ester (prepared as described in Procedure 41 using 3-cyano-3-methyl-2-oxopropanoic acid ethyl ester (U.S. Pat. No. 4,6526,69) and 4-hydrazinopyridine hydrochloride (Apin Chemical, 25637 h)) in place of compound 20, was coupled to 2-(3,4,5,6-tetrahydro-2H-[1,4']bipyridin-4-yl)ethylamine (prepared as described in Procedure 14) using the method of Procedure 10.

MS+=544.2

$^1$H-NMR (DMSO-d6) δ 10.68 (s, 1H), 8.74 (m, 2H), 8.32 (m, 2H), 8.75 (m, 2H), 7.51 (m, 4H), 6.76 (m, 2H), 3.89 (m, 2H), 3.29 (m, 4H), 2.75 (m, 2H), 2.20 (s, 3H), 1.79 (m, 2H), 1.51 (m, 3H), 1.21 (m, 2H).

Example 214

Preparation of 4-Bromo-5-(2-chlorobenzoylamino)-1H-pyrazole-3-carboxylic acid [N-(benzyloxycarbonyl)azapin-3-yl]amide

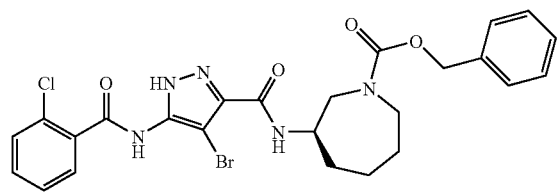

General Procedure 8 was used to synthesize the pyrazole acid for the title compound. The amine was prepared as shown in General Procedure 30 using [(3S)-hexahydro-1H-azepin-3-yl]carbamic acid 1,1-dimethylethyl ester which was prepared as shown in General Procedure 2 using [(3R)-hexahydro-2-oxo-1H-azepin-3-yl]carbamic acid 1,1-dimethylethyl ester which was prepared as shown in General Procedure 23 using Boc-D-Lys-OH (Bachem, A-2705). Coupling of the pyrazole acid and the amine was accomplished using General Procedure 3.

MS+=574.0

$^1$H-NMR (CD$_3$OD) δ 7.66 (m, 1H), 7.54 (m, 3H), 7.33 (m, 5H), 4.28 (m, 1H), 3.70 (m, 2H), 3.59 (m, 1H), 3.39 (m, 3H), 1.98 (m, 1H), 1.68 (m, 5H).

Example 215

Preparation of 4-Bromo-5-(2-chlorobenzoylamino)-1H-pyrazole-3-carboxylic acid azepan-3-ylamide

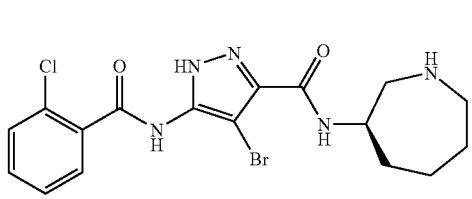

The pyrazole acid, prepared as described in Procedure 8, was coupled to (R)-3-tert-butoxycarbonylaminoazepane-1-carboxylic acid benzyl ester (prepared as described in Procedure 23 using Boc-D-Lys-OH (Bachem, A-2705) followed by Cbz protection of the piperidine amine using the method of Procedure 30) using Procedure 3. Removal of the Cbz group using the method of Procedure 20 afforded the title compound.

MS+=440.0

$^1$H-NMR (CD$_3$OD) δ 7.63 (m, 1H), 7.48 (m, 3H), 4.30 (m, 1H), 3.46 (m, 1H), 3.28 (m, 3H), 2.14 (m, 1H), 1.90 (m, 4H), 1.71 (m, 1H).

Example 216

Preparation of 4-Chloro-5-(2-methylbenzoylamino)-1H-prazole-3-carboxylic acid (1-ethyl-2-oxo-5-phenyl-2,3-dihydro-1H-benzo[e][1,4]diazepin-3-yl)amide

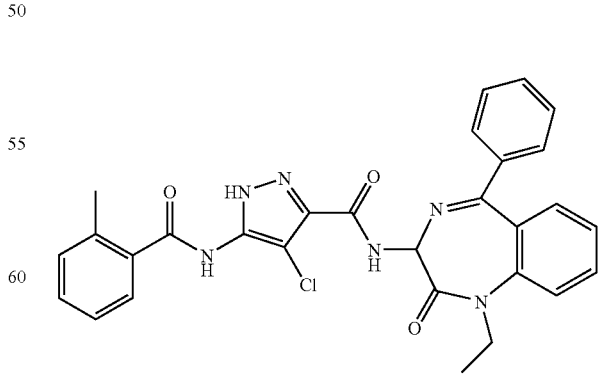

The pyrazole acid, prepared as described in Procedure 18 using 2-methylbenzoyl chloride (Aldrich, 12,201-7) instead of compound 21 was coupled to 3-amino-1-ethyl-5-phenyl-1,3-dihydro-benzo[e][1,4]diazepin-2-one (WO 00/0038618) using the method of Procedure 10.

MS+=541.1

$^1$H-NMR (DMSO-d6) δ 7.74 (m, 2H), 7.47 (m, 1H), 5.42 (s, 1H), 4.03 (2 multiplets, 2H), 2.43 (s, 3H), 0.98 (m, 3H).

Example 217

Preparation of 4-Bromo-5-(2-chlorobenzoylamino)-1H-pyrazole-3-carboxylic acid indan-2-ylamide

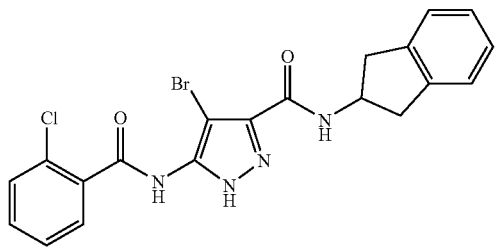

The pyrazole acid, prepared as described in Procedure 8, was coupled to 2-aminoindane hydrochloride (Aldrich, A5,952-2) using the method of Procedure 10.

MS+=459.0

$^1$H-NMR (DMSO-d6) δ 8.36 (d, J=7.2 Hz, 1H), 7.55-7.42 (m, 4H), 7.21-7.14 (m, 4H), 4.67 (m, 1H), 3.20 (dd, J=15.6, 7.6 Hz, 2H), 2.95 (dd, J=15.5, 6.9 Hz, 2H).

Example 218

Preparation of 4-Bromo-5-(2-chlorobenzoylamino)-1-methyl-1H-pyrazole-3-carboxylic acid [2-(3,4,5,6-tetrahydro-2H-[1,4']bipyridin-4-yl)ethyl]amide

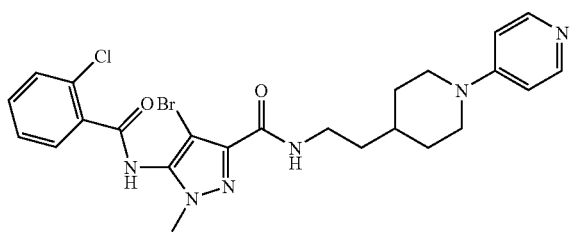

The pyrazole acid was prepared by coupling methyl ester 85 (General Procedure 26) with 2-chlorobenzoyl chloride (21), followed by hydrolysis and bromination as shown in General Procedure 8. General Procedure 14 was used to prepare the appropriate amine. Coupling of the pyrazole acid and the amine was accomplished using General Procedure 3.

MS+=545.1

$^1$H-NMR (DMSO-d6) δ 13.41 (bs, 1H), 10.74 (s, 1H), 8.27 (m, 1H), 8.17 (t, J=6.0 Hz, 2H), 7.19-7.67 (m, 3H), 7.18 (d, J=9.0 Hz, 2H), 4.22 (d, J=15.0 Hz, 2H), 3.81 (s, 3H), 3.26 (m, 2H), 3.12 (t, J=12.0 Hz, 2H), 1.87 (d, J=12.0 Hz, 2H), 1.70 (m, 1H), 1.47 (m, 2H), 1.14 (m, 2H).

Example 219

Preparation of 5-(2-Chlorobenzoylamino)-1-methyl-1H-pyrazole-3-carboxylic acid (2-oxo-5-phenyl-2,3-dihydro-1H-benzo[e][1,4]diazepin-3-yl)amide

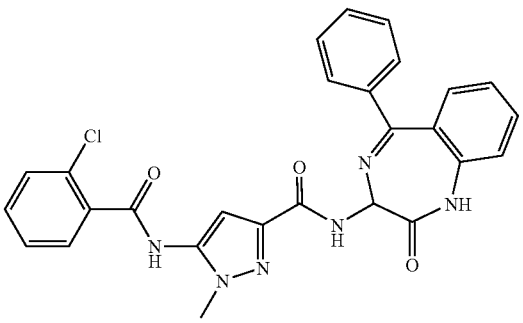

The pyrazole acid was prepared by coupling methyl ester 85 (General Procedure 26) with 2-chlorobenzoyl chloride (21) and hydrolysis as shown in General Procedure 8. The amine was prepared using General Procedure 20. The final coupling was accomplished using General Procedure 10.

MS+=513.1

$^1$H-NMR (DMSO-d6) δ 11.08 (s, 1H), 10.86 (s, 1H), 8.51 (d, J=9.0 Hz, 1H), 7.43-7.68 (m, 10H), 7.32 (m 3H), 6.81 (s, 1H), 5.38 (d, J=6.0 Hz, 1H), 3.88 (s, 3H).

Example 220

Preparation of 3-(2-Chlorobenzoylamino)-1-methyl-1H-pyrazole-5-carboxylic acid (2-oxo-5-phenyl-2,3-dihydro-1H-benzo[e][1,4]diazepin-3-yl)amide

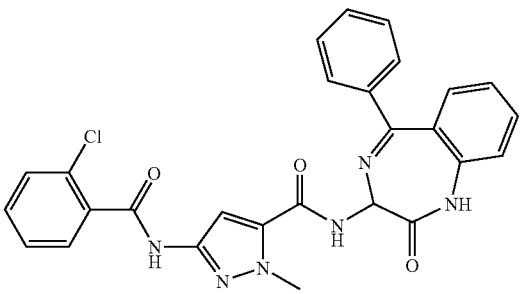

The pyrazole acid was prepared by coupling methyl ester 86 (General Procedure 26) with 2-chlorobenzoyl chloride (21) and hydrolysis as shown in General Procedure 8. The amine was prepared using General Procedure 20. The final coupling was accomplished using General Procedure 10.

MS+=513.1

$^1$H-NMR (CDCl$_3$) δ 9.66 (s, 1H), 9.12 (s, 1H), 8.33 (d, J=8.1 Hz, 1H), 7.72 (m, 1H), 7.65 (s, 1H), 7.35-7.57 (m, 1H), 7.27 (m, 1H), 7.18 (m, 1H), 5.71 (d, J=7.80 Hz, 1H), 3.93 (s, 3H).

Example 221

Preparation of 5-(2-Chlorobenzoylamino)-1-methyl-1H-pyrazole-3-carboxylic acid [2-(3,4,5,6-tetrahydro-2H-[1,4']bipyridin-4-yl)ethyl]amide

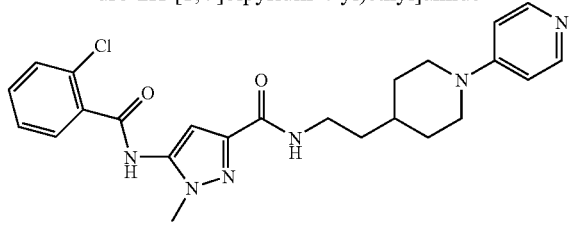

Prepared by coupling methyl ester 85 (General Procedure 26) with 2-chlorobenzoyl chloride (21) and hydrolysis as shown in General Procedure 8. General Procedure 14 was used to prepare the appropriate amine. Coupling of the pyrazole acid and the amine was accomplished using General Procedure 3.

MS+=467.2

$^1$H-NMR (CD$_3$OD) δ 8.05 (dd, J=1.2, 5.4 Hz, 2H), 7.63 (m, 1H), 7.41-7.7.55 (m, 3H), 6.81 (m, 3H), 3.98 (m, 2H), 3.87 (s, 3H), 3.43 (m, 2H), 2.88 (m, 2H), 1.86 (m, 2H), 1.57 (m, 3H), 1.26 (m, 2H).

Example 222

Preparation of 4-bromo-5-(2-chlorobenzoylamino)-1H-pyrazole-3-carboxylic acid [2-(N-(2,2,2-trichloroethoxycarbonyl)piperidine-4-yl)eth-1-yl]amide

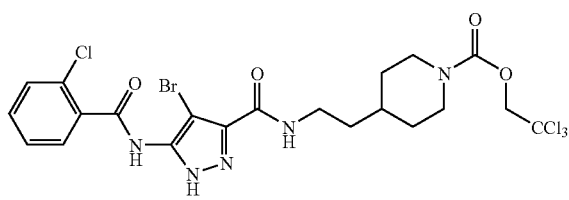

General Procedure 8 was used to synthesize the pyrazole acid for the title compound. The amine was prepared using as shown for compound 185 in General Procedure 30 using 4-(2-tert-butoxycarbonylaminoethyl) piperidine and 2,2,2-trichloroethyl chloroformate. Coupling of the pyrazole acid and the amine was accomplished using General Procedure 3.

MS+=627.9

$^1$H-NMR (CDCl$_3$) δ 12.40 (bs, 1H), 9.05 (s, 1H), 7.99 (d, J=7.5 Hz, 1H), 7.55 (m, 2H), 7.49 (m, 1H), 7.27 (m, 1H), 5.31 (s, 2H), 4.75 (m, 2H), 4.16 (m, 2H), 3.50 (m, 2H), 2.82 (m, 2H), 1.76 (m, 2H), 1.58 (m, 1H), 1.20 (m, 2H).

Example 223

Preparation of 3-(2-Chlorobenzoylamino)-1-methyl-1H-pyrazole-5-carboxylic acid [2-(3,4,5,6-tetrahydro-2H-[1,4']bipyridin-4-yl)ethyl]amide

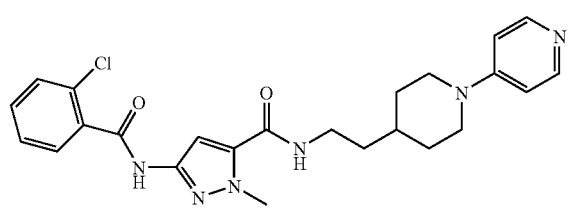

The pyrazole acid was prepared by coupling methyl ester 86 (General Procedure 26) with 2-chlorobenzoyl chloride (21) and hydrolysis as shown in General Procedure 8. General Procedure 14 was used to prepare the appropriate amine. Coupling of the pyrazole acid and the amine was accomplished using General Procedure 3.

MS+=467.2

$^1$H-NMR (DMSO-d6) δ 11.08 (s, 1H), 8.60 (s, 1H), 8.10 (m, 2H), 7.38-7.51 (m, 4H), 7.28 (s, 1H), 6.79 (, 2H), 3.98 (s, 3H), 3.93 (m, 2H), 3.30 (m, 2H), 2.78 (m, 2H), 1.76 (m, 2H), 1.57 (m, 1H), 1.45 (m, 2H), 1.14 (m, 2H).

Example 224

Preparation of 4-Bromo-5-(2-chlorobenzoylamino)-1H-pyrazole-3-carboxylic acid {2-[1-(1H-benzoimidazol-2-yl)-piperidin-4-yl]ethyl}amide

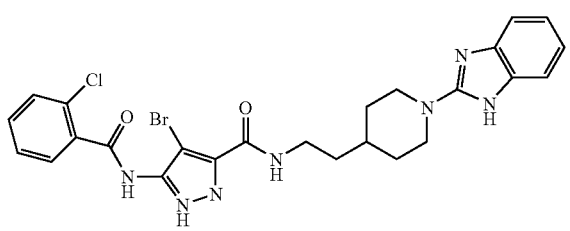

General Procedure 8 was used to synthesize the pyrazole acid for the title compound. The amine was as shown for compound 35 in General Procedure 14 using 4-(2-tert-butoxycarbonylaminoethyl) piperidine and 2-chlorobenzimidazole (Aldrich, 59,227-7). Coupling of the pyrazole acid and the amine was accomplished using General Procedure 3.

MS+=570.1

$^1$H-NMR (DMSO-d6) δ 13.84 (s, 1H), 11.25 (s, 1H), 12.40 (s, 1H), 8.17 (s, 1H), 7.47-7.58 (m, 4H), 7.14 (m, 2H), 6.88 (m, 2H), 4.07 (m, 2H), 3.33 (m, 2H), 2.90 (m, 2H), 1.78 (m, 2H), 1.49 (m, 3H), 1.17 (m, 2H).

Example 225

Preparation of 4-Bromo-5-(2-chlorobenzoylamino)-2H-pyrazole-3-carboxylic acid {2-[4-(1H-benzoimidazol-2-yl)-phenyl]ethyl}amide

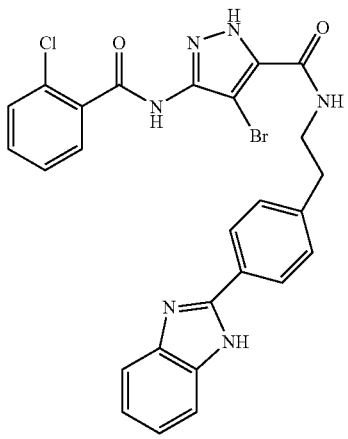

239

The title compound was prepared as shown in General Procedure 10 using pyrazole acid 7 amine 169 (shown in General Procedure 34) followed by formation of the amidine as shown in General Procedure 33.

MS+=563.0

$^1$H-NMR (CD$_3$OD) δ 8.08 (d, J=8.4 Hz, 2H), 7.83-7.78 (m, 2H), 7.69-7.43 (m, 8H), 3.73 (t, J=6.6 Hz, 2H), 3.12 (t, J=6.9 Hz, 2H).

Example 226

Preparation of 5-(2-Chlorobenzoylamino)-4-methyl-1H-pyrazole-3-carboxylic acid (2-oxo-5-phenyl-2,3-dihydro-1H-benzo[e][1,4]diazepin-3-yl)amide

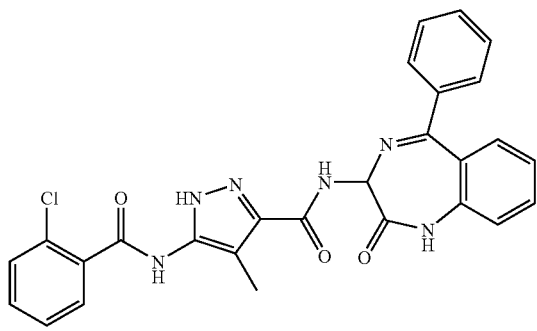

The pyrazole acid was prepared using General Procedure 18 and the amine was prepared using General procedure 20. The final coupling was accomplished using General Procedure 10.

MS+=513.0

Example 227

Preparation of 4-Bromo-5-(2-chlorobenzoylamino)-1H-pyrazole-3-carboxylic acid [1-(pyridine-4-carbonyl)-piperidin-4-yl]amide

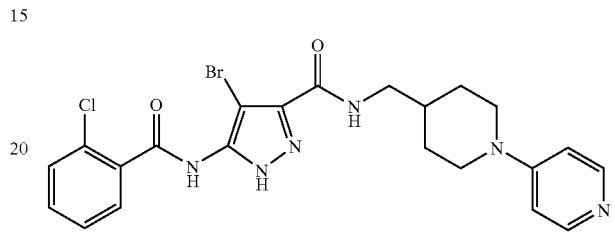

General Procedure 8 was used to synthesize the pyrazole acid for the title compound. The amine was prepared as shown for compound 22 in General Procedure 8 using compound 183 (shown in General Procedure 30) and isonicotinoyl chloride hydrochloride (Aldrich, 22,875-3). Coupling of the pyrazole acid and the amine was accomplished using General Procedure 3.

MS+=531.0

$^1$H-NMR (DMSO-d6) δ 8.66 (d, J=5.5 Hz, 2H), 8.07 (d, J=7.7 Hz, 1H), 7.51 (m, 3H), 7.36 (d, J=6.0 Hz, 2H), 4.36 (m, 1H), 4.03 (m, 1H), 3.47 (m, 1H), 3.22 (m, 1H), 2,99 (m, 1H), 1.87 (m, 1H), 1.73 (m, 1H), 1.57 (m, 2H).

Example 228

Preparation of 4-Bromo-5-(2-chlorobenzoylamino)-1H-pyrazole-3-carboxylic acid (3,4,5,6-tetrahydro-2H-[1,4']bipyridin-4-ylmethyl)amide

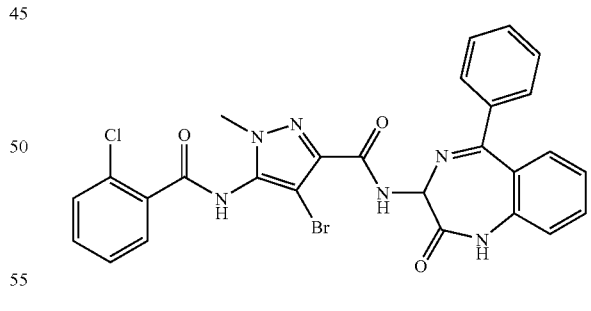

General Procedure 8 was used to synthesize the pyrazole acid for the title compound. General Procedure 14 was used to prepare the appropriate amine. Coupling of the pyrazole acid and the amine was accomplished using General Procedure 3.

MS+=517.0

$^1$H-NMR (CD$_3$OD) δ 8.07 (d, J=6.7 Hz, 2H), 7.63 (d, J=7.5 Hz, 1H), 7.55-7.42 (m, 3H), 7.14 (d, J=6.8 Hz, 2H), 4.29 (d, J=13.2 Hz, 2H), 3.33 (d, J=7.7 Hz, 2H), 3.23 (m, 2H), 2.09 (m, 1H), 1.98 (d, J=13.2 Hz, 2H), 1.36 (m, 2H).

Example 229

Preparation of 4-Bromo-5-(2-chlorobenzoylamino)-1-methyl-1H-pyrazole-3-carboxylic acid (2-oxo-5-phenyl-2,3-dihydro-1H-benzo[e][1,4]diazepin-3-yl)amide The pyrazole acid was prepared by coupling methyl ester 85 (General Procedure 26) with 2-chlorobenzoyl chloride (21), followed by hydrolysis and bromination as shown in General Procedure 8. The amine was prepared using General Procedure 20. The final coupling was accomplished using General Procedure 10.

MS+=593.0

$^1$H-NMR (DMSO-d6) δ 11.09 (s, 1H), 10.78 (s, 1H), 8.52 (d, J=6.0 Hz, 1H), 7.40-7.69 (m, 10H), 7.25-7.38 (m, 3H), 5.37 (d, J=6.0 Hz, 1H), 3.91 (s, 3H).

Example 230

Preparation of (R)-4-Bromo-5-(2-chloro-benzoylamino)-1H-pyrazole-3-carboxylic acid (5-methyl-2-oxo-2,3,4,5-tetrahydro-1H-benzo[b][1,4]diazepin-3-yl)amide

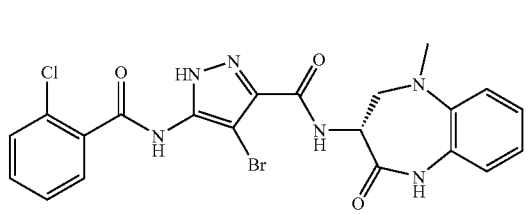

General Procedure 8 was used to synthesize the pyrazole acid for the title compound. The amine was prepared using methods well known in the art and described in General Procedure 38. Coupling of the pyrazole acid and the amine was accomplished using General Procedure 3.

MS+=517.0

$^1$H-NMR (CD$_3$OD) δ 7.66 (m, 4H), 6.90 (m, 4H), 5.17 (m, 1H), 3.74 (m, 2H), 3.15 (two s, 3H).

Example 231

Synthesis of (R)-4-Bromo-5-(2-chloro-benzoylamino)-1H-pyrazole-3-carboxylic acid (1-cyclopropylmethyl-5-methyl-2-oxo-2,3,4,5-tetrahydro-1H-benzo[b][1,4]diazepin-3-yl)amide

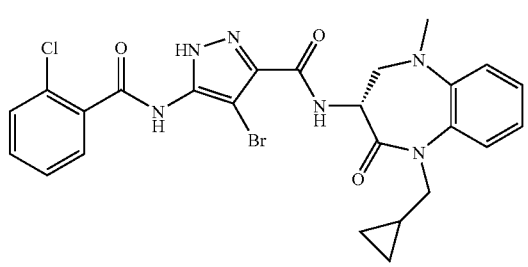

General Procedure 8 was used to synthesize the pyrazole acid for the title compound. The amine was prepared using methods well known in the art and described in General Procedure 38. Coupling of the pyrazole acid and the amine was accomplished using General Procedure 3.

MS+=571.1

$^1$H-NMR (CDCl$_3$) δ 9.04 (m, 1H), 8.00 (m, 1H), 7.48 (m, 4H), 6.99 (m, 4H), 5.42 (m, 1H), 3.71 (m, 2H), 3.37 (s, 3H), 0.86 (m, 3H), 0.39 (m, 2H), 0.26 (m, 1H), 0.06(m, 1H).

Example 232

Preparation of 5-(2-chlorobenzoylamino)-1H-pyrazole-3-carboxylic acid {2-[4-(4,5-dihydro-1H-imidazol-2-yl)-phenyl]ethyl}amide

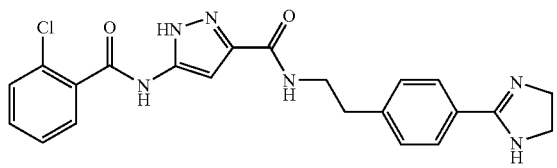

The title compound was prepared as shown in General Procedure 10 using pyrazole acid 23 and amine 169 (shown in General Procedure 34) followed by formation of the amidine using ethylene diamine as shown in General Procedure 33.

MS+=437.1

$^1$H-NMR (DMSO-d6) δ 7.87 (d, J=8.1 Hz, 2H), 7.59 (m, 4H), 7.46 (d, J=9.5 Hz, 2H), 3.61 (m, 2H), 3.43 (m, 4H), 3.00 (m, 2H).

Example 233

Preparation of 4-Bromo-5-(2-chlorobenzoylamino)-1H-pyrazole-3-carboxylic acid {2-[3-methoxy-4-hydroxyphenyl]ethyl}amide

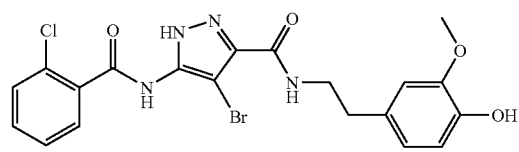

General Procedure 8 was used to synthesize the pyrazole acid for the title compound. The amine was purchased (Aldrich: 16,431-1). The final coupling was accomplished using General Procedure 11.

MS+=493.0

$^1$H-NMR (DMSO-d6) δ 13.85 (br, 1H), 8.72 (s, 1H), 7.51 (m, 4H), 6.78 (s, 1H), 6.64 (m, 2H), 3.73 (s, 3H), 3.41 (m, 2H), 2.71 (m, 2H)

Example 234

Preparation of (R)-4-Bromo-5-(2-fluoro-benzoylamino)-1H-pyrazole-3-carboxylic acid (1,5-dimethyl-2-oxo-2,3,4,5-tetrahydro-1H-benzo[b][1,4]diazepin-3-yl)amide

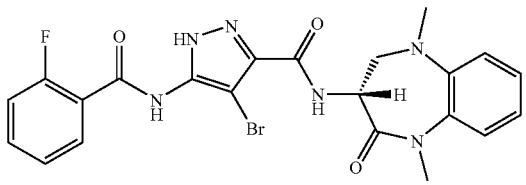

The pyrazole acid was prepared as described for compound 22 using amine 20 and 2-fluorobenzoyl chloride (Aldrich, 12,084-7) followed by bromination as shown in General Procedure 8. The amine was prepared using General Procedure 27. Coupling of the pyrazole acid and the amine was accomplished using General Procedure 3.

MS+=515.1

$^1$H-NMR (CDCl$_3$) δ 9.06 (m, 1H), 8.27 (m, 1H), 7.60 (m, 1H), 7.35 (m, 1H), 7.21 (m, 2H), 6.93 (m, 4H), 5.43 (m, 1H), 3.81 (m, 2H), 3.38 (s, 3H), 3.34 (s, 3H).

Example 235

Preparation of 5-(2-chloro-benzoylamino)-1H-pyrazole-3-carboxylic acid [2-(3,4,5,6-tetrahydro-2H-[1,4']bipyridin-4-yl)methyl]amide

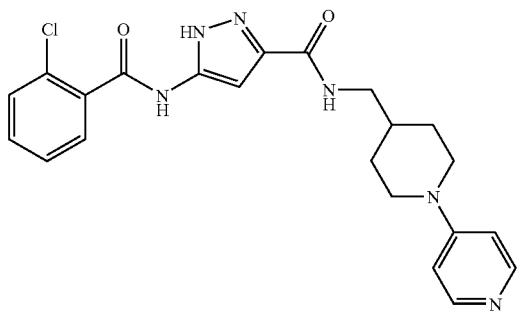

General Procedure 8 was used to synthesize the pyrazole acid for the title compound. General Procedure 14 was used to prepare the appropriate amine. Coupling of the pyrazole acid and the amine was accomplished using General Procedure 3.

MS+=439.1

$^1$H-NMR (CD$_3$OD) δ 8.21 (d, J=6.9 Hz, 2H), 7.65 (m, 4H), 7.29 (d, J=7.2 Hz, 2H), 4.43 (m, 2H), 3.40 (m, 4H), 2.23 (m, 1H), 2.12 (m, 2H), 1.49 (m, 2H).

Example 236

Preparation of 4-bromo-5-(2-chloro-benzoylamino)-1H-pyrazole-3-carboxylic acid [1-benzyloxycarbonyl-5-oxo-[1,4]diazepin-6-yl

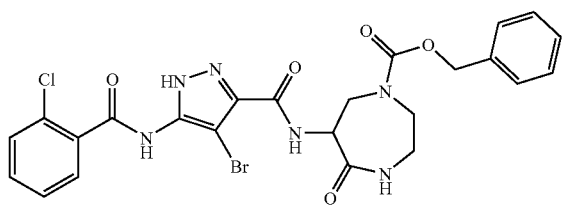

General Procedure 8 was used to synthesize the pyrazole acid for the title compound. The amine was commercially available (Astatech, 46012). Coupling of the pyrazole acid and the amine was accomplished using General Procedure 10.

MS+=589.0

$^1$H-NMR (CD$_3$OD) δ 7.64 (m, 1H), 7.44 (m, 7H), 5.18 (s, 2H), 4.82 (m, 1H), 4.43 (m, 1H), 4.15 (m, 1H), 3.49 (m, 1H), 3.43 (m, 1H), 3.11 (m, 2H).

Example 237

Preparation of 4-Bromo-5-(2-chloro-benzoylamino)-1H-pyrazole-3-carboxylic acid [2-(1'-methyl-[1,4']bipiperidin-4-yl)-methyl]amide

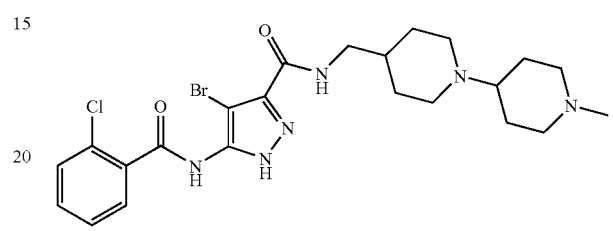

General Procedure 8 was used to synthesize the pyrazole acid for the title compound. The amine was prepared using methods well known in the art and described in General Procedure 35. Coupling of the pyrazole acid and the amine was accomplished using General Procedure 3.

MS+=537.1

$^1$H-NMR (CD$_3$OD) δ 8.37 (br, 1H), 7.64 (m, 1H), 7.56-7.43 (m, 3H), 3.72-3.50 (m, 5H), 3.35 (m, 2H), 3.11 (m, 4H), 2.91 (s, 3H), 2.41 (m, 2H), 2.14-1.94 (m, 5H), 1.61 (m, 2H).

Example 238

Preparation of 4-Bromo-5-(2-fluoro-benzoylamino)-1H-pyrazole-3-carboxylic acid [2-(3,4,5,6-tetrahydro-2H-[1,4']bipyridin-4-yl)methyl]amide

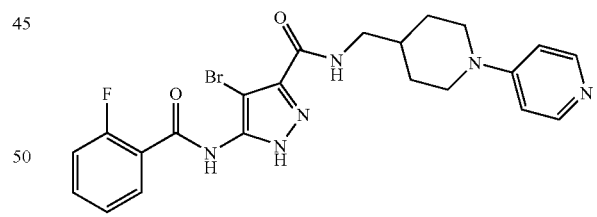

The pyrazole acid was prepared as described for compound 22 using compound 20 and 2-fluorobenzoyl chloride (Aldrich, 12,084-7) followed by hydrolysis and bromination as shown in General Procedure 8. General Procedure 14 was used to prepare the appropriate amine. Coupling of the pyrazole acid and the amine was accomplished using General Procedure 3.

MS+=501.1

$^1$H-NMR (CD$_3$OD) δ 8.09 (d, J=7.7 Hz, 2H), 7.90 (m, 1H), 7.64 (m, 1H), 7.35 (m, 2H), 7.17 (d, J=7.7 Hz, 2H), 4.30 (d, J=13.6 Hz, 2H), 3.35 (d, J=6.7 Hz, 2H), 3.25 (m, 2H), 2.11 (m, 1H), 2.00 (d, J=13.5 Hz, 2H), 1.38 (m, 2H).

Example 239

Preparation of 4-Bromo-5-(2-chlorobenzoylamino)-1H-pyrazole-3-carboxylic acid (2-(4-methylpiperidinyl)ethyl)amide

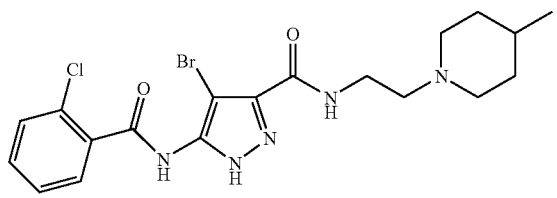

General Procedure 8 was used to synthesize the pyrazole acid for the title compound. The amine was purchased (TimTec, Inc.: OVS1009601) and the final coupling was accomplished using General Procedure 10.
MS+=468.0
$^1$H-NMR (CD$_3$OD) δ 7.66 (d, J=6.9 Hz, 1H), 7.56-7.43 (m, 3H), 3.55 (t, J=6.5 Hz, 2H), 3.00 (d, J=11.1, Hz, 2H), 2.62 (t, J=6.5 Hz, 2H), 2.12 (t, J=11.2 Hz, 2H), 1.68 (d, J=12.3 Hz, 2H), 1.42 (m, 1H), 1.29 (m, 2H), 0.96 (d, J=6.2 Hz, 3H).

Example 240

Preparation of 1-methyl-4-bromo-5-(2-chloro-benzoylamino)-1H-pyrazole-3-carboxylic acid [2-(3,4,5,6-tetrahydro-2H-[1,4']bipyridin-4-yl)methyl]amide

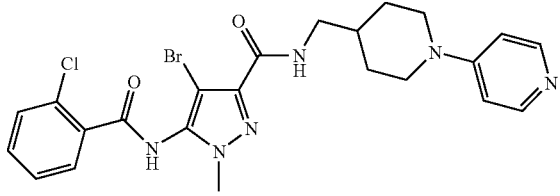

The pyrazole acid was prepared by coupling methyl ester 85 (General Procedure 26) with 2-chlorobenzoyl chloride (21), followed by hydrolysis and bromination as shown in General Procedure 8. General Procedure 14 was used to prepare the appropriate amine. Coupling of the pyrazole acid and the amine was accomplished using General Procedure 3.
MS+=531.1
$^1$H-NMR (DMSO-d6) δ 10.72 (bs, 1H), 8.29 (t, J=5.7 Hz, 1H), 8.10 (d, J=4.5 Hz, 2H), 7.47-7.66 (m, 4H), 6.78 (d, J=5.4 Hz, 2H), 3.90 (m, 2H), 3.81 (s, 3H), 3.11 (m, 2H), 2.78 (m, 2H), 1.81 (m, 1H), 1.70 (m, 2H), 1.14 (m, 2H).

Example 241

Preparation of 1-methyl-4-bromo-5-(2-fluoro-benzoylamino)-1H-pyrazole-3-carboxylic acid [2-(3,4,5,6-tetrahydro-2H-[1,4']bipyridin-4-yl)ethyl]amide

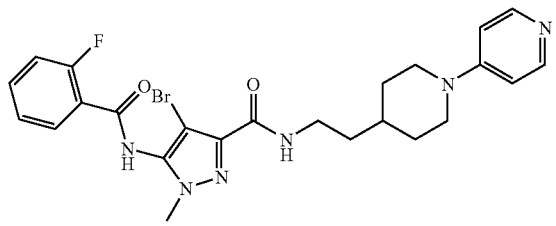

The pyrazole acid was prepared by coupling methyl ester 85 (General Procedure 26) with 2-fluorobenzoyl chloride (Aldrich, 12,084-7), followed by hydrolysis and bromination as shown in General Procedure 8. General Procedure 14 was used to prepare the appropriate amine. Coupling of the pyrazole acid and the amine was accomplished using General Procedure 3.
MS+=529.1
$^1$H-NMR (CD$_3$OD) δ 8.06 (d, J=7.8 Hz, 2H), 7.86 (m, 1H), 7.65 (m, 1H), 7.32 (m, 2H), 7.14 (d, J=7.5 Hz, 2H), 4.27 (d, J=13.5 Hz, 2H), 3.86 (s, 3H), 3.45 (m, 2H), 3.22 (m, 2H), 2.01 (m, 2H), 1.85 (m, 1H), 1.61 (m, 2H), 1.31 (m, 2H).

Example 242

Preparation of 5-(2-chlorobenzoylamino)-1H-pyrazole-3-carboxylic acid [2-(pyridin-4-yl)ethyl]amide

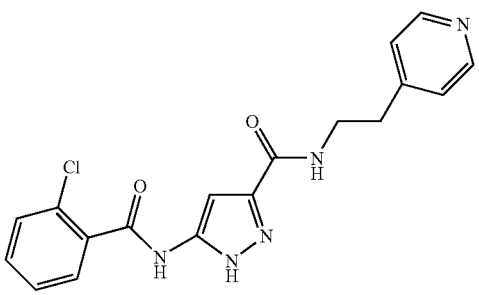

General Procedure 8 was used to synthesize the pyrazole acid for the title compound. The amine was purchased (TCI, A1264) and the coupling of the pyrazole acid and the amine was accomplished using General Procedure 3.
MS+=370.1
$^1$H-NMR (DMSO-d6) δ 13.15 (s, 1H), 11.06 (s, 1H), 8.67 (s, 1H), 8.45 (d, J=6.0 Hz, 2H), 7.45 (m, 4H), 7.26 (m, 3H), 3.51 (m, 2H), 2.86 (t, J=6.0 Hz, 2H).

Example 243

Preparation of 4-Bromo-5-(2-chlorobenzoylamino)-1H-pyrazole-3-carboxylic acid (2-[2-phenyl-1H-benzo[d]imidazol-5-yl]ethyl)amide

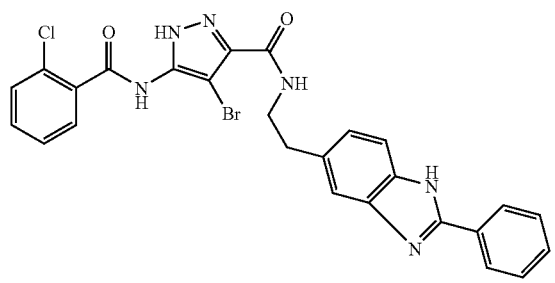

General Procedure 8 was used to synthesize the pyrazole acid for the title compound. The amine was prepared using methods well known in the art and described in General Procedure 31. The final coupling was accomplished using General Procedure 10.

MS+=564.0

$^1$H-NMR (CD$_3$OD) δ 8.05 (dd, J=8.1, 1.8 Hz, 2H), 7.61-7.42 (m, 9H), 7.21 (d, J=8.7 Hz, 1H), 3.67 (t, J=7.2 Hz, 2H), 3.04 (t, J=6.9 Hz, 2H).

Example 244

Preparation of 4-Bromo-5-(2-chlorobenzoylamino)-1H-pyrazole-3-carboxylic acid (5-(t-butoxycarbamoyl)aminopent-1-yl)amide

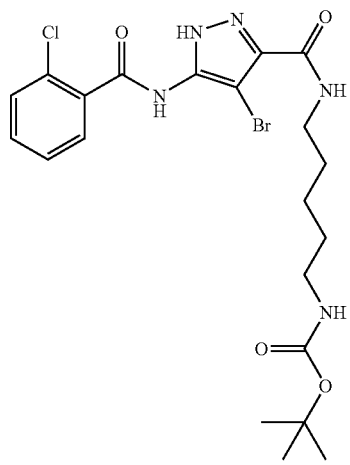

The pyrazole acid, prepared as described in Procedure 8, was coupled to N-Boc-cadaverine (Fluka, 15406) using the method of Procedure 1.

MS+=428.0

$^1$H-NMR (CD$_3$OD) δ 7.66 (dd, J=6.6, 1.8 Hz, 1H), 7.52-7.46 (m, 3H), 6.61 (bs, 1H), 3.40 (t, J=6.9 Hz, 2H), 3.33 (p, J=3.0 Hz, 2H), 3.09-3.04 (m, 2H), 1.70-1.59 (m, 2H), 1.56-1.49 (m, 2H), 1.44 (s, 9H).

Example 245

Preparation of 4-Bromo-5-(2-chlorobenzoylamino)-1H-pyrazole-3-carboxylic acid (5-aminopentyl)amide

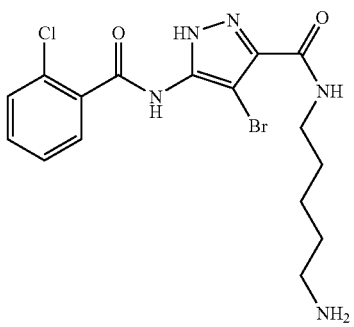

The pyrazole acid, prepared as described in Procedure 8, was coupled to N-Boc-cadaverine (Fluka, 15406) using the method of Procedure 1. Removal of the Boc-protecting group by treatment with TFA as shown for compound 33 in Procedure 13 afforded the title compound.

MS+=428.0

$^1$H-NMR (CD$_3$OD) δ 7.65 (d, J=7.8 Hz, 1H), 7.57-7.44 (m, 3H), 3.42 (t, J=6.9 Hz, 2H), 2.93 (t, J=7.5 Hz, 2H), 1.77-1.64 (m, 4H), 1.54-1.46 (m, 2H).

Example 246

Preparation of 4-methyl-5-(2-chlorobenzoylamino)-1H-pyrazole-3-carboxylic acid {2-[4-(4,5-dihydro-1H-imidazol-2-yl)-phenyl]ethyl}amide

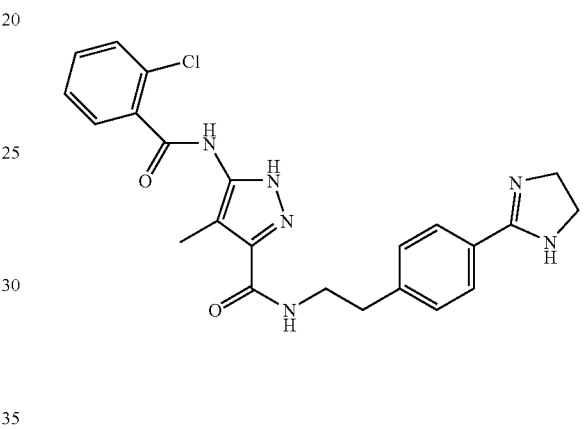

The title compound was prepared as shown in General Procedure 10 using pyrazole acid 51 amine 169 (shown in General Procedure 34) followed by formation of the amidine using ethylene diamine as shown in General Procedure 33.

MS+=451.1

$^1$H-NMR (CD$_3$OD) δ 7.79 (d, 2H, J=7.8 Hz), 7.55 (m, 6H), 3.65 (t, 2H, J=7.1 and 6.7 Hz), 3.04 (t, 2H, J=6.7 and 7.1 Hz), 2.19 (s, 3H).

Example 247

Preparation of 4-methyl-5-(2-chloro-benzoylamino)-1H-pyrazole-3-carboxylic acid [2-(3,4,5,6-tetrahydro-2H-[1,4']bipyridin-4-yl)-ethyl]amide

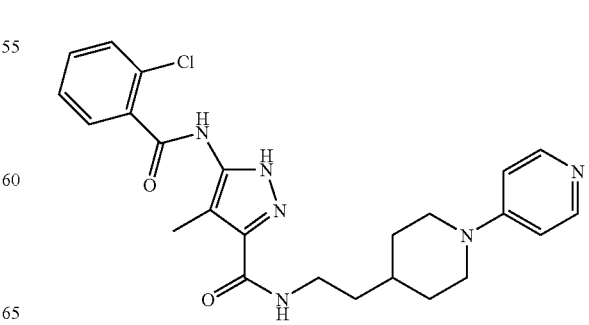

The pyrazole acid was prepared using General Procedure 18. General Procedure 14 was used to prepare the appropriate amine. Coupling of the pyrazole acid and the amine was accomplished using General Procedure 3.

MS+=467.1

$^1$H-NMR (CD$_3$OD) δ 8.06 (d, 2H, J=7.3 Hz), 7.62-7.42 (m, 6H), 7.14 (d, 2H, J=7.3 Hz), 4.27 (bd, 2H, J=13.4 Hz), 3.45 (m, 2H), 3.22 (t, 2H, J=12.5 Hz), 2.24 (s, 3H), 2.00 (bd, 2H, J=13.4 Hz), 1.85 (m, 1H), 1.61 (m, 2H), 1.31 (m, 2H).

Example 248

Preparation of 1-t-butyl-4-methyl-5-(2-chloro-benzoylamino)-1H-pyrazole-3-carboxylic acid [2-(3,4,5,6-tetrahydro-2H-[1,4']bipyridin-4-yl)-ethyl]amide

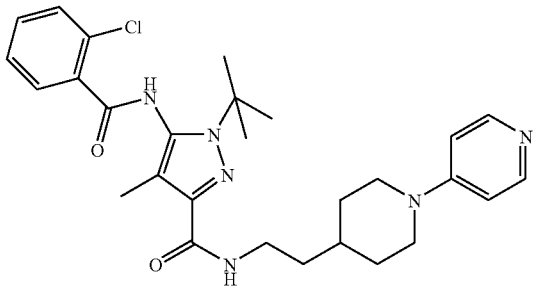

The pyrazole acid was prepared using General Procedure 18. General Procedure 14 was used to prepare the appropriate amine. Coupling of the pyrazole acid and the amine was accomplished using General Procedure 3.

MS+=523.2

$^1$H-NMR (CD$_3$OD) δ 8.06 (d, 2H, J=7.3 Hz), 7.62-7.42 (m, 6H), 7.14 (d, 2H, J=7.3 Hz), 4.27 (bd, 2H, J=13.4 Hz), 3.45 (m, 2H), 3.22 (t, 2H, J=12.5 Hz), 2.24 (s, 3H), 2.00 (bd, 2H, J=13.4 Hz), 1.85 (m, 1H), 1.69 (s, 3H), 1.61 (m, 2H), 1.31 (m, 2H).

The following compounds can be prepared using methods well known in the art and/or methods similar to those described herein or in U.S. Pat. No. 4,873,334.

Example 249

Preparation of 4-bromo-5-(2-chloro-benzoylamino)-1H-pyrazole-3-carboxylic acid [2-(4-(1,4,5,6-tetrahydropyrimidin-2-yl)phenyl)ethyl]amide

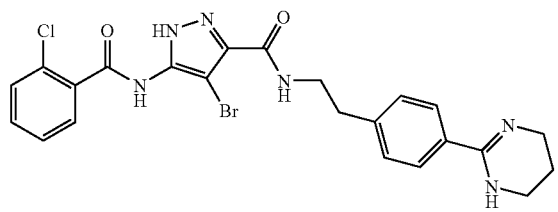

The pyrazole acid, prepared as described in Procedure 8, was coupled to compound 169 using the method of Procedure 10. Formation of the amidine as shown in Procedure 33 using propylene diamine afforded the title compound.

MS+=529.0

$^1$H-NMR (DMSO-d6) δ 9.84 (br, 1H), 8.34 (m, 1H), 7.57 (m, 8H), 3.57 (m, 6H), 2.97 (m, 2H), 2.08 (m, 2H).

Example 250

Preparation of 4-fluoro-5-(2-chloro-benzoylamino)-1H-pyrazole-3-carboxylic acid [2-(3,4,5,6-tetrahydro-2H-[1,4']bipyridin-4-yl)-ethyl]amide

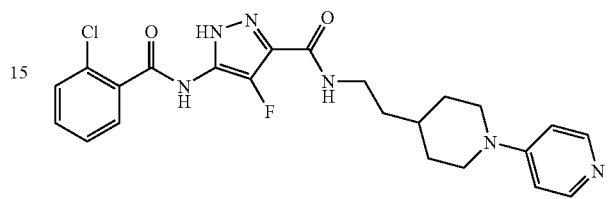

The pyrazole acid, prepared using compound 23 and SELECTFLUOR™ (Aldrich, 43,947-9) using a procedure similar to that described in Katoch-Rouse, R. et al., J. Med. Chem. 2003, 46, 642, was coupled to 2-(1-pyrimidin-2-yl-piperidin-4-yl)ethylamine (prepared as described in Procedure 14) using the method of Procedure 10.

MS+=471.1

$^1$H-NMR (DMSO-d6) δ 8.16 (d, J=7.2 Hz, 2H), 7.50 (m, 4H), 7.17 (d, J=6.9 Hz, 2H), 4.21 (d, J=13.8 Hz, 2H), 3.31 (m, 2H), 3.12 (t, J=12.9 Hz, 2H), 1.85 (d, J=12.3 Hz, 2H), 1.71 (m, 1H), 1.47 (m, 2H), 1.14 (m, 2H).

Example 251

Preparation of 1-(pyridin-2-yl)-4-methyl-5-(2-chloro-benzoylamino)-1H-pyrazole-3-carboxylic acid [2-(3,4,5,6-tetrahydro-2H-[1,4']bipyridin-4-yl)-ethyl]amide

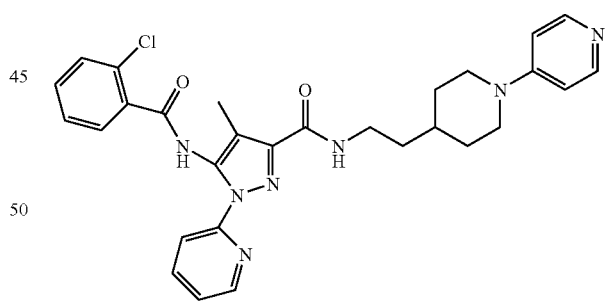

The pyrazole acid, prepared as described in Procedure 8 using 5-amino-4-methyl-1-pyridin-2-yl-1H-pyrazole-3-carboxylic acid ethyl ester (prepared as described in Procedure 41 using 3-cyano-3-methyl-2-oxopropanoic acid ethyl ester (U.S. Pat. No. 4,652,669) and 2-hydrazinopyridine dihydrochloride (Aldrich, H1,710-4)) in place of compound 20, was coupled to 2-(3,4,5,6-tetrahydro-2H-[1,4']bipyridin-4-yl) ethylamine (prepared as described in Procedure 14) using the method of Procedure 10.

MS+=544.2

$^1$H-NMR (DMSO-d6) δ 10.58 (s, 1H), 8.55 (d, J=6.0 Hz, 1H), 8.35 (m, 1H), 8.05 (m, 3H), 7.88 (d, J=9.0 Hz, 1H), 7.51

(m, 5H), 6.78 (d, J=6.0 Hz, 2H), 3.90 (m, 2H), 2.78 (m, 2H), 2.18 (s, 3H), 1.78 (m, 2H), 1.51 (m, 3H), 1.14 (m, 2H).

Example 252
Preparation of 4-bromo-5-(2-chloro-benzoylamino)-1H-pyrazole-3-carboxylic acid [4-oxo-[1,4]diazepin-5-yl]amide

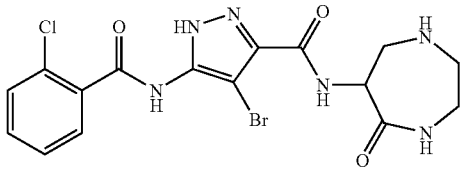

The compound of Example 236 was treated with HBr in AcOH using the method of Procedure 20 to afford the title compound.
MS+=454.9
$^1$H-NMR (CD$_3$OD) δ 7.63 (m, 1H), 7.48 (m, 3H), 5.07 (m, 1H), 3.64 (m, 4H), 3.19 (m, 2H).

Example 253
Preparation of 4-bromo-5-(2-chlorobenzoylamino)-1H-pyrazole-3-carboxylic acid (1-methyl-5-oxo-4-(2-(N,N-dimethylamino)ethyl)-2,3,4,5-tetrahydro-1H-benzo[b][1,4]diazepin-6-yl)amide

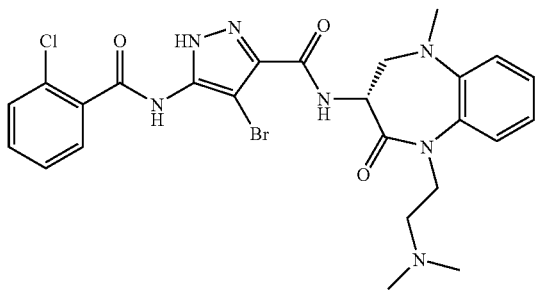

The pyrazole acid, prepared as described in Procedure 8, was coupled to [1-(2-dimethylaminoethyl)-5-methyl-2-oxo-2,3,4,5-tetrahydro-1H-benzo[b][1,4]diazepin-3-yl]carbamic acid tert-butyl ester (prepared as described for compound 139 in Procedure 38 using beta-dimethylaminoethyl bromide hydrobromide (Narchem, 2862-39-7)) using the method of Procedure 3.
MS+=588.0
$^1$H-NMR (CD$_3$OD) δ 7.54 (m, 4H), 7.20 (m, 4H), 5.18 (m, 1H), 4.54 (m, 1H), 3.36 (m, 1H), 4.06 (m, 2H), 3.76 (m, 2H), 3.37 (s, 3H), 3.00 (s, 3H), 2.94 (s, 3H).

Example 254
Preparation of 4-bromo-5-(2-chloro-benzoylamino)-1H-pyrazole-3-carboxylic acid [4-methyl-5-oxo-1-(benzyloxycarbonyl)-[1,4]diazepin-6-yl]amide

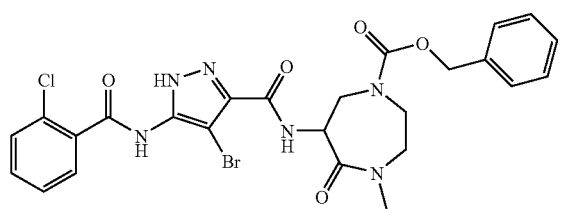

The pyrazole acid, prepared as described in Procedure 8, was coupled to 6-amino-4-methyl-5-oxo-[1,4]diazepane-1-carboxylic acid benzyl ester (prepared from 6-tert-butoxycarbonylamino-4-methyl-5-oxo-[1,4]diazepane-1-carboxylic acid benzyl ester (Astatech, 46012) which was Boc protected as shown for compound 31 in Procedure 13 followed by methylation as shown for compound 16 in Procedure 7) using the method of Procedure 3.
MS+=603.0
$^1$H-NMR (CD$_3$OD) δ 7.49 (m, 9H), 5.14 (s, 2H), 4.25 (m, 1H), 3.84 (m, 2H), 3.42 (m, 2H), 3.25 (m, 2H), 3.06 (m, 3H).

EXAMPLE 255

Preparation of 4-bromo-5-(3-chloro-pyridin-4-ylcarbonyl)amino)-1H-pyrazole-3-carboxylic acid[2-(3,4,5,6-tetrahydro-2H-[1,4']bipyridin-4-yl)-ethyl]amide

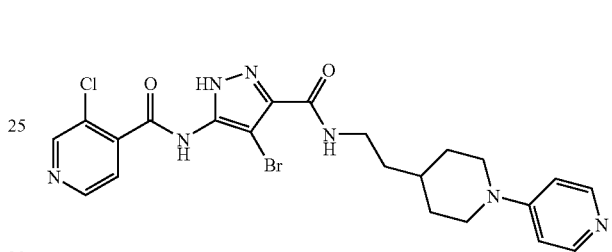

The pyrazole acid, prepared as described in Procedure 8 using 3-chloroisonicotinic acid (Aldrich, 63,341-0) instead of compound 21, was coupled to 2-(3,4,5,6-tetrahydro-2H-[1,4']bipyridin-4-yl)-ethylamine (prepared as described in Procedure 14) using the method of Procedure 10.
MS+=532.0
$^1$H-NMR (DMSO-d6) δ 8.78 (br, 1H), 8.67 (m, 1H), 8.12 (m, 3H), 7.59 (m, 1H), 6.80 (m, 2H), 3.90 (m, 2H), 3.31 (m, 2H), 2.79 (m, 2H), 1.76 (m, 2H), 1.59 (m, 1H), 1.46 (m, 2H), 1.10 (m, 2H).

EXAMPLE 256

Preparation of 4-bromo-5-(2-chloro-benzoylamino)-1H-pyrazole-3-carboxylic acid [4-methyl-5-oxo-[1,4]diazepin-6-yl]amide

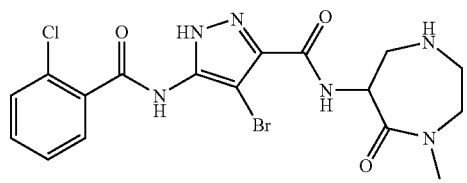

The compound of Example 255 was treated with HBr in AcOH using the method of Procedure 20 to afford the title compound.
MS+=469.0
$^1$H-NMR (CD$_3$OD) δ 7.64 (m, 1H), 7.49 (m, 3H), 5.15 (m, 1H), 4.10 (m, 1H), 3.59 (m, 3H), 3.19 (m, 2H), 3.12 (s, 3H).

EXAMPLE 257
Preparation of (R)-4-Bromo-5-(2-chloro-benzoylamino)-1H-pyrazole-3-carboxylic acid (1-pyridin-4-yl)azepan-3-yl)-amide

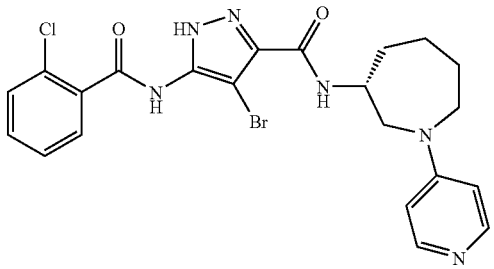

The pyrazole acid, prepared as described in Procedure 8, was coupled to (1-pyridin-4-yl-azepan-3-yl)carbamic acid tert-butyl ester (prepared by cyclization of Boc-D-Lys-OH (Bachem, A-2705) using the method of Procedure 23 followed by reduction using the method of Procedure 2 and arylation as shown for compound 35 in Procedure 14) using the method of Procedure 10.
MS+=517.0
¹H-NMR (DMSO-d6) δ 8.28 (m, 2H), 7.52 (m,4H), 7.36 (m, 1H), 7.10 (m, 1H), 3.95 (m, 3H), 3.51 (m, 2H), 3.28 (m, 2H), 1.84 (m, 3H), 1.24 (m, 1H).

EXAMPLE 258

Preparation of 4-bromo-5-(2-chlorobenzoylamino)-1H-pyrazole-3-carboxylic acid (2,3,4,5-tetrahydro-1H-benzo[b]azepin-3-yl)amide

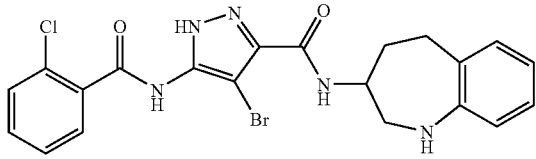

The pyrazole acid, prepared as described in Procedure 8, was coupled to 2,3,4,5-tetrahydro-1H-benzo[b]azepin-3-ylamine (prepared from 3-amino-1,3,4,5-tetrahydro-benzo[b]azepin-2-one (WO 9838177) using the method of Procedure 2) using the method of Procedure 10.
MS+=488.0
¹H-NMR (CDCl₃) δ 9.26 (br, 1H), 7.92 (m, 2H), 7.40 (m, 3H), 7.08 (m, 2H), 6.87 (m, 1H), 6.77 (d, J=7.7 Hz, 1H), 4.34 (m, 1H), 3.17 (m, 2H), 2.92 (m, 1H), 2.65 (m, 1H), 2.01 (m, 1H), 1.77 (m, 1H).

EXAMPLE 259
Preparation of 4-Bromo-5-(2-chloro-benzoylamino)-1H-pyrazole-3-carboxylic acid [6-(benzothiazol-2-yl)hex-1-yl]amide

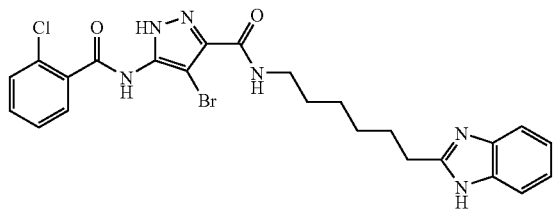

The pyrazole acid, prepared as described in Procedure 8, was coupled to 1H-benzimidazole-2-hexanamine (prepared by displacement of bromine from N-(6-bromohexyl)phthalimide (Alfa, B25128) using KCN in DMF followed by formation of the amidine as shown in Procedure 33 and treatment with hydrazine hydrate) using the method of Procedure 10.
MS+=543.0

¹H-NMR (DMSO-d6) δ 8.12 (br, 1H), 7.51 (m, 6H), 7.07 (m, 2H), 3.21 (m, 2H), 2.77 (m, 2H), 1.75 (m, 2H), 1.50 (m, 2H), 1.34 (m, 4H).

EXAMPLE 260

Preparation of (R)-5-(2-chloro-benzoylamino)-1-(phenyl)-pyrazole-3-carboxylic acid (2-oxo-azepan-3-yl)-amide

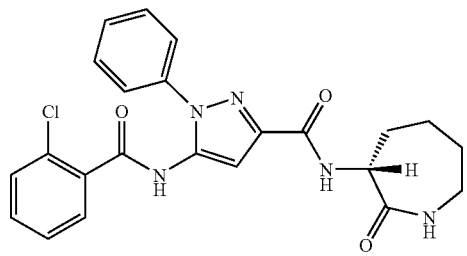

The pyrazole acid, prepared as described in Procedure 8 using compound 188 (Procedure 41) in place of compound 20, was coupled to (2-oxo-azepan-3-yl)carbamic acid tert-butyl ester (prepared as described in Martin G. Banwell and Kenneth J. McRae; *J. Org. Chem.* 2001, 66, 6768, which is incorporated herein by reference in its entirety) using the method of Procedure 3.
MS+=452.1

¹H-NMR (CD₃OD) δ 8.43 (m, 1H), 7.60 (m, 2H), 7.44 (m, 7H), 4.66 (m, 1H), 3.26 (m, 2H), 2.04 (m, 2H), 1.84 (m, 2H), 1.57 (m, 1H), 1.37 (m, 1H).

EXAMPLE 261

Preparation of 4-bromo-5-(2-chloro-benzoylamino)-1H-pyrazole-3-carboxylic acid [1,4-dimethyl-5-oxo-[1,4]diazepan-6-yl]amide

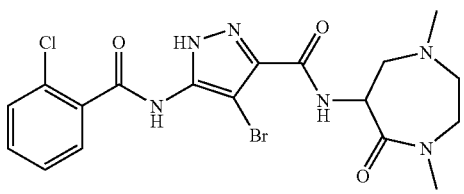

The pyrazole acid, prepared as described in Procedure 8, was coupled to (1,4-dimethyl-5-oxo-[1,4]diazepan-6-yl)-carbamic acid tert-butyl ester (prepared from 6-tert-butoxy-carbonylamino-4-methyl-5-oxo-[1,4]diazepane-1-carboxylic acid benzyl ester (Astatech, 46012) which was Boc protected as shown for compound 31 in Procedure 13 followed by methylation as shown for compound 16 in Procedure 7, deprotected as shown in Procedure 20 and finally methylated as for compound 16 in Procedure 7) using the method of Procedure 3.

MS+=483.0

¹H-NMR (DMSO-d6) δ 8.31 (br, 1H), 7.53 (m, 4H), 5.06 (m, 1H), 3.98 (m, 1H), 3.23 (m, 1H), 2.98 (m, 2H), 2.86 (m, 2H), 2.48 (s, 6H).

EXAMPLE 262

Preparation of 4-bromo-5-(2-chloro-benzoylamino)-1H-pyrazole-3-carboxylic acid [4-(4,5-dihydro-1H-imidazol-2-yl)benzyl]amide

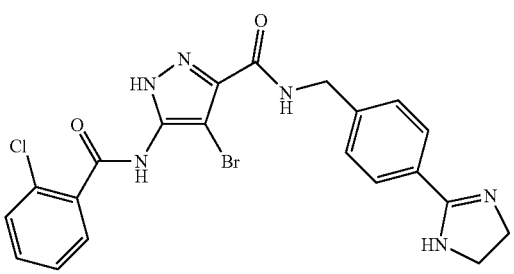

The pyrazole acid, prepared as described in Procedure 8, was coupled to 4-aminomethylbenzonitrile (Apin, 35480 c) using the method of Procedure 10. Amidine formation as described in Procedure 33 using ethylene diamine afforded the title compound.

MS+=501.0

¹H-NMR (DMSO-d6) δ 8.95 (m, 1H), 7.95 (m, 2H), 7.56 (m, 6H), 4.56 (m, 2H), 4.03 (s, 4H).

EXAMPLE 263

Preparation of 4-Bromo-5-(2-chloro-benzoylamino)-1H-pyrazole-3-carboxylic acid [5-(benzothiazol-2-yl)pent-1-yl]amide

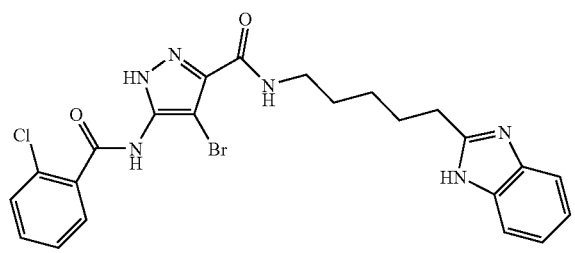

The pyrazole acid, prepared as described in Procedure 8, was coupled to 5-(1H-benzoimidazol-2-yl)pentylamine (Matrix Scientific, 10423) using the method of Procedure 10.

MS+=529.0

¹H-NMR (DMSO-d6) δ 7.75 (m, 2H), 7.53 (m, 6H), 3.25 (m, 2H), 3.11 (m, 2H), 1.88 (m, 2H), 1.58 (m, 2H), 1.40 (m, 2H).

EXAMPLE 264

Preparation of 4-Bromo-5-(2-chloro-benzoylamino)-1H-pyrazole-3-carboxylic acid [N -(benzothiazol-2-yl)piperidin-4-ylmethyl]amide

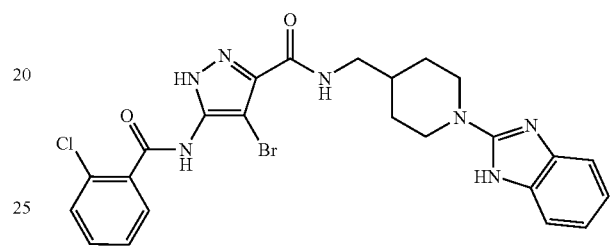

The pyrazole acid, prepared as described in Procedure 8, was coupled to [1-(1H-benzoimidazol-2-yl)-piperidin-4-yl-methyl]carbamic acid tert-butyl ester (prepared as shown for compound 35 in Procedure 14 using 2-chlorobenzimidazole (Aldrich, 59,227-7)) using the method of Procedure 3.

MS+=556.0

¹H-NMR (DMSO-d6) δ 12.86 (br, 1H), 8.31 (br, 1H), 7.50 (m, 4H), 7.38 (m, 2H), 7.25 (m, 2H), 3.98 (m, 4H), 3.26 (m, 2H), 1.87 (m, 3H), 1.35 (m, 2H).

EXAMPLE 265

Preparation of 4-bromo-5-(2-fluoro-benzoylamino)-1H-pyrazole-3-carboxylic acid [N -(pyridin-4-yl)piperidin-4-ylmethyl]amide

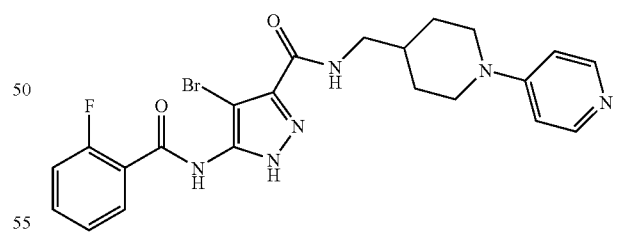

The pyrazole acid, prepared as described in Procedure 8 using 2-fluorobenzoyl chloride instead of compound 21, was coupled to 1-(4-pyridinyl)-4-piperidinemethanamine (prepared as described in Procedure 14) using the method of Procedure 10.

MS+=501.1

¹H-NMR (CD₃OD) δ 8.09 (d, J=7.7 Hz, 2H), 7.90 (m, 1H), 7.64 (m, 1H), 7.35 (m, 2H), 7.17 (d, J=7.7 Hz, 2H), 4.30 (d, J=0.6 Hz, 2H), 3.35 (d, J=6.7 (Hz, 2H), 3.25 (m, 2H), 2.11 (m, 1H), 2.00 (d, J=13.5 Hz, 2H), 1.38 (m, 2H).

EXAMPLE 266

Preparation of 4-bromo-5-(2-chloro-benzoylamino)-1H-pyrazole-3-carboxylic acid [2-(4-methyl-piperidin-1-yl)ethyl]amide

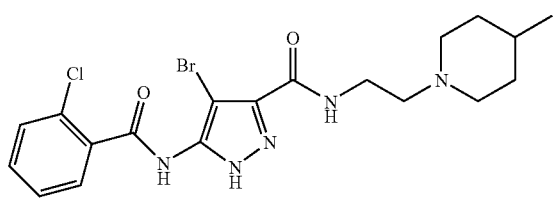

The pyrazole acid, prepared as described in Procedure 8, was coupled to 4-methyl-1-piperidineethanamine (TimTec, OVS1009601) using the method of Procedure 10.
MS+=468.0
$^1$H-NMR (CD$_3$OD) δ 7.66 (d, J=6.9 Hz, 1H), 7.56-7.43 (m, 3H), 3.55 (t, J=6.5 Hz, 2H), 3.00 (d, J=11.1 Hz, 2H), 2.62 (t, J=6.5 Hz, 2H), 2.12 (t, J=11.2 Hz, 2H), 1.68 (d, J=12.3 Hz, 2H), 1.42 (m, 1H), 1.29 (m, 2H), 0.96 (d, J=6.2 Hz, 3H).

EXAMPLE 267

Preparation of 4-bromo-5-(2-fluoro-benzoylamino)-1H-pyrazole-3-carboxylic acid [2-(4-(pyridin-4-yl)-piperazin-1-yl)ethyl]amide

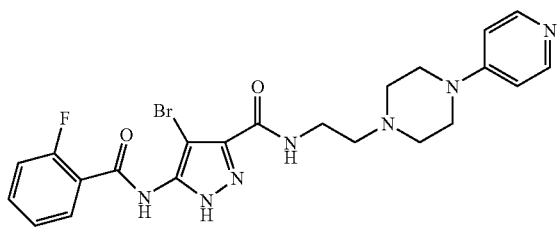

The pyrazole acid, prepared as described in Procedure 8 using 2-fluorobenzoyl chloride instead of compound 21, was coupled to 2-(4-pyridin-4-yl-piperazin-1-yl)ethylamine (CA 985683) using the method of Procedure 10.
MS+=516.0
$^1$H-NMR (CD$_3$OD) d 8.27 (d, J=7.3 Hz, 2H), 7.90 (m, 1H), 7.66 (m, 1H), 7.40-7.29 (m, 4H), 4.03 (br, 4H), 3.80 (m, 2H), 3.48 (br, 4H), 3.35 (m, 2H).

EXAMPLE 268

Preparation of 4-Bromo-5-(2-bromo-benzoylamino)-1H-pyrazole-3-carboxylic acid [N-(2-aminopyridin-6-yl)piperidin-4-ylmethyl]amide

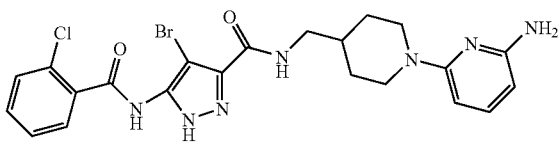

The pyrazole acid, prepared as described in Procedure 8, was coupled to (6'-Amino-3,4,5,6-tetrahydro-2H-[1,2']bipyridin-4-ylmethyl)carbamic acid tert-butyl ester (prepared as described in Procedure 40) using the method of Procedure 3.
MS+=532.0
$^1$H-NMR (CD$_3$OD) δ 8.28 (br, 1H), 7.63 (m, 2H), 7.56-7.42 (m, 3H), 6.22 (d, J=8.4 Hz, 1H), 6.10 (d, J=8.4 Hz, 1H), 3.97 (d, J=13.2 Hz, 2H), 3.33 (m, 2H), 3.11 (t, J=12.1 Hz, 2H), 1.94 (m, 3H), 1.40 (m, 2H).

EXAMPLE 269

Preparation of 5-(2-chloro-benzoylamino)-1H-pyrazole-3-carboxylic acid [2-(pyridine-4-yl)ethyl]amide

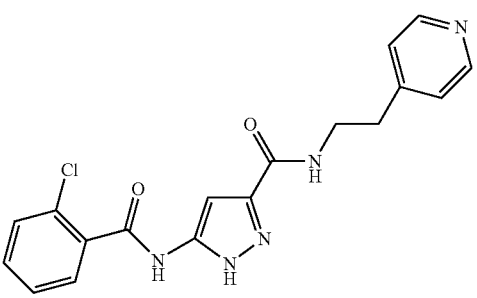

The pyrazole acid, prepared as described in Procedure 8, was coupled to 4-(2-aminoethyl)pyridine (TCI America, A1264) using the method of Procedure 10.
MS+=370.1
$^1$H-NMR (DMSO-d6) δ 13.15 (s, 1H), 11.06 (s, 1H), 8.67 (s, 1H), 8.45 (d, J=6.0 Hz, 2H), 7.39-7.54 (m, 4H), 7.26 (m, 3H), 3.51 (m, 2H), 2.86 (t, J=6.0 Hz, 2H).

EXAMPLE 270

Preparation of 4-bromo-5-(2-chloro-benzoylamino)-1H-pyrazole-3-carboxylic acid [2-(1-(4,5-dihydro-1H-imidazol-2-yl)piperidin-4-yl)-ethyl]amide

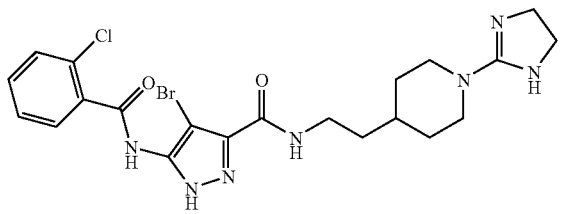

The pyrazole acid, prepared as described in Procedure 8, was coupled to {2-[1-(4,5-dihydro-1H-imidazol-2-yl)piperidin-4-yl]ethyl}carbamic acid tert-butyl ester (prepared from (2-piperidin-4-yl-ethyl)carbamic acid tert-butyl ester (Procedure 14) and 2-methylthio-2-imidazoline hydriodide (Aldrich, 15,884-4) using the method described by M. Dubey, et al. Pharmazie, 1978, 33, 268) using the method of Procedure 3.
MS+=522.0
$^1$H-NMR (CD$_3$OD) δ 7.62 (d, J=1.5 Hz, 1H), 7.40-7.55 (m, 3H), 3.73 (m, 4H), 3.45 (m, 2H), 3.31 (m, 2H), 3.14 (m, 2H), 1.91 (m, 2H), 1.55-1.80 (m, 3H), 1.30 (m, 2H).

EXAMPLE 271

Preparation of 4-Bromo-5-(2-chloro-benzoylamino)-1-methyl-pyrazole-3-carboxylic acid [2-(N-(benzothiazol-2-yl)piperidin-4-yl)ethyl]amide

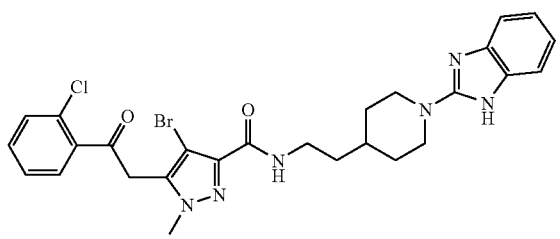

The pyrazole acid, prepared by coupling methyl ester 85 (Gen. Proc. 26) with 2-chlorobenzoyl chloride (21) followed by hydrolysis and bromination as shown in Gen. Proc. 8. was coupled to {2-[1-(1H-benzoimidazol-2-yl)piperidin-4-yl]ethyl}carbamic acid tert-butyl ester (prepared as shown for compound 35 in Procedure 14 using 2-chlorobenzimidazole (Aldrich, 59,227-7)) using the method of Procedure 3.

MS+=584.0

$^1$H-NMR (CD$_3$OD) δ 7.65 (d, J=6.3 Hz, 1H), 7.42-7.60 (m, 3H), 7.38 (m, 2H), 7.30 (m, 2H), 4.01 (m, 2H), 3.92 (s, 3H), 3.47 (m, 2H), 3.36 (m, 2H), 2.04 (m, 2H), 1.78 (m, 1H), 1.64 (m, 2H), 1.35-1.53 (m, 2H).

EXAMPLE 272

Preparation of 4-bromo-5-(2-chloro-benzoylamino)-1H-pyrazole-3-carboxylic acid [4-(N-pyridin-4-yl)amino)butyl]amide

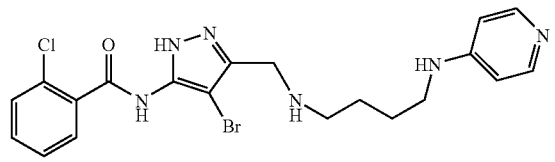

The pyrazole acid, prepared as described in Procedure 8, was coupled to [4-(pyridin-4-ylamino)butyl]carbainic acid tert-butyl ester (prepared by coupling N-Boc-4-amino butyric acid (Aldrich, 46,957-2) and 4-aminopyridine (Aldrich, A7,840-3) using the method of Procedure 10 followed by reduction using the method of Procedure 2) using the method of Procedure 3.

MS+=491.0

$^1$H-NMR (CD$_3$OD) δ 8.40 (d, J J=6.3 Hz, 2H), 7.78 (d, J J=6.0 Hz, 2H), 7.61 (d, J=6.6 Hz, 1H), 7.53-7.41 (m, 3H), 3.47 (t, J=6.6 Hz, 2H), 2.54 (t, J=7.2 Hz, 2H), 1.99 (m, 2H), 1.29 (m, 2H)

EXAMPLE 273

Preparation of 4-Bromo-5-(2-chloro-benzoylamino)-1-methyl-pyrazole-3-carboxylic acid [2-N,N-dimethylamino)ethyl]amide

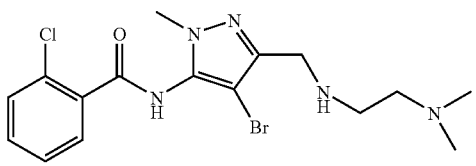

The pyrazole acid, prepared by coupling methyl ester 85 (Gen. Proc. 26) with 2-chlorobenzoyl chloride (21) followed by hydrolysis and bromination as shown in Gen. Proc. 8. was coupled to N1,N1-dimethylethane-1,2-diamine (Fluka, 39030) using the method of Procedure 10.

MS+=428.0

$^1$H-NMR (CDCl$_3$) δ 7.66 (d, J=7.5 Hz, 1H), 7.44-7.28 (m, 3H), 3.83 (s, 3H), 3.35 (t, J=6.0 Hz, 2H), 2.45 (t, J=6.0 Hz, 2H), 2.23 (s, 6H)

EXAMPLE 274

Preparation of (R)-4-bromo-5-(2-chlorobenzoylamino)-1-methyl-pyrazole-3-carboxylic acid (1,5-dimethyl-2-oxo-2,3,4,5-tetrahydro-1H-benzo[b][1,4]diazepin-3-yl)amide

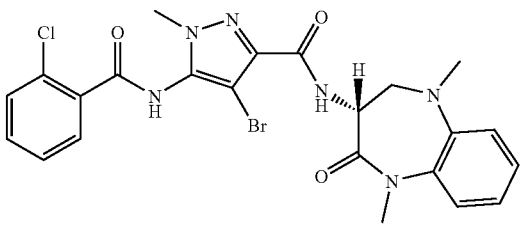

The pyrazole acid, prepared by coupling methyl ester 85 (Gen. Proc. 26) with 2-chlorobenzoyl chloride (21) followed by hydrolysis and bromination as shown in Gen. Proc. 8. was coupled to compound 92 (Procedure 27) using the method of Procedure 3.

MS+=545.0

$^1$H-NMR (CDCl$_3$) δ 9.48 (s, 1H), 7.42 (dd, J=8.1, 1.5 Hz, 1H), 7.33-6.88 (m, 7H), 5.49-5.32 (m, 1H), 4.01-3.94 (m, 2H), 3.79 (s, 3H), 3.62 (s, 3H), 3.20 (s, 3H).

EXAMPLE 275

Preparation of (R)-4-bromo-5-(2-chloro-benzoylamino)-1-methyl-pyrazole-3-carboxylic acid (2-oxo-azepan-3-yl)-amide

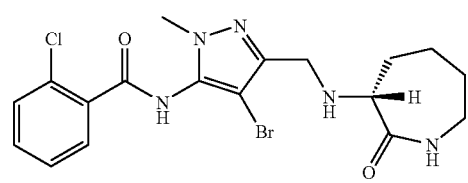

The pyrazole acid, prepared by coupling methyl ester 85 (Gen. Proc. 26) with 2-chlorobenzoyl chloride (21) followed by hydrolysis and bromination as shown in Gen. Proc. 8. was coupled to (2-oxo-azepan-3-yl)carbamic acid tert-butyl ester (prepared as described in Martin G. Banwell and Kenneth J. McRae; J. Org. Chem. 2001, 66, 6768, which is incorporated herein by reference in its entirety) using the method of Procedure 3.

MS+=468.0

$^1$H-NMR (CDCl$_3$) δ 8.70 (bs, 1H), 8.02 (d, J=6 Hz, 1H), 7.69 (d, J=9 Hz, 1H), 7.43-7.31 (m, 3H), 6.43 (t, J=6 Hz, 1H), 4.58 (dd, J=12, 6 Hz, 1H), 3.86 (s, 3H), 3.25 (m, 2H), 2.13-2.01 (m, 2H), 1.86-1.75 (m, 2H), 1.54-1.38 (m, 2H).

EXAMPLE 276

Preparation of 4-methyl-5-(2-fluoro-benzoylamino)-1-phenyl-pyrazole-3-carboxylic acid [2-(3,4,5,6-tetrahydro-2H-[1,4']bipyridin-4-yl)-ethyl]amide

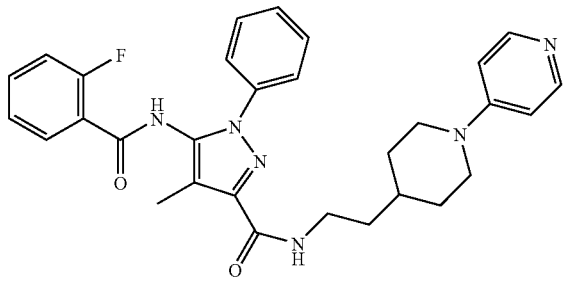

The pyrazole acid, prepared as described in Procedure 8 using 5-amino-4-methyl-1-phenyl-1H-pyrazole-3-carboxylic acid ethyl ester (prepared as described in Procedure 41 using 3-cyano-3-methyl-2-oxopropanoic acid ethyl ester (U.S. Pat. No. 4,652,669)) in place of compound 20 and 2-fluorobenzoyl chloride in place compound 21, was coupled to 2-(3,4,5,6-tetrahydro-2H-[1,4']bipyridin-4-yl)ethylamine (prepared as described in Procedure 14) using the method of Procedure 10.

MS+=527.2

$^1$H-NMR (DMSO-d6) δ 10.34 (bs, 1H), 8.23 (bs, 1H), 8.09 (d, 2H, J=4.7 Hz), 7.58-7.28 (m, 8H), 6.77 (d, 2H, J J=4.7 Hz), 3.89 (d, 2H, J=7 Hz), 2.73 (t, 2H, J=12 Hz), 2.15 (s, 3H), 1.78 (d, 2H, J J=12 Hz), 1.56-1.46 (m, 4H), 1.12 (m, 2H).

EXAMPLE 277

Preparation of (R)-4-Bromo-5-(2-chloro-benzoylamino)-1H-pyrazole-3-carboxylic acid (1-(benzyl-carbonyl)azepan-3-yl)-amide

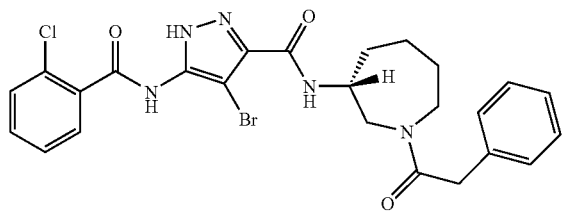

The pyrazole acid, prepared as described in Procedure 8, was coupled to (R)-(1-Phenylacetyl-azepan-3-yl)carbamic acid tert-butyl ester (prepared by cyclization of Boc-D-Lys-OH (Bachem, A-2705) using the method of Procedure 23 followed by reduction using the method of Procedure 2 and acylation with phenylacetic acid using the method of Procedure 10) using the method of Procedure 3.

MS+=558.0

$^1$H-NMR (CDCl$_3$) δ 9.19 (two br, 1H), 7.89 (two d, J=7.7 Hz, 1H), 7.32 (m, 8H), 4.19 (m, 2H), 3.81 (m, 3H), 3.28 (m, 2H), 2.03 (m, 2H), 1.63 (m, 2H), 1.35 (m, 2H).

EXAMPLE 278

Preparation of 4-methyl-5-(2-fluoro-benzoylamino)-1-t-butyl-pyrazole-3-carboxylic acid [2-(3,4,5,6-tetrahydro-2H-[1,4']bipyridin-4-yl)-ethyl]amide

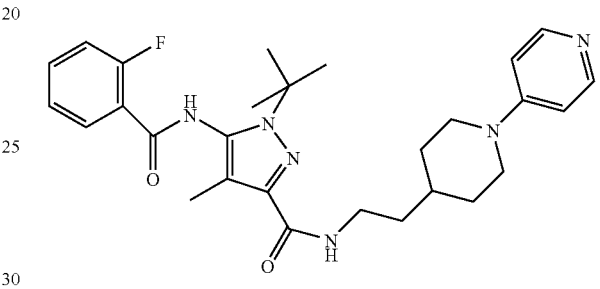

The pyrazole acid, prepared as described in Procedure 18 using 2-fluorobenzoyl chloride instead of compound 21, was coupled to 2-(3,4,5,6-tetrahydro-2H-[1,4']bipyridin-4-yl) ethylamine (prepared as described in Procedure 14) using the method of Procedure 10.

MS+=507.2

$^1$H-NMR (CD$_3$OD) δ 8.06 (d, 2H, J=6.4 Hz), 7.78 (t, 1H, J=7.6 Hz), 7.62 (m, 1H), 7.38-7.27 (m, 2H), 6.82 (d, 2H, J=6.4 Hz), 4.01 (d, 2H, J=13.3 Hz), 3.43 (t, 2H, J=7.2 Hz)), 2.91 (t, 2H, J=12.5 Hz), 1.89 (d, 2H, J=12.5 Hz), 1.65 (s, 9H), 1.60 (q, 2H, J=7.2 Hz), 1.27 (m, 2H).

EXAMPLE 279

Preparation of 5-(2-chloro-benzoylamino)-1-(phenyl)-pyrazole-3-carboxylic acid [2-(3,4,5,6-tetrahydro-2H-[1,4']bipyridin-4-yl)-ethyl]amide

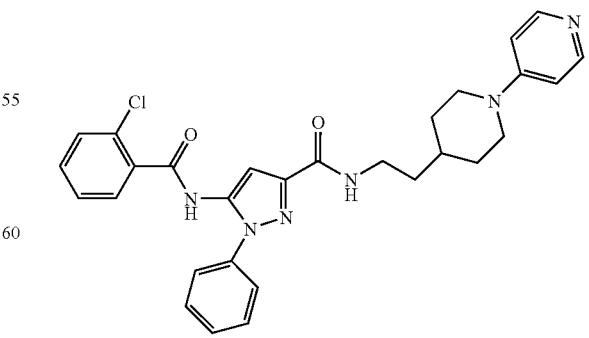

The pyrazole acid, prepared as described in Procedure 8 using compound 188 (Procedure 41) in place of compound 20, was coupled to 2-(3,4,5,6-tetrahydro-2H-[1,4']bipyridin-4-yl)ethylamine (prepared as described in Procedure 14) using the method of Procedure 10.

MS+=529.2

¹H-NMR (CDCl₃) δ 8.89 (b, 1H), 8.13 (d, J=6.5 Hz, 2H), 7.82 (d, J=7.5 Hz, 1H), 7.54 (m, 6H), 7.37 (m, 3H), 6.91 (m, 1H), 6.61 (d, J=6.5 Hz, 2H), 3.85 (d, J=13.0 hz, 2H), 3.50 (dt(app.q), J=6.5 Hz, 2H), 2.82 (dd(app. t), J=12.4 Hz, 2H), 1.84 (d, J=12.4 Hz, 2H), 1.57 (m, 3H), 1.25 (m, 2H).

EXAMPLE 280

Preparation of 4-bromo-5-(2-chloro-benzoylamino)-1-(phenyl)-pyrazole-3-carboxylic acid [2-(3,4,5,6-tetrahydro-2H-[1,4']bipyridin-4-yl)-ethyl]amide

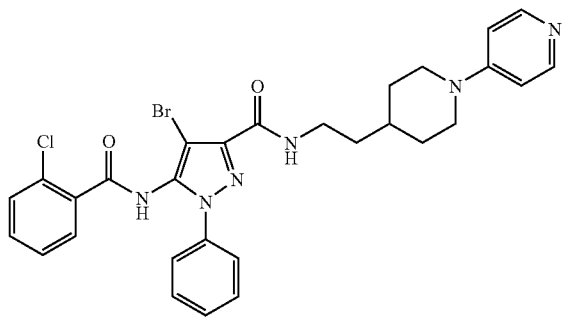

The pyrazole acid, prepared as described in Procedure 8 using compound 188 (Procedure 41) in place of compound 20, was coupled to 2-(3,4,5,6-tetrahydro-2H-[1,4']bipyridin-4-yl)ethylamine (prepared as described in Procedure 14) using the method of Procedure 10.

MS+=607.0

¹H-NMR (CD₃OD) δ 8.05 (d, J=7.8 Hz, 2H), 7.65-7.37 (m, 9H), 7.13 (d, J=7.8 Hz, 2H), 4.26 (d, J=13.4 Hz, 2H), 3.49 (m, 2H), 3.32 (m, 2H), 3.22 (m, 2H), 2.02 (d, J=13.5 Hz, 2H), 1.86 (m, 1H), 1.63 (dt(app. q.), J=6.9 Hz, 2H), 1.32 (m, 2H).

EXAMPLE 281

Preparation of 5-(2-chloro-benzoylamino)-1-(3,4-dichlorophenyl)-pyrazole-3-carboxylic acid [2-(3,4,5,6-tetrahydro-2H-[1,4']bipyridin-4-yl)-ethyl]amide

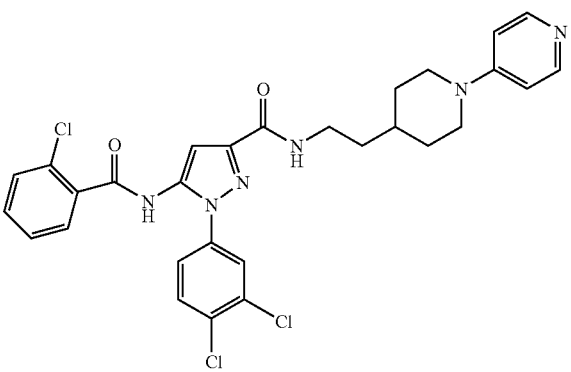

The pyrazole acid, prepared as described in Procedure 8 using 5-amino-1-(3,4-dichlorophenyl)-1H-pyrazole-3-carboxylic acid ethyl ester (prepared as described for compound 188 in Procedure 41 using 3,4-dichlorophenyl hydrazine) in place of compound 20, was coupled to 2-(3,4,5,6-tetrahydro-2H-[1,4']bipyridin-4-yl)ethylamine (prepared as described in Procedure 14) using the method of Procedure 10.

MS+=597.1

¹H-NMR (CDCl³) δ 8.55 (s, 1H), 8.16 (d, J=7.4 Hz, 2H), 7.73 (d, J=2.3 Hz, 1H), 7.59 (d, J=8.6 Hz, 1H), 7.42 (m, 3H), 7.17 (s, 1H), 6.92 (m, 1H), 6.81 (d, J=7.6 Hz, 2H), 4.07 (d, J=13.4, 2H), 3.53 (dt(app. q.), J=6.6 Hz, 2H), 3.16 (t, J=12.3 Hz, 2H), 2.02 (d, J=10.9 Hz, 2H), 1.82 (m, 1 h), 1.63 (dt(app. q.), J=6.8 Hz, 2H), 1.30 (m, 2H).

EXAMPLE 282

Preparation of 5-(2-chloro-benzoylamino)-1-(m-trifluoromethyl-phenyl)-pyrazole-3-carboxylic acid [2-(3,4,5,6-tetrahydro-2H-[1,4']bipyridin-4-yl)-ethyl]amide

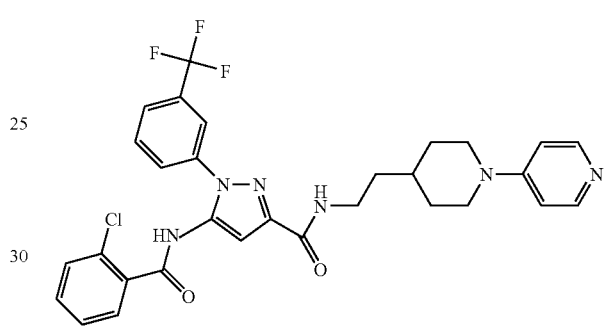

The pyrazole acid, prepared as described in Procedure 8 using 5-amino-1-(3-difluoromethylphenyl)-1H-pyrazole-3-carboxylic acid ethyl ester (prepared as described for compound 188 in Procedure 41 using 3-difluoromethylphenyl hydrazine) in place of compound 20, was coupled to 2-(3,4,5,6-tetrahydro-2H-[1,4']bipyridin-4-yl)ethylamine (prepared as described in Procedure 14) using the method of Procedure 10.

MS+=597.1

¹H-NMR (CDCl₃) δ 8.05 (d, 2H, J=7.3 Hz), 7.98 (s, 1H), 7.93 (d, 1H, J=7.2 Hz), 7.72-7.81 (m, 2H), 7.32-7.48 (m, 4H), 7.00 (s, 1H), 6.86 (d, 2H, J=6.4 Hz), 4.04 (d, 2H, J=13.7 Hz), 3.48 (t, 2H, J=7.2 Hz), 2.96 (t, 2H, J=12.8 Hz), 1.91 (d, 2H, J=12.9 Hz), 1.57-1.77 (m, 3H), 1.28 (q, 2H, J=12.0 Hz).

EXAMPLE 283

Preparation of 4-bromo-5-(2-chloro-benzoylamino)-1-(m-trifluoromethyl-phenyl)-pyrazole-3-carboxylic acid [2-(3,4,5,6-tetrahydro-2H-[1,4']bipyridin-4-yl)-ethyl]amide

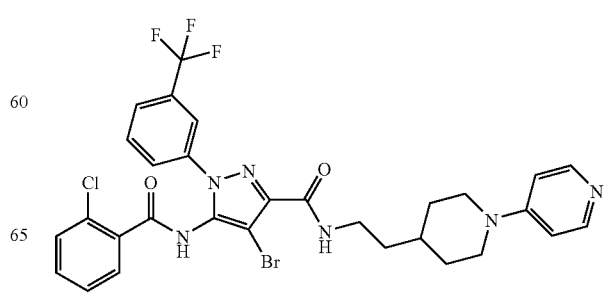

The pyrazole acid, prepared as described in Procedure 8 using 5-amino-1-(3-difluoromethylphenyl)-1H-pyrazole-3-carboxylic acid ethyl ester (prepared as described for compound 188 in Procedure 41 using 3-difluoromethylphenyl hydrazine) in place of compound 20, was coupled to 2-(3,4,5,6-tetrahydro-2H-[1,4']bipyridin-4-yl)ethylamine (prepared as described in Procedure 14) using the method of Procedure 10.

MS+=677.0

EXAMPLE 284

Preparation of 4-bromo-5-(2-chloro-benzoylamino)-1H-pyrazole-3-carboxylic acid [2-(piperidin-4-yl)-ethyl]amide

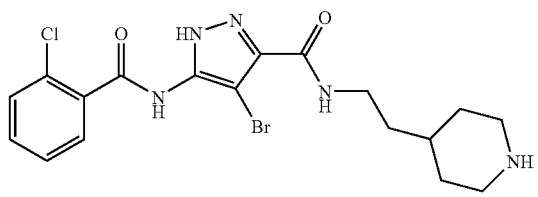

The pyrazole acid, prepared as described in Procedure 8, was coupled to 4-(2-aminoethyl)piperidine-1-carboxylic acid tert-butyl ester (Astatech, 56036) using the method of Procedure 10. Subsequent treatment with TFA afforded the title compound.

MS+=454.0

$^1$H-NMR (DMSO-d6) δ 8.25 (br, 1H), 7.53 (m, 4H), 3.51 (m, 2H), 3.24 (m, 2H), 2.84 (m, 2H), 1.86 (m, 2H), 1.55 (m, 3H), 1.28 (m, 2H).

EXAMPLE 285

Preparation of 4-Bromo-5-(2-fluoro-benzoylamino)-1H-pyrazole-3-carboxylic acid [N -(benzothiazol-2-yl)piperidin-4-ylmethyl]amide

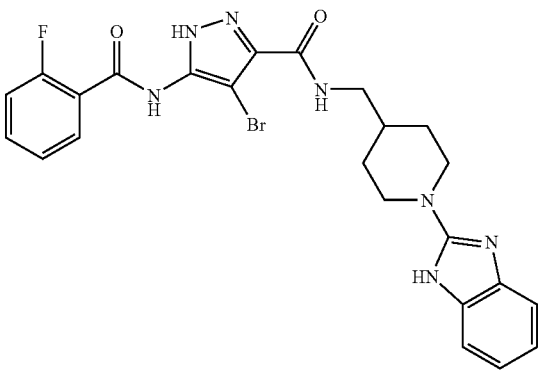

The pyrazole acid, prepared as described in Procedure 8 using 2-fluorobenzoyl chloride instead of compound 21, was coupled to [1-(1H-benzoimidazol-2-yl) -piperidin-4-ylmethyl]carbamic acid tert-butyl ester (prepared as shown for compound 35 in Procedure 14 using 2-chlorobenzimidazole (Aldrich, 59,227-7)) using the method of Procedure 3.

MS+=540.0

$^1$H-NMR (DMSO-d6) δ 7.68 (m, 2H), 7.39 (m, 4H), 7.25 (m, 2H), 4.01 (m, 2H), 3.24 (m, 4H), 1.87 (m, 3H), 1.38 (m, 2H).

EXAMPLE 286

Preparation of 4-Bromo-5-(2-chloro-benzoylamino)-1H-pyrazole-3-carboxylic acid (azepan-3-ylmethyl)-amide

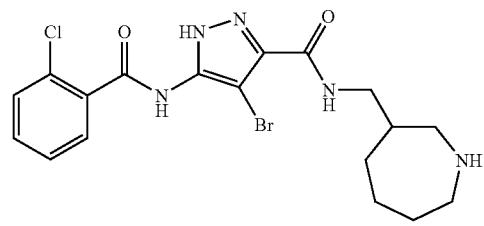

The pyrazole acid, prepared as described in Procedure 8, was coupled to 3-aminomethylazepane-1-carboxylic acid tert-butyl ester (prepared by Boc protection of azepan-3-ylmethanol (WO 02/22572) as shown for compound 31 in Procedure 13 followed by bromination as described in Procedure 42, azide displacement and reduction as shown for compounds 168 and 169 in Procedure 34) using the method of Procedure 10. Subsequent treatment with TFA afforded the title compound.

MS+=454.0

$^1$H-NMR (CD$_3$OD) δ 7.63 (d, J=7.1 Hz, 1H), 7.49 (m, 3H), 3.29 (m, 5H), 2.99 (m, 1H), 2.20 (m, 1H), 1.88 (m, 4H), 1.63 (m, 1H), 1.44 (m, 1H).

EXAMPLE 287

Preparation of 4-bromo-5-(2-chloro-benzoylamino)-1H-pyrazole-3-carboxylic acid [5-(4,5-dihydro-1H-imidazol-2-yl)-pent-1-yl]amide

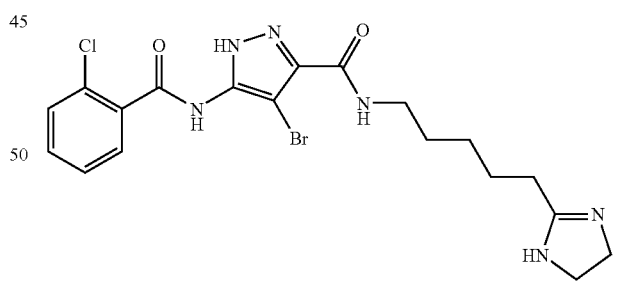

The pyrazole acid, prepared as described in Procedure 8, was coupled to 7-aminoheptanenitrile (prepared by displacement of bromine from N-(6-bromohexyl)phthalimide (Alfa, B25128) using KCN in DMF followed by treatment with hydrazine hydrate) using the method of Procedure 10. Formation of the amidine as shown in Procedure 33 using ethylene diamine afforded the title compound.

MS+=481.0

$^1$H-NMR (DMSO-d6) δ 7.56 (m, 4H), 3.82 (s, 4H), 3.26 (m, 2H), 2.49 (m, 2H), 1.66 (m, 2H), 1.56 (m, 2H), 1.36 (m, 2H).

EXAMPLE 288
Preparation of 4-bromo-5-(2-chloro-benzoylamino)-1-methyl-pyrazole-3-carboxylic acid [2-(4-(pyridin-4-yl)-piperazin-1-yl)ethyl]amide

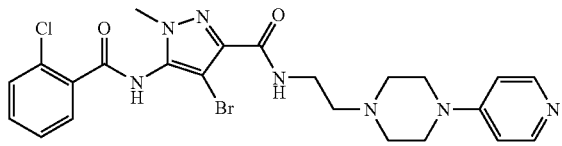

The pyrazole acid, prepared by coupling methyl ester 85 (Gen. Proc. 26) with 2-chlorobenzoyl chloride (21) followed by hydrolysis and bromination as shown in Gen. Proc. 8. was coupled to 2-(4-pyridin-4-yl-piperazin-1-yl)ethylamine (CA 985683) using the method of Procedure 10.

MS+=546.0

$^1$H-NMR (DMSO-d6) δ 8.15 (m, 2H), 7.58 (m, 4H), 6.83 (m, 2H), 3.82 (s, 3H), 3.36 (m, 2H), 2.49 (m, 10H).

EXAMPLE 289

Preparation of (R)-4-Bromo-5-(2-chloro-benzoylamino)-1-methyl-pyrazole-3-carboxylic acid (azepan-3-yl)-amide

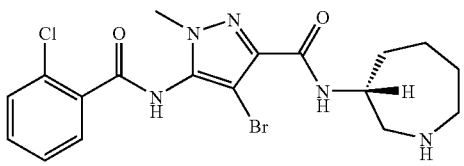

The pyrazole acid, prepared by coupling methyl ester 85 (Procedure 26) with 2-chlorobenzoyl chloride (21) followed by hydrolysis and bromination as shown in Procedure 8, was coupled to (R)-3-tert-butoxycarbonylaminoazepane-1-carboxylic acid benzyl ester (prepared as described in Procedure 23 using Boc-D-Lys-OH (Bachem, A-2705) followed by Cbz protection of the piperidine amine using the method of Procedure 30) using Procedure 3. Removal of the Cbz group using the method of Procedure 20 afforded the title compound.

MS+=454.0

$^1$H-NMR ($_{CD3OD}$) δ 7.66 (d, J=7.7 Hz, 1H), 7.51 (m, 3H), 4.32 (m, 1H), 3.91 (s, 3H), 3.36 (m, 4H), 2.12 (m, 1H), 1.94 (m, 4H), 1.70 (m, 1H).

EXAMPLE 290

Preparation of 4-bromo-5-(2-chloro-benzoylamino)-1H-pyrazole-3-carboxylic acid [3-(pyridin-4-yl)-[1,4]diazepin-5-yl]amide

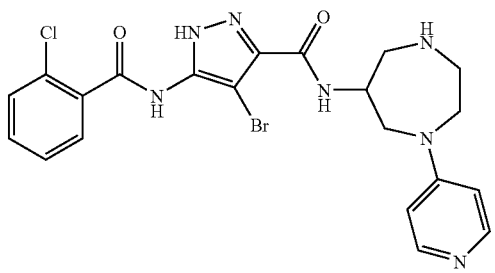

The pyrazole acid, prepared as described in Procedure 8, was coupled to 5-tert-butoxycarbonylamino-3-pyridin-4-yl-[1,3]diazepane-1-carboxylic acid benzyl ester (prepared by Boc protection of 5-amino-4-oxo-[1,3]diazepane-1-carboxylic acid benzyl ester (Astatech, 46012) followed by reduction as described in Procedure 2 and arylation as shown for compound 35 in Procedure 14) using the method of Procedure 3. Removal of the Cbz protecting group using the method of Procedure 20 afforded the title compound.

MS+=517.9

$^1$H-NMR (CD$_3$OD) δ 8.23 (d, J=6.9 Hz, 2H), 7.58 (m, 1H), 7.41 (m, 5H), 4.53 (m, 1H), 4.21 (m, 2H), 3.87 (m, 2H), 3.61 (m, 2H), 3.25 (m, 2H).

EXAMPLE 291
Preparation of 4-bromo-5-(2-chloro-benzoylamino)-1-methyl-pyrazole-3-carboxylic acid [2-(N-methyl-piperidin-4-yl)-ethyl]amide

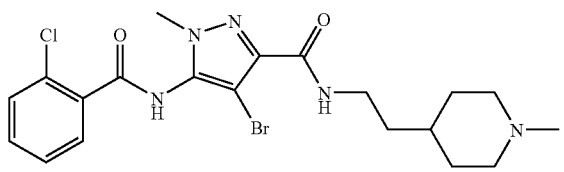

The pyrazole acid, prepared by coupling methyl ester 85 (Procedure 26) with 2-chlorobenzoyl chloride (21) followed by hydrolysis and bromination as shown in Procedure 8, was coupled to amine 169 (Procedure 34) using the method of Procedure 10. Formation of the amidine using the method of Procedure 33 using ethylene diamine afforded the title compound.

MS+=482.1

$^1$H-NMR (DMSO-d6) δ 8.16 (m, 1H), 7.58 (m, 4H), 3.83 (s, 3H), 3.24 (m, 2H), 2.74 (m, 1H), 2.14 (s, 3H), 1.84 (m, 2H), 1.66 (m, 2H), 1.43 (m, 2H), 1.17 (m, 4H).

EXAMPLE 292
Preparation of 4-bromo-5-(2-chloro-benzoylamino)-1-methyl-pyrazole-3-carboxylic acid {2-[4-(4,5-dihydro-1H-imidazol-2-yl)-phenyl]ethyl}amide

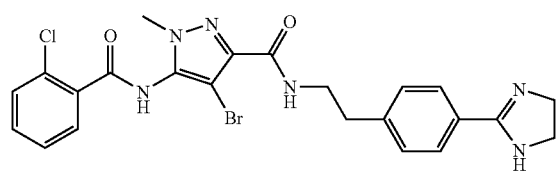

The pyrazole acid, prepared by coupling methyl ester 85 (Procedure 26) with 2-chlorobenzoyl chloride (21) followed by hydrolysis and bromination as shown in Procedure 8, was coupled to amine 169 (Procedure 34) using the method of Procedure 10. Formation of the amidine using the method of Procedure 33.

MS+=529.0

$^1$H-NMR (DMSO-d6) δ 8.23 (m, 1H), 7.73 (m, 2H), 7.56 (m, 4H), 7.29 (m, 2H), 3.80 (3H), 3.60 (s, 4H), 3.45 (m, 2H), 2.86 (m, 2H).

EXAMPLE 293

Preparation of 4-methyl-5-(2-chloro-benzoylamino)-1-methyl-pyrazole-3-carboxylic acid [2-(3,4,5,6-tetrahydro-2H-[1,4']bipyridin-4-yl)-ethyl]amide

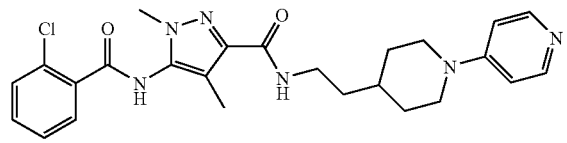

The pyrazole acid, prepared as described in Procedure 8 using 5-amino-1,4-dimethyl-1H-pyrazole-3-carboxylic acid ethyl ester (prepared as described in Procedure 41 using 3-cyano-3-methyl-2-oxopropanoic acid ethyl ester (U.S. Pat. No. 4,6526,69) and methylhydrazine hydrochloride) in place of compound 20, was coupled to 2-(3,4,5,6-tetrahydro-2H-[1,4']bipyridin-4-yl)ethylamine (prepared as described in Procedure 14) using the method of Procedure 10.

MS+=481.2

$^1$H-NMR (DMSO-d6) δ 8.16 (m, 2H), 7.57 (m, 4H), 7.17 (m, 2H), 4.20 (m, 2H), 3.73 (s, 3H), 3.66 (m, 2H), 3.13 (m, 2H), 2.11 (s, 3H), 1.87 (m, 2H), 1.71 (m, 1H), 1.45 (m, 2H), 1.13 (m, 2H).

EXAMPLE 294

Preparation of 4-methyl-5-(2-chloro-benzoylamino)-1-(2-methyl-phenyl)-pyrazole-3-carboxylic acid [2-(3,4,5,6-tetrahydro-2H-[1,4']bipyridin-4-yl)-ethyl]amide

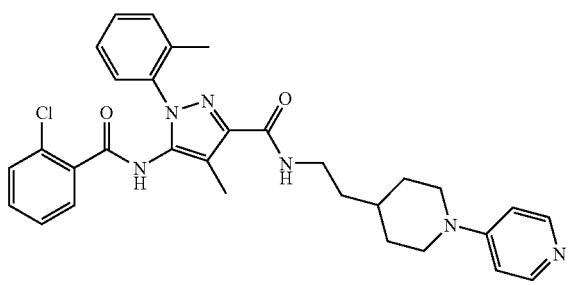

The pyrazole acid, prepared as described in Procedure 8 using 5-amino-4-methyl-1-o-tolyl-1H-pyrazole-3-carboxylic acid ethyl ester (prepared as described in Procedure 41 using 3-cyano-3-methyl-2-oxopropanoic acid ethyl ester (U.S. Pat. No. 4,652,669) and o-tolylhydrazine hydrochloride) in place of compound 20, was coupled to 2-(3,4,5,6-tetrahydro-2H-[1,4']bipyridin-4-yl)ethylamine (prepared as described in Procedure 14) using the method of Procedure 10.

MS+=556.9

$^1$H-NMR (DMSO-d6) δ 8.16 (m, 2H), 7.35 (m, 8H), 7.17 (m, 2H), 4.19 (m, 2H), 3.75 (m, 2H), 3.13 (m, 2H), 2.25 (s, 3H), 2.02 (s, 3H), 1.87 (m, 2H), 1.71 (m, 1H), 1.46 (m, 2H), 1.122 (m, 2H).

EXAMPLE 295

Preparation of 4-methyl-5-(2-chloro-benzoylamino)-1-(3-methoxyphenyl)-pyrazole-3-carboxylic acid [2-(3,4,5,6-tetrahydro-2H-[1,4']bipyridin-4-yl)-ethyl]amide

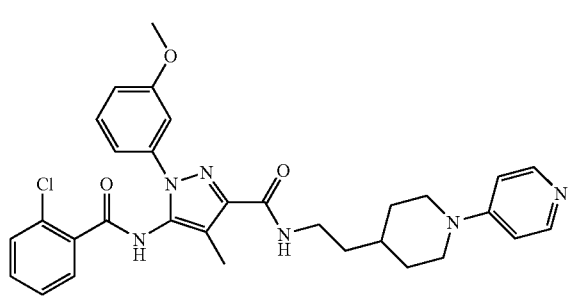

The pyrazole acid, prepared as described in Procedure 8 using 5-amino-1-(3-methoxyphenyl)-4-methyl-1H-pyrazole-3-carboxylic acid ethyl ester (prepared as described in Procedure 41 using 3-cyano-3-methyl-2-oxopropanoic acid ethyl ester (U.S. Pat. No. 4,652,669) and 3-methoxyphenylhydrazine hydrochloride) in place of compound 20, was coupled to 2-(3,4,5,6-tetrahydro-2H-[1,4']bipyridin-4-yl) ethylamine (prepared as described in Procedure 14) using the method of Procedure 10.

MS+=573.2

$^1$H-NMR (DMSO-d6) δ 8.16 (m, 2H), 7.47 (m, 4H), 7.10 (m, 6H), 4.21 (m, 2H), 3.78 (s, 3H), 3.50 (m, 2H), 3.13 (m, 2H), 2.17 (s, 3H), 1.88 (m, 2H), 1.73 (m, 1H), 1.48 (m, 2H), 1.12 (m, 2H).

EXAMPLE 296

Preparation of 4-methyl-5-(2-chloro-benzoylamino)-1-(p-fluorophenyl)-pyrazole-3-carboxylic acid [2-(3,4,5,6-tetrahydro-2H-[1,4']bipyridin-4-yl)-ethyl]amide

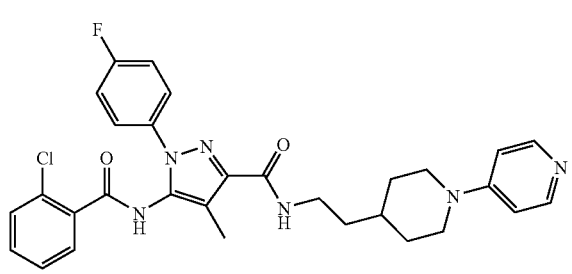

The pyrazole acid, prepared as described in Procedure 8 using 5-amino-1-(4-fluorophenyl)-4-methyl-1H-pyrazole-3-carboxylic acid ethyl ester (prepared as described in Procedure 41 using 3-cyano-3-methyl-2-oxopropanoic acid ethyl ester (U.S. Pat. No. 4,652,669) and 4-fluorophenylhydrazine hydrochloride) in place of compound 20, was coupled to 2-(3,4,5,6-tetrahydro-2H-[1,4']bipyridin-4-yl)ethylamine (prepared as described in Procedure 14) using the method of Procedure 10.

MS+=560.8

¹H-NMR (DMSO-d6) δ 8.18 (m, 2H), 7.53 (m, 8H), 7.19 (m, 2H), 4.22 (m, 2H), 3.32 (m, 2H), 3.16 (m, 2H), 2.21 (s, 3H), 1.91 (m, 2H), 1.74 (m, 1H), 1.49 (m, 2H), 1.16 (m, 2H).

EXAMPLE 297

Preparation of 4-methyl-5-(2-chloro-benzoylamino)-1-phenyl-pyrazole-3-carboxylic acid [2-(3,4,5,6-tetrahydro-2H-[1,4']bipyridin-4-yl)-ethyl]amide

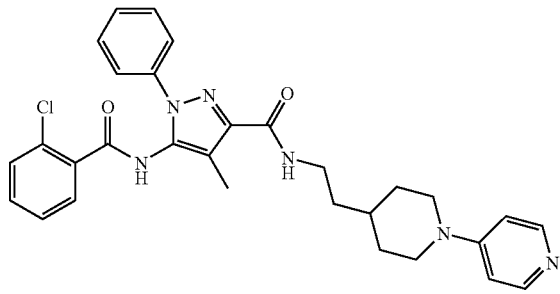

The pyrazole acid, prepared as described in Procedure 8 using 5-amino-4-methyl-1-phenyl-1H-pyrazole-3-carboxylic acid ethyl ester (prepared as described in Procedure 41 using 3-cyano-3-methyl-2-oxopropanoic acid ethyl ester (U.S. Pat. No. 4,652,669)) in place of compound 20, was coupled to 2-(3,4,5,6-tetrahydro-2H-[1,4']bipyridin-4-yl) ethylamine (prepared as described in Procedure 14) using the method of Procedure 10.

MS+=543.2

¹H-NMR (DMSO-d6) δ 8.16 (m, 2H), 7.50 (m, 9H), 7.16 (m, 2H), 4.20 (m, 22H), 3.31 (m, 2H), 3.14 (m, 2H), 2.19 (s, 3H), 1.89 (m, 2H), 1.75 (m, 1H), 1.48 (m, 2H), 1.16 (m, 2H).

EXAMPLE 298

Preparation of 5-(2-chloro-benzoylamino)-1-(pyridine-2-yl)-pyrazole-3-carboxylic acid [2-(3,4,5,6-tetrahydro-2H-[1,4']bipyridin-4-yl)-ethyl]amide

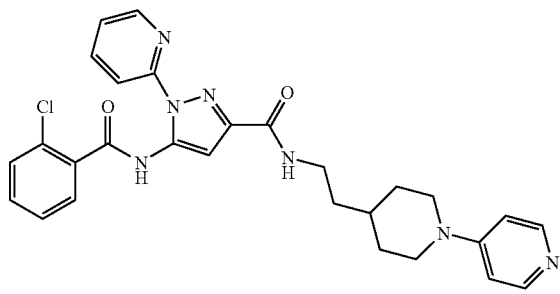

The pyrazole acid, prepared as described in Procedure 8 using 5-amino-1-pyridin-2-yl-1H-pyrazole-3-carboxylic acid ethyl ester (prepared as described for compound 188 in Procedure 41 using 2-hydrazinopyridine) in place of compound 20, was coupled to 2-(3,4,5,6-tetrahydro-2H-[1,4']bi-pyridin-4-yl)ethylamine (prepared as described in Procedure 14) using the method of Procedure 10.

MS+=530.1

¹H-NMR (DMSO-d6) δ 8.44 (m, 2H), 8.10 (m, 4H), 7.52 (m, 4H), 6.78 (m, 2H), 5.73 (s, 1H), 3.90 (m, 2H), 3.33 (m, 2H), 2.76 (m, 2H), 1.78 (m, 2H), 1.49 (m, 3H), 1.17 (m, 2H).

EXAMPLE 299

Preparation of 4-bromo-5-(2-chloro-benzoylamino)-1-(p-fluorophenyl)-pyrazole-3-carboxylic acid [2-(3,4,5,6-tetrahydro-2H-[1,4']bipyridin-4-yl)-ethyl]amide

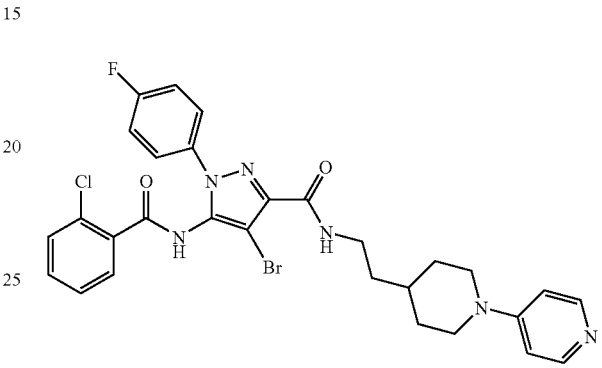

The pyrazole acid, prepared as described in Procedure 8 using 5-amino-1-(4-fluorophenyl)-1H-pyrazole-3-carboxylic acid ethyl ester (prepared as described for compound 188 in Procedure 41 using 4-fluorophenylhydrazine hydrochloride) in place of compound 20, was coupled to 2-(3,4,5,6-tetrahydro-2H-[1,4']bipyridin-4-yl)ethylamine (prepared as described in Procedure 14) using the method of Procedure 10.

MS+=625.0

¹H-NMR (DMSO-d6) δ 8.18 (m, 2H), 7.56 (m, 8H), 7.18 (m, 2H), 4.22 (m, 2H), 3.28 (m, 2H), 3.15 (m, 2H), 1.90 (m, 2H), 1.75 (m, 1H), 1.50 (m, 2H), 1.18 (m, 2H).

EXAMPLE 300

Preparation of 4-bromo-5-(2-chloro-benzoylamino)-1-(pyridin-2-yl)-pyrazole-3-carboxylic acid [2-(3,4,5,6-tetrahydro-2H-[1,4']bipyridin-4-yl)-ethyl]amide

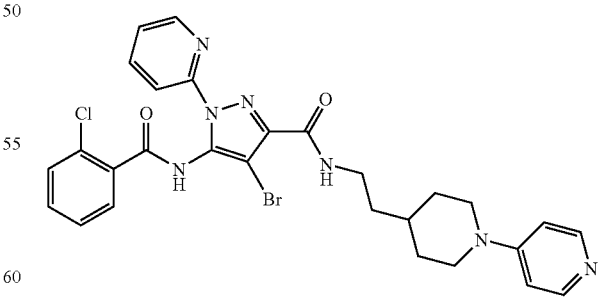

The pyrazole acid, prepared as described in Procedure 8 using 5-amino-1-pyridin-2-yl-1H-pyrazole-3-carboxylic acid ethyl ester (prepared as described for compound 188 in Procedure 41 using 2-hydrazinopyridine) in place of compound 20, was coupled to 2-(3,4,5,6-tetrahydro-2H-[1,4']bipyridin-4-yl)ethylamine (prepared as described in Procedure 14) using the method of Procedure 10.

MS+=608.1

¹H-NMR (DMSO-d6) δ 8.51 (m, 2H), 8.07 (m, 3H), 7.87 (m, 1H), 7.53 (m, 4H), 6.77 (m, 2H), 3.90 (m, 2H), 3.33 (m, 2H), 2.79 (m, 2H), 1.79 (m, 2H), 1.60 (m, 1H), 1.50 (m, 2H), 1.15 (m, 2H).

EXAMPLE 301

Preparation of 5-(2-chloro-benzoylamino)-1-(p-fluorophenyl)-pyrazole-3-carboxylic acid [2-(3,4,5,6-tetrahydro-2H-[1,4']bipyridin-4-yl)-ethyl]amide

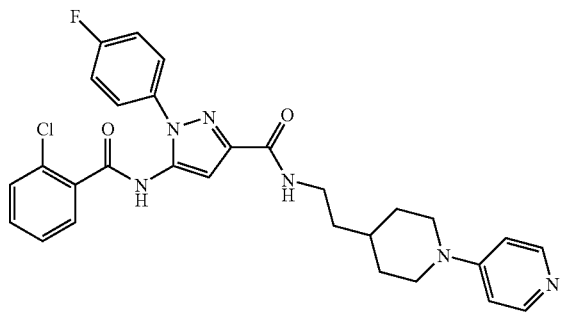

The pyrazole acid, prepared as described in Procedure 8 using 5-amino-1-(4-fluorophenyl)-1H-pyrazole-3-carboxylic acid ethyl ester (prepared as described for compound 188 in Procedure 41 using 4-fluorophenyl hydrazine) in place of compound 20, was coupled to 2-(3,4,5,6-tetrahydro-2H-[1,4']bipyridin-4-yl)ethylamine (prepared as described in Procedure 14) using the method of Procedure 10.

MS+=547.1

¹H-NMR (DMSO-d6) δ 8.34 (m, 1H), 8.16 (m, 2H), 7.62 (m, 2H), 7.44 (m, 6H), 7.17 (m, 2H), 4.21 (m, 2H), 3.42 (m, 2H), 3.12 (m, 2H), 1.87 (m, 2H), 1.71 (m, 1H), 1.46 (m, 2H), 1.12 (m, 2H).

EXAMPLE 302

Preparation of 5-(2-chloro-benzoylamino)-1H-pyrazole-3-carboxylic acid [4-methyl-5-oxo-[1,4]diazepin-6-yl]amide

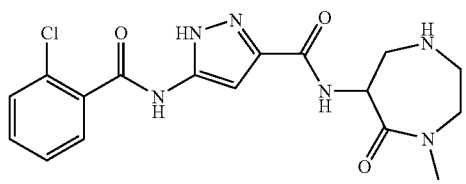

The pyrazole acid, prepared as described in Procedure 8, was coupled to 5-tert-butoxycarbonylamino-3-methyl-4-oxo-[1,3]diazepane-1-carboxylic acid benzyl ester (prepared by Boc protection of 5-amino-4-oxo-[1,3]diazepane-1-carboxylic acid benzyl ester (Astatech, 46012) followed by methylation as described in Procedure 7) using the method of Procedure 3. Removal of the Cbz protecting group as described in Procedure 20 afforded the title compound.

MS+=391.1

¹H-NMR (DMSO-d6) δ 7.49 (m, 4H), 6.45 (s, 1H), 5.11 (m, 1H), 3.99 (m, 1H), 3.36 (m, 5H), 2.98 (s, 3H).

EXAMPLE 303

Preparation of 5-(2-chlorobenzoylamino)-1-phenyl-1H-pyrazole-3-carboxylic acid (2-oxo-5-phenyl-2,3-dihydro-1H-benzo[e][1,4]diazepin-3-yl)amide

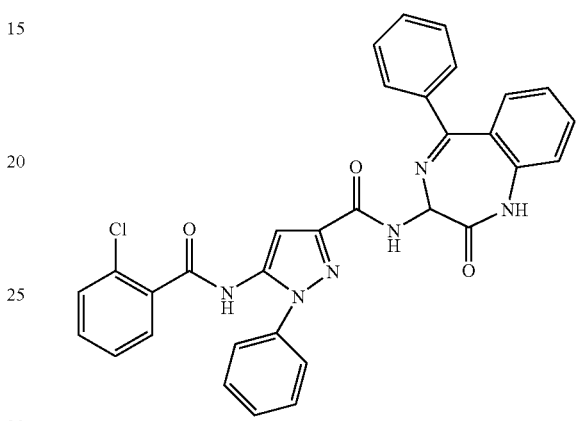

The pyrazole acid, prepared as described in Procedure 8 using compound 188 (Procedure 41) in place of compound 20, was coupled to 3-amino-5-phenyl-1,3-dihydro-benzo[e][1,4]diazepin-2-one (prepared as described in Procedure 20) using the method of Procedure 10.

MS+=575.1

¹H NMR (DMSO-d₆) δ 11.02 (br, 1H), 8.52 (d, J=8.0 Hz, 1H), 8.08 (d, J=7.6 Hz, 2H), 7.67 (dd(app. t), J=7.3 Hz, 1H), 7.52-7.27 (m, 16H), 7.08 (s, 1H), 5.43 (d, J=8.0 Hz, 1H).

EXAMPLE 304

Preparation of 4-Bromo-5-(2-chlorobenzoylamino)-1-phenyl-1H-pyrazole-3-carboxylic acid (2-oxo-5-phenyl-2,3-dihydro-1H-benzo[e][1,4]diazepin-3-yl) amide

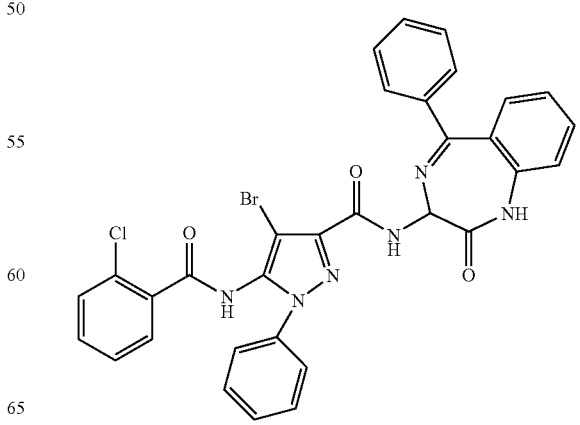

The pyrazole acid, prepared as described in Procedure 8 using compound 188 (Procedure 41) in place of compound 20, was coupled to 3-amino-5-phenyl-1,3-dihydro-benzo[e][1,4]diazepin-2-one (prepared as described in Procedure 20) using the method of Procedure 10.

MS+=653.0

$^1$H NMR (DMSO-d$_6$) δ 11.07 (br, 1H), 10.80 (br, 1H), 8.83 (br, 1H), 7.70-7.36 (m, 18H), 5.45 (br, 1H).

EXAMPLE 305

Preparation of 5-acetylamino-1-phenyl-1H-pyrazole-3-carboxylic acid [2-(3,4,5,6-tetrahydro-2H-[1,4']bipyridin-4-yl)-ethyl]amide

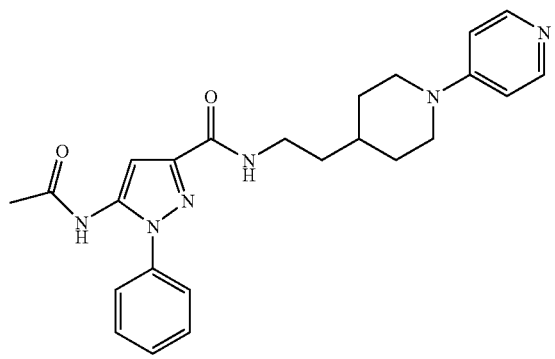

The pyrazole acid, prepared as described in Procedure 8 using compound 188 (Procedure 41) in place of compound 20 and acetyl chloride in place of compound 21, was coupled to 2-(3,4,5,6-tetrahydro-2H-[1,4']bipyridin-4-yl)ethylamine (prepared as described in Procedure 14) using the method of Procedure 10.

MS+=433.2

$^1$H NMR (CDCl$_3$) δ 8.13 (d, J=6.9 Hz, 2H), 7.56-7.48 (m, 5H), 6.94 (m, 1H), 6.83 (d, J=7.6 Hz, 2H), 4.09 (d, J=13.4 Hz, 2H), 3.52 (dt(app. q), J=6.7 Hz, 2H), 3.16 (m, 2H), 2.11 (s, 3H), 2.01 (m, 2H), 1.83 (m, 1H), 1.62 (dt(app. q), J=6.8 Hz, 2H), 1.35 (m, 2H).

EXAMPLE 306

Preparation of 4-bromo-5-(2-chlorobenzoylamino)-1-(4-isopropylphenyl)-1H-pyrazole-3-carboxylic acid [2-(3,4,5,6-tetrahydro-2H-[1,4']bipyridin-4-yl)ethyl]amide

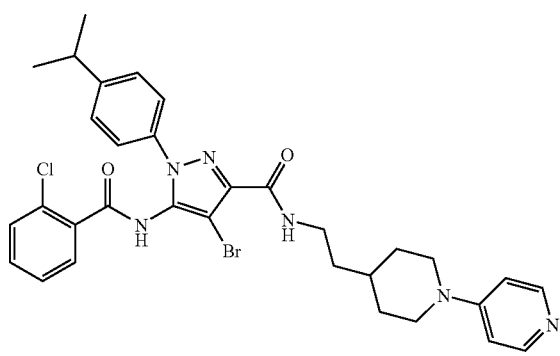

The pyrazole acid, prepared as described in Procedure 8 using 5-amino-1-(4-isopropylphenyl)-1H-pyrazole-3-carboxylic acid ethyl ester (prepared as described for compound 188 in Procedure 41 using 4-isopropylphenylhydrazine hydrochloride) in place of compound 20, was coupled to 2-(3,4,5,6-tetrahydro-2H-[1,4']bipyridin-4-yl)ethylamine (prepared as described in Procedure 14) using the method of Procedure 10.

MS+=649.1

$^1$H-NMR (DMSO-d$_6$) δ 8.40 (m, 1H), 8.18 (d, J=7.5 Hz, 2H), 7.49 (m, 8H), 7.19 (d, J=7.8 Hz, 2H), 4.23 (d, J=13.2 Hz, 2H), 3.32 (m, 2H), 3.16 (t, J=12.3 Hz, 2H), 2.99 (m, 1H), 1.90 (d, J=13.2 Hz, 2H), 1.75 (m, 1H), 1.51 (m, 2H), 1.24 (d, J=6.9 Hz, 6H), 1.17 (m, 2H).

EXAMPLE 307

Preparation of 5-(2-chlorobenzoylamino)-1-(4-isopropylphenyl)-1H-pyrazole-3-carboxylic acid [2-(3,4,5,6-tetrahydro-2H-[1,4']bipyridin-4-yl)ethyl]amide

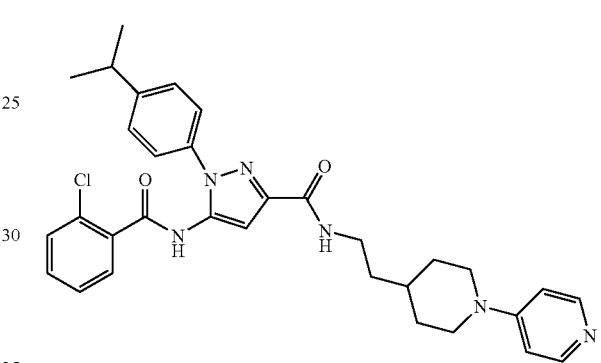

The pyrazole acid, prepared as described in Procedure 8 using 5-amino-1-(4-isopropylphenyl)-1H-pyrazole-3-carboxylic acid ethyl ester (prepared as described for compound 188 in Procedure 41 using 4-isopropylphenylhydrazine hydrochloride) in place of compound 20, was coupled to 2-(3,4,5,6-tetrahydro-2H-[1,4']bipyridin-4-yl)ethylamine (prepared as described in Procedure 14) using the method of Procedure 10.

MS+=575.1

$^1$H-NMR (DMSO-d$_6$) δ 8.18 (d, J=7.5 Hz, 2H), 7.47 (m, 8H), 7.18 (d, J=7.5 Hz, 2H), 6.87 (s, 1H), 4.22 (d, J=13.8 Hz, 2H), 3.32 (m, 2H), 3.14 (t, J=12.9 Hz, 2H), 2.99 (m, 1H), 1.89 (d, J=12.3 Hz, 2H), 1.74 (m, 1H), 1.50 (m, 2H), 1.24 (d, J=6.9 Hz, 6H), 1.16 (m, 2H).

EXAMPLE 308

Preparation of 4-Bromo-5-(2-fluorobenzoylamino)-1-phenyl-1H-pyrazole-3-carboxylic acid [2-(3,4,5,6-tetrahydro-2H-[1,4']bipyridin-4-yl)ethyl]amide

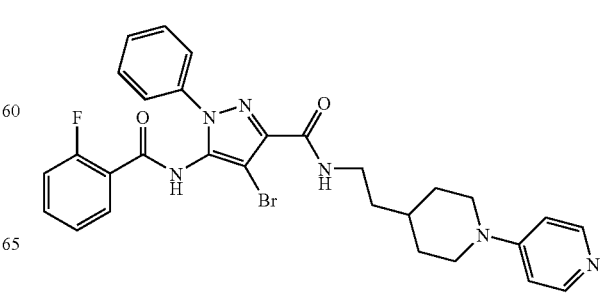

The pyrazole acid, prepared as described in Procedure 8 using compound 188 (Procedure 41) in place of compound 20 and 2-fluorobenzoyl chloride in place of compound 21, was coupled to 2-(3,4,5,6-tetrahydro-2H-[1,4']bipyridin-4-yl)ethylamine (prepared as described in Procedure 14) using the method of Procedure 10.

MS+=591.0

$^1$H-NMR (DMSO-$d_6$) δ 8.42 (m, 1H), 8.11 (d, J=6.3 Hz, 2H), 7.71 (m, 7H), 7.34 (m, 2H), 6.79 (d, J=6.6 Hz, 2H), 3.91 (d, J=12.9 Hz, 2H), 3.32 (m, 2H), 2.80 (t, J=12.3 Hz, 2H), 1.80 (d, J=12.6 Hz, 2H), 1.59 (m, 1H), 1.50 (m, 2H), 1.17 (m, 2H).

EXAMPLE 309

Preparation of 5-(2-Fluorobenzoylamino)-1-phenyl-1H-pyrazole-3-carboxylic acid [2-(3,4,5,6-tetrahydro-2H-[1,4']bipyridin-4-yl)ethyl]amide

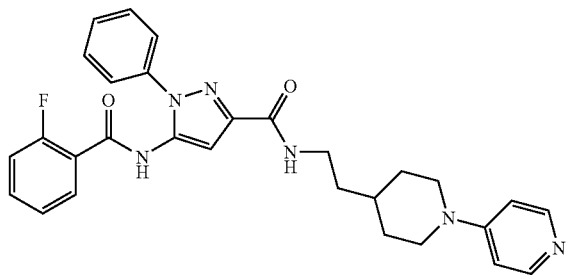

The pyrazole acid, prepared as described in Procedure 8 using compound 188 (Procedure 41) in place of compound 20 and 2-fluorobenzoyl chloride in place of compound 21, was coupled to 2-(3,4,5,6-tetrahydro-2H-[1,4']bipyridin-4-yl)ethylamine (prepared as described in Procedure 14) using the method of Procedure 10.

MS+=513.1

$^1$H-NMR (DMSO-$d_6$) δ 8.27 (m, 1H), 8.11 (d, J=6.0 Hz, 2H), 7.55 (m, 7H), 7.32 (m, 2H), 6.89 (s, 1H), 6.78 (d, J=6.3 Hz, 2H), 3.90 (d, J=12.9 Hz, 2H), 3.30 (m, 2H), 2.79 (t, J=11.4 Hz, 2H), 1.79 (d, J=12.0 Hz, 2H), 1.57 (m, 1H), 1.48 (m, 2H), 1.15 (m, 2H).

EXAMPLE 310

Preparation of 4-Bromo-5-(2-chlorobenzoylamino)-1-(4-methoxyphenyl)-1H-pyrazole-3-carboxylic acid [2-(3,4,5,6-tetrahydro-2H-[1,4']bipyridin-4-yl)ethyl]amide

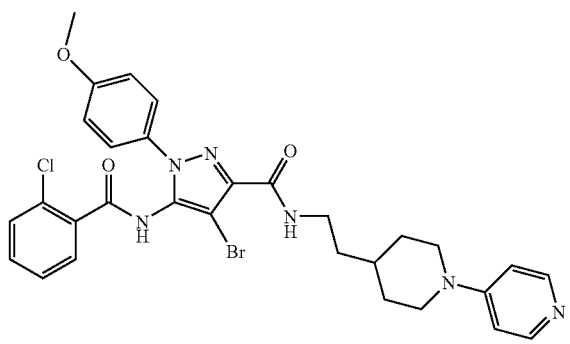

The pyrazole acid, prepared as described in Procedure 8 using 5-amino-1-(4-methoxyphenyl)-1H-pyrazole-3-carboxylic acid ethyl ester (prepared as described for compound 188 in Procedure 41 using 4-methoxyphenylhydrazine hydrochloride) in place of compound 20, was coupled to 2-(3,4,5,6-tetrahydro-2H-[1,4']bipyridin-4-yl)ethylamine (prepared as described in Procedure 14) using the method of Procedure 10.

MS+=637.0

$^1$H-NMR (DMSO-$d_6$) δ 8.40 (m, 1H), 8.18 (d, J=7.2 Hz, 2H), 7.49 (m, 6H), 7.19 (d, J=7.2 Hz, 2H), 7.12 (d, J=9.0 Hz, 2H), 4.22 (d, J=14.1 Hz, 2H), 3.32 (m, 2H), 3.16 (t, J=11.7 Hz, 2H), 1.90 (d, J=9.9 Hz, 2H), 1.73 (m, 1H), 1.51 (m, 2H), 1.19 (m, 2H).

EXAMPLE 311

Preparation of 4-Bromo-5-(2-chlorobenzoylamino)-1-(2-N,N-diemthylamino)eth-1-yl)-pyrazole-3-carboxylic acid [2-(3,4,5,6-tetrahydro-2H-[1,4']bipyridin-4-yl)ethyl]amide

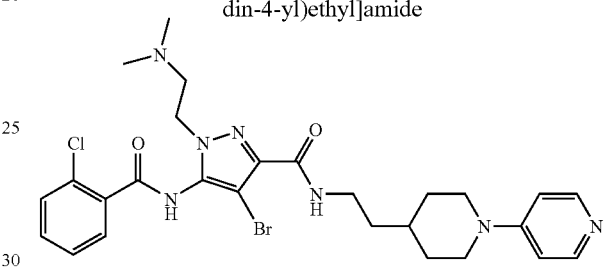

The pyrazole acid, prepared as described in Procedure 8 using 5-amino-1-(2-dimethylaminoethyl)-1H-pyrazole-3-carboxylic acid ethyl ester (prepared as described in Procedure 26 using 2-chloro-N,N-dimethylethylamine hydrochloride) in place of compound 20, was coupled to 2-(3,4,5,6-tetrahydro-2H-[1,4']bipyridin-4-yl)ethylamine (prepared as described in Procedure 14) using the method of Procedure 10.

MS+=602.1 $^1$H NMR (DMSO-$d_6$) δ 8.12 (m, 2H), 7.52 (m, 4H), 6.81 (m, 2H), 4.30 (m, 2H), 3.93 (m, 2H), 3.34 (m, 2H), 2.78 (m, 2H), 2.60 (m, 2H), 2.14 (s, 6H), 1.79 (m, 2H), 1.70 (m, 1H), 1.51 (m, 2H), 1.18 (m, 2H).

Biological Example

The potency and efficacy to inhibit the bradykinin $B_1$ receptor was determined for the compounds of this invention in a cell-based fluorescent calcium-mobilization assay. The assay measures the ability of test compounds to inhibit bradykinin $B_1$ receptor agonist-induced increase of intracellular free $Ca^{+2}$ in a native human bradykinin $B_1$ receptor-expressing cell line.

In this example, the following additional abbreviations have the meanings set forth below. Abbreviations heretofore defined are as defined previously. Undefined abbreviations have the art recognized meanings.

| | |
|---|---|
| BSA = | bovine serum albumin |
| DMSO = | dimethylsulfoxide |
| FBS = | fetal bovine serum |
| MEM = | minimum essential medium |
| mM = | millimolar |
| nM = | nanomolar |
| ng = | nanogram |
| μg = | micrograms |
| μM = | micromolar |

Specifically, calcium indicator-loaded cells are pre-incubated in the absence or presence of different concentrations of test compounds followed by stimulation with selective bradykinin $B_1$ receptor agonist peptide while Ca-dependent fluorescence is monitored.

IMR-90 human lung fibroblast cells (CCL 186, American Type Tissue Collection) are grown in MEM supplemented with 10% FBS as recommended by ATCC. Confluent cells are harvested by trypsinization and seeded into black wall/clear bottom 96-well plates (Costar #3904) at approximately 13,000 cells/well. The following day, cells are treated with 0.35 ng/mL interleukin-1β in 10% FBS/MEM for 2 hours to up-regulate bradykinin $B_1$ receptors. Induced cells are loaded with fluorescent calcium indicator by incubation with 2.3 µM Fluo-4/AM (Molecular Probes) at 37° C. for 1.5 hrs in the presence of an anion transport inhibitor (2.5 mM probenecid in 1% FBS/MEM). Extracellular dye is removed by washing with assay buffer (2.5 mM probenecid, 0.1% BSA, 20 mM HEPES in Hank's Balanced Salt Solution without bicarbonate or phenol red, pH 7.5) and cell plates are kept in dark until used. Test compounds are assayed at 7 concentrations in triplicate wells. Serial dilutions are made in half log-steps at 100-times final concentration in DMSO and then diluted in assay buffer. Compound addition plates contain 2.5-times final concentrations of test compounds or controls in 2.5% DMSO/assay buffer. Agonist plates contain 5-times the final concentration of 2.5 nM (3×EC50) bradykinin $B_1$ receptor agonist peptide des-$Arg^{10}$-kallidin (DAKD, Bachem) in assay buffer. Addition of test compounds to cell plate, incubation for 5 min at 35° C., followed by the addition of bradykinin $B_1$ receptor agonist DAKD is carried out in the Fluorometric Imaging Plate Reader (FLIPR, Molecular Devices) while continuously monitoring Ca-dependent fluorescence. Peak height of DAKD-induced fluorescence is plotted as function of concentration of test compounds. $IC_{50}$ values are calculated by fitting a 4-parameter logistic function to the concentration-response data using non-linear regression (Xlfit, IDBS (ID Business Solutions Ltd.)).

Typical potencies observed for bradykinin $B_1$ receptor agonist peptides are $EC_{50}$ approximately 0.8 nM and approximately 100 nM for des-$Arg^{10}$-kallidin and des-$Arg^9$-bradykinin, respectively, while for bradykinin $B_1$ receptor antagonist peptide des-$Arg^{10}$, $Leu^9$-kallidin $IC_{50}$ is approximately 1 nM.

The compounds of this invention have potency in the above assay as demonstrated by results of less than 50 micromolar. It is advantageous that the assay results be less than 1 micromolar, even more advantageous for the results to be less than 0.5 micromolar.

In view of the above, all of these compounds exhibit bradykinin $B_1$ receptor antagonistic properties and, accordingly, are useful in treating disease conditions mediated at least in part by bradykinin $B_1$ receptor.

What is claimed is:
1. A compound of Formula (I) or Formula (II):

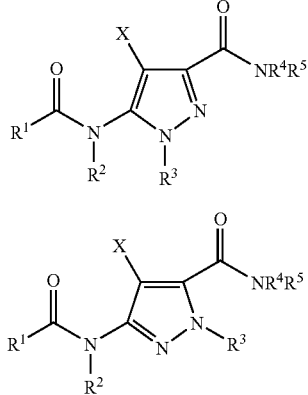

wherein
R$^1$ is phenyl optionally substituted with a group selected from the group consisting of hydroxy, nitro, acyl, acyloxy, alkoxy, phenoxy, benzyloxy, phenyl, alkenyl, halogen, alkyl, and alkyl substituted with hydroxy or halogen;
R$^2$ is selected from hydrogen and alkyl;
R$^3$ is selected from the group consisting of hydrogen, alkyl, aryl optionally substituted with a group selected from the group consisting of halo, alkoxy, alkyl, and alkyl substituted with halo;
R$^4$ is selected from the group consisting of R$^{40}$ and alkyl substituted with R$^{40}$ or R$^{41}$ and further optionally substituted with phenyl;
R$^{40}$ is a 6-membered heterocycle having one heteroatom and is optionally substituted with alkyl optionally substituted with aryl or heteroaryl, aryl, benzyl, oxo, —SO$_2$-aryl, heteroaryl optionally substituted with amino or alkyl, aminoacyl, heterocyclic, heteroarylacetyl, benzyloxyacyl, and haloalkoxyacyl, and combinations thereof with the proviso that the heteroaryl and heterocyclic groups of R$^{40}$ are 6-membered rings and have one heteroatom;
R$^{41}$ is a 6-membered heteroaryl having one heteroatom and is optionally substituted with alkyl optionally substituted with aryl or heteroaryl, aryl, benzyl, oxo, —SO$_2$-aryl, heteroaryl optionally substituted with amino or alkyl, aminoacyl, heterocyclic, heteroarylacetyl, benzyloxyacyl, and haloalkoxyacyl, and combinations thereof with the proviso that the heteroaryl and heterocyclic groups of R$^{41}$ are 6-membered rings and have one heteroatom;
R$^5$ is hydrogen or alkyl;
or R$^4$ and R$^5$, together with the nitrogen atom pendent thereto are joined to form a heterocyclic or a heteroaryl wherein each of the heterocyclic and heteroaryl groups are 6-membered rings and contain only one heteroatom,
X is selected from the group consisting of hydrogen, halogen, and alkyl;
or a pharmaceutically acceptable salt or stereoisomer thereof.

2. A compound according to claim 1 wherein R$^1$ is selected from the group consisting of
2-chlorophenyl, 2-fluorophenyl, 2-bromophenyl, 2-hydroxyphenyl,
2-nitrophenyl, 2-methylphenyl, 2-methoxyphenyl,
2-phenoxyphenyl, 2-trifluoromethylphenyl, 4-fluorophenyl, 4-chlorophenyl,
4-bromophenyl, 4-nitrophenyl, 4-methylphenyl, 4-hydroxyphenyl,
4-methoxyphenyl, 4-ethoxyphenyl, 4-butoxyphenyl, 4-isopropylphenyl,
4-phenoxyphenyl, 4-trifluoromethylphenyl, 4-hydroxymethylphenyl,
3-methoxyphenyl, 3-hydroxyphenyl, 3-nitrophenyl, 3-fluorophenyl,
3-chlorophenyl, 3-bromophenyl, 3-phenoxyphenyl, 3-thiomethoxyphenyl,
3-methylphenyl, 3-trifluoromethylphenyl, 2,3-dichlorophenyl,
2,3-difluorophenyl, 2,4-dichlorophenyl, 2,5-dimethoxyphenyl,
3,4-dichlorophenyl, 3,4-difluorophenyl,
3,4-dimethoxyphenyl, 3,5-difluorophenyl, 3,5-dichlorophenyl,
3,5-di-(trifluoromethyl)phenyl, 3,5-dimethoxyphenyl, 2,4-dichlorophenyl,
2,4-difluorophenyl, 2,6-difluorophenyl, 3,4,5-trifluorophenyl,
3,4,5-trimethoxyphenyl, 3,4,5-tri-(trifluoromethyl)phenyl, 2,4,6-trifluorophenyl,
2,4,6-trimethylphenyl, 2,4,6-tri-(trifluoromethyl)phenyl, 2,3,5-trifluorophenyl,
2,4,5-trifluorophenyl, 2,5-difluorophenyl, 2-fluoro-3-trifluoromethylphenyl,
4-fluoro-2-trifluoromethylphenyl, 2-fluoro-4-trifluoromethylphenyl,
4-benzyloxyphenyl, 2-chloro-6-fluorophenyl, 2,3,4,5,6-pentafluorophenyl,
2,5-dimethylphenyl, 4-phenylphenyl, 2-fluoro-3-trifluoromethylphenyl, and phenyl.

3. A compound according to claim 1 wherein R$^1$ is 2-chlorophenyl.

4. A compound according to claim 1 wherein R$^2$ is selected from the group consisting hydrogen, methyl, ethyl, and isopropyl.

5. A compound according to claim 1 wherein R$^3$ is selected from the group consisting of hydrogen, C$_{1-4}$ alkyl, monocyclic aryl optionally substituted with a group selected from the group consisting of halo, alkoxy, alkyl, and alkyl substituted with halo.

6. A compound according to claim 1 wherein —NR$^4$R$^5$ is selected from the group consisting of (1'-methyl-[1,4']bipiperidin-4-yl)methylamino; (1-methyl-piperidin-4-ylmethyl)amino; (1-pyridin-4-ylmethyl-piperidin-4-yl)amino; (1-pyridin-4-ylmethyl-piperidin-4-ylmethyl)amino; (3,4,5,6-tetrahydro-2H-[1,4']bipyridin-4-yl)methylamino; (N-(benzyloxyacetyl)piperidin-4-yl)amino; (N-(pyridin-4-ylcarbonyl)piperidin-4-yl)methylamino; [1-(2-pyridin-4-yl-ethyl)-piperidin-4-yl]amino; [1-(2-pyridin-4-yl-ethyl)-piperidin-4-ylmethyl]amino; [1-(pyridin-4-ylcarbonyl)-piperidin-4-yl]amino; [2-(1'-methyl-[1,4']bipiperidin-4-yl)-ethyl]amino; [2-(1-pyridin-4-ylmethyl-piperidin-4-yl)-ethyl]amino; [2-(pyridine-4-yl)ethyl]amino; {2-[1-(2-pyridin-4-yl-ethyl)-piperidin-4-yl]-ethyl}amino; {2-[1-(N,N-dimethylaminocarbonyl)-piperidin-4-yl]ethyl}amino; {2-[1-(pyridin-4-ylcarbonyl)-piperidin--4-yl]ethyl}amino;
2-(N-methyl-N-pyridin-4-yl)ethylamino; 2-[1,4']bipiperidinyl-2-cyano-ethylamino; 2-[1,4']bipiperidinylethylamino; 2-[4-(pyridin-4-yl)piperidin-1-yl]ethylamino; 2-[N-((pyridin-4-yl)acetyl)piperidin-4-yl]ethylamino; 2-[N-(2,2,2-trichloroethoxyacetyl) piperidin-4-yl]ethyl amino; 5-(t-butoxycarbonyl)aminopentylamino; N-((pyridin-4-yl)acetyl)piperidin-4-ylamino; and piperidin-4-ylamino.

7. A compound according to claim 1 wherein $R^4$ is selected from 2-[N-(α-aminoacetyl)piperid-4-yl]eth-1-yl; 2-[N-(1-amino-1-methylethylcarbonyl)piperid-4-yl]eth-1-yl; (2-aminopyrid-4-yl)methyl; 2-(N-cyclopropylpiperidin-4-yl)eth-1-yl; 2-(N-hydroxypyrid-4-yl)eth-1-yl; (N-methylpiperidin-2-yl)methyl; 2-(N-methylpiperidin-2-yl)eth-1-yl; 2-(N-methylpiperidin-3-yl)eth-1-yl; 2-(N-methyl-1,2,5,6-tetrahydropyrid-4-yl)eth-1-yl; 2-(piperidin-2-yl)eth-1-yl; 2-(piperidin-3-yl)eth-1-yl; 2-(piperidin-4-yl)eth-1-yl; (piperidin-1-yl)carbonylmethyl; 2-(pyrid-2-yl)eth-1-yl; 2-(pyrid-3-yl)eth-1-yl; pyrid-3-yl-methyl; and 2-[N-(t-butoxycarbonylmethyl)piperid-4-yl]eth-1-yl.

8. A compound according to claim 7 wherein $R^5$ is selected from the group consisting or hydrogen, methyl, ethyl, and isopropyl.

9. The compound according to claim 1, wherein X is selected from the group consisting of hydrogen, bromo, chloro, fluoro and methyl.

10. A compound selected from the group consisting of:
4-Bromo-5-(2-chloro-benzoylamino)-1H-pyrazole-3-carboxylic acid [2-(1-methyl-piperidin-4-yl)-ethyl]-amide;
4-Bromo-5-(2-chloro-benzoylamino)-1H-pyrazole-3-carboxylic acid [2-(1 -phenyl-piperidin-4-yl)-ethyl]-amide;
5-(2-Chloro-benzoylamino)-4-methyl-2H-pyrazole-3-carboxylic acid (2-piperidin-1 -yl-ethyl)-amide;
5-(2-Chloro-benzoylamino)-4-methyl-1H-pyrazole-3-carboxylic acid (1 -benzyl-piperidin-4-yl)-amide;
4-Benzyl-5-(2-Chloro-benzoylamino)-1H-pyrazole-3-carboxylic acid (2-piperidin-1 -yl-ethyl)-amide;
4-Bromo-5-(2-chloro-benzoylamino)-1H-pyrazole-3-carboxylic acid (2-pyridin-4-yl-ethyl)-amide;
4-Bromo-5-(2-chloro-benzoylamino)-1H-pyrazole-3-carboxylic acid (1-benzyl-piperidin-4-yl)-amide;
(S)-4-Bromo-5-(2-chloro-benzoylamino)-1H-pyrazole-3-carboxylic acid (1-methyl-2-piperidin-1-yl-ethyl)-amide;
4-Bromo-5-(2-chloro-benzoylamino)-1H-pyrazole-3-carboxylic acid [2-(1-methyl-piperidin-4-yl)-ethyl]-amide;
4-Bromo-5-(2-chloro-benzoylamino)-1H-pyrazole-3-carboxylic acid (1 -benzenesulfonyl-piperidin-4-yl)-amide;
4-Bromo-5-(2-chloro-benzoylamino)-1H-pyrazole-3-carboxylic acid (1-methyl-piperidin-4-yl)-amide;
(R)-4-Bromo-5-(2-chloro-benzoylamino)-1H-pyrazole-3-carboxylic acid (1-methyl-2-piperidin-1-yl-ethyl)-amide;
(R)-4-Bromo-5-(2-chloro-benzoylarnino)-1H-pyrazole-3-carboxylic acid (1-phenyl-2-piperidin-1-yl-ethyl)-amide;
(S)-4-Bromo-5-(2-chloro-benzoylamino)-1H-pyrazole-3-carboxylic acid (1-phenyl-2-piperidin-1-yl-ethyl)-amide;
4-Bromo-5-(2-chloro-benzoylamino)-1H-pyrazole-3-carboxylic acid (pyridin-2-ylmethyl)-amide;
4-Bromo-5-(2-chloro-benzoylamino)-1H-pyrazole-3-carboxylic acid (pyridin-3 -ylmethyl)-amide;
4-Bromo-5-(2-chloro-benzoylamino)-1H-pyrazole-3-carboxylic acid (pyridin-4-ylmethyl)-amide;
4-Bromo-5-(2-chloro-benzoylamino)-1H-pyrazole-3-carboxylic acid (2-piperidin-1 -yl-ethyl)-amide;
4-Bromo-5-(2-chloro-benzoylamino)-1H-pyrazole-3-carboxylic acid piperidin-1-ylamide;
(R)-4-Bromo-5-(2-chloro-benzoylamino)-1H-pyrazole-3-carboxylic acid (3-phenyl-1-piperidin-1-ylmethyl-propyl)amide;
4-Bromo-5-(2-chloro-benzoylamino)-1H-pyrazole-3-carboxylic acid (3-methyl-2-oxo-piperidin-3-yl)amide;
4-Bromo-5-(2-chloro-benzoylamino)-1H-pyrazole-3-carboxylic acid (1-methyl-2-oxo-piperidin-3-yl)amide;
4-Bromo-5-(2-chloro-benzoylamino)-1H-pyrazole-3-carboxylic acid (1-methyl-piperidin-3-yl)-amide;
4-Bromo-5-[(2-chloro-benzoyl)-methyl-amino]-1H-pyrazole-3-carboxylic acid [2-(1-methyl-piperidin-4-yl)-ethyl]amide;
4-Bromo-5-(2-chlorobenzoylamino)-1H-pyrazole-3-carboxylic acid [2-(3,4,5,6-tetrahydro-2H-[1,4']bipyridin-4-yl)ethyl]amide;
4-Chloro-5-(2-chloro-benzoylamino)-1H-pyrazole-3-carboxylic acid [2-(3,4,5,6-tetrahydro-2H-[1,4']bipyridin-4-yl)-ethyl]amide;
4-Bromo-5-(2-chloro-benzoylamino)-1H-pyrazole-3-carboxylic acid [1-methyl-2-(1-methyl-piperidin-4-yl)ethyl]amide;
4-Bromo-5-(2-chlorobenzoylamino)-1H-pyrazole-3-carboxylic acid (3,4,5,6-tetrahydro-2H-[1,4']bipyridin-4-yl)amide;
4-Bromo-5-(2-chloro-benzoylamino)-1H-pyrazole-3-carboxylic acid [2-(3,4,5,6-tetrahydro-2H-[1,2']bipyridin-4-yl)-ethyl]amide;
5-(2-Chlorobenzoylamino)-1H-pyrazole-3-carboxylic acid [2-(1-methyl-piperidin-4-yl)-ethyl]amide;
4-Bromo-5-(2-chloro-benzoylamino)-1H-pyrazole-3-carboxylic acid [2-(N-methyl-N-pyridin-4-yl)eth-1-yl]amide;
4-Bromo-5-(2-chloro-benzoylamino)-1H-pyrazole-3-carboxylic acid (1-methyl-piperidin-4-ylmethyl)amide;
5-(3-Chloro-benzoylamino)-1H-pyrazole-3-carboxylic acid [2-(3,4,5,6-tetrahydro-2H-[1,4']bipyridin-4-yl)-ethyl]amide;
4-Bromo-5-(2-methyl-benzoylamino)-1H-pyrazole-3-carboxylic acid [2-(3,4,5,6-tetrahydro-2H-[1,4']bipyridin-4-yl)-ethyl]amide;
4-Bromo-5-(2-fluoro-benzoylamino)-1H-pyrazole-3-carboxylic acid [2-(3,4,5,6-tetrahydro-2H-[1,4']bipyridin-4-yl)-ethyl]amide;
4-Bromo-5-(2-chloro-benzoylamino)-1H-pyrazole-3-carboxylic acid (2-(N—(N,N-dimethylaminocarbonyl)piperidin-4-yl)eth-1-yl)amide;
4-Bromo-5-(2-chloro-benzoylamino)-1H-pyrazole-3-carboxylic acid {2-[1-(pyridin-4-carbonyl)-piperidin-4-yl]-ethyl}amide;
4-Bromo-5-(2-chloro-benzoylamino)-1H-pyrazole-3-carboxylic acid (1-pyridin-4-ylmethyl-piperidin-4-yl)amide;
4-Methyl-5-(2-chlorobenzoylamino)-1-(pyrimidin-2-yl)-pyrazole-3-carboxylic acid [2-(3,4,5,6-tetrahydro-2H-[1,4']bipyridin-4-yl)ethyl]amide;
4-Bromo-5-(2-chloro-benzoylamino)-1H-pyrazole-3-carboxylic acid [2-(1-pyridin-4-ylmethyl-piperidin-4-yl)-ethyl]amide;
4-Bromo-5-(2-chloro-benzoylamino)-1H-pyrazole-3-carboxylic acid {2[-1-(2-pyridin-4-yl-ethyl)-piperidin-4-yl]-ethyl}amide;
4-Bromo-5-(2-chloro-benzoylamino)-1H-pyrazole-3-carboxylic acid (1-pyridin-4-ylmethyl-piperidin-4-ylmethyl)amide;
4-Bromo-5-(2-chloro-benzoylamino)-1H-pyrazole-3-carboxylic acid [1-(2-pyridin-4-yl-ethyl)-piperidin-4-yl]amide;

4-Bromo-5-(2-chloro-benzoylamino)-1H-pyrazole-3-carboxylic acid [1-(2-pyridin-4-yl-ethyl)-piperidin-4-yl]amide;
4-Bromo-5-(2-chloro-benzoylamino)-1H-pyrazole-3-carboxylic acid [2-(1'-methyl-[1,4']bipiperidin-4-yl)-ethyl]amide;
4-Bromo-3-(2-chloro-benzoylamino)-1-methyl-pyrazole-5-carboxylic acid [2-(3,4,5,6-tetrahydro-2H-[1,4']bipyridin-4-yl)-ethyl]amide;
4-Bromo-5-(2-chloro-benzoylamino)-1H-pyrazole-3-carboxylic acid [(1-(2-pyridin-4-yl-acetyl)-piperidin-4-yl]amide;
4-Bromo-5-(2-chlorobenzoylamino)-1H-pyrazole-3-carboxylic acid [(1-pyridine-4-carbonyl)-piperidin-4-ylmethyl]amide;
4-Bromo-5-(2-chlorobenzoylamino)-1H-pyrazole-3-carboxylic acid (2-[1,4']bipiperidin-1'-yl-ethyl)amide
4-Bromo-5-(2-chlorobenzoylamino)-1H-pyrazole-3-carboxylic acid (2-[1,4']bipiperidin-1'-yl-2--cyanoethyl)amide;
4-Bromo-5-(2-chloro-benzoylamino)-1H-pyrazole-3-carboxylic acid [(1-(2-pyridin-4-yl-acetyl)-piperidin-4-yl]amide;
4Bromo-5-(2-chlorbenzoylamino)-1H-pyrazole-3-carboxylic acid {2-[1-(2-pyridin-4-yl-acetyl)-piperidin-4-yl]methyl}amide;
4-Bromo-5-(2-chlorobenzoylamino)-1H-pyrazole-3-carboxylic acid [2-(3,4,5,6-tetrahydro-2H-[4,4']bipiperidin-1-yl)ethyl]amide;
4Bromo-5-(2-chlorbenzoylamino)-1H-pyrazole-3-carboxylic acid [N-(benzyloxycarbonyl)piperidin-4yl]amide;
4Bromo-5-(2-chlorbenzoylamino)-1H-pyrazole-3-carboxylic acid piperidin-4-ylamide;
4Bromo-5-(2-chlorbenzoylamino)-1-methyl-1H-pyrazole-3-carboxylic acid [2-(3,4,5,6tetrahydro-2H-[1,4']bipyridin-4yl)methyl]amide;
5-(2-Chlorobenzoylamino)-1-methyl-1H-pyrazole-3-carboxylic acid [2-(3,4,5,6-tetrahydro-2H-[1,4']bipyridin-4-yl)ethyl]amide;
4-Bromo-5-(2-chlorobenzoylamino)-1H-pyrazole-3-carboxylic acid [2-(N-(2,2,2-trichloroethoxycarbonyl)piperidin-4-yl)eth-1-yl]amide;
3-(2-Chlorobenzoylamino)-1-methyl-1H-pyrazole-5-carboxylic acid [2-(3,4,5,6-tetrahydro-2H-[1,4']bipyridin-4-yl)ethyl]amide;
4-Bromo-5-(2-chlorobenzoylamino)-1H-pyrazole-3-carboxylic acid [1-(pyridine-4-carbonyl)-piperidin-4-yl]amide;
4-Bromo-5-(2-chlorobenzoylamino)-1H-pyrazole-3-carboxylic acid (3,4,5,6-tetrahydro-2H-[1,4']bipyridin-4-yl)methyl]amide;
5-(2-Chloro-benzoylamino)-1H-pyrazole-3-carboxylic acid [2-(3,4,5,6-tetrahydro-2H-[1,4']bipyridin-4-yl)methyl]amide;
4-Bromo-5-(2-Chloro-benzoylamino)-1H-pyrazole-3-carboxylic acid [2-(1'-methyl-[1,4']bipiperidin-4-yl)-methyl]amide;
4-Bromo-5-(2-fluoro-benzoylamino)-1H-pyrazole-3-carboxylic acid [2-(3,4,5,6-tetrahydro-2H-[1,4']bipyridin-4-yl)methyl]amide;
4-Bromo-5-(2-chlorobenzoylamino)-1H-pyrazole-3-carboxylic acid (2-(4-methylpiperidinyl)ethyl)amide;
1-Methyl-4-bromo-5-(2-chloro-benzoylamino)-1H-pyrazole-3-carboxylic acid [2-(3,4,5,6-tetrahydro-2H-[1,4']bipyridin-4-yl)methyl]amide;

1-Methyl-4-bromo-5-(2-fluoro-benzoylamino)-1H-pyrazole-3-carboxylic acid [2-(3,4,5,6-tetrahydro-2H-[1,4']bipyridin-4-yl)-ethyl]amide;
5-(2-Chlorobenzoylamino)-1H-pyrazole-3-carboxylic acid [2-(pyridin-4-yl)ethyl]amide;
4-Methyl-5-(2-chloro-benzoylamino)-1H-pyrazole-3-carboxylic acid [2-(3,4,5,6-tetrahydro-2H-[1,4']bipyridin-4-yl)-ethyl'amide;
1-t-Butyl-4-methyl-5-(2-chloro-benzoylamino)-1H-pyrazole-3-carboxylic acid [2-(3,4,5,6-tetrahydro-2H-[1,4']bipyridin-4-yl)-ethyl]amide;
4-Fluoro-5-(2-chloro-benzoylamino)-1H-pyrazole-3-carboxylic acid [2-(3,4,5,6-tetrahydro-2H-[1,4']bipyridin-4-yl)-ethyl]amide;
1-(Pyridin-2-yl)-4-methyl-5-(2-chloro-benzoylamino)-1H-pyrazole-3-carboxylic acid [2-(3,4,5,6-tetrahydro-2H-[1,4']bipyridin-4-yl)-ethyl]amide;
4-Bromo-5-(3-chloro-pyridin-4-ylcarbonyl)amino)-1H-pyrazole-3-carboxylic acid [2-(3,4,5,6-tetrahydro-2H-[1,4']bipyridin-4-yl)-ethyl]amide;
4-Bromo-5-(2-fluoro-benzoylamino)-1H-pyrazole-3-carboxylic acid [N-(pyridin-4-yl)piperidin-4-ylmethyl]amide;
4-Bromo-5-(2-chloro-benzoylamino)-1H-pyrazole-3-carboxylic acid [2-(4-methyl-piperidin-1-yl)ethyl]amide;
4-Bromo-5-(2-bromo-benzoylamino)-1H-pyrazole-3-carboxylic acid [N-(2-aminopyridin-6-yl)piperidin-4-ylmethyl]amide;
5-(2-Chloro-benzoylamino)-1H-pyrazole-3-carboxylic acid [2-(pyridine-4-yl)ethyl]amide;
4-Bromo-5-(2-chloro-benzoylamino)-1H-pyrazole-3-carboxylic acid [4-(N-pyridin-4-yl)amino)butyl]amide;
4-methyl-5-(2-fluoro-benzoylamino)-1-phenyl-pyrazole-3-carboxylic acid [2-(3,4,5,6-tetrahydro-2H-[1,4']bipyridin-4-yl)-ethyl]amide;
4-methyl-5-(2-fluoro-benzoylamino)-1-phenyl-pyrazole-3-carboxylic acid [2-(3,4,5,6-tetrahydro-2H-[1,4']bipyridin-4-yl)-ethyl]amide;
4-Methyl-5-(2-fluoro-benzoylamino)-1-t-butyl-pyrazole-3-carboxylic acid [2-(3,4,5,6-tetrahydro-2H-[1,4']bipyridin-4-yl)-ethyl]amide;
5-(2-Chloro-benzoylamino)-1-(phenyl)-pyrazole-3-carboxylic acid [2-(3,4,5,6-tetrahydro-2H-[1,4']bipyridin-4-yl)-ethyl]amide;
4-Bromo-5-(2-chloro-benzoylamino)-1-(phenyl)-pyrazole-3-carboxylic acid [2-(3,4,5,6-tetrahydro-2H-[1,4']bipyridin-4-yl)-ethyl]amide;
5-(2-Chloro-benzoylamino)-1-(3,4-dichlorophenyl)-pyrazole-3-carboxylic acid [2-(3,4,5,6-tetrahydro-2H-[1,4']bipyridin-4-yl)-ethyl]amide;
5-(2-Chloro-benzoylamino)-1-(m-trifluoromethyl-phenyl)-pyrazole-3-carboxylic acid [2-(3,4,5,6-tetrahydro-2H-[1,4']bipyridin-4-yl)-ethyl]amide;
4-Bromo-5-(2-chloro-benzoylamino)-1-(m-trifluoromethyl-phenyl)-pyrazole-3-carboxylic acid [2-(3,4,5,6-tetrahydro-2H-[1,4']bipyridin-4-yl)-ethyl]amide;
4-Bromo-5-(2-chloro-benzoylamino)-1H-pyrazole-3-carboxylic acid [2-(piperidin-4-yl)-ethyl]amide;
4-Bromo-5-(2-chloro-benzoylamino)-1-methyl-pyrazole-3-carboxylic acid [2-(3,4,5,6-tetrahydro-2H-[1,4']bipyridin-4-yl)-ethyl]amide;
4-Methyl-5-(2-chloro-benzoylamino)-1-methyl-pyrazole-3-carboxylic acid [2-(3,4,5,6-tetrahydro-2H-[1,4']bipyridin-4-yl)-ethyl]amide;
4-Methyl-5-(2-chloro-benzoylamino)-1-(2-methyl-phenyl)-pyrazole-3-carboxylic acid [2-(3,4,5,6-tetrahydro-2H-[1,4']bipyridin-4-yl)-ethyl]amide;

4-Methyl-5-(2-chloro-benzoylamino)-1-(3-methoxyphenyl)-pyrazole-3-carboxylic acid [2-(3,4,5,6-tetrahydro-2H-[1,4']bipyridin-4-yl)-ethyl]amide;

4-Methyl-5-(2-chloro-benzoylamino)-1-(p-fluorophenyl)-pyrazole-3-carboxylic acid [2-(3,4,5,6-tetrahydro-2H-[1,4']bipyridin-4-yl)-ethyl]amide;

4-Methyl-5-(2-chloro-benzoylamino)-1-phenyl-pyrazole-3-carboxylic acid [2-(3,4,5,6-tetrahydro-2H-[1,4']bipyridin-4-yl)-ethyl]amide;

5-(2-Chloro-benzoylamino)-1-(pyridine-2-yl)-pyrazole-3-carboxylic acid [2-(3,4,5,6-tetrahydro-2H-[1,4']bipyridin-4-yl)-ethyl]amide;

4-Bromo-5-(2-chloro-benzoylamino)-1-(p-fluorophenyl)-pyrazole-3-carboxylic acid [2-(3,4,5,6-tetrahydro-2H-[1,4']bipyridin-4-yl)-ethyl]amide;

4-Bromo-5-(2-chloro-benzoylamino)-1-(pyridin-2-yl)-pyrazole-3-carboxylic acid [2-(3,4,5,6-tetrahydro-2H-[1,4']bipyridin-4-yl)-ethyl]amide;

5-(2-Chloro-benzoylamino)-1-(p-fluorophenyl)-pyrazole-3-carboxylic acid [2-(3,4,5,6-tetrahydro-2H-[1,4']bipyridin-4-yl)-ethyl]amide;

5-Acetylamino-1-phenyl-1H-pyrazole-3-carboxylic acid [2-(3,4,5,6-tetrahydro-2H-[1,4']bipyridin-4-yl)-ethyl]amide;

4-Bromo-5-(2-chlorobenzoylamino)-1-(4-isopropylphenyl)-1H-pyrazole-3-carboxylic acid [2-(3,4,5,6-tetrahydro-2H-[1,4']bipyridin-4-yl)ethyl]amide;

5-(2-Chlorobenzoylamino)-1-(4-isopropylphenyl)-1H-pyrazole-3-carboxylic acid [2-(3,4,5,6-tetrahydro-2H-[1,4']bipyridin-4-yl)ethyl]amide;

4-Bromo-5-(2-fluorobenzoylamino)-1-phenyl-1H-pyrazole-3-carboxylic acid [2-(3,4,5,6-tetrahydro-2H-[1,4']bipyridin-4-yl)ethyl]amide;

5-(2-Fluorobenzoylamino)-1-phenyl-1H-pyrazole-3-carboxylic acid [2-(3,4,5,6-tetrahydro-2H-[1,4']bipyridin-4-yl)ethyl]amide;

4-Bromo-5-(2-chlorobenzoylamino)-1-(4-methoxyphenyl)-1H-pyrazole-3-carboxylic acid [2-(3,4,5,6-tetrahydro-2H-[1,4']bipyridin-4-yl)ethyl]amide; and 4-Bromo-5-(2-chlorobenzoylamino)-1-(2-N,N-diemthylamino)eth-1-yl)-pyrazole-3-carboxylic acid [2-(3,4,5,6-tetrahydro-2H-[1,4']bipyridin-4-yl)ethyl]amide;

or a pharmaceutically acceptable salt or stereoisomer thereof.

11. A pharmaceutical composition comprising a pharmaceutically acceptable carrier and a therapeutically effective amount of a compound of claim 1, or mixtures thereof.

12. A compound according to claim 1 wherein —$NR^4R^5$ is selected from the group consisting of (1-(phenylsulfonyl)piperidin-4-yl)amino;(1-benzylpiperidin-4-yl)amino; (1-methylpiperidin-4-yl)amino; (2-(1-phenylpiperidin-4-yl)eth-1-yl)amino; (2-(4-methylpiperidinyl)ethyl)amino; (2-(piperidin-1-yl)eth-1-yl)amino; (2-(R or S)-1-(1-methyl-piperidin-4-yl)prop-2-yl)amino; (2-(R or S)-1-(piperidin-1-yl)-2-(phenyl)eth-2-yl)amino; (2-(R or S)-1-(piperidin-1-yl)-4-(phenyl)but-2-yl)amino; (3-(R or S)-1-methyl-2-oxo-piperidin-3-yl)amino; (3-(R or S)-1-methylpiperidin-3-yl)amino; (3-(R or S)-3-methyl-2-oxo- piperidin-3-yl)amino; (piperidin-1-yl)amino; (pyridin-2-ylmethyl)amino; (pyridin-4-ylmethyl)amino; (R or S)-(1-methyl-2-piperidin-1-yl-ethlyl)amino; [2-(1-pryimidin-2-yl-piperidin-4-yl)ethyl]amino; [2-(3,4,5,6-tetrahydro-2H-[1,2']bipyridin-4-yl)-eth-1-yl]amino; [2-(3,4,5,6-tetrahydro-2H-[1,4']bipyridin-4-yl)-eth-1-yl]amino; [2-(3,4,5,6-tetrahydro-2H-[4,4']bipyridin-4-yl)-eth-l-yl]amino; [2-(N-(benzothiazol-2-yl)piperidin-4-yl)ethyl]amino; [2-(N-methyl-piperidin-4-yl)-ethyl]amino; [2-(pyridine-4-yl)ethyl]amino; [4-(N-pyridin-4-yl)amino)butyl]amino; [N-(2-aminopyridin-6-yl)piperidin-4-ylmethyl]amino; [N-(benzothiazol-2-yl)piperidin-4-ylmethyl]amino; [N-(benzyloxycarbonyl)piperidin-4-yl]amino; 2-(N-(4-1H-benzimidazol-2-yl)piperin-4-yl)ethylamino; and N-((pyridin-4yl)acetyl)piperidin-4-ylamino.

* * * * *

UNITED STATES PATENT AND TRADEMARK OFFICE
CERTIFICATE OF CORRECTION

| | | |
|---|---|---|
| PATENT NO. | : 7,432,379 B2 | Page 1 of 1 |
| APPLICATION NO. | : 10/837231 | |
| DATED | : October 7, 2008 | |
| INVENTOR(S) | : Tung et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 560 days.

Delete the phrase "by 560 days" and insert -- by 814 days --

Signed and Sealed this

Fourth Day of May, 2010

David J. Kappos
*Director of the United States Patent and Trademark Office*